United States Patent [19]
Rose et al.

[11] Patent Number: 6,015,565
[45] Date of Patent: Jan. 18, 2

```
RFHV    V  Y  K  K  N  I  V  P  Y  I  E  K  V  R  R  Y  I  K  I  A
        GTGTACAAGAAGAACATCGTGCCGTACATTTTCAAGGTACGCAGGTACATAAAATAGCA   60
        ** ***** ** ** ***** ***** ***** ***** **  ** **  ***** **
        GTGTACAAGAAGAACATCGTGCCGTATATTTTTAAGGTGCGGCGTATAGGAAAATTGCC   60
KSHV    V  Y  K  K  N  I  V  P  Y  I  E  K  V  R  R  Y  R  K  I  A (NIVPA>) gtg

```
            (<TDRDB) atgcaagtggctagccctact
         S   M   K   I   V   V   N   G   V   E   N   T   F   T   D   R   D   D   V   N
RFHV     TCCATGAAAATTGTAGTAGTGAACGGAGTCAACGGGATCGAAATAGTTCACCGATCGGATGACGTAAAC  240
         ****** * *   ** ****** ** **** *  **  ** ** *** ** *    *   **
         TCCATGAAGGTAAATGTCAACGGGTAAACGGGGTAGAAAAGAGATTTACTGACAGAGACGATGTTAAC  240
         S   M   K   V   N   V   N   G   V   E   N   T   F   T   D   R   D   D   V   N
KSHV     cttccattacagttgcccca (<VNVNB)
         (<TFTDB) gtgtaaatgactgtctctgct (<CFSSB)
         -agntacttctaacaacacttg
         (ENTFA>)   gtcaacggagtagaraayacnttyacnga

FIG. 1B
```

```
                                                                                  (PVLYA>)  agc-
            (<VEGLB)  gcagcttccagattgactgtt                                                  S
   (VEGLA>) cccgtcgaaggtctaactgaC                              L  T  D  N  I  Q  R  Y  E  F  S
         K  T  V  F  L  Q  P  V  E  G  L  T  D  N  I  Q  R  Y  E  F  S
RFHV    AAAACCGTATTCCTCCAGCCCGTCGAAGGTCTAACTGACAACATACAAAGATACTTTAGC  300
         * ****** ****** ****** ****** ***** **** ******* ****** ****
KSHV    ACCACAGTAT

Glycoprotein B encoding region

FRFDA  NIVPA  TVNCA  FAYDA  IYGKA  CYSRA           FREYA
⇒      ⇒      ⇒      ⇒      ⇒      ⇒                ⇐

⇐                    ⇐      ⇐      ⇐
          TVNCB               NIDFB  NVFDB  FREYB

Signal-Peptide Domain

```
KSHV    MPTSRLRA

HVS     MVPNKHLL
bHV4    MYYKTILF
mHV68   MYPTVKSM
EBV     MTRRRVLS
hHV6    MSKMVLF
hHVS1   MRQGAARG
```

```
KSHV   TLGTVILLVCFCAGAAHSRGDTFQTSSSPTPPGSSSKAPTKPGEE----------------
HVS    LIILSFSTACGQTTPTTAVEKNKTQAI---------------------------------
bHV4   FALIKVCSFNQTTHSTTTSPSISSTTTSSTTSTKPSNTTSTN-------------------
mHV68  RVAHLTNLLTLLCLLCHTHHLYVCQPTTLRQPSDMPAQDAPTETPPLSTNTN---------
EBV    VVVLLAALACRLGAQTPEQPAPPATTVQPTATRQ---------------------------
hHV6   LAVFLMNSVLMIYCDPDHYIRAGYN-----------------------------------
hHVS1  CRWFVVWALLGLTLGVLVASAAPSSPGTPGVAAATQAANGGPATPAPPAPGPAPTGDTKPKKNK
```

_FRFDA>_
```
KSHV   --------------ASGPKSVDFYQFRVCSASIT-GELFRFNLEQTC
HVS    --------------------YQEYFKYRVCSASTT-GELFTFDLDRTC
bHV4   SSLAASPQNTSTSKPSTDNQGTSTPTIPTVTDDTASK-NFYKYRVCSASSSGELFRFDLDQTC
mHV68  RTHLYVCQPTTLRQPSDMTPAQDAPTETPPLSTNTNRGFEYFRVCGVAAT-GETFRFDLDKTC
EBV    QLSVVVLLAALACRLGAQTPEQPAPPATTVQPTATRQQTSFPFRVCELSSH-GDLFRFSSDIQC
hHV6   ------------------------HKYPFRICSIAKG-TDLMRFDRDISC
hHVS1  KPKNPPPPRPAGDNATVAAGHATLREHLRDIKAENTDANFY----VCPPPTG-ATVVQFEQPRRC*
```

```
                         NIVPH>    VRRYIKIATSVTVYRGM--TEAAITNKYETPRPVPLY
RFHVMn                             VRRYRKVATPVTLYRGM--TDAAITNKYEIPRPVPLY
RFHVMm
KSHV     PDTKDKY-HQEGILLVYKKNIVPHIFKVRRYRKIATSVTVYRGL--TESAITNKYELPRPVPLY

HVS      PSTEDKV-HKEDILLVYKKNIVPYIFKVRRYKKITTSVRIFNGWTREGVAITNKWELSRAVPKY
bHV4     PDTKDKK-HVEGILLVLKKNIVPYIFKVRKYRKIATSVTVYRGW--SQAAVTNRDDISRAIPYN
mHV68    PSTQDKK-HVEGILLVYKINIVPYIFKIRRYRKIITQLTIWRGL--TTSSVTGKFEMATQAHEW
EBV      PSFGTRENHTEGLLMVEKDNIIPYSFKVRSYTKIVTNILIYNGW--YADSVTNRHEEKFSVDSY
hHV6     SPYKSNAKMSEGFFIYKTNIETYTFPVRTYKKELTFQSSYRDV--GVVYFLDRTVMGLAMPVY
hHSV1    PTRPEGQNYTEGIAVVFEKENIAPYKFKATMYYKDVTVSQWFGH-RYSQFMGIFEDRAPVPFEE
                   *           *  *  **  *  *

RFHVMn   EISHMDSTYQCFSSMKIVVNGVENTFTDRDDVNKTVFELQPVEGLTDNIQRYFSQ--PVLYSEPG
RFHVMm   EISHMDSTYQCFSSMKIVVNGVENTFTGRDDVNKSVFLQPVEGLTDNIKRYFSQ--PVLYSEPG
KSHV     EISHMDSTYQCFSSMKVVNVNGVENTFTDRDDVNTTVFELQPVEGLTDNIQRYFSQ--PVIYAEPG

HVS      EIDIMDKTYQCHNCMQIEVNGMLNSYYDRDGNNKTVDLKPVDGLTGAITRYISQ--PKVFADPG
bHV4     EISMIDRTYHCFSAMATVINGILNTYIDRDSENKSVPLQPVAGLTENINRYFSQ--PLIYAEPG
mHV68    EVGDFDSIYQCYNSATMVVNNVRQVYVDRDGVNKTVNIRPVDGLTGNIQRYFSQ--PTLYSEPG
EBV      EDTQMDTIYQCYNAVKMTKDGLTRVYVDRDGVNITVNLKPTGGLANGVRRYASQ--TELYDAPG
hHV6     EANLVNSHAQCYSAVAMKRPDGTVFSAFHEDNNKNNTLNLFPLNFKSITNKRFITTKEPYFARG
hHSV1    VIDKINAKGVCRSTAKYVRNNLETTAFHRDDHETDMELKPANAATRTSRGWH--TTDLKYN--PS
                *                                                    *
```

FIG. 3C

```
RFHVMn  WFPGIYRVG
RFHVMm  WFPGIYRVR
KSHV    WFPGIYRVRTTVNCEIVDMIARSAEPYNYFVTSLGDTVEVSPFCYNESS--CSTTPSNKN-GLS

HVS     WLWGTYRTRTTVNCEIVDMFARSADPYTYFVTALGDTVEVSPFCDVDNS--CPNAT----DVLS
bHV4    WFPGIYRVRTTVNCEVVDMYARSVEPYTHFITALGDTIEISPFCH--NNSQCTGNSTSRDATK
mHV68   WMPGFYRVRTTVNCEIVDMVARSMDPYNYIATALGDSLELSPFQTFDNTSQCTAPKRA--DMRV
EBV     WLIWTYRTRTTVNCLITDMMAKSNSPFDFVTTGQTVEMSPFYDGKNKETFHE-----RADS
hHV6    P-LMLYSTSTSLNCIVTEATAKAYPFSYFALTGEIVEGSPFENGSNGKHFAEPLEK--LTIL
hHSV1   RVEAFHRYGTTVNCIVEEVDARSVYPYDEFVLATGDFVYNSPFYGTREGSHTEHTSYAADRFKQ
                   *                                 ***

KSHV    VQVVLNHTVVTYSDRGTSPTPQNRIFVETGAYTLSWASESKTTAVCPLALWKTFPRSIQTTHED
                                                    *

HVS     VQIDLNHTVVDYGNRATSQQHKKRIFAHTLDYSVSWEAVNKSASVCSMVFWKSFQRAIQTEHDL
bHV4    VWIEENHQTVDY-ERRGHPTKDKRIFLKDEEYTISWKAEDRERAICDFVIWKTFPRAIQTIHNE
mHV68   REVK-NYKFVDYNNRGTAPAGQSRTFLETPSATYSWKTATRQTATCDLVHWKTFPRAIQTAHEH
EBV     FHVRTNYKIVDYDNRGTNPQGERRAFLDKGTYTLSWKLENRTA--YCPLQHWQTFDSTIATETGK
hHV6    ENYTMIEDLMNG-MNGATTLVRKIAFLEKADTLFSWEIKEENESVCMLKHWTVTHGLRAETDE
hHVS1   -VDGFYARDLTTKARATAPTTRN---LLTTPKFTVAWDWVPKRPSVCTMTKWQEVDEMLRSEGG
                                                    *               *

KSHV    SEHFVANEITATFTAPLTP---VANEFTDTYSCLTSDINTTLNA-SKAKLASTHVPNGTVQYFHT
HVS     TYHFIANEITAGFSTVKEP---LANEFTSDYNCLMTHINTTLED-KIARVNNTHTPNGTAEYYQT
bHV4    SEHFVANEVTASFLTSNQEETELRGNTEILNCMNSTINETLEE--TVKKFENKSHIRDGEVKYYKT
mHV68   SYHFVANEVTATFNTPLIE---VENFTSTYSCVSDQINKTISE-YIQKLNNSYVASGKTQYFKT
EBV     SIAVFTDEGTSSFVINTTV---GIELPDAFKCIEEQVNKTMHEKYEAVQDRYTKGQEAITYFIT
hHV6    TYHFISKELTAAFVAPKES---LNLTDPKQTCIKDEFEKIINEVYMSDYNDTYSMNGSYQIFKT
hHVS1   SFRFSSDAISTFTNLTE--YPLSRVDLGDCIGKDARDAMDRIFARRYNATHIKVGQPQYYLA
                                  *
```

FIG. 3D

```
KSHV    TGGLYLVWQPMSAINLTHAQGDSGNPTSSPPPSASPMTTSASRRK----------------

HVS     EGGMILVWQPLIAIELEEAMLEATTSPVTPSAPTSSSRSKRAI---------------------
bHV4    NGGLFLIWQAMKPLNLSE-------HTNYTIERNNKTGNKSRQK--------------------
mHV68   DGNLYLIWQPLEHPEIEDIDEDSDPEP-TPAPPKSTRRKREAA---------------------
EBV     SGGLLAWLPLTPRSLATVKNLTELTTPTSSPSSPSPPSAARGSTPAAVLRRRRDAGNAT
hHV6    TGDLILIWQPLVQKSL--MFLEQGSEKIRRRDVVDVKSRHDI----------------------
hHVS1   NGGFLIAYQPLLSNTLAELYVREHLREQSRKPPNPTPPPGAS----------------------
            *
                              FAYDA>
KSHV    RRSASTAAAGGGGSTDNLSYTQLQFAYDKLRDGINQVLEELSRAWCREQVRDNLMWYELSKINP

HVS     ------RSIRDVSAGSENNVFLSQIQYAYDKLRQSINNVLEELAITWCREQVRQTMVWYEIAKINP
bHV4    ------RSVDTKTFQGAKGLSTAQVQYAYDHLRTSMNHILEELTKTWCREQKKDNLMWYELSKINP
mHV68   -DNGNSTSEVSKGSENPLITAQIQFAYDKLTTSVNNVLEELSRAWCREQVRDTLMWYELSKVNP
EBV     TPVPPTAPGKSLGTLNNPATVQIQFAYDSLRRQINRMLGDLARAWCLEQKRQNMVLRELTKINP
hHV6    ---------------LYVQLQYLYDTLKDYINDALGNLAESWCLDQKRTITMLHELSKISP
hHVS1   ------ANASVERIKTTSSIEFARLQFTYNHIQRHVNDMLGRVAIAWCELQNHELTLWNEARKLNP
                 *         *                  *         *      *
```

FIG. 3E

```
                     <IYGKA>                                                      <CYSRA>
KSHV    TSVMTAIYGKRPVSAKFVGDAISVTECINVDQSSVNIHKSLRTNSK------DVCYARPLBTFKF

HVS     TSVMTAIYGKPVSRKALGDVISVTECINVDQSSVSIHKSLKTENN-------DICYSRPPVTFKF
bHV4    VSVMAAIYGKPVAVKAMGDAFMVSECINVDQASVNIHKSMRTDDP-------KVCYSRPLVTFKF
mHV68   TSVMSAIYGKPVAARYVGDAISVTDCIYVDQSSVNIHQSLRLQHD-------KTTCYSRPLVTFKF
EBV     TTVMSSIYGKAVAAKRLGDVISVSQCVPVNQATVTLRKSMRVPGS-------ETMCYSRPLVSFSF
hHV6    SSIVSEVYGRPISAQLHGDVLAISKCIEVNQSSVQLHKSMRVVDAKGVRSETMCYNRPLVTFSF
hHVS1   NAIASATVGRRVSARMLGDVMAVSTCVPVAADNVIVQNSMRISSR-------PGACYSRPLVSFRY
                 *                *       *                        *  * * *

KSHV    LNSS-NLFTGQLGARNEIILTNNQVETCKDTCEHYFITRNETLVYKDYAYLRTINTTDISTLNT

HVS     VNSS-QLFKGQLGARNEILLSESLVENCHQNAETFFTAKNETYHFKNYVHVETLPVNNISTLDT
bHV4    VNST-ATFRGQLGTRNEILLTNTHVETCRPTADHYFFVKNMTHYFKDYKFVKTMDTNNISTLDT
mHV68   INST-DPLTGQLGPRKEIILSNTNIETCKDESEHYFIBGEYIYYYKNYIFEEKLNLSSIATLFT
EBV     INDT-KTYEGQLGTDNEIFLTKKMTEVCQATSQYYFQSGNEIHVYNDYHHFKTIELDGIATLQT
hHV6    VNSTPEVVPGQLGLDNEILLGDHRTEECEIPSTKIFLSGNHAHVYTDYTHTNSTPIEDIEVLDA
hHVS1   EDQG-PLIVEGQVGENNELRLTRDAIEPCTVGHRRYFTFGGGVYFEEYAYSHQLSRADITTVST
                    *  *                                                 *

<NIDFB>    <NVFDB>     <FREYB
                                               FREYA>
KSHV    FIALNLSFIQNIDFKAIELYSSAEKRLASSVFDLETMFREYNYYTHRLAGLREDLDNTIDMNKE

HVS     FLALNLTFIENIDFKAVELYSSGERKLA-NVFDLETMFREYNYYAQSISGLRKDFDNSQRNNRD
bHV4    FLTLNLTFIDNIDFKTVELYSETERKMA-SALDLETMFREYNYTQKLASLREDLDNTIDLNRD
mHV68   FIALNISFIENIDFKTVELYSSTERKLASSVEDIESMFREYNYTYSLAGIKKDLDNTIDYNRD
EBV     FISLKIDPLENADFKVLDLYSPDELSRA-NVFDLEGIFREYNFQAQNIAGLRKDLDNAVSNGRN
hHV6    FIRLKIDPLENADFKVLDLYSPDELSRA-NVFDLENILREYNSYKSALYTIEAKI----AANTP
hHVS1   FIDLNITMLEDHEFVPLEVYTRHEIKDSGLLDYTEVQRRNQLHDLRFADIDTVIHADANAAMV-
              *       *      *                *
```

FIG. 3F

```
                                                              Membrane-spanning domain
KSHV   RFVRDLSEIVADLGGIGKTVVNVASSVVTLCGSLVTGFIN--------FIKHPLGGMLMIIIVIA
HVS    RIIQDFSEILADLGSIGKVIVNVASGAFSLFGGIVTGILN--------FIKNPLGGMFTFLLIGA
bHV4   RLVKDLSEMMADLGDIGKVVVNTFSGIVTVFGSIVGGFVS--------FTNPIGGVTILLLIV
mHV68  RLVQDLSDMMADLGDIGRSVVNVSSVVTFFSSIVTGFIK--------FFTNPLGGIFLLIGG
EBV    QFVDGLGELMDSLGSVGQDITNLVSTVGGLFSSLBSGFIS--------FLKNPFGGGIMLILAIV
hHV6   SYVNGINSFLQGLGAIGTGLGSVISVTAGALGDIVGGVVS--------FLKNPFGGGIMLILAIV
hHVS1  IHADANAAMFAGLGAFFEGMGDLGRAVGKVVMGIVGGVVSAVSGVSSFMSNPFGALAVGLLVLA
                                                             *  **        **

KSHV   ------TREEIKNILLGMHQLQQE
HVS    VIILVILIVRRTNNMSQAPIRMIYPDVEKSKSTVTP------------MEPETIKQILLGMHNMQQE
bHV4   VVFVFETVSRRTNNMNEAPIKMIYPNIDKASEQENIQP---------LPGEEIKRILLGMHQLQQS
mHV68  IIFLVVVINRRNSQFHDAPIKMLYPSVENYAARQAPPYSASPPAIDKEEIKRILLGMHQVHQE
EBV    VVILVISITRRTRQMSQQPVQMLYPGIDELAQQHASGEGPGINP-ISKTELQAIMLALHEQNQE
hHV6   VVVIIVVFVRQRHVLSKPIDMMFPYATNPVTTVSSVTGTTVVKTPSVKDVDGGTSVAVSEKEE
hHVS1  GLAAAFFAFRYVMRLQSNPMKALYPLTTKELKNPTNPDASGEGEEGGDFDEAKLAEAREMIRYM
                *
```

FIG. 3G

```
KSHV   ERQKADDLKKSTPSVFQRTANG-LRQRLGYKPLTQSLDISPETGE
HVS    AYKKEEQRAARPSIFRQAAETELR-KRSGYKQISTEDKIV
bHV4   EHGKSEEEASHKPGLFQLLGDGLQLLRRGYTR-LPTFDPSPGNDTSETHQKYV
mHV68  EKEAQKQLTNSGPTLWQK-ATGFLRNRRKGYSQ-LPLEDESTSL
EBV    QKRAAQRAAGPSVASRALQAARDRFPGLRRRYHDPETAAALLGEAETEF
hHV6   ADVSGQVSDDEYSQEAALKMLKAIKSLDESYRR-KPSSSESHASKPSLIDRIRYRGYKSVNVEEA
hHVS1  ALVSAMERTEHKAKKKGTSALLSAKVTDMVMRKRRNTNYTQVPNKDGDADEDDL
```

FIG. 4

| | |
|---|---|
| EBV | GGCGACCTGTGTTCCGCTTCCTCCGGACATCCAGTGTCCC |
| sHV1 | GGAGAATTGTTAGATTTGATTTAGACAGAACTGTCCA |
| mHV68 | GGGGAGACCTTCAGGTTTGATTTAGACAAAACATGCCCC |
| bHV4 | GGAGAACTATTCAGATTTCAGATTTGACCTTGATCAGACATGTCCA |

5'-gctgttcagatttgacttagaymanmcntgycc-3'
<FRFDA 256-fold 33mer>

FIG. 5

| | |
|---|---|
| EBV | GAGGGCCCTGTTGATGGTGTTTAAAGACAACATTATTCCCTACTCGTTTAAG |
| sHV1 | GAAGCATTCTTTTAGTGCTCTGTAGTGCAAAAAAATATAGTTCCATATATCTTTAAA |
| mHV68 | GAGGCATCTTCTTGCTCTGTGTATAAGATCAACATCGTGCCCTACATCTTCAAA |
| bHV4 | GAAGCATCCTGCTGGTACTAAAAAAGAATATTGTCCATACATCTTCAAA |

5'-gtgtacaagaagaacatcgtgccntayatnttyaa-3'
<NIVPA 64-fold 32mer>

5'-gtgtacaagaagaacatcgtgcc-3'
<NIVPASQ 23MER>

| | |
|---|---|
| EBV | AACAATCCCGCCACCGTCCAGATCCAATTGCCTACGAC |
| sHV1 | AATAATGTGTTCTATCACAAATACAATATGCATATGAT |
| mHV68 | AATCCGCTCATTACGGCCCAAATTCAATTGCCTATGAC |
| bHV4 | AAGGGCCTGTCCACTGCCGCCCAGTTCAATATGCCTATGAC |

5'--aataacctctttacggcccaaattcartwygcntayga-3'
   FAYDA 64-fold 38mer>

FIG. 8

| | |
|---|---|
| EBV | AATCCAACCACCGTCATGTCCAGCATCTACGGTAAGGCGGTG |
| sHV1 | AATCCAACAAGTGTTATGACAGCAATATATGGAAAACCTGTC |
| mHV68 | AACCCTACGACGTGTGATGTCTGCCATTTATGAAAGCCTGTC |
| bHV4 | AACCCAGTGAGTGTCATGGCAGCATTTATGGAAACCTGTG |

5'--ccaacgagtgtgatgtcagccatttayggnaarccngt-3'
   IYGKA 64-fold 38mer>

5'--ccaacgagtgtgatgtcagcc-3'
   ITGKASQ 21mer>

FIG. 9

| | |
|---|---|
| EBV | TGCTACTCGCGCCCCTGGTGTCCTTCAGCTTTATCAACGAC |
| sHV1 | TGCTATTCACGGCCTCCAGTTACACATTTAAATTTGTTAACAGT |
| mHV68 | TGCTACTCGAGACCTAGAGTCACCTTCAAATTTATAAACAGT |
| bHV4 | TGTTACTCCAGACCCCTGGTCACATTTAAATTTGTGAATAGT |

5'--tgctactcgacctctagtcaccttyaarttyrtnaa-3'
   CYSRA 64-fold 38mer>

5'--tgctactcgacctctagtcacc-3'
   CYSRASQ 24mer>

FIG. 10

```
EBV     AACATTGACTTTGCCTCCCTGAGCTGTACTCACGGGACGAACAGCGT
sHV1    AATATTGACTTTAAAGCTGTGAATTGTATTCAAGTGAGAGAGAAAG
mHV68   AATATCGACTTCAAAACAGTAGAACTGTACTCCTCTACTGAAAGAAA
bHV4    AATATAGATTTCAAGACAGTGGAACTTTACAGTGAGACTGAAAGAAAG
                       3'-ttrtadctraarttytgtcacctgacatgaggcca-3'
                                <NIDFB 48-fold 36mer>
                       3'-tgtcacctgacatgaggcca-5'
                                <NIDFBSQ 21mer>
```

FIG. 11

```
EBV     AACGTCTTTGACCTGGAGGGCATCTTCCGGGAGTACAACTTCCAGGCGCAAAAC
sHV1    AACGTTTGATTTAGAGACTATGTTTAGAATATAACTATTACGCTCAGAGT
mHV68   AGCGTCTTTGATATAGAATCCATGTTTAGGAATATAACTATTACACCTACAGC
bHV4    AGTGCCCTCGACCTGGAGACGATGTTTAGAGATGTTAGAGTATAATTACTACACAGAAG
                       5'-tttgacctggagactatgttymgnartyaa-3'
                                FREYA 64-fold 32mer>
                       3'-tacaartcyctyatrttgatgatgtgggtctcg-5'
                                <FREYB 16-fold 33mer
                       3'-ttrcanaarctgacctctcgtacaaggctct-5'
                                <NVFDB 32-fold 32mer
```

FIG. 12

```
EBV     TTCATCTCCTTCTTCAAAAACCCCTTCGGGCGGCATGCTC
sHV1    ATATTAAATTTATTAAAAATCCTTTAGTGGCATGTTC
mHV68   TTCATTAAATTCTTTACCAACCCTCTAGGGGGTGACG
bHV4    TTTGTCAGTTTTTCACAAACCCCATTGGGGGCGTGACG
                       5'-accttcatcaaaaatcccttnggnggnatgyt-3'
                                GGMA 128-fold 32mer>
```

FIG. 13A

```
         V   R   R   Y   R   K   I   A   T   S   V   T   V   Y   R   G   L   T   E
KSHV   GGTGCGGCGCTATAGAAGAAAATTGCCACCTCTGTCACGGTCTACAGGGGCTTGACAGAG---
RFHV   ...A..CA.G..C.TA.....A..A..A.........C.C..TA.......A---
bHV4   A...A..AAA....A.............A..G..A..T.....A..G.G.T.CC..---
sHV1   A..CA..AA.A...C.AA....CA..A..A...CGTA.T.TT.AT...G...TAGAGA
eHV2   T..CA..AAAG.........G..CATG....GAC...CA.....A...T.G..GC..---
mHV68  AA.CA..A.A......A..A..AATT..TCAAC.G..CA...GGC.A....C.A..CACT---
hEBV   ...C...CTC....C.CC...G..A.TG......AACA.TCTCA......AT....G.TAC.C..---

S   A   I   T   N   K   Y   E   L   P   R   P   V   P   L   Y   E   I   S
KSHV   ----TCCGCCATCACCAACAAGTATGAACTCCCCGAGACCCGTGCCACTCTATGAGATAAG
RFHV   ----G.A..A....A......A......GA....C.G.......T....C....C..
bHV4   ----G.A..TG.T....G.....TA..AGC...G..A.A..CTATA....A..TTC
sHV1   AGGTGTT..T..T..A.....A.GG....TT.T..G.T..T...AAA.........GA
eHV2   ----GAT.....A..A...C..C.CACGAGAGCTACG....C..C...C...G.CCA
mHV68  ----AGTT.AG...TGGT..A.T...A.GG.C.CT.AG.CC.ACGAG.GG..AG.GG.
hEBV   ----GA.T..G.G.......CG.C.C..GGAGAA.TTCT....TGACAG....C..A.CTGA

H   M   D   S   T   Y   Q   C   F   S   S   M   K   V   N   V   N   G   V   E
KSHV   CCACATGGACAGCACCTATCAGTGCTTTAGTTCCATGAAGGTAAATGTCAACGGGTAGA
RFHV   T................C..............AA.TGTA..G..C..A..C..
bHV4   AATG..A..T..G.....T.....T..CTC.G.T...GCAAC.GTCA.T..T..A.TCT
sHV1   TATT....T.AG..T..C..A..TCAT.A..G...C..A..G..A....AA..GTT
eHV2   GATG......CA.TAT..............CG..G.AC...C..C.AGGGG...CAC.T
mHV68  .G..T.T......T.........AC.A.AG.GCC.CCA.GGTG..A...AAC..CAG
hEBV   ...G........T.C..T.....C.........AC.ACG.GG.C...A.G.CAAAAG.T...C.GAC
```

FIG. 13B

```
        N  T  F  T  D  R  D  D  V  N  T  T  V  F  L  Q  P  V  E  G
        AACACATTACTGACAGACGATGTTAACACCAGTATTCCTCCAACCAGTAGAGG
KSHV    AACACATTACTGACAGACGATGTTAACACCAGTATTCCTCCAACCAGTAGAGG
RFHV    ...T..G.C.C..TC.G..T.C..A...AA..C....T....G..C..C..A..
bHV4    G.....C.A..TA......G..TTC..AA..T.AGT.T..TCC....G.....G.CC..
sHV1    ...TT.T.ACTA..........T.GAAA....AA.T...GA.T.AA.G..T...T..
eHV2    C....C.ACTA.......G....GGTGG...GAG..C.CC....A....G.CC..T..
mHV68   .C.GGTG.A.GTG.........T.GG..C..T.AA..T..GAA.A.A.GC..T..T..T..
hEBV    GCG.GTG.A.GTA........C.C.......GA......T....C..CAA....AA.G..CACC..G...

L  T  D  N  I  Q  R  Y  F  S  Q  P  V  I  Y  A  E  P  G  W
        GCTTACGGATAACATTCAAAGGTACTTTAGCCAGCCGGTCATCTACGCGGAACCCGGCTG
KSHV    GCTTACGGATAACATTCAAAGGTACTTTAGCCAGCCGGTCATCTACGCGGAACCCGGCTG
RFHV    T..A..T..C...A........A.........A..A.AC.G..TT.......A..
bHV4    A..G..T..G...TAA.C..A........T..A..TC...A.T..A..T.......
sHV1    T..A....G.GCA.T.AC..A.....A.T...A.....TAAAG.T.TT..T..T.....
eHV2    T..C...CTC..G..TAACGC.C.TCAG..T..A..A.AGG.G....CACC....A.AAA
mHV68   T..A..A.GG..T..C...A..........T......CAC.C.T..TT.A...T..T..
hEBV    C..GG.CA.CGGGG.G.GCC.C...GCC.....A....AGC....T.AC.CC......G..

F  P  G  I  Y  R  V  R
        GTTTCCCGGCATATACAGAGTTAGG
KSHV    GTTTCCCGGCATATACAGAGTTAGG
RFHV    ...C..A..T.C......G..G...
bHV4    .....A..G..T....G..A
sHV1    .C.ATGG..A.CT.....GAC.C.A
eHV2    CC.GTTGT.GTCT....C.ACA..A
mHV68   .A.G..T...T.T..TC.T...C.A
hEBV    ...GATAT.G.CT.......ACA..A
```

FIG. 14

```
KSHV   VRRYRKIATSVTVYRGLTES--AITNKYELPRPVPLYEISHMDSTYQCFSSMKVNVNGVE
RFHV   ...I..........M..A--.....I..............IV..........
bHV4   ..K..............WSQA--V..RDDIS.AI.YN...MI.R..H..A.ATVI..IL
sHV1   ..K..T...RIFN.W.REGV.....W..S.A..K...DIM.K.....HNC.QIE....ML
mHV68  I....I.QL.IW....T.--SV.G.F.MATQAHEW.VGDF..I...YN.ATMV..N.R
eHV2   ..K....M..T.I.K.WS.D--....QHTRSYA......VQM..HY.......AVQ..EG.HV
hEBV   ..S.T..V.NILI.N.WYAD--SV..RH.EKFS.DS...TDQ..TI...YNAV.MTKD..LT

VTVYRG   AITNKYE          SHMDSTY     VE-
              rgltesa
              rgmteaa KSHV   NTFTDRDDVNTTVFLQPVEGLTDNIQRYFSQPVIYAEPGWFPGIYRVR
RFHV   .........K................L.S.............G
bHV4   ..YI...SE.KS.P....A....E..N....L............
sHV1   .SYY...GN.K..D.K..D...GA.T..I...KVF.D...LW.T...T.
mHV68  QVYV....G..K..NIR..D...G.........TL.S...M..F....
eHV2   ..YY...GW.E.A..K.AD...SS.T..Q....EV..T.RNLLWS.TT.
hEBV   RVYV....G..I..N.K.TG..ANGVR..A..TEL.DA...LIWT...T.

-NTFTD     TVELQPV      TDNIQRY   pviyaep
                                  pvlysep
                        RFYSQP (-) Deletions
(.) Amino acids identical to KSHV
```

FIG. 15

| | | |
|---|---|---|
| KSHV | VRRYRKIATSVTVYRGLTES---AITNKYELPRPVPLYEISHMDSTYQCFSSMKVN | V-NGVENTFTDRDDD-NTTVFLQPVEGLTDNIQRYFSQPVIYAEPGWFPGIYRVR |
| RFHV | VRRYIKIATSVTVYRGMTEA---AITNKYEIPRPVPLYEISHMDSTYQCFSSMKIV | V-NGVENTFTDRDDV-NKTVFLQPVEGLTDNIQRYFSQPVLYSEPGWFPGIYRVG |
| bHV4 | VRKYRKIATSVTVYRGWSQA---AVTNRDDISRAIPYNEISMIDRTYHCFSAMATV | I-NGILNTYIDRDSE-NKSVPLQPVAGLTENINRYFSQPLIYAEPGWFPGIYRVR |
| sHV1 | VRRYKKITTSVRIFNGWTREGVAITNKWELSRAVPKYEIDIMDKTYQCHNCMQIE | V-NGMLNSYDRDGN-NKTVDLKPVDGLTGAITRYISQPKVFADPGWLWGTYRTR |
| eHV2 | VRKYRKIMTSTTIYKGWSED---AITNQHTRSYAVPLYEVQMDHYYQCFSAVQVN | E-GGHVNTYYDRDGW-NETAFLKPADGLYSSITRYQSQPEVYATPRNLLWSYTTR |
| mHV68 | IRRYRKIITQLTIWRGLTTS---SVTGKFEMATQAHEWEVGDFDSIYQCYNSATMV | V-NNVRQVYVDRDGV-NKTVNIRPVDGLTGNIQRYFSQPTLYSEPGWMPGFYRVR |
| hEBV | VRSYTKIVTNLILYNGWYAD---SVTNRHEEKFSVDSYETDQMDTIYQCYNAVKMT | K-DGLTRVYVDRDGV-NITVNLKPTGGLANGVRRYASQTELYDAPGWLIWTYRTR |
| hCMV | VRVYQKVLTFRRSYAYIHTT---YLLGSNTEYVAPPMWEIHHINSHSQCYSSYSRV | I-AGTVFVAYHRDSYENKTMQLMPDDYSNTHSTRYVTVKDQWHSRGSTW--LYRET |
| hHHV6 | VRTYKKELTFQSSYRDVGVV---YFLDRTBMGLAMPVYEANLVNSHAQCYSAVAMK | RPDGTVFSAFHEDNNKNNTLNLFPLNFKSITNKRFITTKEPYFARGPLW--LYSTS |
| hVZV | ATVYYKDVIVSTAWAGSSYT-QITNRYADRVPIPVSEITDTIDKFGKCSSKATYV | R-NNHKVEAFNEDKN--PQDMPLIASKYNSVGSKAWHTTNDTYMVAG--TPGTYRTG |
| sHVSA8 | ATMYYKDVTVSQWFGHRYS-QFMGIFEDRAPVPFEEVMDKINAKGVCRSTAKYV | R-NNMESTAFHRDDH--ESDMALKPAKAATRTSRGWHTTDLKYNPARVEAFHRYGT |
| hHSV1 | ATMYYKDVTVSQWFGHRYS-QFMGIFEDRAPVPFEEVIDKINAKGVCRSTAKYV | R-NNLETTAFHRDDH--ETDMELKPANAATRTSRGWHTTDLKYNPSRVEAFHRYGT |

FIG. 17A

```
KSHV   GGTGCGGGCGCTATAGGAAAATTGCCACCCTCTGTCACGGGTCTACAGGGGCTTGACAGAG---
RFHV   ...A..CA.G..C.TA.........A.A..A..............C.C..TA......A---
bHV4   A...A..AAA....A.................A..G..A..T.....A..G.G.T.CC..--
sHV1   A...CA.AA.A...C.AA.......CA.A..A..A...CGTA.T.TT.AT.....G...TAGAGA
eHV2   T..CA.AAAG............G..CATG....GAC....CA........A...T.G..GC...--
mHV68  AA.CA...A.A.....A...A...A..AATT..TCAAC.G..CA.....GGC.A.....C.A..CACT---
hEBV   ...C...CTC....C.CC...C.G..A.TG...AACA.TCTCA......AT.....G.TAC.C..--

KSHV   ----TCCGCCATCACCAACAAGTATGAACTCCCGAGACCCGTGCCACTCTATGAGATAAG
RFHV   ----G.A..A......A......A.......GA......C..G..........T....C...C..
bHV4   ----G.A..TG.T......T.G.G...TA..AGC....G..A.A..CTATA....A..TTC
sHV1   AGGTGTT..T..T..A.....A.GG......TT.T..G.T...AAA.........GA
eHV2   ----GAT.....A..A....C..C.CACGAGGAGCTACG.....C..C..G..C...G.CCA
mHV68  ----AGTT..AG....TGGT..A.T.....A.GG.C.CT.AG.CC.ACGAG.GG..AG.GG.
hEBV   ----GA.T..G.G........CG.C.C...GGAGAA.TTCT....TGACAG.....C..A.CTGA (SHMDA>) agacccgtgccactctatgarathag- KSHV   CCACATGGACAGCACCTATCAGTGCTTTAGTTCCATGAAGGTAAATGTCAACGGGGTAGA
RFHV   T..............C........C...........AA.TGTA..G..C..A..C..
bHV4   AATG...A..T..G.....C.....T...T..CTC.G.T...GCAAC.GTCA.T..T...A.TCT
sHV1   TATT.....T.AG..T..C..A..TCAT.A..G....C..A..G.A..A......AA.GTT
eHV2   GATG.....CA.TAT..............CG...G.AC.....C..C.AGGGG...CAC.T
mHV68  .G..T..T......T........T.........AC.A.AG.GCC.CCA.GGTG..A...AAC..CAG
hEBV   ...G......T.C..T...C..........AC.ACG.GG.C...A.G.CAAAAG.T...C.GAC (<CFSSB)                  (ENTFA>)
            (SHMDA>)          acraartcragntacttctaacaacacttg
       ycayatgga                              gtcaacggagtaga-
```

FIG. 17B

```
KSHV    AAACACATTTACTGACAGAGACGATGTTAACACCACAGTATTCCTCCAACCAGTAGAGG
RFHV    ...T..G..C..C..TC.G..T..C..A...AA..C.....T.....G..C..C..A..
bHV4    G......C..A..TA......G..TTC..AA..T.AGT.T..TCC..........G..CC.
sHV1    ....TT.T.ACTA........T.GAAA......AA..T....GA.T.AA.G..T....T..
eHV2    C......C.ACTA.......G....GGTGG...GAG..C.CC......A.....G.CC..T..
mHV68   .C.GGTG.A.GTG...........T.GG..C..T.AA..T..GAA.A.A.GC..T..T..T..
hEBV    GCG.GTG.A.GTA......C.C....GA..........T.....C..CAA...AA.G..CACC.G...

-raayacnttyacnga    (ENTFA>)

KSHV    GCTTACGGATAACATTCAAAGGTACTTTAGCCAGCCGGTCATCTTACGCGGAACCCGGCTG
RFHV    T..A..T..C.....A......A.............A..A..AC.G..TT........A..
bHV4    A..G..T..G....TAA.C..A.......T.A..TC...A.T.A...T..........
sHV1    T..A.....G.GCA.T.AC...A.....A.T......A..TAAAG.T.TT..T..T......
eHV2    T..C...CTC..G..TAACGC.C..TCAG..T..A.A.AGG.G...CACC...A.AAA
mHV68   T..A..A.GG..T..C...A.....T.......T.....CAC.C.T..TT.A...T..T..
hEBV    C..GG..CA.CGGGG.G.GCC.C...GCC......A...AGC...T.AC.CC......G..

tgnctrttrtaagtttccatgaaatcggtcggtca    (<DNIQB)

KSHV    GTTTCCCGGCATATACAGAGTTAGG
RFHV    ...C..A..T..C.....G....G...
bHV4    .....A..G..T..T.....G..A
sHV1    .C.ATGG..A.CT......GAC.C.A
eHV2    CC.GTTGT.GTCT....C.ACA..A
mHV68   .A.G..T...T..TC.T...C.A
hEBV    ...GATAT.G.CT......ACA..A
```

FIG. 19A

Capsid/Maturation/Tranpsort Gene

```
  G  G  M  F  P  I  Q  K  M  M  V  S  E  M  I  W  P  S  I  E
TGGGGCATGTTTCCATTCAAAAGATGATGGTATCAGAGATGATCTGGCCCAGCATAGA     60

R  K  D  W  I  E  P  N  F  N  Q  F  Y  S  F  E  N  Q  D  I
GCGGAAGACTGGATAGAGCCCAACTTCAACCAGTTCTATAGCTTTGAGAATCAAGACAT    120

N  H  L  Q  K  R  A  W  E  Y  I  R  E  L  V  L  S  V  S  L
AAACCATCTGCAAAAGAGAGCTTGGGAATATCAGAGAGCTGGTATTATCGGTTTCTCT    180

N  N  R  T  W  E  R  E  L  K  I  L  L  T  P  Q  G  S  P  G
GAACAACAGAACTTGGGAGAGGAGCTAAAAATACTTCTCACGCCTCAGGCTCACCGGG    240

F  E  E  P  K  P  A  G  L  T  T  G  L  Y  L  T  F  E  I  S
GTTTGAGGAACCGAAACCCGCAGGACTCACAACGGGGCTGTACCTAACATTTGAGATATC   300

A  P  L  V  L  V  D  K  K  Y  G  W  I  F  K  D  L  Y  A  L
TGCGCCCTTGGTGTTGGTGGATAAAAAATATGGCTGGATATTTAAAGACCTGTACGCCCT  360

L  Y  H  H  L  Q  L  S  N  H  N  D  S  Q  V  *    Glycoprotein B Gene
                                             M  T  P  R  S  R  L  A  T  L
TCTGTACCACCACCTGCAACTGAGCAACCACAATGACTCCCAGTCTAGATTGGCCACCC   420

G  T  V  I  L  L  V  C  F  C  A  G  A  A  H  S  R  G  D  T
TGGGGACTGTCATCCCTGTTGGTCTGCTTTTGCGCCAGGGCGGCCACTGAGGGGTGACA  480
```

FIG. 19B

```
  F   Q   T   S   S   S   P   T   P   P   G   S   S   S   K   A   P   T   K   P
CCTTTCAGACGTCCAGTTCCCCACACCCCAGGATCTTCCTCTAAGGCCCCCACCAAAC                              540

G   E   E   A   S   G   P   K   S   V   D   F   Y   Q   F   R   V   C   S   A
CTGGTGAGGAAGCATCTGGTCCTAAGAGTGTGGACTTTTACCAGTTCAGAGTGTGTAGTG                            600

S   I   T   G   E   L   F   R   F   N   L   E   Q   T   C   P   D   T   K   D
CATCGATCACCGGGGAGCTTTTTCGGTTCAACCTGGAGCAGACGTGCCCAGACACCAAAG                            660

K   Y   H   Q   E   G   I   L   L   V   Y   K   K   N   I   V   P   H   I   F
ACAAGTACCACCAAGAAGGAATTTTACTGGTGTACAAAAAAACATAGTGCCTCATATCT                             720

K   V   R   R   Y   R   K   I   A   T   S   V   T   V   Y   R   G   L   T   E
TTAAGGTGCGGCGCTATAGGAAAATTGCCACCTCTGTCACGGTCTACAGGGGCTTGACAG                            780

S   A   I   T   N   K   Y   E   L   P   R   P   V   P   L   Y   E   I   S   H
AGTCCGCCATCACCAACAAGTATGAACTCCCGAGACCCGTGCCACTCTATGAGATAAGCC                            840

M   D   S   T   Y   Q   C   F   S   S   M   K   V   N   V   N   G   V   E   N
ACATGGACAGCACCTATCAGTGCTTTAGTTCCATGAAGGTAAATGTCAACGGGGTAGAAA                            900
```

FIG. 19C

```
  T  F  T  D  R  D  D  V  N  T  T  V  F  L  Q  P  V  E  G  L
ACACATTTACTGACAGAGACGATGTTAACCACAGTATTCCTCCAACCAGTAGAGGGC       960

T  D  N  I  Q  R  Y  F  S  Q  P  V  I  Y  A  E  P  G  W  F
TTACGGATAACATTCAAAGGTACTTTAGCCAGCCGGTCATCTACGCGGAACCCGGCTGGT   1020

P  G  I  Y  R  V  R  T  V  N  C  E  I  V  D  M  I  A  R
TTCCCGGCATATACAGAGTTAGGACCACTGTCAATTGCGAGATAGTGGACATGATAGCCA   1080
                                  > C

S  A  E  P  Y  N  Y  F  V  T  S  L  G  D  T  V  E  V  S  P
GGTCTGCTGAACCATACAATTACTTTGTCACGTCACTGGGTGACACGGTGGAAGTCTCCC   1140

F  C  Y  N  E  S  S  C  S  T  T  P  S  N  K  N  G  L  S  V
CTTTTTGCTATAACGAATCCTCATGCAGCAGCACAACCCCAGCAACAAAAATGCCTTAGCG   1200

Q  V  V  L  N  H  T  V  V  T  Y  S  D  R  G  T  S  P  T  P
TCCAAGTAGTTCTCAACCACACTGTGGTCACGTACTCTGACAGAGGAACCAGTCCCACTC   1260

Q  N  R  I  F  V  E  T  G  A  Y  T  L  S  W  A  S  E  S  K
CCCAAAACAGGATCTTTGTGGAAACGGGAGCGTACACGCTTTCGTGGGCCTCCGAGAGCA   1320

T  A  V  C  P  L  A  L  W  K  T  F  P  R  S  I  Q  T  T
AGACCACGGCCGTGTCCGCTGGCACTGTGGAAAACCTTCCCGCTCCATCCAGACTA      1380
```

FIG. 19D

```
  H   E   D   S   F   H   F   V   A   N   E   I   T   A   T   F   T   A   P   L
CCCACGAGGACAGCTTCCACTTTGTGGCCAACGAGATCACGGCCACCTTCACGGCTCCTC                    1440

T   P   V   A   N   F   T   D   Y   S   C   L   T   S   D   I   N   T   T
TAACGCCAGTGGCCAACTTTACCGACTACTCTTGTCTGACCTCGGATATCAACACCA                       1550

L   N   A   S   K   A   K   L   A   S   T   H   V   P   N   G   T   V   Q   Y
CGCTTAACGCCAGCAAGGCCAAACTGGCCAGCACTCACGTCCCTAACGGGACGGTCCAGT                    1560

F   H   T   T   G   G   L   Y   L   V   W   Q   P   M   S   A   I   N   L   T
ACTTCCACACAACAGGCGACAGCTCTATTTGGTCTGGCAGCCCATGTCCGCGATTAACCTGA                  1620

H   A   Q   G   D   S   G   N   P   T   S   S   P   P   P   S   A   S   P   M
CTCACGCTCAGGGCGACAGCGGAAACCCCACGTCATCGCCCCTCCGCCATCCCCCA                        1680

T   S   A   S   R   R   K   R   R   S   A   S   T   A   A   A   G   G   G
TGACCACCTCTGCCAGCCGCCAGAAAGAGACGGTCAGCACCGCAGCCGCCGGGGCG                        1740

G   S   T   D   N   L   S   Y   T   Q   L   Q   F   A   Y   D   K   L   R   D
GGGGTCCACGGACAACCTGTCTTACACGCAGTTGCTACAGTTTGCCTACGACAAACTGCGGG                  1800

G   I   N   Q   V   L   E   E   L   S   R   A   W   C   R   E   Q   V   R   D
ATGGCATTAATCAGGTGTTAGAAGAACTCTCCAGGGCATGGTGTCGCGAGCAGGTCAGGG                    1860
```

FIG. 19E

```
  N   L   M   W   Y   E   L   S   K   I   N   P   T   S   V   M   T   A   I   Y
ACAACCTAATGTGGTACGAGCTCAGTAAAATCAACCCCACCAGCGTTATGACAGCCATCT          1920

G   R   P   V   S   A   K   F   V   G   D   A   I   S   V   T   E   C   I   N
ACGGTCGACCTGTATCCGCCAAGTTCGTAGGAGACGCCATTTCCGTGACCGAGTGCATTA          1980

V   D   Q   S   S   V   N   I   H   K   S   L   R   T   N   S   K   D   V   C
ACGTGGACCAGAGCTCCGTAAACATCCACAAGAGCCTCAGAACCAATAGTAAGGACGTGT          2040

Y   A   R   P   L   V   T   F   K   F   L   N   S   S   N   L   F   T   G   Q
GTTACGCGCCCCTGGTGACGTTTAAGTTTTTGAACAGTTCCAACCTATTCACCGGCC            2100

L   G   A   R   N   E   I   I   L   T   N   N   Q   V   E   T   C   K   D   T
AGCTGGGGCGCGCAATGAGATAATACTGACCAACAACCAGGTGGAAACCTGCAAAGACA          2160

C   E   H   Y   F   I   T   R   N   E   T   L   V   Y   K   D   Y   A   Y   L
CCTGCGAACACTACTTCATCACCCGCAACGAGACTCTGGTGTATAAGGACTACGCGTACC        2220

R   T   I   N   T   D   I   S   T   L   N   T   F   I   A   L   N   L   S
TGCGCACTATAAACACCGACATATCCACCCTGAAGAGTTTTATCGCCCTGAATCTAT            2280

F   I   Q   N   I   D   F   K   A   I   E   L   Y   S   S   A   E   K   R   L
CCTTTATTCAAAACATAGACTTCAAGGCCATCGAGCTGTACAGCAGTGCAGAGAAACGAC        2340

A   S   S   V   F   D   L   E   T   M   F   R   E   Y   N   Y   Y   T   H   R
TCGCGAGTAGCGTGTTTGACCTGGAGACGATGTTCAGGGAGTACAACTACTACACACATC        2400
```

FIG. 19F

```
      L   A   G   L   R   E   D   L   D   N   T   I   D   M   N   K   E   R   F   V
GTCTCGCGGGTTTGCGCGAGATCTGGACAACACCATAGATATGAACAAGGAGCGCTTCG                         2460

R   D   L   S   E   I   V   A   D   L   G   G   I   G   K   T   V   V   N   V
TAAGGGACTTGTCGGAGATAGTGGCGGACCTGGGCATCGGAAAAACGGTGGTGAACG                           2520
                                                          >T

A   S   S   V   V   T   L   C   G   S   L   V   T   G   F   I   N   F   I   K
TGGCCAGCAGCGTGGTCACTCTATGTGGCTCATTGGTTACCGGATTCATAAATTTATTA                         2580

H   P   L   G   G   M   L   M   I   I   V   I   A   I   L   L   I   E
AACACCCCCTAGGTGGCATGCTGATGATCATTATCGTTATAGCAATCATCCTGATCATT                         2640

M   L   S   R   R   T   N   T   I   A   Q   A   P   V   K   M   I   Y   P   D
TTATGCTCAGTCGCCGCCACCAATACCAGCCCAGGCGGTGAAGATGATCTACCCCG                            2700

V   D   R   R   A   P   P   S   G   G   A   P   T   R   E   E   I   K   N   I
ACGTAGATCGCAGGGCACCTCCTAGCGGGGGAGCCCCAACACGGGAGAAATCAAAAACA                         2760
```

FIG. 19G

```
       L  L  G  M  H  Q  L  Q  Q  E  E  R  Q  K  A  D  D  L  K  K
       TCCTGCTGGGAATCACGAGCTACAACAGAGAGGAGCAGAAGGCGGATGATCTGAAAA         2820
                                                             > T

S  T  P  S  V  F  Q  R  T  A  N  G  L  R  Q  R  L  R  G  Y
       AAAGTACACCCCTCGGTGTTTCAGCGTACGGCAAACGGCCTTCGTCAGCGTCTGAGAGGAT     2880

> L
       K  P  L  T  Q  S  L  D  I  S  P  E  T  G  E  *
       ATAAACCTCTGACTCAATCAGTCCTAGACATCAGTCCGGAAACGGGGAGTGACAGTGGATTC    2940
                                > T

GAGGTTATTGTTTGATGTAAATTTAGGAAACACGGCCCGCCCTCTGAAGCACCACATACAG     3000
                                                       DNA POLYMERASE GENE
                                                                M  D
       ACTGCAGTTATCAACCCTACTCGTTGCACACAGACACAAATTACCGTCCGCAGATCATGG      3060

F  F  N  P  F  I  D  P  T  R  G  G  P  R  N  T  V  R  Q  P
       ATTTTTTCAATCCATTTATCGACCCAACTCGCGGAGCCCGAGAAACACTGTGAGGCAAC       3120

T  P  S  Q  S  P  T  V  P  S  E  T  R  V  C  R  L  I  P  A
       CCACGCCGTCACAGTCGCCAACTGTCCCCTCGGAGACAAGAGTATGCAGGCTTATACCGG      3180
```

FIG. 19H

```
    C   F   Q   T   P   G   R   P   G   V   V   A   V   D   T   T   F   P   P   T
CCTGTTTCCAAACCCCGGGGGCCAGACCCGGGGGTGTTGCCGTGGATGACACCTTCCACCCA                    3240

Y   F   Q   G   P   K   R   G   E   V   F   A   G   E   T   G   S   I   W   K
CCTACTTCCAGGGCCCCAAGCGGGGAGAAGTATTCGCGGGAGAGACTGGTCTATCTGGA                       3300

T   R   R   G   Q   A   R   N   A   P   M   S   H   L   I   F   H   V   Y   D
AAACAAGGCGGGAGACAGGCACGCAATGCTCCTATGTCGACCTCATATTCCACGTATACG                      3360

I   V   E   T   T   Y   T   A   D   R   C   E   D   V   P   F   S   E   Q   T
ACATCGTGGAGACCACCTACACGGCCGACCGTGCGAGGACGTGCCATTAGCTTCCAGA                        3420

D   I   P   S   G   T   V   L   K   L   L   G   R   T   L   D   G   A   S
CTGATATCATTCCCAGCGGCACCGTCCTCAAGCTGCTCGGACAGAACACTAGATGGCGCCA                     3480

V   C   V   N   V   F   R   Q   R   C   Y   F   Y   T   L   A   P   Q   G   V
GTGTCTGCGTGAACGTTTTCAGGCAGCGGTGCTACTTCTACACACTAGCACCCCAGGGGG                      3540

N   L   T   H   V   L   Q   Q   A   L   Q   A   G   F   G   R   A   S   C   G
TAAACCTGACCCACGTCCTCCAGCAGGCCCTCCAGGCTGGGTTCGGCCATCCTGCCG                         3600

F   S   T
GCTTCTCCACCG                                                                      3612
```

FIG. 23

```
    V   Y   K   K   N   I   V   P   N   M   F   K   V   R   R   Y   R   K   V   A
    GTGTACAAGAAGAACATCGTGCCTAACATGTTCAAGGTACGCAGGTACAGAAAGTAGCA              60

T   P   V   T   L   Y   R   G   M   T   D   A   A   I   T   N   K   Y   E   I
    ACGCCTGTCACACTCTACCGGTATGACAGACGCAGCAATAACTAACAAATATGAAATT              120

P   R   P   V   P   L   Y   E   I   S   H   M   D   S   T   Y   Q   C   F   S
    CCCAGACCCGTACCACTATACGAGATCAGTCACATGGACAGCACCTACCCAGTGCTTTAGT           180

S   M   K   I   V   V   N   G   V   E   N   T   F   G   R   D   D   V   N
    TCCATGAAAATTGTAGTGAACGGAGTCGAAAACACGTTCACCGGTCGGATGACGTAAAC             240

K   S   V   F   L   Q   P   V   E   G   L   T   D   N   I   K   R   Y   F   S
    AAAAGCGTATTTCTCCAGCCAGTCGAAGGTCTAACTGACAACATAAAGAGATACTTTAGC           300

Q   P   V   L   Y   S   E   P   G   W   F   P   G   I   Y   R   V   R   T   T
    CAGCCAGTGCTATATTCTGAACCCGGATGGTTTCCAGGTATATCTACAGGGTTAGACAACA          360

V   N   C   E   I   V   D   M
    GTTAATTGTGAGATTGTAGACATGTT                                             380
```

```
KSHV GLYB         C A G A A H S R G D T F Q T S S S P T

FIBRINOGEN (1)            N I M E I L R G D T F S S A N N R D N
FIBRINOGEN (2)            S S T S Y N R G D S T F E E S K S Y K
LAMININ (1)         A L G G D V E K R G D R E E A H V P F F
LAMININ (2)         C Q A G T F A L R G D S T F E E S K S
FIBRONECTIN         I T V Y A V T G D S P A S S K P I S
VON WILLEBRAND      C E V T G P R G D S Q S S W K S V G
VITRONECTIN         C K P Q V T R G D V F T M P E D E Y
```

Potential Signal Peptidase Cleavage Sites

```
KSHV   MTPRSRLATLGTVILLVCFCAGAAHSRGDTFQTSSSPTPPGSSSSKAP...
HVS    MVPNKHLLILSFSTA CGQTPTTAVEKNKTQAIYQEYFKYR...
BHV4   MYYKTILFFALIKVCSFNQTTHSTTTSPSISSTTSSTTTSTSKP...
MHV68  MYPTVKSM

GLYCOPROTEIN B OF THE RFHV/KSHV SUBFAMILY OF HERPES VIRUSES

CROSS-REFERENCE TO RELATED APPLICATIONS

This application is a continuation-in-part of International Application PCT/US96/15702 designating the U.S., which was filed on Sep. 26, 1996; for which the priority application is U.S. provisional patent application Ser. No. 60/004,297, filed Sep. 26, 1995. This application is also a continuation-in-part of U.S. non-provisional application Ser. No. 08/720,229, filed Sep. 26, 1996, pending; for which the priority application is U.S. provisional patent application Ser. No. 60/004,297, filed Sep. 26, 1995, now abandoned. This application claims priority benefit of all the above-referenced applications, which are hereby incorporated herein by reference in their entirety.

FIELD OF THE INVENTION

The present invention relates generally to the field of virology, particularly viruses of the herpes family. More specifically, it relates to the identification and characterization of herpes virus Glycoprotein B molecules which are associated with fibroproliferative and neoplastic conditions in primates, including humans.

BACKGROUND

Kaposi's Sarcoma is a disfiguring and potentially fatal form of hemorrhagic sarcoma. It is characterized by multiple vascular tumors that appear on the skin as darkly colored plaques or nodules. At the histological level, it is characterized by proliferation of relatively uniform spindle-shaped cells, forming fascicles and vascular slits. There is often evidence of plasma cells, T cells and monocytes in the inflammatory infiltrate. Death may ultimately ensue due to bleeding from gastrointestinal lesions or from an associated lymphoma. (See generally Martin et al., Finesmith et al.)

Once a relatively obscure disease, it has leapt to public attention due to its association with AIDS. As many as 20% of certain AIDS-affected populations acquire Kaposi's during the course of the disease. Kaposi's Sarcoma occurs in other conditions associated with immunodeficiency, including kidney dialysis and therapeutic immunosuppression. However, the epidemiology of the disease has suggested that immunodeficiency is not the only causative factor. In particular, the high degree of association of Kaposi's with certain sexual practices suggests the involvement of an etiologic agent which is not the human immunodeficiency virus (Berel et al.).

A herpes-virus-like DNA sequence has been identified in tissue samples from Kaposi's lesions obtained from AIDS patients (Chang et al., confirmed by Ambroziuk et al.). The sequence was obtained by representational difference analysis (Lisitsyn et al.), in which DNA from affected and unaffected tissue were amplified using unrelated priming oligonucleotides, and then hybridized together to highlight differences between the cells. The sequence was partly identical to known sequences of the Epstein Barr Virus and herpesvirus saimiri. It coded for capsid and tegument proteins, two structural components sequestered in the viral interior. In a survey of tissues from various sources, the sequence was found in 95% of Kaposi's sarcoma lesions, regardless of the patients' HIV status (Moore et al. 1995a). 21% of uninvolved tissue from the same patients was positive, while 5% of samples from a control population was positive. There was approximately 0.5% sequence variation between samples.

The same sequence has been detected in body cavity lymphoma, a lymphomatous effusion with B-cell features, occurring uniquely in AIDS patients (Cesarman et al.). The copy number was higher in body cavity lymphoma, compared with Kaposi's Sarcoma. Other AIDS-associated lymphomas were negative. The sequence has also been found in peripheral blood mononuclear cells of patients with Castleman's disease (Dupin et al.). This is a condition characterized by morphologic features of angiofolicular hyperplasia, and associated with fever, adenopathy, and splenomegaly. The putative virus from which the sequence is derived has become known as Kaposi's Sarcoma associated Herpes Virus (KSHV).

Using PCR in situ hybridization, Boshoff et al. have detected KSHV polynucleotide sequences in the cell types thought to represent neoplastic cells in Kaposi's sarcoma. Serological evidence supports an important role for KSHV in the etiology of Kaposi's sarcoma (O'Leary). Kedes et al. developed an immunofluorescence serological assay that detects antibody to a latency-associated nuclear antigen in B cells latently infected with KSHV, and found that KSHV seropositivity is high in patients with Kaposi's sarcoma. Gao et al. found that of 40 patients with Kaposi's sarcoma, 32 were positive for antibodies against KSHV antigens by an immunoblot assay, as compared with only 7 of 40 homosexual men without Kaposi's sarcoma immediately before the onset of AIDS. Miller et al. prepared KSHV antigens from a body cavity lymphoma cell line containing the genomes of both KSHV and Epstein-Barr virus. Antibodies to one antigen, designated p40, were identified in 32 of 48 HIV-1 infected patients with Kaposi's sarcoma, as compared with only 7 of 54 HIV-1 infected patients without Kaposi's sarcoma.

Zhong et al. analyzed the expression of KSHV sequences in affected tissue at the messenger RNA level. Two small transcripts were found that represent the bulk of the virus specific RNA transcribed from the KSHV genome. One transcript was predicted to encode a small membrane protein; the other is an unusual poly-A RNA that accumulates in the nucleus and may have no protein encoding sequence. Messenger RNA was analyzed by cloning a plurality of overlapping KSHV genomic fragments that spanned the ~120 kb KSHV genome from a lambda library of genomic DNA. The clones were used as probes for Northern analysis, but their sequences were not obtained or disclosed.

Moore et al. have partially characterized a KSHV genome fragment obtained from a body-cavity lymphoma. A 20.7 kb region of the genome was reportedly sequenced, although the sequence was not disclosed. 17 partial or complete open reading frames were present in this fragment, all except one having sequence and positional homology to other known gamma herpes virus genes, including the capsid maturation gene and the thymidine kinase gene. Phylogenetic analysis showed that KSHV was more closely related to equine herpes virus 2 and Saimiri virus than to Epstein Barr virus. The 20.7 kb region did not contain sequences encoding either Glycoprotein B or DNA polymerase.

The herpes virus family as a whole comprises a number of multi-enveloped viruses about 100 nm in size, and capable of infecting vertebrates. (For general reviews, see, e.g., Emery et al., Fields et al.). The double-stranded DNA genome is unusually large—from about 88 to about 229 kilobases in length. It may produce over 50 different transcripts at various stages in the life cycle of the virus. A number of glycoproteins are expressed at the viral surface, and play a role in recognition of a target cell by the virus, and penetration of the virus into the cell. These surface proteins are relatively more variant between species, compared with internal viral components (Karlin et al.). The same surface proteins are also present on defective viral particles produced by cells harboring the virus. One such non-infectious form is the L-particle, which comprises a tegument and a viral envelope, but lacks the nucleocapsid.

The herpes virus family has been divided into several subfamilies. Assignments to each of the categories were originally based on biologic properties, and are being refined as genomic sequence data emerges. The alpha subfamily comprises viruses that have a broad host range, a short replicative cycle, and an affinity for the sensory ganglia. They include the human simplex virus and the Varicella-zoster virus. The beta subfamily comprises viruses that have a restricted host range, and include Cytomegalovirus and human Herpes Virus 6. The gamma subfamily comprises viruses that are generally lymphotrophic. The DNA is marked by a segment of about 110 kilobases with a low GC content, flanked by multiple tandem repeats of high GC content. The gamma subfamily includes Epstein Barr Virus (EBV), herpes virus saimiri, equine Herpes Virus 2 and 5, and bovine Herpes Virus 4.

Herpes viruses are associated with conditions that have a complex clinical course. A feature of many herpes viruses is the ability to go into a latent state within the host for an extended period of time. Viruses of the alpha subfamily maintain latent forms in the sensory and autonomic ganglia, whereas those of the gamma subfamily maintain latent forms, for example, in cells of the lymphocyte lineage. Latency is associated with the transcription of certain viral genes, and may persist for decades until conditions are optimal for the virus to resume active replication. Such conditions may include an immunodeficiency. In addition, some herpes viruses of the gamma subfamily have the ability to genetically transform the cells they infect. For example, EBV is associated with B cell lymphomas, oral hairy leukoplakia, lymphoid interstitial pneumonitis, and nasopharyngeal carcinoma.

A number of other conditions occur in humans and other vertebrates that involve fibroproliferation and the generation of pre-neoplastic cells. Examples occurring in humans are retroperitoneal fibrosis, nodular fibromatosis, pseudosarcomatous fibromatosis, and sclerosing mesenteritis. Another condition known as Enzootic Retroperitoneal Fibromatosis (RF) has been observed in a colony of macaque monkeys at the University of Washington Regional Primate Research Center (Giddens et al.). Late stages of the disease are characterized by proliferating fibrous tissue around the mesentery and the dorsal part of the peritoneal cavity, with extension into the inguinal canal, through the diaphragm, and into the abdominal wall. Once clinically apparent, the disease is invariably fatal within 1–2 months. The condition has been associated with simian immunodeficiency (SAIDS) due to a type D simian retrovirus, SRV-2 (Tsai et al.). However, other colonies do not show the same frequency of RF amongst monkeys affected with SAIDS, and the frequency of RF at Washington has been declining in recent years.

The study of such conditions in non-human primates is important not only as a model for human conditions, but also because one primate species may act as a reservoir of viruses that affect another species. For example, the herpes virus saimiri appears to cause no disease in its natural host, the squirrel monkey (*Saimiri sciureus*), but it causes polyclonil T-cell lymphomas and acute leukemias in other primates, particularly owl monkeys.

There is a need to develop reagents and methods for use in the detection and treatment of herpes virus infections. The etiological linkage between KSHV and Kaposi's sarcoma, confirmed by the serological evidence, indicates the importance of this need.

For example, there is a need to develop reagents and methods which can be used in the diagnosis and assessment of Kaposi's sarcoma, and similar conditions. Being able to detect the etiologic agent in a new patient may assist in differential diagnosis; being able to assess the level of the agent in an ongoing condition may assist in clinical management. Desirable markers include those that provide a very sensitive indication of the presence of both active and latent forms viral infection, analogous to the HBsAg of Hepatitis B. Desirable markers also include those that are immunogenic, and can be used to assess immunological exposure to the viral agent as manifest in the antibody response. Glycoprotein antigens from the viral envelope are particularly suitable as markers with these characteristics. They may be expressed at high abundance near the surface not only of replicative forms of the virus, but also on L-particles produced by virally infected cells.

Second, there is a need to develop reagents and methods that can be used for treatment of viral infection—both prophylactically, and following a viral challenge. Such reagents include vaccines that confer a level of immunity against the virus. Passive vaccines, such as those comprising an anti-virus antibody, may be used to provide immediate protection or prevent cell penetration and replication of the virus in a recently exposed individual. Active vaccines, such as those comprising an immunogenic viral component, may be used to elicit an active and ongoing immune response in an individual. Antibody elicited by an active vaccine may help protect an individual against a subsequent challenge by live virus. Cytotoxic T cells elicited by an active vaccine may help eradicate a concurrent infection by eliminating host cells involved in viral replication. Suitable targets for a protective immune response, particularly antibody, are protein antigens exposed on the surface of viral particles, and those implicated in fusion of the virus with target cells.

Third, there is a need to develop reagents and methods which can be used in the development of new pharmaceuticals for Kaposi's sarcoma, and similar conditions. The current treatment for Kaposi's is radiation in combination with traditional chemotherapy, such as vincristine (Northfelt, Mitsuyasu). While lesions respond to these modalities, the response is temporary, and the downward clinical course generally resumes. Even experimental therapies, such as treatment with cytokines, are directed at the symptoms of the disease rather than the cause. Drug screening and rational drug design based upon the etiologic agent can be directed towards the long-felt need for a clinical regimen with long-term efficacy. Suitable targets for such pharmaceuticals are viral components involved in recognition and penetration of host cells. These include glycoprotein components of the viral envelope.

Fourth, there is a need to develop reagents and methods which can be used to identify new viral agents that may be associated with other fibroproliferative conditions. The representational difference analysis technique used by Chang et al. is arduously complex, and probably not appropriate as a general screening test. More desirable are a set of oligonucleotide probes, peptides, and antibodies to be used as reagents in more routine assays for surveying a variety of tissue samples suspected of containing a related etiologic agent. The reagents should be sufficiently specific to avoid identifying unrelated viruses and endogenous components of the host, and may be sufficiently cross-reactive to identify related but previously undescribed viral pathogens.

SUMMARY OF THE INVENTION

It is an objective of this invention to provide isolated polynucleotides, polypeptides, and antibodies derived from or reactive with the products of novel genes encoding Glycoprotein B molecules of the RFHV/KSHV subfamily of herpes viruses. Two members of the family are Retroperitoneal Fibromatosis associated Herpes Virus (RFHV) and Kaposi's Sarcoma associated Herpes Virus (KSHV). These materials and related methods can be used in the diagnosis and treatment of herpes virus infection in primates, including humans. Isolated or recombinant Glycoprotein B fragments or polynucleotides encoding them may be used as components of an active herpes vaccine, while antibodies specific for Glycoprotein B may be used as components of a passive vaccine.

Accordingly, one of the embodiments of the invention is an isolated polynucleotide with a region encoding a Glycoprotein B of a herpes virus of the RFHV/KSHV subfamily, the polynucleotide comprising a sequence of 319 nucleotides at least 65% identical to nucleotides 36 to 354 of SEQ. ID NO:1 or SEQ. ID NO:3, which are 319 nucleotide fragments encoding Glycoprotein B from RFHV and KSHV, respectively. Also embodied is an isolated polynucleotide with a region encoding a Glycoprotein B, the polynucleotide comprising a sequence selected from the group consisting of: a sequence of 35 nucleotides at least 74% identical to oligonucleotide SHMDA (SEQ. ID NO:41); a sequence of 30 nucleotides at least 73% identical to oligonucleotide CFSSB (SEQ. ID NO:43); a sequence of 29 nucleotides at least 72% identical to oligonucleotide ENTFA (SEQ. ID NO:45); and a sequence of 35 nucleotides at least 80% identical to oligonucleotide DNIQB (SEQ. ID NO:46).

Another embodiment of the invention is an isolated polynucleotide comprising a fragment of at least 21, preferably 35, more preferably 50, still more preferably 75, and even more preferably 100 consecutive nucleotides of the Glycoprotein B encoding region of the polynucleotide of the preceding embodiments. The polynucleotide is preferably from a virus capable of infecting primates. Included are Glycoprotein B encoding polynucleotide fragments from RFHV and KSHV. Another embodiment of the invention is an isolated polynucleotide comprising a linear sequence of at least about 21 nucleotides identical to a the Glycoprotein B encoding sequence between nucleotides 36 to 354 inclusive of SEQ. ID NO:1, SEQ. ID NO:3, or SEQ. ID NO:92, or anywhere within SEQ. ID NO:96, but not in SEQ. ID NO:98.

A further embodiment of this invention is an isolated polypeptide encoded by any of the previous embodiments. Also embodied is an isolated polypeptide, comprising a linear sequence of at least 17 amino acids essentially identical to the Glycoprotein B protein sequence shown in SEQ. ID NO:2, SEQ. ID NO:4, or SEQ. ID NO:97, or anywhere within SEQ. ID NO:94 (KSHV), but not in SEQ. ID NO:99. This includes fusion polypeptides, immunogenic polypeptides, and polypeptides occurring in glycosylated and unglycosylated form. Some preferred antigen peptides are listed in SEQ. ID NOS:67–76. Also embodied are isolated and non-naturally occurring polynucleotides encoding any of the aforementioned polypeptides, along with cloning vectors, expression vectors and transfected host cells derived therefrom. Further embodiments are method for producing polynucleotides or polypeptides of this invention, comprising replicating vectors of the invention or expressing polynucleotides in suitable host cells.

Yet another embodiment of this invention is a monoclonal or isolated polyclonal antibody specific for a Glycoprotein B polypeptide embodied in this invention, or a Glycoprotein B encoded in the encoding region of a polynucleotide embodied in this invention. The antibodies are specific for members of the RFHV/KSHV subfamily, and do not cross-react with more distantly related Glycoprotein B sequences, particularly SEQ. ID NOS:30–41.

Still another embodiment of this invention is a vaccine comprising a polypeptide of this invention in a pharmaceutically compatible excipient, and optionally also comprising an adjuvant. In certain embodiments, the polypeptide of the vaccine comprises an RGD sequence. Another embodiment of this invention is a vaccine comprising a polynucleotide of this invention, which may be in the form of a live virus or viral expression vector. Another embodiment of this invention is a vaccine comprising an antibody of this invention in a pharmaceutically compatible excipient. Other embodiments are methods for treating a herpes virus infection, either prophylactically or during an ongoing infection, comprising administering one of the aforementioned embodiments.

Also embodied in this invention are methods of inhibiting attachment of a herpes virus to a cell, or preventing infection or pathology due to a member of the RFHV/KSHV virus subfamily, comprising contacting the cell or introducing into the environment a polypeptide according to this invention comprising an RGD sequence.

Further embodiments of this invention are oligonucleotides specific for Glycoprotein B encoding sequences of the gamma herpes subfamily, the RFHV/KSHV subfamily, RFHV, and KSHV, especially those listed in SEQ. ID NOS:24–63. Also embodied are methods for obtaining an amplified copy of a polynucleotide encoding a Glycoprotein B, comprising contacting the polynucleotide with one or more of the aforementioned oligonucleotides. The polynucleotide to be amplified may be taken from an individual affected with a disease featuring fibroblast proliferation and collagen deposition, including but not limited to Retroperitoneal Fibromatosis or Kaposi's Sarcoma, or a malignancy of the lymphocyte lineage.

Additional embodiments of this invention are methods for detecting viral DNA or RNA in a sample. One method comprises the steps of contacting the DNA or RNA in the sample with a probe comprising a polynucleotide or oligonucleotide of this invention under conditions that would permit the probe to form a stable duplex with a polynucleotide having the sequence shown in SEQ. ID NO:1 or SEQ. ID NO:3, or both, but not with a polynucleotide having a sequence of herpes viruses outside the RFHV/KSHV subfamily, particularly SEQ. ID NOS:5–13, and detecting the presence of any duplex formed thereby. The conditions referred to are a single set of reaction parameters, such as incubation time, temperature, solute concentrations, and washing steps, that would permit the polynucleotide to form a stable duplex if alternatively contacted with a polynucleotide with SEQ. ID NO:1, or with a polynucleotide with SEQ. ID NO:3, or with both, but not with a polynucleotide of any of SEQ ID NO:5–13. Another method comprises the steps of amplifying the DNA or RNA in the sample using an oligonucleotide of this invention as a primer in the amplification reaction, and detecting the presence of any amplified copies. Also embodied are isolated polynucleotides identified by the aforementioned methods, as may be present in the genome of a naturally occurring virus or affected tissue.

Further embodiments of this invention are diagnostic kits for detecting components related to herpes virus infection in a biological sample, such as may be obtained from an individual suspected of harboring such an infection, comprising a polynucleotide, oligonucleotide, polypeptide, or antibody of this invention in suitable packaging. Also embodied are methods of detecting infection of an individual, comprising applying the reagents, methods, or kits of this invention on biological samples obtained from the individual.

Still other embodiments of this invention are therapeutic compounds and compositions for use in treatment of an individual for infection by a gamma herpes virus. Included are therapeutic agents that comprise polynucleotides and vectors of this invention for the purpose of gene therapy. Also included are pharmaceutical compounds identified by contacting a polypeptide embodied in this invention with the compound and determining whether a biochemical function of the polypeptide is altered. Also included are pharmaceutical compounds obtained from rational drug design, based on structural and biochemical features of a Glycoprotein B molecule.

BRIEF DESCRIPTION OF THE FIGURES

FIG. 2 is a map of the Glycoprotein B encoding DNA sequence believed to be contained in the KSHV genome, and other members of the RFHV/KSHV subfamily. Shown are the approximate location of the KSHV Glycoprotein B sequence described herein. Also shown are the putative conserved segments that represent hybridization sites for Type 1 consensus/degenerate oligonucleotides useful in probing and amplifying Glycoprotein B sequences from gamma herpes viruses.

FIGS. 3A–3D are listings of some previously known herpes virus Glycoprotein B protein sequences, aligned with the complete KSHV Glycoprotein B protein sequence and fragments of RFHV1 and RFHV2. Boxed regions indicate the putative pre-processing signal sequence and the transmembrane domain. Cysteine residues are underlined. Residues that are highly conserved amongst herpes virus Glycoprotein B sequences are underscored with an asterisk (*). Cysteines appearing uniquely in the KSHV Glycoprotein B are underscored with a bullet (●).

FIG. 4 is a listing of previously known Glycoprotein B polynucleotide sequences of gamma herpes viruses, showing a conserved region, and the Type 1 oligonucleotide FRFDA designed therefrom.

FIG. 5 is a listing of previously known Glycoprotein B polynucleotide sequences of gamma herpes viruses, showing a conserved region, and the Type 1 oligonucleotides NIVPA and NIVPASQ designed therefrom.

FIG. 6 is a listing of previously known Glycoprotein B polynucleotide sequences of gamma herpes viruses, showing a conserved region, and the Type 1 oligonucleotides TVNCA, TVNCB and TVNCBSQ designed therefrom.

FIG. 7 is a listing of previously known Glycoprotein B polynucleotide sequences of gamma herpes viruses, showing a conserved region, and the Type 1 oligonucleotide FAYDA designed therefrom.

FIG. 8 is a listing of previously known Glycoprotein B polynucleotide sequences of gamma herpes viruses, showing a conserved region, and the Type 1 oligonucleotides IYGKA and IYGKASQ designed therefrom.

FIG. 9 is a listing of previously known Glycoprotein B polynucleotide sequences of gamma herpes viruses, showing a conserved region, and the Type 1 oligonucleotides CYSRA and CYSRASQ designed therefrom.

FIG. 10 is a listing of previously known Glycoprotein B polynucleotide sequences of gamma herpes viruses, showing a conserved region, and the Type 1 oligonucleotides NIDFB and NMDFBSQ designed therefrom.

FIG. 11 is a listing of previously known Glycoprotein B polynucleotide sequences of gamma herpes viruses, showing a conserved region, and the Type 1 oligonucleotides FREYA, FREYB and NVFDA designed therefrom.

FIG. 12 is a listing of previously known Glycoprotein B polynucleotide sequences of gamma herpes viruses, showing a conserved region, and the Type 1 oligonucleotide GGMA designed therefrom.

FIGS. 13A and 13B are listings of a portion of the Glycoprotein B polynucleotide sequence from RFHV and KSHV, aligned with previously known gamma herpes Glycoprotein B polynucleotide sequences. Each shared residue is indicated as a period.

FIG. 14 is a comparison listing of the polypeptide sequences of Glycoprotein B from various gamma herpes viruses, encoded between the hybridization sites of NIVPA and TVNCB in the polynucleotide sequences. The Class II sequence fragments shown underlined are predicted to be RFHV/KSHV cross-reactive antigen peptides. The Class III sequences shown in lower case are predicted to be RFHV or KSHV virus-specific peptides.

FIG. 15 is an alignment of the polypeptide sequences of Glycoprotein B over a broader spectrum of herpes viruses in the gamma, beta, and alpha subfamilies.

FIGS. 17A and 17B are listings of exemplary Type 2 (subfamily-specific) oligonucleotides, aligned with the nucleotide sequences from which they were derived.

FIGS. 19A–19D of a KSHV DNA sequence obtained by amplifying fragments upstream and downstream from the sequence in FIG. 1. An open reading frame is shown for the complete KSHV Glycoprotein B sequence, flanked by open reading frames for the capsid maturation gene and DNA polymerase. Underlined in the nucleotide sequence is a putative Glycoprotein B promoter

FIG. 23 is a listing of DNA and protein sequences for a Glycoprotein B fragment of a third member of the RFHV/KSHV subfamily, designated RFHV2. The 319-base polynucleotide segment between residues 36 to 354 is underlined, and represents the Glycoprotein B encoding segment between the primers used to amplify it.

FIG. 24 is an alignment of protein sequences showing an RGD triplet near the N-terminal of mature KSHV Glycoprotein B. The upper panel shows alignment of the Glycoprotein B with RGD domains in other proteins. The lower panel shows predicted signal peptidase cleavage sites for producing the mature form of Glycoprotein B.

DETAILED DESCRIPTION

We have discovered and characterized polynucleotides encoding Glycoprotein B from herpes viruses of the RFHV/KSHV subfamily. The polynucleotides, oligonucleotides, polypeptides and antibodies embodied in this invention are useful in the diagnosis, clinical monitoring, and treatment of herpes virus infections and related conditions.

The source for the polynucleotide for the RFHV Glycoprotein B was affected tissue samples taken from *Macaque nemestrina* monkeys with retroperitoneal fibromatosis ("RF"). The polynucleotide for the KSHV Glycoprotein B was obtained from affected tissue samples taken from humans with Kaposi's Sarcoma ("KS"). The tissues used for the present invention were known to contain genetic material from RFHV or KSHV, because they had previously been used successfully to clone corresponding DNA Polymerase encoding fragments. The amplification of the DNA Polymerase regions have been described in commonly owned U.S. patent application Ser. No. 60/001,148.

In order to amplify the Glycoprotein B sequences from these samples, we designed oligonucleotides from those of other herpes viruses. Glycoprotein B is expected to be less well conserved between herpes viruses, because it is externally exposed on the viral envelope and therefore under selective pressure from the immune system of the hosts they infect. Accordingly, the oligonucleotides were designed from sequences of herpes viruses believed to be most closely related to RFHV and KSHV. These two viruses are known from the DNA polymerase sequences to be closely related gamma type herpes viruses.

Oligonucleotides were designed primarily from Glycoprotein B sequences previously known for four gamma herpes viruses: sHV1, eHV2, bHV4, mHV68 and hEBV. Comparison of the amino acid sequences of these four Glycoprotein B molecules revealed nine relatively conserved regions. Based on the sequence data, oligonucleotides were constructed comprising a degenerate segment and a consensus segment, as described in a following section. Three of these oligonucleotides have been used as primers in amplification reactions that have yielded fragments of the RFHV and KSHV Glycoprotein B encoding segments from the RF and KS tissue.

Figure 1:
FIG. 1 is a listing of polynucleotide sequences amplified from a Glycoprotein B encoding region of RFHV and KSHV. The 319-base polynucleotide segment between residues 36 to 354 is underlined, and represents the respective viral gene segment between the primers used to amplify it. Aligned with the polynucleotide sequences are oligonucleotides that may be used as hybridization probes or PCR primers. Type 1 oligonucleotides comprise a gamma herpes consensus sequence, and can be used to amplify a Glycoprotein B gene segment of a gamma herpes virus. Examples shown are NIVPA and TVNCB. Type 2 oligonucleotides comprise a consensus sequence from the RFHV/KSHV subfamily, and can be used to amplify Glycoprotein B gene segment of a virus belonging to the subfamily. Examples shown are SHMDA, CFSSB, ENTFA and DNIQB. The other oligonucleotides shown are Type 3 oligonucleotides. These comprise sequences taken directly from the RFHV or KSHV sequence, and are specific for sequences from the respective virus. Oligonucleotides that initiate amplification in the direction of the coding sequence (with designations ending in "A") are listed 5'→3'. Oligonucleotides that initiate amplification in the direction opposite to that of the coding sequence (with designations ending in "B") are listed 3'→5'. Also shown are the polypeptides encoded by the RFHV and KSHV polynucleotide sequences. The asparagine encoded by nucleotides 238–240 in both sequences is a potential N-linked glycosylation site conserved with other herpes viruses.
Figure 16:
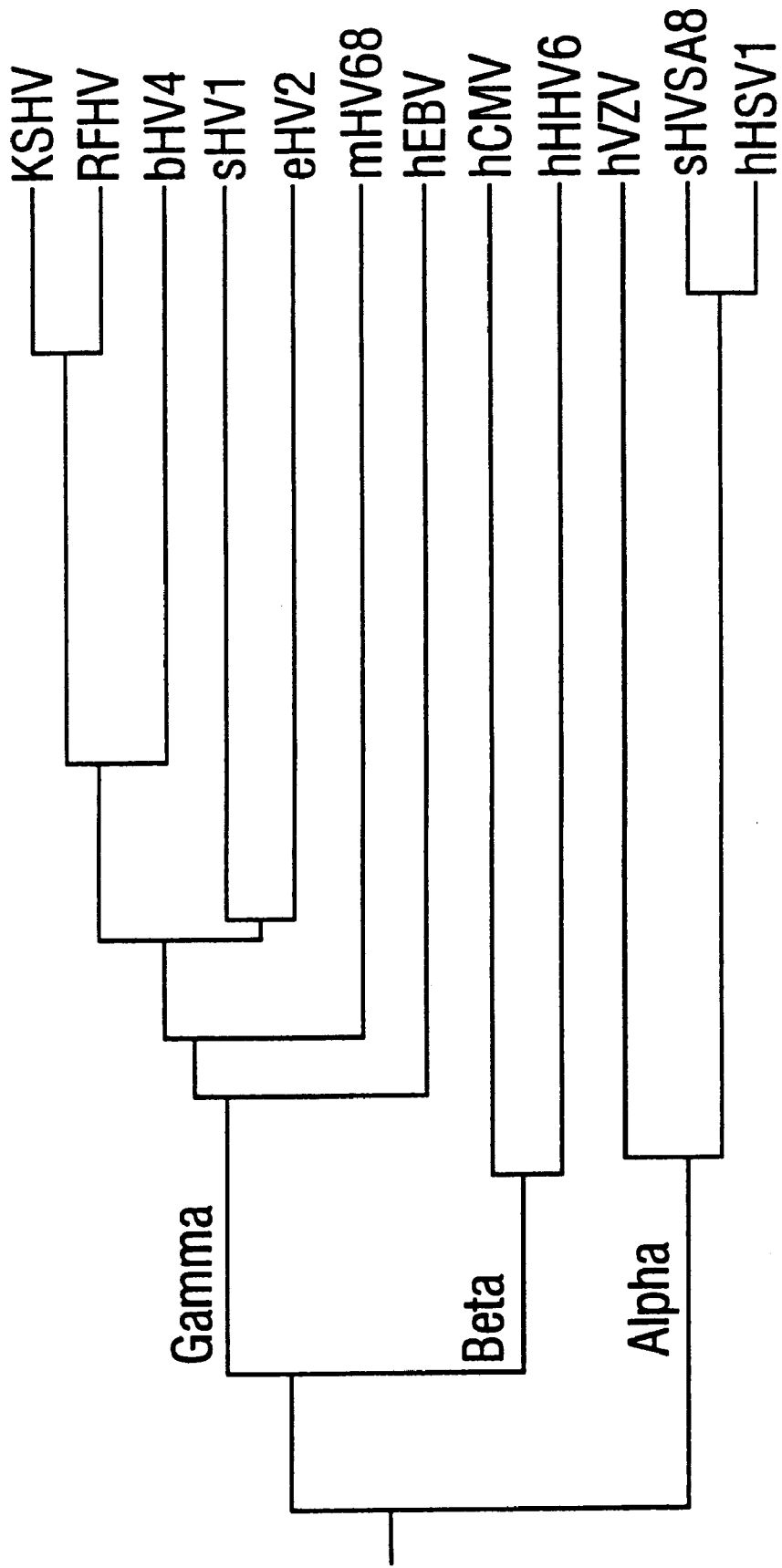
FIG. 16 is a relationship map of Glycoprotein B, based on the polypeptide sequences shown in FIG. 15.

The RFHV and KSHV polynucleotide sequence fragments obtained after the final amplification step are shown in FIG. 1 (SEQ ID NO:1 and SEQ. ID NO:3, respectively). Included are segments at each end corresponding to the hybridizing regions of the NIVPA and TVNCB primers used in the amplification. The fragment between the primer binding segments is 319 base pairs in length (residues 36–354), and believed to be an accurate reflection of the sequences of the respective Glycoprotein B encoding regions of the RFHV and KSHV genomes.

The 319 base pair Glycoprotein B encoding polynucleotide segment from RFHV is only 60% identical with that from sHV1 and bHV4, the most closely related sequences from outside the RFHV/KSHV subfamily. The 319 base pair polynucleotide segment from KSHV is only 63% identical with sHV1 and bHV4. The segments are 76% identical between RFHV and KSHV.

Also shown are the corresponding predicted amino acid sequences (SEQ ID NO:2 and SEQ ID NO:4). The polypeptide sequences are novel, and are partly homologous to Glycoprotein B sequences from other herpes viruses. The fragments shown are predicted to be about ⅛ of the entire Glycoprotein B sequence. They begin about 80 amino acids downstream from the predicted N-terminal methionine of the pre-processed protein. There is a potential N-linked glycosylation site at position 80 of the amino acid sequence, according to the sequence Asn-Xaa-(Thr/Ser). This site is conserved between RFHV and KSHV, and is also conserved amongst other known gamma herpes viruses. There is also a cysteine residue at position 58 that is conserved across herpes viruses of the gamma, beta, and alpha subfamilies, which may play a role in maintaining the three-dimensional structure of the protein.

The 106 amino acid segment of Glycoprotein B encoded by the 319 base pairs between the amplification primers is 91% identical between RFHV and KSHV, but only 65% identical between KSHV and that of bHV4, the closest sequence outside the RFHV/KSHV subfamily.

Glycoprotein B molecules expressed by the RFHV/KSHV herpes virus subfamily are expected to have many of the properties described for Glycoprotein B of other herpes viruses. Glycoprotein B molecules are generally about 110 kDa in size, corresponding to about 800–900 amino acids or about 2400–2700 base pairs. Hydrophobicity plots indicate regions from the N terminus to the C terminus in the following order: a hydrophobic region corresponding to a membrane-directing leader sequence; a mixed polarity region corresponding to an extracellular domain; a hydrophobic region corresponding to a transmembrane domain; and another mixed polarity region corresponding to a cytoplasmic domain.

The full sequence of the KSHV Glycoprotein B, shown in FIG. 19, confirms these predictions: The gene encodes about 845 amino acids including the signal peptide and a transmembrane region near the C-terminus. Cysteine residues are conserved with other Glycoprotein B sequences, and an additional potential disulfide may help stabilize the three-dimensional structure.

Glycoprotein B is generally expressed on the envelope of infectious and defective viral particles, and on the surface of infected cells. It is generally glycosylated, and may comprise 5–20 glycosylation sites or more. It is also generally expressed as a protein dimer, which assembles during translocation to the surface of the host cell, prior to budding of the virus. The site responsible for dimerization appears to be located between about amino acid 475 and the membrane spanning segment (Navarro et al.).

Previous studies have mapped several biochemical functions related to infectivity to different regions of the Glycoprotein B molecule. Glycoprotein B and Glycoprotein C are both implicated in initial binding of HSV1 and bovine herpes virus 1 to target cells (Herold et al., Byrne et al.). The moiety on the cells recognized by Glycoprotein B appears to be heparan sulfate; the binding is inhibitable by fluid-phase heparin. Mutants that lack Glycoprotein C can still bind target cells, but mutants that lack both Glycoprotein C and Glycoprotein B are severely impaired in their ability to gain access to the cells.

Another apparently important function is the ability of Glycoprotein B to promote membrane fusion and entry of the virus into the cell. In human CMV, the fusogenic role appears to map to the first hydrophobic domain of Glycoprotein B, and may be associated with conserved glycine residues within this region (Reschke et al.). In HSV1 mutants, the ability of Glycoprotein B to promote syncytia formation maps to multiple sites in the cytoplasmic domain of the protein, near the C-terminus (Kostal et al.).

In order to exercise some of these more complicated functions, it seems likely that Glycoprotein B associates not only with a second Glycoprotein B molecule, but with other components encoded by the virus. For example, the UMA5 gene product appears to be required for Glycoprotein B induced fusion (Haanes et al.). It has been hypothesized that Glycoprotein B cooperates with other surface proteins to form a hydrophobic fusion pore in the surface of the target cell (Pereira et al.). Glycoprotein B has been found to elicit a potent antibody response capable of neutralizing the intact virus. Monoclonal antibodies with neutralizing activity may be directed against many different sites on the Glycoprotein B molecule.

Consequently, it is expected that the Glycoprotein B molecule bears sites that interact with the target cell, help promote fusion, and associate with other viral proteins. It is predicted that Glycoprotein B molecules of RFHV/KSHV subfamily viruses will perform many of the functions of Glycoprotein B in other species of herpes virus, and bear active regions with some of the same properties. Interfering with any of these active regions with a drug, an antibody, or by mutation, may impair viral infectivity or virulence.

Subsequent to discovery of the Glycoprotein B of RFHV and KSHV, a third member of the RFHV/KSHV subfamily was identified in a sample of affected tissue from a Macaca mulatta (Example 12). This Glycoprotein B is closely related but not identical to RFHV, and is designated RFHV2. It is predicted that other members of the RFHV/KSHV subfamily will emerge, including some that are pathogenic to humans. This disclosure teaches how new members of the subfamily can be detected and characterized.

The homology between Glycoprotein B sequences within the RFHV/KSHV subfamily means that the polynucleotides and polypeptides embodied in this invention are reliable markers amongst different strains of the subfamily. The polynucleotides, polypeptides, and antibodies embodied in this invention are useful in such applications as the detection and treatment of viral infection in an individual, due to RFHV, KSHV, or other herpes viruses in the same subfamily. The polynucleotides, oligonucleotide probes, polypeptides, antibodies, and vaccine compositions relating to Glycoprotein B, and the preparation and use of these compounds, is described in further detail in the sections that follow.

Abbreviations

The following abbreviations are used herein to refer to species of herpes viruses, and polynucleotides and polypeptides derived therefrom:

TABLE 1

Abbreviations for Herpes Virus Strains

| Designation | Virus | Provisional Subfamily Assignment |
| --- | --- | --- |
| RFHV | simian Retroperitoneal Fibromatosis-associated HerpesVirus | gamma-HerpesVirus |
| KSHV | human Kaposi's Sarcoma-associated HerpesVirus | |
| mHV68 | murine HerpesVirus 68 | |
| bHV4 | bovine Herpesvirus 4 | |
| eHV2 | equine HerpesVirus 2 | |
| sHV1 | saimiri monkey HerpesVirus 1 | |
| hEBV | human Epstein-Barr Virus | |
| hCMV | human CytoMegaloVirus | beta-HerpesVirus |
| mCMV | murine CytoMegaloVirus | |
| gpCMV | guinea pig CytoMegaloVirus | |
| hHV6 | human HerpesVirus 6 | |
| hVZV | human Varicella-Zoster Virus | alpha-HerpesVirus |
| HSV1 | human Herpes Simplex Virus 1 | |
| HSV2 | human Herpes Simplex Virus 2 | |
| sHVSA8 | simian HerpesVirus A8 | |
| eHV1 | equine HerpesVirus 1 | |
| iHV1 | ictalurid catfish HerpesVirus | |

General Definitions

"Glycoprotein B" is a particular protein component of a herpes virus, encoded in the viral genome and believed to be expressed at the surface of the intact virus. Functional studies with certain species of herpes virus, especially HSV1, hCMV, and bovine herpes virus 1, have implicated Glycoprotein B in a number of biochemical functions related to viral infectivity. These include binding to components on the surface of target cells, such as heparan sulfate, fusion of the viral membrane with the membrane of the target cell, penetration of the viral capsid into the cell, and formation of polynucleated syncytial cells. Glycoprotein B has been observed as a homodimer, and may interact with other viral surface proteins in order to exert some of its biochemical functions. Different biochemical functions, particularly heparan sulfate binding and membrane fusion, appear to map to different parts of the Glycoprotein B molecule. A Glycoprotein B molecule of other herpes viruses, including members of the RFHV/KSHV subfamily, may perform any or all of these functions. As used herein, the term Glycoprotein B includes unglycosylated, partly glycosylated, and filly glycosylated forms, and both monomers and polymers.

As used herein, a Glycoprotein B fragment, region, or segment is a fragment of the Glycoprotein B molecule, or a transcript of a subregion of a Glycoprotein B encoding polynucleotide. The intact Glycoprotein B molecule, or the full-length transcript, will exert biochemical functions related to viral activity, such as those described above. Some or all of these functions may be preserved on the fragment, or the fragment may be from a part of the intact molecule which is unable to perform these functions on its own.

"Glycoprotein B activity" refers to any biochemical function of Glycoprotein B, or any biological activity of a herpes virus attributable to Glycoprotein B. These may include but are not limited to binding of the protein to cells, cell receptors such as heparan sulfate, and receptor analogs; viral binding or penetration into a cell, or cell fusion.

The term "Glycoprotein B gene" refers to a gene comprising a sequence that encodes a Glycoprotein B molecule as defined above. It is understood that a Glycoprotein B gene may give rise to processed and altered translation products, including but not limited to forms of Glycoprotein B with or without a signal or leader sequence, truncated or internally deleted forms, multimeric forms, and forms with different degrees of glycosylation.

As used herein, a "DNA Polymerase" is a protein or a protein analog, that under appropriate conditions is capable of catalyzing the assembly of a DNA polynucleotide with a sequence that is complementary to a polynucleotide used as a template. A DNA Polymerase may also have other catalytic activities, such as 3'–5' exonuclease activity; any of the activities may predominate. A DNA Polymerase may require association with additional proteins or co-factors in order to exercise its catalytic function.

"RFHV" is a virus of the herpes family detected in the tissue samples of *Macaque nemestrina* monkeys affected with Retroperitoneal Fibromatosis (RF). RFHV is synonymous with the terms "RFHV1", "RFHVMn", and "RFMn". "KSHV" is a virus of the herpes virus family detected in the tissue samples of humans affected with Kaposi's Sarcoma (KS). A third member of the RFHV/KSHV subfamily is a virus identified in a *%M. mulatta* monkey. The virus is referred to herein as "RFHV2". "RFHV2" is synonymous with the terms "RFHVMm" and "RFMm".

The "RFHV/KSHV subfamily" is a term used herein to refer to a collection of herpes viruses capable of infecting vertebrate species. The subfamily consists of members that have Glycoprotein B sequences that are more closely related to that of the corresponding sequences of RFHV or KSHV than other herpes viruses, including sHV1, eHV2, bHV4, mHV68 and hEBV. Preferably, the polynucleotide encoding Glycoprotein B comprises a segment that is at least 65% identical to that of RFHV (SEQ. ID NO: 1) or KSHV (SEQ. ID NO:3) between residues 36 and 354; or at least about 74% identical to the oligonucleotide SHMDA, or at least about 73% identical to the oligonucleotide CFSSB, or at least about 72% identical to the nucleotide ENTFA, or at least about 80% identical to the nucleotide DNIQB. RFHV and KSHV are exemplary members of the RFHV/KSHV subfamily. The RFHV/KSHV subfamily represents a subset of the gamma subfamily of herpes viruses.

The terms "polynucleotide" and "oligonucleotide" are used interchangeably, and refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: a gene or gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

The term polynucleotide, as used herein, refers to both double- and single-stranded molecules. Unless otherwise specified or required, any embodiment of the invention described herein that is a polynucleotide encompasses both the double-stranded form and each of two complementary single-stranded forms known or predicted to make up the double-stranded form.

In the context of polynucleotides, a "linear sequence" or a "sequence" is an order of nucleotides in a polynucleotide in a 5' to 3' direction in which residues that neighbor each other in the sequence are contiguous in the primary structure of the polynucleotide. A "partial sequence" is a linear sequence of part of a polynucleotide which is known to comprise additional residues in one or both directions.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogsteen binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR, or the enzymatic cleavage of a polynucleotide by a ribozyme.

Hybridization reactions can be performed under conditions of different "stringency". Conditions that increase the stringency of a hybridization reaction are widely known and published in the art: see, for example, Sambrook Fritsch & Maniatis. Examples of relevant conditions include (in order of increasing stringency): incubation temperatures of 25° C., 37° C., 50° C., and 68° C.; buffer concentrations of 10×SSC, 6×SSC, 1×SSC, 0.1×SSC (where SSC is 0.15 M NaCl and 15 mM citrate buffer) and their equivalent using other buffer systems; formamide concentrations of 0%, 25%, 50%, and 75%; incubation times from 5 min to 24 h; 1, 2, or more washing steps; wash incubation times of 1, 5, or 15 min; and wash solutions of 6×SSC, 1×SSC, 0.1×SSC, or deionized water.

"$T_m$" is the temperature in degrees Centigrade at which 50% of a polynucleotide duplex made of complementary strands hydrogen bonded in an antiparallel direction by Watson-Crick base paring dissociates into single strands under the conditions of the experiment. $T_m$ may be predicted according to standard formula; for example:

$$T_m=81.5+16.6 \log [Na^+]+0.41(\% G/C)-0.61(\% F)-600/L$$

where $[Na^+]$ is the cation concentration (usually sodium ion) in mol/L; (% G/C) is the number of G and C residues as a percentage of total residues in the duplex; (% F) is the percent formamide in solution (wt/vol); and L is the number of nucleotides in each strand of the duplex.

A "stable duplex" of polynucleotides, or a "stable complex" formed between any two or more components in a biochemical reaction, refers to a duplex or complex that is sufficiently long-lasting to persist between the formation of the duplex or complex, and its subsequent detection. The duplex or complex must be able to withstand whatever conditions exist or are introduced between the moment of formation and the moment of detection, these conditions being a function of the assay or reaction which is being performed. Intervening conditions which may optionally be present and which may dislodge a duplex or complex include washing, heating, adding additional solutes or solvents to the reaction mixture (such as denaturants), and competing with additional reacting species. Stable duplexes or complexes may be irreversible or reversible, but must meet the other requirements of this definition. Thus, a transient complex may form in a reaction mixture, but it does not constitute a stable complex if it dissociates spontaneously or as a result of a newly imposed condition or manipulation introduced before detection.

When stable duplexes form in an antiparallel configuration between two single-stranded polynucleotides, particularly under conditions of high stringency, the strands are essentially "complementary". A double-stranded polynucleotide can be "complementary" to another polynucleotide, if a stable duplex can form between one of the strands of the first polynucleotide and the second. A complementary sequence predicted from the sequence of a single stranded polynucleotide is the optimum sequence of standard nucleotides expected to form hydrogen bonding with the single-stranded polynucleotide according to generally accepted base-pairing rules.

A "sense" strand and an "antisense" strand when used in the same context refer to single-stranded polynucleotides which are complementary to each other. They may be opposing strands of a double-stranded polynucleotide, or one strand may be predicted from the other according to generally accepted base-pairing rules. If not specified, the assignment of one or the other strand as "sense" or "antisense" may be arbitrary. In relation to a polypeptide-encoding segment of a polynucleotide, the "sense" strand is generally the strand comprising the encoding segment.

When comparison is made between polynucleotides for degree of identity, it is implicitly understood that complementary strands are easily generated, and the sense or antisense strand is selected or predicted that maximizes the degree of identity between the polynucleotides being compared. For example, where one or both of the polynucleotides being compared is double-stranded, the sequences are identical if one strand of the first polynucleotide is identical with one strand of the second polynucleotide. Similarly, when a polynucleotide probe is described as identical to its target, it is understood that it is the complementary strand of the target that participates in the hybridization reaction between the probe and the target.

A linear sequence of nucleotides is "essentially identical" to another linear sequence, if both sequences are capable of hybridizing to form duplexes with the same complementary polynucleotide. Sequences that hybridize under conditions of greater stringency are more preferred. It is understood that hybridization reactions can accommodate insertions, deletions, and substitutions in the nucleotide sequence. Thus, linear sequences of nucleotides can be essentially identical even if some of the nucleotide residues do not precisely correspond or align. Sequences that correspond or align more closely to the invention disclosed herein are comparably more preferred. Generally, a polynucleotide region of about 25 residues is essentially identical to another region, if the sequences are at least about 85% identical; more preferably, they are at least about 90% identical; more preferably, they are at least about 95% identical; still more preferably, the sequences are 100% identical. A polynucleotide region of 40 residues or more will be essentially identical to another region, after alignment of homologous portions if the sequences are at least about 75% identical; more preferably, they are at least about 80% identical; more preferably, they are at least about 85% identical; even more preferably, they are at least about 90% identical; still more preferably, the sequences are 100% identical.

In determining whether polynucleotide sequences are essentially identical, a sequence that preserves the functionality of the polynucleotide with which it is being compared is particularly preferred. Functionality can be determined by different parameters. For example, if the polynucleotide is to be used in reactions that involve hybridizing with another polynucleotide, then preferred sequences are those which hybridize to the same target under similar conditions. In general, the $T_m$ of a DNA duplex decreases by about 1° C. for every 1% decrease in sequence identity for duplexes of 200 or more residues; or by about 5° C. for duplexes of less than 40 residues, depending on the position of the mismatched residues (see, e.g., Meinkoth et al.). Essentially identical sequences of about 100 residues will generally form a stable duplex with each other's respective complementary sequence at about 20° C. less than $T_m$; preferably, they will form a stable duplex at about 15° C. less; more preferably, they will form a stable duplex at about 10° C. less; even more preferably, they will form a stable duplex at about 5° C. less; still more preferably, they will form a stable duplex at about $T_m$. In another example, if the polypeptide encoded by the polynucleotide is an important part of its functionality, then preferred sequences are those which encode identical or essentially identical polypeptides. Thus, nucleotide differences which cause a conservative amino acid substitution are preferred over those which cause a non-conservative substitution, nucleotide differences which do not alter the amino acid sequence are more preferred, while identical nucleotides are even more preferred. Insertions or deletions in the polynucleotide that result in insertions or deletions in the polypeptide are preferred over those that result in the down-stream coding region being rendered out of phase; polynucleotide sequences comprising no insertions or deletions are even more preferred. The relative importance of hybridization properties and the encoded polypeptide sequence of a polynucleotide depends on the application of the invention.

A polynucleotide has the same "characteristics" of another polynucleotide if both are capable of forming a stable duplex with a particular third polynucleotide under similar conditions of maximal stringency. Preferably, in addition to similar hybridization properties, the polynucleotides also encode essentially identical polypeptides.

"Conserved" residues of a polynucleotide sequence are those residues which occur unaltered in the same position of two or more related sequences being compared. Residues that are relatively conserved are those that are conserved amongst more related sequences or with a greater degree of identity than residues appearing elsewhere in the sequences.

"Related" polynucleotides are polynucleotides that share a significant proportion of identical residues.

As used herein, a "degenerate" oligonucleotide sequence is a designed sequence derived from at least two related originating polynucleotide sequences as follows: the residues that are conserved in the originating sequences are preserved in the degenerate sequence, while residues that are not conserved in the originating sequences may be provided as several alternatives in the degenerate sequence. For example, the degenerate sequence AYASA may be designed from originating sequences ATACA and ACAGA, where Y is C or T and S is C or G. Y and S are examples of "ambiguous" residues. A degenerate segment is a segment of a polynucleotide containing a degenerate sequence.

It is understood that a synthetic oligonucleotide comprising a degenerate sequence is actually a mixture of closely related oligonucleotides sharing an identical sequence, except at the ambiguous positions. Such an oligonucleotide is usually synthesized as a mixture of all possible combinations of nucleotides at the ambiguous positions. Each of the oligonucleotides in the mixture is referred to as an "alternative form". The number of forms in the mixture is equal to $$\prod_{i=1}^{n} k_i$$

where $k_i$ is the number of alternative nucleotides allowed at each position.

As used herein, a "consensus" oligonucleotide sequence is a designed sequence derived from at least two related originating polynucleotide sequences as follows: the residues that are conserved in all originating sequences are preserved in the consensus sequence; while at positions where residues are not conserved, one alternative is chosen from amongst the originating sequences. In general, the nucleotide chosen is the one which occurs in the greatest frequency in the originating sequences. For example, the consensus sequence AAAAA may be designed from originating sequences CAAAA, AAGAA, and AAAAT. A consensus segment is a segment of a polynucleotide containing a consensus sequence.

A polynucleotide "fragment" or "insert" as used herein generally represents a sub-region of the full-length form, but the entire full-length polynucleotide may also be included.

Polynucleotides "correspond" to each other if they are believed to be derived from each other or from a common ancestor. For example, encoding regions in the genes of different viruses correspond if they share a significant degree of identity, map to the same location of the genome, or encode proteins that perform a similar biochemical function. Messenger RNA corresponds to the gene from which it is transcribed. cDNA corresponds to the RNA from which it has been produced, and to the gene that encodes the RNA. A protein corresponds to a polynucleotide encoding it, and to an antibody that is capable of binding it specifically.

A "probe" when used in the context of polynucleotide manipulation refers to an oligonucleotide which is provided as a reagent to detect a target potentially present in a sample of interest by hybridizing with the target. Usually, a probe will comprise a label or a means by which a label can be attached, either before or subsequent to the hybridization reaction. Suitable labels include, but are not limited to radioisotopes, fluorochromes, chemiluminescent compounds, dyes, and proteins, including enzymes.

A "primer" is an oligonucleotide, generally with a free 3'-OH group, that binds to a target potentially present in a sample of interest by hybridizing with the target, and thereafter promotes polymerization of a polynucleotide complementary to the target.

Processes of producing replicate copies of the same polynucleotide, such as PCR or gene cloning, are collectively referred to herein as "amplification" or "replication". For example, single or double-stranded DNA may be replicated to form another DNA with the same sequence. RNA may be replicated, for example, by an RNA-directed RNA polymerase, or by reverse-transcribing the DNA and then performing a PCR. In the latter case, the amplified copy of the RNA is a DNA with the identical sequence.

A "polymerase chain reaction" ("PCR") is a reaction in which replicate copies are made of a target polynucleotide using one or more primers, and a catalyst of polymerization, such as a reverse transcriptase or a DNA polymerase, and particularly a thermally stable polymerase enzyme. Generally, a PCR involves reiteratively performing three steps: "annealing", in which the temperature is adjusted such that oligonucleotide primers are permitted to form a duplex with the polynucleotide to be amplified; "elongating", in which the temperature is adjusted such that oligonucleotides that have formed a duplex are elongated with a DNA polymerase, using the polynucleotide to which they've formed the duplex as a template; and "melting", in which the temperature is adjusted such that the polynucleotide and elongated oligonucleotides dissociate. The cycle is then repeated until the desired amount of amplified polynucleotide is obtained. Methods for PCR are taught in U.S. Pat. No. 4,683,195 (Mullis) and U.S. Pat. No. 4,683,202 (Mullis et al.).

A "control element" or "control sequence" is a nucleotide sequence involved in an interaction of molecules that contributes to the functional regulation of a polynucleotide, including replication, duplication, transcription, splicing, translation, or degradation of the polynucleotide. The regulation may affect the frequency, speed, or specificity of the process, and may be enhancing or inhibitory in nature. Control elements are known in the art. For example, a "promoter" is an example of a control element. A promoter is a DNA region capable under certain conditions of binding RNA polymerase and initiating transcription of a coding region located downstream (in the 3' direction) from the promoter.

"Operatively linked" refers to a juxtaposition of genetic elements, wherein the elements are in a relationship permitting them to operate in the expected manner. For instance, a promoter is operatively linked to a coding region if the promoter helps initiate transcription of the coding sequence. There may be intervening residues between the promoter and coding region so long as this functional relationship is maintained.

The terms "polypeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation, such as conjugation with a labeling component.

In the context of polypeptides, a "linear sequence" or a "sequence" is an order of amino acids in a polypeptide in an N-terminal to C-terminal direction in which residues that neighbor each other in the sequence are contiguous in the primary structure of the polypeptide. A "partial sequence" is a linear sequence of part of a polypeptide which is known to comprise additional residues in one or both directions.

A linear sequence of amino acids is "essentially identical" to another sequence if the two sequences have a substantial degree of sequence identity. It is understood that the folding and the biochemical function of proteins can accommodate insertions, deletions, and substitutions in the amino acid sequence. Thus, linear sequences of amino acids can be essentially identical even if some of the residues do not precisely correspond or align. Sequences that correspond or align more closely to the invention disclosed herein are more preferred. It is also understood that some amino acid substitutions are more easily tolerated. For example, substitution of an amino acid with hydrophobic side chains, aromatic side chains, polar side chains, side chains with a positive or negative charge, or side chains comprising two or fewer carbon atoms, by another amino acid with a side chain of like properties can occur without disturbing the essential identity of the two sequences. Methods for determining homologous regions and scoring the degree of homology are well known in the art; see for example Altschul et al. and Henikoff et al. Well-tolerated sequence differences are referred to as "conservative substitutions". Thus, sequences with conservative substitutions are preferred over those with other substitutions in the same positions; sequences with identical residues at the same positions are still more preferred.

Generally, a polypeptide region will be essentially identical to another region, after alignment of homologous portions, if the sequences are at least about 92% identical; more preferably, they are at least about 95% identical; more preferably, they are at least about 95% identical and comprise at least another 2% which are either identical or are conservative substitutions; more preferably, they are at least about 97% identical; more preferably, they are at least about 97% identical, and comprise at least another 2% which are either identical or are conservative substitutions; more preferably, they are at least about 99% identical; still more preferably, the sequences are 100% identical.

In determining whether polypeptide sequences are essentially identical, a sequence that preserves the functionality of the polypeptide with which it is being compared is particularly preferred. Functionality may be established by different parameters, such as enzymatic activity, the binding rate or affinity in a substrate-enzyme or receptor-ligand interaction, the binding affinity with an antibody, and X-ray crystallographic structure.

A polypeptide has the same "characteristics" of another polypeptide if it displays the same biochemical function, such as enzyme activity, ligand binding, or antibody reactivity. Preferred characteristics of a polypeptide related to a Glycoprotein B or a Glycoprotein B fragment are the ability to bind analogs of the cell surface receptor bound by Glycoprotein B of other herpes species, the ability to promote membrane fusion with a target cell, the ability to promote viral penetration of the host cell. Also preferred is a polypeptide that displays the same biochemical function as the polypeptide with which it is being compared, and in addition, is believed to have a similar three-dimensional conformation, as predicted by computer modeling or determined by such techniques as X-ray crystallography.

The "biochemical function", "biological function" or "biological activity" of a polypeptide includes any feature of the polypeptide detectable by suitable experimental investigation. "Altered" biochemical function can refer to a change in the primary, secondary, tertiary, or quaternary structure of the polypeptide; detectable, for example, by molecular weight determination, circular dichroism, antibody binding, difference spectroscopy, or nuclear magnetic resonance. It can also refer to a change in reactivity, such as the ability to catalyze a certain reaction, or the ability to bind a cofactor, substrate, inhibitor, drug, hapten, or other polypeptide. A substance may be said to "interfere" with the biochemical function of a polypeptide if it alters the biochemical function of the polypeptide in any of these ways.

A "fusion polypeptide" is a polypeptide comprising regions in a different position in the sequence than occurs in nature. The regions may normally exist in separate proteins and are brought together in the fusion polypeptide; or they may normally exist in the same protein but are placed in a new arrangement in the fusion polypeptide. A fusion polypeptide may be created, for example, by chemical synthesis, or by creating and translating a polynucleotide in which the peptide regions are encoded in the desired relationship.

An "antibody" (interchangeably used in plural form) is an immunoglobulin molecule capable of specific binding to a target, such as a polypeptide, through at least one antigen recognition site, located in the variable region of the immunoglobulin molecule. As used herein, the term encompasses not only intact antibodies, but also fragments thereof, mutants thereof, fusion proteins, humanized antibodies, and any other modified configuration of the immunoglobulin molecule that comprises an antigen recognition site of the required specificity.

"Immunological recognition" or "immunological reactivity" refers to the specific binding of a target through at least one antigen recognition site in an immunoglobulin or a related molecule, such as a B cell receptor or a T cell receptor.

The term "antigen" refers to the target molecule that is specifically bound by an antibody through its antigen recognition site. The antigen may, but need not be chemically related to the immunogen that stimulated production of the antibody. The antigen may be polyvalent, or it may be a monovalent hapten. Examples of kinds of antigens that can be recognized by antibodies include polypeptides, polynucleotides, other antibody molecules, oligosaccharides, complex lipids, drugs, and chemicals.

An "immunogen" is a compound capable of stimulating production of an antibody when injected into a suitable host, usually a mammal. Compounds with this property are described as "immunogenic". Compounds may be rendered immunogenic by many techniques known in the art, including crosslinking or conjugating with a carrier to increase valency, mixing with a mitogen to increase the immune response, and combining with an adjuvant to enhance presentation.

A "vaccine" is a pharmaceutical preparation for human or animal use, which is administered with the intention of conferring the recipient with a degree of specific immunological reactivity against a particular target, or group of targets. The immunological reactivity may be antibodies or cells (particularly B cells, plasma cells, T helper cells, and cytotoxic T lymphocytes, and their precursors) that are immunologically reactive against the target, or any combination thereof. Possible targets include foreign or pathological compounds, such as an exogenous protein, a pathogenic virus, or an antigen expressed by a cancer cell. The immunological reactivity may be desired for experimental purposes, for the treatment of a particular condition, for the elimination of a particular substance, or for prophylaxis against a particular condition or substance. Unless specifically indicated, a vaccine referred to herein may be either a passive vaccine or an active vaccine, or it may have the properties of both.

A "passive vaccine" is a vaccine that does not require participation of the recipient's immune response to exert its effect. Usually, it is comprised of antibody molecules reactive against the target. The antibodies may be obtained from a donor subject and sufficiently purified for administration to the recipient, or they may be produced in vitro, for example, from a culture of hybridoma cells, or by genetically engineering a polynucleotide encoding an antibody molecule.

An "active vaccine" is a vaccine administered with the intention of eliciting a specific immune response within the recipient, that in turn has the desired immunological reactivity against the target. An active vaccine comprises a suitable immunogen. The immune response that is desired may be either humoral or cellular, systemic or secretory, or any combination of these.

A "reagent" polynucleotide, polypeptide, or antibody, is a substance provided for a reaction, the substance having some known and desirable parameters for the reaction.

A reaction mixture may also contain a "target", such as a polynucleotide, antibody, or polypeptide that the reagent is capable of reacting with. For example, in some types of diagnostic tests, the amount of the target in a sample is determined by adding a reagent, allowing the reagent and target to react, and measuring the amount of reaction product. In the context of clinical management, a target may also be a cell, collection of cells, tissue, or organ that is the object of an administered substance, such as a pharmaceutical compound. A cell that is a target for a viral infection is one to which a virus preferentially localizes for such purposes as replication or transformation into a latent form.

An "isolated" polynucleotide, polypeptide, protein, antibody, or other substance refers to a preparation of the substance devoid of at least some of the other components that may also be present where the substance or a similar substance naturally occurs or is initially obtained from. Thus, for example, an isolated substance may be prepared by using a purification technique to enrich it from a source mixture. Enrichment can be measured on an absolute basis, such as weight per volume of solution, or it can be measured in relation to a second, potentially interfering substance present in the source mixture. Increasing enrichments of the embodiments of this invention are increasingly more preferred. Thus, for example, a 2-fold enrichment is preferred, 10-fold enrichment is more preferred, 100-fold enrichment is more preferred, 1000-fold enrichment is even more preferred. A substance can also be provided in an isolated state by a process of artificial assembly, such as by chemical synthesis or recombinant expression.

A polynucleotide used in a reaction, such as a probe used in a hybridization reaction, a primer used in a PCR, or a polynucleotide present in a pharmaceutical preparation, is referred to as "specific" or "selective" if it hybridizes or reacts with the intended target more frequently, more rapidly, or with greater duration than it does with alternative substances. Similarly, a polypeptide is referred to as "specific" or "selective" if it binds an intended target, such as a ligand, hapten, substrate, antibody, or other polypeptide more frequently, more rapidly, or with greater duration than it does to alternative substances. An antibody is referred to as "specific" or "selective" if it binds via at least one antigen recognition site to the intended target more frequently, more rapidly, or with greater duration than it does to alternative substances. A polynucleotide, polypeptide, or antibody is said to "selectively inhibit" or "selectively interfere with" a reaction if it inhibits or interferes with the reaction between particular substrates to a greater degree or for a greater duration than it does with the reaction between alternative substrates.

A "pharmaceutical candidate" or "drug candidate" is a compound believed to have therapeutic potential, that is to be tested for efficacy. The "screening" of a pharmaceutical candidate refers to conducting an assay that is capable of evaluating the efficacy and/or specificity of the candidate. In this context, "efficacy" refers to the ability of the candidate to affect the cell or organism it is administered to in a beneficial way: for example, the limitation of the pathology due to an invasive virus.

The "effector component" of a pharmaceutical preparation is a component which modifies target cells by altering their function in a desirable way when administered to a subject bearing the cells. Some advanced pharmaceutical preparations also have a "targeting component", such as an antibody, which helps deliver the effector component more efficaciously to the target site. Depending on the desired action, the effector component may have any one of a number of modes of action. For example, it may restore or enhance a normal function of a cell, it may eliminate or suppress an abnormal function of a cell, or it may alter a cell's phenotype. Alternatively, it may kill or render dormant a cell with pathological features, such as a virally infected cell. Examples of effector components are provided in a later section.

A "cell line" or "cell culture" denotes higher eukaryotic cells grown or maintained in vitro. It is understood that the descendants of a cell may not be completely identical (either morphologically, genotypically, or phenotypically) to the parent cell.

A "host cell" is a cell which has been transformed, or is capable of being transformed, by administration of an exogenous polynucleotide. A "host cell" includes progeny of the original transformant.

"Genetic alteration" refers to a process wherein a genetic element is introduced into a cell other than by natural cell division. The element may be heterologous to the cell, or it may be an additional copy or improved version of an element already present in the cell. Genetic alteration may be effected, for example, by transfecting a cell with a recombinant plasmid or other polynucleotide through any process known in the art, such as electroporation, calcium phosphate precipitation, contacting with a polynucleotide-liposome complex, or by transduction or infection with a DNA or RNA virus or viral vector. The alteration is preferably but not necessarily inheritable by progeny of the altered cell.

An "individual" refers to vertebrates, particularly members of a mammalian species, and includes but is not limited to domestic animals, sports animals, and primates, including humans.

The term "primate" as used herein refers to any member of the highest order of mammalian species. This includes (but is not limited to) prosimians, such as lemurs and lorises; tarsioids, such as tarsiers; new-world monkeys, such as squirrel monkeys (*Saimiri sciureus*) and tamarins; old-world monkeys such as macaques (including *Macaca nemestrina, Macaca fascicularis,* and *Macaca fuscata*); hylobatids, such as gibbons and siamangs; pongids, such as orangutans, gorillas, and chimpanzees; and hominids, including humans.

The "pathology" caused by a herpes virus infection is anything that compromises the well-being or normal physiology of the host. This may involve (but is not limited to) destructive invasion of the virus into previously uninfected cells, replication of the virus at the expense of the normal metabolism of the cell, generation of toxins or other unnatural molecules by the virus, irregular growth of cells or intercellular structures (including fibrosis), irregular or suppressed biological activity of infected cells, malignant transformation, interference with the normal function of neighboring cells, aggravation or suppression of an inflammatory or immunological response, and increased susceptibility to other pathogenic organisms and conditions.

"Treatment" of an individual or a cell is any type of intervention in an attempt to alter the natural course of the individual or cell. For example, treatment of an individual may be undertaken to decrease or limit the pathology caused by a herpes virus infecting the individual. Treatment includes (but is not limited to) administration of a composition, such as a pharmaceutical composition, and may be performed either prophylactically, or therapeutically, subsequent to the initiation of a pathologic event or contact with an etiologic agent.

It is understood that a clinical or biological "sample" encompasses a variety of sample types obtained from a subject and useful in an in vitro procedure, such as a diagnostic test. The definition encompasses solid tissue samples obtained as a surgical removal, a pathology specimen, or a biopsy specimen, tissue cultures or cells derived therefrom and the progeny thereof, and sections or smears prepared from any of these sources. Non-limiting examples are samples obtained from infected sites, fibrotic sites, unaffected sites, and tumors. The definition also encompasses blood, spinal fluid, and other liquid samples of biologic origin, and may refer to either the cells or cell fragments suspended therein, or to the liquid medium and its solutes. The definition also includes samples that have been solubilized or enriched for certain components, such as DNA, RNA, protein, or antibody.

Oligonucleotide primers and probes described herein have been named as follows: The first part of the designation is the single amino acid code for a portion of the conserved region of the polypeptide they are based upon, usually 4 residues long. This is followed with the letter A or B, indicating respectively that the oligonucleotide is complementary to the sense or anti-sense strand of the encoding region. Secondary consensus oligonucleotides used for sequencing and labeling reactions have the letters SQ at the end of the designation.

General techniques

The practice of the present invention will employ, unless otherwise indicated, conventional techniques of molecular biology, microbiology, recombinant DNA, and immunology, which are within the skill of the art. Such techniques are explained fully in the literature. See, for example, "Molecular Cloning: A Laboratory Manual", Second Edition (Sambrook, Fritsch & Maniatis, 1989), "Oligonucleotide Synthesis" (M. J. Gait, ed., 1984), "Animal Cell Culture" (R. I. Freshney, ed., 1987); the series "Methods in Enzymology" (Academic Press, Inc.); "Handbook of Experimental Immunology" (D. M. Weir & C. C. Blackwell, eds.), "Gene Transfer Vectors for Mammalian Cells" (J. M. Miller & M. P. Calos, eds., 1987), "Current Protocols in Molecular Biology" (F. M. Ausubel et al., eds., 1987); and "Current Protocols in Immunology" (J. E. Coligan et al., eds., 1991).

All patents, patent applications, articles and publications mentioned herein, both supra and infra, are hereby incorporated herein by reference.

Polynucleotides encoding Glycoprotein B of the herpes virus RFHV/KSHV subfamily

This invention embodies isolated polynucleotide segments derived from Glycoprotein B genes present in herpes viruses that encode a fragment of a Glycoprotein B polypeptide. The polynucleotides are related to the RFHV/KSHV subfamily of herpes viruses. Exemplary polynucleotides encode Glycoprotein B fragments from either RFHV or KSHV. Preferred fragments include those shown in FIG. 1, and subfragments thereof, obtained as described in the Example section below. Especially preferred is the polynucleotide comprising the sequence between residues 36–354 of SEQ. ID NO:1, SEQ. ID NO:3, or SEQ. ID NO:96, or polynucleotides contained in SEQ. ID NO:92.

The polynucleotide segments of RFHV and KSHV between residues 36 and 354 are 76% identical. Shared residues are indicated in FIG. 1 by "*". The longest subregions that are identically shared between RFHV and KSHV within this segment are 15, 17, and 20 nucleotides in length.

The 319 base pair fragments of RFHV and KSHV between the amplification primer binding sites are more identical to each other than either of them are to that of any previously sequenced herpes virus. The next most closely related sequences are sHV1 and bHV4, which are 63% identical to the corresponding sequence of KSHV, and 60% identical to the corresponding sequence of RFHV. The longest number of consecutive bases shared between the Glycoprotein B fragment and any of the previously sequenced viruses is 14. It is believed that any subfragment of the RFHV or KSHV sequence of 16 base pairs or longer will be unique to the RFHV/KSHV subfamily, or to particular herpes virus species and variants within the subfamily.

This invention embodies subfragments contained in the Glycoprotein B gene of the RFHV/KSHV subfamily, preferably contained in the region corresponding to the 319 base pair fragment between residues 36–354 of SEQ. ID NO:1, SEQ. ID NO:3, or SEQ. ID NO:96, or anywhere in SEQ. ID NO:92. Preferably, the sub-fragments are at least about 16 nucleotides in length; more preferably they are at least 18 nucleotides in length; more preferably they are at least 21 nucleotides in length; more preferably they are at least about 25 nucleotides in length; more preferably they are at least about 35 nucleotides in length; still more preferably they are at least about 50 nucleotides in length; yet more preferably they are at least about 75 nucleotides in length, and even more preferably they are 100 nucleotides in length or more. Also embodied in this invention are polynucleotides comprising the entire open reading frame of each respective herpes virus Glycoprotein B.

The RFHV/KSHV subfamily consists of members that have sequences that are more closely identical to the corresponding sequences of RFHV or KSHV, than RFHV or KSHV are to any other virus listed in Table 1. Preferred members of the family may be identified on the basis of the sequence of the Glycoprotein B gene in the region corresponding to that of FIG. 1. Table 2 provides the degree of sequence identities in this region:

TABLE 2

Sequence Identities Between Glycoprotein B of KSHV and other Herpes Viruses

| Glycoprotein B Sequence | | SEQ. ID NO: | Identity to polynucleotide fragment: RFHV (SEQ. ID NO:1) Bases 36–354 | KSHV (SEQ. ID NO:3) Bases 36–354 |
|---|---|---|---|---|
| RFHV/KSHV subfamily | RFHV | 1 | (100%) | 76% |
| | KSHV | 3 | 76% | (100%) |
| Other gamma herpes viruses | sHV1 | 5 | 60% | 63% |
| | bHV4 | 6 | 60% | 63% |
| | eHV2 | 7 | 52% | 54% |
| | mHV68 | 8 | 56% | 54% |
| | hEBV | 9 | <50% | 52% |
| alpha and beta herpes viruses | hCMV | 10 | <50% | <50% |
| | hHV6 | 11 | <50% | <50% |
| | hVZV | 12 | <50% | <50% |
| | HSV1 | 13 | <50% | <50% |

The percentage of sequence identity is calculated by first aligning the encoded amino acid sequence, determining the corresponding alignment of the encoding polynucleotide, and then counting the number of residues shared between the sequences being compared at each aligned position. No penalty is imposed for the presence of insertions or deletions, but insertions or deletions are permitted only where required to accommodate an obviously increased number of amino acid residues in one of the sequences being aligned. Offsetting insertions just to improve sequence alignment are not permitted at either the polypeptide or polynucleotide level. Thus, any insertions in the polynucleotide sequence will have a length which is a multiple of 3. The percentage is given in terms of residues in the test sequence that are identical to residues in the comparison or reference sequence.

Preferred Glycoprotein B encoding polynucleotide sequences of this invention are those derived from the RFHV/KSHV herpes virus subfamily. They include those sequences that are at least 65% identical with the RFHV or KSHV sequence between bases 36 and 354; more preferably, the sequences are at least 67% identical; more preferably, the sequences are at least about 70% identical; more preferably, the sequences are at least about 75% identical; more preferably, the sequences are at least about 80% identical; more preferably, the sequences are at least about 85% identical; more preferably, the sequences are at least about 90% identical; even more preferably, the sequences are over 95% identical. Also included are Glycoprotein B encoding regions that are upstream or downstream of a region fulfilling the identity criteria indicated.

Other preferred Glycoprotein B encoding polynucleotide sequences may be identified by the percent identity with RFHV/KSHV subfamily-specific oligonucleotides (Type 2 oligonucleotides) described in more detail in a later section. The percent identity of RFHV and KSHV Glycoprotein B with exemplary Type 2 oligonucleotides is shown in Table 3:

TABLE 3

Sequence Identities Between Glycoprotein B of Select Herpes Viruses and RFHV/KSHV Subfamily Specific Oligonucleotides

| Glycoprotein B Sequence | SEQ ID NO: | Identity to SHMDA (SEQ ID NO:41) | Identity to CFSSB (SEQ ID NO:43) | Identity to ENTFA (SEQ ID NO:45) | Identity to DNIQB (SEQ ID NO:46) |
|---|---|---|---|---|---|
| RFHV | 1 | 91% | 91% | 89% | 91% |
| KSHV | 3 | 100% | 85% | 89% | 97% |
| sHV1 | 5 | 71% | 70% | 66% | 66% |
| bHV4 | 6 | 57% | 64% | 69% | 74% |
| eHV2 | 7 | 57% | 61% | 54% | 60% |
| mHV68 | 8 | <50% | 55% | 54% | 77% |
| hEBV | 9 | 57% | 55% | 60% | 51% |
| hCMV | 10 | 57% | 55% | 60% | 51% |
| hHV6 | 11 | <50% | 52% | 60% | 57% |
| hVZV | 12 | 54% | 58% | 66% | 57% |
| HSV1 | 13 | 57% | 60% | 54% | 54% |

Percent identity is calculated for oligonucleotides of this length by not allowing gaps in either the oligonucleotide or the polypeptide for purposes of alignment. Throughout this disclosure, whenever at least one of two sequences being compared is a degenerate oligonucleotide comprising an ambiguous residue, the two sequences are identical if at least one of the alternative forms of the degenerate oligonucleotide is identical to the sequence with which it is being compared. As an illustration, AYAAA is 100% identical to ATAAA, since AYAAA is a mixture of ATAAA and ACAAA.

Preferred Glycoprotein B encoding sequences are those which over the corresponding region are at least 72% identical to SHMDA; more preferably they are at least 74% identical; more preferably they are at least about 77% identical; more preferably they are at least about 80% identical; more preferably they are at least about 85% identical; more preferably they are at least about 91% identical. Other preferred Glycoprotein B encoding sequences are those which over the corresponding region are at least 71% identical to CFSSB; more preferably they are at least 73% identical; more preferably they are at least about 77% identical; more preferably they are at least about 80% identical; more preferably they are at least about 85% identical. Other preferred Glycoprotein B encoding sequences are those which over the corresponding region are at least 70% identical to ENTFA; more preferably they are at least 72% identical; more preferably they are at least about 75% identical; more preferably they are at least about 80% identical; more preferably they are at least about 85% identical; more preferably, they are at least about 89% identical. Other preferred Glycoprotein B encoding sequences are those which over the corresponding region are at least about 78% identical to DNIQB; more preferably they are at least 80% identical; more preferably they are at least about 85% identical; more preferably they are at least about 91% identical. Also included are Glycoprotein B encoding regions that are upstream or downstream of a region fulfilling the identity criteria indicated.

Glycoprotein B encoding sequences from members of the RFHV/KSHV subfamily identified by any of the aforementioned sequence comparisons, using either RFHV or KSHV sequences, or the subfamily-specific oligonucleotides, are equally preferred. Exemplary sequences are the Glycoprotein B encoding sequences of RFHV and KSHV. Also embodied in this invention are fragments of any Glycoprotein B encoding sequences of the subfamily, and longer polynucleotides comprising such polynucleotide fragments.

The polynucleotide sequences described in this section provide a basis for obtaining the synthetic oligonucleotides, proteins and antibodies outlined in the sections that follow. These compounds may be prepared by standard techniques known to a practitioner of ordinary skill in the art, and may be used for a number of investigative, diagnostic, and therapeutic purposes, as described below.

Preparation of polynucleotides

Polynucleotides and oligonucleotides of this invention may be prepared by any suitable method known in the art. For example, oligonucleotide primers can be used in a PCR amplification of DNA obtained from herpes virus infected tissue, as in Example 3 and Example 11, described below. Alternatively, oligonucleotides can be used to identify suitable bacterial clones of a DNA library, as described below in Example 8.

Polynucleotides may also be prepared directly from the sequence provided herein by chemical synthesis. Several methods of synthesis are known in the art, including the triester method and the phosphite method. In a preferred method, polynucleotides are prepared by solid-phase synthesis using mononucleoside phosphoramidite coupling units. See, for example Horise et al., Beaucage et al., Kumar et al., and U.S. Pat. No. 4,415,732.

A typical solid-phase synthesis involves reiterating four steps: deprotection, coupling, capping, and oxidation. This results in the stepwise synthesis of an oligonucleotide in the 3' to 5' direction.

In the first step, the growing oligonucleotide, which is attached at the 3'-end via a (—O—) group to a solid support, is deprotected at the 5' end. For example, the 5' end may be protected by a —ODMT group, formed by reacting with 4,4'-dimethoxytrityl chloride (DMT-Cl) in pyridine. This group is stable under basic conditions, but is easily removed under acid conditions, for example, in the presence of dichloroacetic acid (DCA) or trichloroacetic acid (TCA). Deprotection provides a 5' -OH reactive group.

In the second step, the oligonucleotide is reacted with the desired nucleotide monomer, which itself has first been converted to a 5'-protected, 3'-phosphoramidite. The 5'-OH of the monomer may be protected, for example, in the form of a —ODMT group, and the 3'-OH group may be converted to a phosphoramidite, such as —OP(OR')NR$_2$; where R is the isopropyl group —CH(CH$_3$)$_2$; and R' is, for example, —H (yielding a phosphoramidite diester), or —CH$_3$, —CH$_2$CH$_3$, or the beta-cyanoethyl group —CH$_2$CH$_2$CN (yielding a phosphoramidite triester). The 3'-phosphoramidite group of the monomer reacts with the 5'-OH group of the growing oligonucleotide to yield the phosphite linkage 5'-OP(OR')O-3'.

In the third step, oligonucleotides that have not coupled with the monomer are withdrawn from further synthesis to prevent the formation of incomplete polymers. This is achieved by capping the remaining 5'-OH groups, for example, in the form of acetates (—OC(O)CH$_3$,) by reaction with acetic anhydride (CH$_3$C(O)—O—C(O)CH$_3$).

In the fourth step, the newly formed phosphite group (i.e., 5'-OP(OR')O-3') is oxidized to a phosphate group (i.e., 5'-OP(=O)(OR')O-3'); for example, by reaction with aqueous iodine and pyridine.

The four-step process may then be reiterated, since the oligonucleotide obtained at the end of the process is 5'-protected and is ready for use in step one. When the desired full-length oligonucleotide has been obtained, it may be cleaved from the solid support, for example, by treatment with alkali and heat. This step may also serve to convert phosphate triesters (i.e., when R' is not —H) to the phosphate diesters (—OP(=O)$_2$O—), and to deprotect base-labile protected amino groups of the nucleotide bases.

Polynucleotides prepared by any of these methods can be replicated to provide a larger supply by any standard technique, such as PCR amplification or gene cloning.

Cloning and expression vectors comprising a Glycoprotein B encoding polynucleotide Cloning vectors and expression vectors are provided in this invention that comprise a sequence encoding a herpes virus Glycoprotein B or variant or fragment thereof. Suitable cloning vectors may be constructed according to standard techniques, or may be selected from the large number of cloning vectors available in the art. While the cloning vector selected may vary according to the host cell intended to be used, useful cloning vectors will generally have the ability to self-replicate, may possess a single target for a particular restriction endonuclease, and may carry genes for a marker that can be used in selecting transfected clones. Suitable examples include plasmids and bacterial viruses; e.g., pUC18, mp18, mp19, pBR322, pMB9, ColE1, pCR1, RP4, phage DNAs, and shuttle vectors like pSA3 and pAT28.

Expression vectors generally are replicable polynucleotide constructs that encode a polypeptide operatively linked to suitable transcriptional and translational controlling elements. Examples of transcriptional controlling elements are promoters, enhancers, transcription initiation sites, and transcription termination sites. Examples of translational controlling elements are ribosome binding sites, translation initiation sites, and stop codons. Protein processing elements may also be included: for example, regions that encode leader or signal peptides and protease cleavage sites required for translocation of the polypeptide across the membrane or secretion from the cell. The elements employed would be functional in the host cell used for expression. The controlling elements may be derived from the same Glycoprotein B gene used in the vector, or they may be heterologous (i.e., derived from other genes and/or other organisms).

Polynucleotides may be inserted into host cells by any means known in the art. Suitable host cells include bacterial cells such as E. coli, mycobacteria, other prokaryotic microorganisms and eukaryotic cells (including fungal cells, insect cells, plant cells, and animal cells). The cells are transformed by inserting the exogenous polynucleotide by direct uptake, endocytosis, transfection, f-mating, or electroporation. Subsequently, the exogenous polynucleotide may be maintained within the cell as a non-integrated vector, such as a plasmid, or may alternatively be integrated into the host cell genome.

Cloning vectors may be used to obtain replicate copies of the polynucleotides they contain, or as a means of storing the polynucleotides in a depository for future recovery. Expression vectors and host cells may be used to obtain polypeptides transcribed by the polynucleotides they contain. They may also be used in assays where it is desirable to have intact cells capable of synthesizing the polypeptide, such as in a drug screening assay.

Synthetic Type 1 oligonucleotides for Glycoprotein B of gamma herpes virus

Oligonucleotides designed from sequences of herpes virus Glycoprotein B, as embodied in this invention, can be used as probes to identify related sequences, or as primers in an amplification reaction such as a PCR.

Different oligonucleotides with different properties are described in the sections that follow. Oligonucleotides designated as Type 1 are designed from previously known gamma herpes virus Glycoprotein B polynucleotide sequences. They are designed to hybridize with polynucleotides encoding any gamma herpes virus Glycoprotein B, and may be used to detect previously known species of gamma herpes virus. They may also be used to detect and characterize new species of gamma herpes virus. Oligonucleotides designated as Type 2 are designed from the RFHV and KSHV Glycoprotein B polynucleotide sequences together. They are designed to hybridize with polynucleotides encoding Glycoprotein B of the RFHV/KSHV subfamily, including but not limited to RFHV and KSHV. Oligonucleotides designated as Type 3 are designed from RFHV or KSHV Glycoprotein sequences that are relatively unique to the individual virus. They are designed to hybridize specifically with polynucleotides encoding Glycoprotein B only from RFHV or KSHV and closely related viral strains.

Some preferred examples of Type 1 oligonucleotides are listed in Table 4. These oligonucleotides have a specificity for Glycoprotein B encoding polynucleotides of a broad range of herpes viruses.

TABLE 4

Type 1 Oligonucleotides used for Detecting, Amplifying, or Characterizing Herpes
Virus Polynucleotides encoding Glycoprotein B
Target: Herpes Glycoprotein B, especially from gamma Herpes Viruses

| Desig-<br>nation | Sequence<br>(5' to 3') | Length | No. of<br>forms | Orien-<br>tation | SEQ<br>ID: |
|---|---|---|---|---|---|
| FRFDA | GCTGTTCAGATTTGACTTAGAYMANMCNTGYCC | 33 | 256 | sense | 13 |
| NIVPA | GTGTACAAGAAGAACATCGTGCCNTAYATNTTYA<br>A | 32 | 64 | sense | 14 |
| NIVPASQ | GTGTACAAGAAGAACATCGTGCC | 23 | 1 |  | 15 |
| TVNCB | AACATGTCTACAATCTCACARTTNACNGTNGT | 32 | 128 | anti-<br>sense | 16 |
| TVNCBSQ | AACATGTCTACAATCTCACA | 20 | 1 |  | 17 |
| FAYDA | AATAACCTCTTTACGGCCCAAATTCARTWYGCN<br>TAYGA | 38 | 64 | sense | 18 |
| IYGKA | CCAACGAGTGTGATGTCAGCCATTTAYGGNAAR<br>CCNGT | 38 | 64 | sense | 19 |
| IYGKASQ | CCAACGAGTGTGATGTCAGCC | 21 | 1 |  | 20 |
| CYSRA | TGCTACTCGCGACCTCTAGTCACCTTYAARTTYR<br>TNAA | 38 | 64 | sense | 21 |
| CYSRASQ | TGCTACTCGCGACCTCTAGTCACC | 24 | 1 |  | 22 |
| NIDFB | ACCGGAGTACAGTTCCACTGTYTTRAARTCDATR<br>TT | 36 | 48 | anti-<br>sense | 23 |
| NIDFBSQ | TGTCACCTTGACATGAGGCCA | 21 | 1 |  | 24 |
| FREYA | TTTGACCTGGAGACTATGTTYMGNGARTAYAA | 32 | 64 | sense | 25 |
| FREYB | GCTCTGGGTGTAGTAGTTRTAYTCYCTRAACAT | 33 | 16 | anti-<br>sense | 26 |
| NVFDB | TCTCGGAACATGCTCTCCAGRTCRAAMACRTT | 32 | 32 | anti-<br>sense | 27 |
| GGMA | ACCTTCATCAAAAATCCCTTNGGNGGNATGYT | 32 | 128 | sense | 28 |
| TVNCA | TGGACTTACAGGACTCGAACNACNGTNAAYTG | 32 | 128 | sense | 29 |

The orientation indicated in Table 4 is relative to the encoding region of the polynucleotide. Oligomers with a "sense" orientation will hybridize to the strand antisense to the coding strand and initiate amplification in the direction of the coding sequence. Oligomers with an "antisense" orientation will hybridize to the coding strand and initiate amplification in the direction opposite to the coding sequence.

These oligonucleotides have been designed with several properties in mind: 1) sensitivity for target DNA even when present in the source material at very low copy numbers; 2) sufficient specificity to avoid hybridizing with unwanted sequences; for example, host sequences with limited similarity; 3) sufficient cross-reactivity so that differences between an unknown target and the sequence used to design it do not prevent the oligonucleotide from forming a stable duplex with the target.

For some applications, a particularly effective design is oligonucleotides that have a degenerate segment at the 3' end, designed from a region of at least 2 known polynucleotides believed to be somewhat conserved with the polynucleotide target. The various permutations of the ambiguous residues help ensure that at least one of the alternative forms of the oligonucleotide will be able to hybridize with the target. Adjacent to the degenerate segment at the 5' end of the oligonucleotide is a consensus segment which strengthens any duplex which may form and permits hybridization or amplification reactions to be done at higher temperatures. The degenerate segment is located at the 3' end of the molecule to increase the likelihood of a close match between the oligonucleotide and the target at the site where elongation begins during a polymerase chain reaction.

The ambiguous residues in the degenerate part of the sequences are indicated according to the following code:

TABLE 5

Single Letter Codes for Ambiguous
Positions

| Code | Represents |
|---|---|
| R | A or G (purine) |
| Y | C or T (pyrimidine) |
| W | A or T |
| S | C or G |
| M | A or C |
| K | G or T |
| B | C or G or T (not A) |
| D | A or G or T (not C) |
| H | A or C or T (not G) |
| V | A or C or G (not T) |
| N | A or C or G or T |

The Type 1 oligonucleotides shown in Table 4 are generally useful for hybridizing with Glycoprotein B encoding polynucleotide segments. This may be conducted to detect the presence of the polynucleotide, or to prime an amplification reaction so that the polynucleotide can be characterized further. Suitable targets include polynucleotides encoding a region of a Glycoprotein B from a wide spectrum of gamma herpes viruses, including members of the RFHV/KSHV subfamily. Suitable are those infecting any vertebrate animal, including humans and non-human primates, whether or not the Glycoprotein B or the virus has been previously known or described. Non-limiting examples include polynucleotides encoding Glycoprotein B from any of the gamma herpes viruses listed in Table 1.

The oligonucleotides may be used, inter alia, to prime a reaction to amplify a region of the target polynucleotide in the 3' direction from the site where the oligonucleotide hybridizes. FRFDA, HIVPA, TVNCB, FAYDA, IYGKA, CYSRA, NIDFB, FREYA, FREYB, NVFDB, GGMA, and TVNCA are oligonucleotides with a consensus segment adjoining a degenerate segment, and are useful for this purpose.

FIG. 2 shows the position along the Glycoprotein B polynucleotide sequence of the RFHV/KSHV subfamily where the aforementioned oligonucleotide primers are expected to hybridize. The map is not drawn to scale, but accurately depicts the order of the predicted hybridization sites in the 5' to 3' direction along the Glycoprotein B encoding strand. Also indicated are approximate lengths of amplification products that may be generated by using various sets of primers in an amplification reaction. The lengths shown include the primer binding sites at each end, and the polynucleotide encompassed between them.

A preferred source of DNA for use as a target for the oligonucleotides of Table 4 is any biological sample (including solid tissue and tissue cultures), particularly of vertebrate animal origin, known or suspected to harbor a herpes virus. DNA is extracted from the source by any method known in the art, including extraction with organic solvents or precipitation at high salt concentration.

A preferred method of amplification is a polymerase chain reaction: see generally U.S. Pat. No. 4,683,195 (Mullis) and U.S. Pat. No. 4,683,202 (Mullis et al.); see U.S. Pat. No. 5,176,995 (Sninsky et al.) for application to viral polynucleotides. An amplification reaction may be conducted by combining the target polynucleotide to be amplified with short oligonucleotides capable of hybridizing with the target and acting as a primer for the polymerization reaction. Also added are substrate mononucleotides and a heat-stable DNA-dependent Glycoprotein B, such as Taq. The conditions used for amplification reactions are generally known in the art, and can be optimized empirically using sources of known viruses, such RFHV, KSHV, hEBV or HSV1. Conditions can be altered, for example, by changing the time and temperature of the amplification cycle, particularly the hybridization phase; changing the molarity of the oligonucleotide primers; changing the buffer composition; and changing the number of amplification cycles. Fine-tuning the amplification conditions is a routine matter for a practitioner of ordinary skill in the art.

In one method, a single primer of this invention is used in the amplification, optionally using a second primer, such as a random primer, to initiate replication downstream from the first primer and in the opposite direction. In a preferred method, at least two of the primers of this invention are used in the same reaction to initiate replication in opposite directions. The use of at least two specific primers enhances the specificity of the amplification reaction, and defines the size of the fragment for comparison between samples. For example, amplification may be performed using primers NIVPA and TVNCB. More preferred is the use of several sets of primers in a nested fashion to enhance the amplification. Nesting is accomplished by performing a first amplification using primers that generate an intermediate product, comprising one or more internal binding sites for additional primers. This is followed by a second amplification, using a new primer in conjunction with one from the previous set, or two new primers. The second amplification product is therefore a subfragment of the first product. If desired, additional rounds of amplification can be performed using additional primers.

Accordingly, nesting amplification reactions can be performed with any combination of three or more oligonucleotide primers comprising at least one primer with a sense orientation and one primer with an antisense orientation. Preferably, primers are chosen so that intermediate amplification products are no more than about 2000 base pairs; more preferably, they are no more than about 1500 base pairs; even more preferably, they are no more than about 750 base pairs. Preferably, the innermost primers provide a final amplification product of no more than about 1200 base pairs; more preferably, they are no more than about 750 base pairs; even more preferably, they are no more than about 500 base pairs. Accordingly, a preferred combination is at least three primers selected from FAYDA, IYGKA, CYSRA, NIDFB, NVFDB, and FREYB. Another preferred combination is at least three primers selected from FRFDA, NIVPA, TVNCA, NIDFB, NVFDB, and FREYB.

Particularly preferred is a first amplification using primer FRFDA and TVNCB, followed by a second amplification using primer NIVPA and TVNCB. When performed on a polynucleotide from a Glycoprotein B gene of KSHV, the size of the final fragment including the primer binding regions is about 386 bases.

The amplified polynucleotides can be characterized at any stage during the amplification reaction, for example, by size determination. Preferably, this is performed by running the polynucleotide on a gel of about 1–2% agarose. If present in sufficient quantity, the polynucleotide in the gel can be stained with ethidium bromide and detected under ultraviolet light. Alternatively, the polynucleotide can be labeled with a radioisotope such as $^{32}P$ or $^{35}S$ before loading on a gel of about 6% polyacrylamide, and the gel can subsequently be used to produce an autoradiogram. A preferred method of labeling the amplified polynucleotide is to end-label an oligonucleotide primer such as NIVPA with $^{32}P$ using a polynucleotide kinase and gamma-$[^{32}P]$-ATP, and continuing amplification for about 5–15 cycles.

If desired, size separation may also be used as a step in the preparation of the amplified polynucleotide. This is particularly useful when the amplification mixture is found to contain artifact polynucleotides of different size, such as may have arisen through cross-reactivity with undesired targets. A separating gel, such as described in the preceding paragraph, is dried onto a paper backing and used to produce an autoradiogram. Positions of the gel corresponding to the desired bands on the autoradiogram are cut out and extracted by standard techniques. The extracted polynucleotide can then be characterized directly, cloned, or used for a further round of amplification.

The oligonucleotides NIVPASQ, TVNCBSQ, IYGKASQ, CYSRASQ, and NIDFBSQ are each derived from a consensus-degenerate Type 1 oligonucleotide. They retain the consensus segment, but lack the degenerate segment. They are useful, inter alia, in sequencing of a Glycoprotein B polynucleotide fragment successfully amplified using a consensus-degenerate oligonucleotide.

Unwanted polynucleotides in a mixture from an amplification reaction can also be proportionally reduced by shifting to primers of this type. For example, an initial 3–5 cycles of amplification can be conducted using primers NIVPA and TVNCB at ⅕ to ¹⁄₂₅ the normal amount. Then a molar excess (for example, 50 pmol) of NIVPASQ and/or TVNCBSQ is added, and the amplification is continued for an additional 30–35 cycles. This reduces the complexity of the oligonucleotides present in the amplification mixture, and permits the reaction temperatures to be increased to reduce amplification of unwanted polynucleotides.

Type 2 oligonucleotide primers for Glycoprotein B of the RFHV/KSHV subfamily

Type 2 oligonucleotides are intended for detection or amplification reactions for the Glycoprotein B of any virus of the RFHV/KSHV subfamily. They are designed from segments of the Glycoprotein B encoding region that are relatively well conserved between RFHV and KSHV, but not other previously sequenced gamma herpes viruses. Preferred examples are shown in Table 6:

optionally preamplified using Type 1 oligonucleotides such as NIVPA and TVNCB. Other combinations are also suitable. In another example, one of the Type 2 oligonucleotides of Table 6 is used in combination with a suitable Type 1

TABLE 6

Type 2 Oligonucleotides used for Detecting, Amplifying, or Characterizing Herpes Virus Polynucleotides encoding Glycoprotein B
Target: Glycoprotein B from the RFHV/KSHV subfamily of herpes viruses

| Desig-nation | Sequence (5' to 3') | Length | No. of forms | Orien-tation | SEQ ID: |
|---|---|---|---|---|---|
| SHMDA | AGACCCGTGCCACTCTATGARATHAGYCAYATGGA | 35 | 24 | sense | 41 |
| SHMDASQ | AGACCCGTGCCACTCTATGA | 20 | 1 | | 42 |
| CFSSB | GTTCACAACAATCTTCATNGARCTRAARCA | 30 | 32 | anti-sense | 43 |
| CFSSBSQ | GTTCACAACAATCTTCAT | 18 | 1 | | 44 |
| ENTFA | GTCAACGGAGTAGARAAYACNTTYACNGA | 29 | 128 | sense | 45 |
| DNIQB | ACTGGCTGGCTAAAGTACCTTTGAATRTTRTCNGT | 35 | 16 | anti-sense | 46 |
| DNIQBSQ | ACTGGCTGGCTAAAGTACCTTTG | 23 | 1 | | 47 |

Type 2 oligonucleotides may be used for many purposes where specificity for the RFHV/KSHV subfamily specificity is desired. This includes the detection or amplification of Glycoprotein B from known viruses of the RFHV/KSHV subfamily, or characterization of Glycoprotein B from new members of the family.

SHMDA, CFSSB, ENTFA, and DNIQB are consensus-degenerate oligonucleotides with a degenerate 3' end, useful as initial primers for PCR amplifications, including polynucleotides of the RFHV/KSHV subfamily which are not identical to either RFHV or KSHV. SHMDASQ, CFSSBSQ, and DNIQBSQ contain only a consensus segment, and are useful for example in labeling or sequencing polynucleotides already amplified using the consensus-degenerate oligonucleotides.

In one application, these Type 2 oligonucleotides are used individually or in combination as amplification primers. In one example of this application, the oligonucleotides are used directly on DNA obtained from a tissue sample to obtain a Glycoprotein B from the RFHV/KSHV subfamily, but not more distantly related viruses that may be present in the same tissue, such as hEBV, hCMV or HSV1. Thus, SHMDA and DNIQB may be used as primers in a PCR, oligonucleotide listed earlier. Thus, NIVPA may be used in combination with DNIQB, or SHMDA may be used in combination with TVNCB as primers in a PCR. The DNA source may optionally be preamplified using NIVPA and TVNCB. Other combinations are also suitable.

In another application, Type 2 oligonucleotides, or oligonucleotides comprising these sequences or fragments thereof, are used as probes in a detection assay. For example, they can be provided with a suitable label such as $^{32}$P, and then used in a hybridization assay with a suitable target, such as DNA amplified using FRFDA and/or NIVPA, along with TVNCB.

Type 3 oligonucleotide primers specific for Glycoprotein B of RFHV or KSHV

Type 3 oligonucleotides are intended for detection or amplification reactions specific for a particular virus. They are non-degenerate segments of the Glycoprotein B encoding region of RFHV or KSHV that are relatively more variable between these two viruses and against other herpes viruses than are other segments of the region. Preferred examples are shown in Table 7, and in the Example section.

TABLE 7

Type 3 Oligonucleotides used for Detecting, Amplifying, or Characterizing Herpes Virus Polynucleotides encoding Glycoprotein B

| Desig-nation | Sequence (5' to 3') | Length | No. of forms | Orien-tation | SEQ ID: |
|---|---|---|---|---|---|
| Target: Glycoprotein B from RFHV | | | | | |
| GMTEB | TGCTGCTTCTGTCATACCGCG | 21 | 1 | anti-sense | 48 |
| AAITB | TATTTGTTTGTGATTGCTGCT | 21 | 1 | anti-sense | 49 |
| GMTEA | GCGGTATGACAGMGCAGCAA | 21 | 1 | sense | 50 |
| KYEIA | AACAAATATGAGATCCCCAGG | 21 | 1 | sense | 51 |
| TDRDB | TCATCCCGATCGGTGAACGTA | 21 | 1 | anti-sense | 52 |
| VEGLB | TTGTCAGTTAGACCTTCGACG | 21 | 1 | anti-sense | 53 |
| VEGLA | CCCGTCGAAGGTCTAACTGAC | 21 | 1 | sense | 54 |
| PVLYA | AGCCAACCAGTACTGTACTCT | 21 | 1 | sense | 55 |
| Target: Glycoprotein B from KSHV | | | | | |
| GLTEB | TGATGGCGGACTCTGTCAAGC | 21 | 1 | anti-sense | 56 |
| TNKYB | GTTCATACTTGTTGGTGATGG | 21 | 1 | anti-sense | 57 |
| GLTEA | GGGCTTGACAGAGTCCGCCAT | 21 | 1 | sense | 58 |

TABLE 7-continued

Type 3 Oligonucleotides used for Detecting, Amplifying, or Characterizing
Herpes Virus Polynucleotides encoding Glycoprotein B

| Designation | Sequence (5' to 3') | Length | No. of forms | Orientation | SEQ ID: |
|---|---|---|---|---|---|
| YELPA | ACAAGTATGAACTCCCGAGAC | 21 | 1 | sense | 59 |
| VNVNB | ACCCCGTTGACATTTACCTTC | 21 | 1 | anti-sense | 60 |
| TFTDV | TCGTCTCTGTCAGTAAATGTG | 21 | 1 | anti-sense | 61 |
| TVFLA | CCACAGTATTCCTCCAACCAG | 21 | 1 | sense | 62 |
| SQPVA | GGTACTTTAGCCAGCCGGTCA | 21 | 1 | sense | 63 |

GMTEB, AAITB, GMTEA, KYEIA, TDRDB, VEGLB, VEGLA, and PVLYA are specific non-degenerate oligonucleotides for the RFHV Glycoprotein B, and can be used for the amplification or detection of Glycoprotein B encoding polynucleotides of RFHV origin. Amplification is preferably done using the oligonucleotides in a nested fashion: e.g., a first amplification is conducted using GMTEA and VEGLB as primers; then a second amplification is conducted using KYEIA and TDRDB as primers. This provides an extremely sensitive amplification assay that is specific for RFHV Glycoprotein B. GMTEB and AAITB hybridize near the 5' end of the fragment, and may be used in combination with up-stream hybridizing Type 1 oligonucleotides to amplify or detect sequences in the 5' direction. VEGLA and PVLYA hybridize near the 3' end of the fragment, and may be used in combination with down-stream hybridizing Type 1 oligonucleotides to amplify or detect sequences in the 3' direction.

Similarly, GLTEB, TNKYB, GLTEA, YELPA, VNVNB, ENTFB, SQPVA, and TVFLA are specific non-degenerate oligonucleotides for the KSHV Glycoprotein B, and can be used in a similar fashion, including as primers for an amplification reaction. Preferably, the amplification is done using the oligonucleotides in a nested fashion: e.g., a first amplification is conducted using GLTEA and ENTFB as primers; then a second amplification is conducted using YELPA and VNVNB as primers. This provides an extremely sensitive amplification assay that is specific for KSHV Glycoprotein B. GLTEB and TNKYB hybridize near the 5' end of the fragment, and may be used in combination with up-stream hybridizing Type 1 oligonucleotides to amplify or detect sequences in the 5' direction. SQPVA and TVFLA hybridize near the 3' end of the fragment, and may be used in combination with down-stream hybridizing Type 1 oligonucleotides to amplify or detect sequences in the 3' direction.

Practitioners skilled in the art will immediately recognize that oligonucleotides of Types 1, 2 and 3 (in particular, those shown in Tables 4, 6 and 7) can be used in combination with each other in a PCR to amplify different sections of a Glycoprotein B encoding polynucleotide. The specificity of the amplification reaction generally is determined by the primer with the least amount of cross reactivity. The size and location of the amplified fragment is determined by the primers used in the final round of amplification. For example, NIVPA used in combination with SQPVB will amplify about 310 bases of Glycoprotein B encoding polynucleotide from a virus closely related to KSHV. Suitable combinations of oligonucleotides may be used as amplification primers in a nested fashion.

Use of synthetic oligonucleotides to characterize polynucleotide targets

As described in the previous section, the oligonucleotides embodied in this invention, can be used as primers for amplification of polynucleotides encoding a herpes virus Glycoprotein B, particularly in a polymerase chain reaction.

The conditions for conducting the PCR depend on the nature of the oligonucleotide being used. In particular, when using oligonucleotides comprising a degenerate segment, or a consensus segment that is only partly identical to the corresponding segment of the target, and when the target polynucleotide comprises an unknown sequence, the selection of conditions may be important to the success of the amplification. Optimizing conditions for a new primer or new polynucleotide target are routine for a practitioner of ordinary skill. What follows is a guide to assist in that objective.

First, the temperature of the annealing step of the PCR is optimized to increase the amount of target polynucleotide being amplified above the amount of unrelated polynucleotide amplified. Ideally, the temperature permits the primers to hybridize with the target sequence but not with other sequences. For primers comprising a consensus segment (Type 1), the temperature of the annealing step in repeat cycles of a PCR is generally at least about 45° C.; preferably it is at least about 50° C. It is also preferable to conduct the first few cycles of the PCR at even higher temperatures, such as 55° C. or even 60° C. The higher temperature will compel the annealing to be more sequence specific during the cycle and will reduce the background amplification of unrelated sequences. Annealing steps for subsequent cycles may be performed under slightly less stringent conditions to improve the rate of amplification. In an especially preferred procedure, the first PCR amplification cycle comprises an annealing step of about 1 min conducted at 60° C. Annealing steps in subsequent cycles are conducted at 2° C. lower each cycle, until a temperature of 50° C. is reached. Further cycles are then conducted with annealing steps at 50° C., until the desired degree of amplification is achieved.

Primers which are virus-specific and do not contain a consensus segment (Type 3) are more selective, and may be effective over a broader temperature range. Preferred temperatures for the annealing step in PCR amplification cycles are between 50° C. and 65° C.

Second, the buffer conditions are optimized. We have found that buffers supplied with commercial preparations of Taq polymerase are sometimes difficult to use, in part because of a critical dependence on the concentration of magnesium ion. PCRs performed using the oligonucleotides of this invention generally are more easily performed using a buffer such as that suggested by M. Wigler (Lisitsyn et al.). Preferably, the final PCR reaction mixture contains $(NH_4)_2SO_4$ instead of KCl as the principal ion source. Preferably, the concentration of $(NH_4)_2SO_4$ in the final reaction mixture is about 5–50 mM, more preferably about 10–30 mM, even more preferably 16 mM. The buffering component is preferably Tris, preferably at a final concentration of about 67 mM and a pH of about 8.8. Under these conditions, the MgCl$_2$ concentration is less critical. Preferably the final concentration is about 1–10 mM, more preferably it is about 3–6 mM, optimally it is about 4 mM. The reaction mixture may also contain about 10 mM B-mercaptoethanol and 0.05–1 mg/mL bovine serum albumin. An especially preferred buffer is WB4 buffer (67 mM Tris buffer pH 8.8, 4 mM MgCl$_2$, 16 mM (NH$_4$)$_2$SO$_4$, 10 mM β-mercaptoethanol and 0.1 mg/mL albumin. Preferred conditions for performing the reaction are provided below in Example 3.

To conduct the PCR reaction, a mixture comprising the oligonucleotide primers, the four deoxynucleotides, a suitable buffer, the DNA to be amplified, and a heat-stable DNA-dependent DNA polymerase is prepared. The mixture is then processed through temperature cycles for the annealing, elongating, and melting steps until the desired degree of amplification is achieved. The amount of DNA produced can be determined, for example, by staining with ethidium bromide, optionally after separating amplified fragments on an agarose gel.

A possible complication of the amplification reaction is dimerization and amplification of the oligonucleotide primers themselves. This can be easily detected as low molecular weight (<100 base pair) fragments on an agarose gel. Amplified primer can be removed by agarose or polyacrylamide gel separation. The amount of amplified dimer may be reduced by minor adjustments to the conditions of the reaction, particularly the temperature of the annealing step. It is also preferable to pre-mix the primers, the deoxynucleotides, and the buffer, and heat the mixture to 80 degrees before adding the DNA to be amplified.

Amplification reactions using any the oligonucleotides of this invention as primers yield polynucleotide fragments encoding a portion of a Glycoprotein B. These fragments can be characterized by a number of techniques known to a practitioner of ordinary skill in the art. Some non-limiting methods for characterizing a fragment are as follows:

In one method, a fragment may be sequenced according to any method of sequence determination known in the art, including the Maxam & Gilbert method, or the Sanger & Nicholson method. Alternatively, the fragment may be submitted to any of the commercial organizations that provide a polynucleotide sequencing service. The fragment may optionally be cloned and/or amplified before sequencing. The nucleotide sequence can be used to predict the amino acid sequence encoded by the fragment. Sequence data can be used for comparison with other sequenced Glycoprotein B's, either at the polynucleotide level or the amino acid level, to identify the species of herpes virus present in the original source material. Sequence data can also be used in modeling algorithms to predict antigenic regions or three-dimensional structure.

In a second method of characterizing, the size of the fragment can be determined by any suitable method, such as running on a polyacrylamide or agarose gel, or centrifuging through an appropriate density gradient. For example, for RFHV and KSHV, the fragment between NIVPA and TVNCB is about 319 bases. Hence, the length of the entire amplified fragment including primer binding regions is about 386 bases. The corresponding fragment of sHV1 contains an additional 6 base pairs. The sHV1 fragment can therefore be distinguished from that of RFHV or KSHV, for example, by running amplified polynucleotide fragments from each in neighboring lanes of a separating gel, or by running the sHV1 fragment beside suitable molecular weight standards. Polynucleotide fragments identical in size to that of RFHV and KSHV may be from the same or a related viral species. Fragments substantially different in size are more likely to be derived from a different herpes virus.

In a third method of characterizing, a fragment can be tested by attempting to hybridize it with an oligonucleotide probe. In a preferred example, a fragment is tested for relatedness to the Glycoprotein B encoding region of RFHV or KSHV. The test is conducted using a probe comprising a sequence of a Glycoprotein B encoding region, or its genetic complement. Suitable probes are polynucleotides comprising sequences from RFHV or KSHV, such as the Type 3 oligonucleotides listed in Table 7.

The length and nature of the probe and the hybridization conditions are selected depending on the objectives of the test. If the objective is to detect only polynucleotides from RFHV or KSHV, including minor strain variants, then hybridization is performed under conditions of high stringency. A sequence from the respective Glycoprotein B is used. Longer length sequences improve the specificity of the test and can be used under conditions of higher stringency. Preferably, the probe will comprise a Glycoprotein B sequence of at least about 30 nucleotides; more preferably, the sequence will be at least about 50 nucleotides; even more preferably, the sequence will be at least about 75 nucleotides in length.

If the objective is to detect polynucleotides that are closely related but not identical to RFHV or KSHV, such as in a screening test or a test to recruit previously undescribed viruses of the RFHV/KSHV subfamily, then different conditions are chosen. Sequences from RFHV or KSHV may be used, but a mixture of the two or a degenerate probe is generally preferred. The length of the sequence and the conditions of the hybridization reaction are selected to provide sufficient specificity to exclude unwanted sequences, but otherwise provide a maximum degree of cross-reactivity amongst potential targets. Suitable conditions can be predicted using the formulas given earlier, by calculating the $T_m$ and then calculating the corresponding temperature for the maximum degree of mismatch to be tolerated. The suitability of the conditions can be tested empirically by testing the cross-reactivity of the probes with samples containing known target polynucleotides encoding herpes Glycoprotein B.

The minimum degree of complementarity required for a stable duplex to form under the conditions of the assay will determine what Glycoprotein B sequences will hybridize with the probe. Consider, for example, a target obtained from a human or non-human primate, amplified to produce a fragment corresponding to bases 36–354 of SEQ. ID NO:3, and then probed with the corresponding fragment of the KSHV polynucleotide. According to the data in Table 2, if the hybridization reaction is performed under conditions that require only about 50% identity for a stable duplex to form, the probe may hybridize with targets from any of the sequenced gamma herpes Glycoprotein B genes, including hEBV and sHV1. If the reaction is performed under conditions that require at least about 65% identity between probe and target, preferably at least about 67% identity, more preferably at least about 70% identity, and even more preferably at least about 75% identity for a stable duplex to form, the assay will detect a target polynucleotide from the RFHV/KSHV subfamily; i.e., either RHFV, KSHV, or a closely related herpes virus with a Glycoprotein B polynucleotide not yet sequenced. Even under hybridization conditions that required only about 50–55% identity for a stable duplex to form, a positive reaction would not indicate the presence of bHV4, eHV2, or mHV68, since these viruses are not believed to be capable of infecting primates.

It is possible to combine characterization by size and characterization by hybridization. For example, the amplified polynucleotide may be separated on a gel of acrylamide or agarose, blotted to a membrane of suitable material, such as nitrocellulose, and then hybridized with a probe with a suitable label, such as 32p. The presence of the label after washing reflects the presence of hybridizable material in the sample, while the migration distance compared with appropriate molecular weight standards reflects the size of the material. A fragment sequence hybridizing with one of the aforementioned probes under conditions of high stringency but having an unexpected size would indicate a Glycoprotein B sequence with a high degree of identity to the probe, but distinct from either RFHV or KSHV.

Use of polynucleotides and oligonucleotides to detect herpes virus infection

Polynucleotides encoding herpes virus Glycoprotein B, and synthetic oligonucleotides based thereupon, as embodied in this invention, are useful in the diagnosis of clinical conditions associated with herpes virus infection. For example, the presence of detectable herpes Glycoprotein B in a clinical sample may suggest that the respective herpes virus participated as an etiologic agent in the development of the condition. The presence of viral Glycoprotein B in a particular tissue, but not in surrounding tissue, may be useful in the localization of an infected lesion. Differentiating between gamma herpes virus and other herpes viruses in clinical samples may be useful in predicting the clinical course of an infection or selecting a drug suitable for treatment. Since Glycoprotein B is expressed by replicative virus, L-particles, and infected cells, we predict that it will serve as a useful marker for active and quiescent stages of the disease that involve expression of the protein in any of these forms.

The procedures for conducting diagnostic tests are extensively known in the art, and are routine for a practitioner of ordinary skill. Generally, to perform a diagnostic method of this invention, one of the compositions of this invention is provided as a reagent to detect a target in a clinical sample with which it reacts. For example, a polynucleotide of this invention may be used as a reagent to detect a DNA or RNA target, such as might be present in a cell infected with a herpes virus. A polypeptide of this invention may be used as a reagent to detect a target with which it is capable of forming a specific complex, such as an antibody molecule or (if the polypeptide is a receptor) the corresponding ligand. An antibody of this invention may be used as a reagent to detect a target it specifically recognizes, such as a polypeptide expressed by virally infected cells.

The target is supplied by obtaining a suitable tissue sample from an individual for whom the diagnostic parameter is to be measured. Relevant test samples are those obtained from individuals suspected of harboring a herpes virus. Many types of samples are suitable for this purpose, including those that are obtained near the suspected site of infection or pathology by biopsy or surgical dissection, in vitro cultures of cells derived therefrom, solubilized extracts, blood, and blood components. If desired, the target may be partially purified from the sample or amplified before the assay is conducted. The reaction is performed by contacting the reagent with the sample under conditions that will allow a complex to form between the reagent and the target. The reaction may be performed in solution, or on a solid tissue sample, for example, using histology sections. The formation of the complex is detected by a number of techniques known in the art. For example, the reagent may be supplied with a label and unreacted reagent may be removed from the complex; the amount of remaining label thereby indicating the amount of complex formed. Further details and alternatives for complex detection are provided in the descriptions that follow.

To determine whether the amount of complex formed is representative of herpes infected or uninfected cells, the assay result is preferably compared with a similar assay conducted on a control sample. It is generally preferable to use a control sample which is from an uninfected source, and otherwise similar in composition to the clinical sample being tested. However, any control sample may be suitable provided the relative amount of target in the control is known or can be used for comparative purposes. It is often preferable to conduct the assay on the test sample and the control sample simultaneously. However, if the amount of complex formed is quantifiable and sufficiently consistent, it is acceptable to assay the test sample and control sample on different days or in different laboratories.

Accordingly, polynucleotides encoding Glycoprotein B of the RFHV/KSHV subfamily, and the synthetic oligonucleotides embodied in this invention, can be used to detect gamma herpes virus polynucleotide that may be present in a biological sample. General methods for using polynucleotides in specific diagnostic assays are well known in the art: see, e.g., Patent Application JP 5309000 (Iatron).

An assay employing a polynucleotide reagent may be rendered specific, for example: 1) by performing a hybridization reaction with a specific probe; 2) by performing an amplification with a specific primer, or 3) by a combination of the two.

To perform an assay that is specific due to hybridization with a specific probe, a polynucleotide is chosen with the required degree of complementarity for the intended target. Preferred probes include polynucleotides of at least about 16 nucleotides in length encoding a portion of the Glycoprotein B of RFHV, KSHV, or another member of the RFHV/KSHV subfamily. Increasingly preferred are probes comprising at least about 18, 21, 25, 30, 50, or 100 nucleotides of the Glycoprotein B encoding region. Also preferred are degenerate probes capable of forming stable duplexes with polynucleotides of the RFHV/KSHV subfamily under the conditions used, but not polynucleotides of other herpes viruses.

The probe is generally provided with a label. Some of the labels often used in this type of assay include radioisotopes such as $^{32}P$ and $^{33}P$, chemiluminescent or fluorescent reagents such as fluorescein, and enzymes such as alkaline phosphatase that are capable of producing a colored solute or precipitant. The label may be intrinsic to the reagent, it may be attached by direct chemical linkage, or it may be connected through a series of intermediate reactive molecules, such as a biotin-avidin complex, or a series of inter-reactive polynucleotides. The label may be added to the reagent before hybridization with the target polynucleotide, or afterwards. To improve the sensitivity of the assay, it is often desirable to increase the signal ensuing from hybridization. This can be accomplished by using a combination of serially hybridizing polynucleotides or branched polynucleotides in such a way that multiple label components become incorporated into each complex. See U.S. Pat. No. 5,124,246 (Urdea et al.).

If desired, the target polynucleotide may be extracted from the sample, and may also be partially purified. To measure viral particles, the preparation is preferably enriched for DNA; to measure active transcription of Glycoprotein B, the preparation is preferably enriched for RNA. Generally, it is anticipated that the level of polynucleotide of a herpes virus will be low in clinical samples: there may be just a few copies of DNA encoding the Glycoprotein B per cell where the virus is latent, or up to several hundred copies of DNA per cell where the virus is replicating. The level of mRNA will be higher in cells where the protein is actively expressed than those where the gene is inactive. It may therefore be desirable to enhance the level of target in the sample by amplifying the DNA or RNA. A suitable method of amplification is a PCR, which is preferably conducted using one or more of the oligonucleotide primers embodied in this invention. RNA may be amplified by making a cDNA copy using a reverse transcriptase, and then conducting a PCR using the aforementioned primers.

The target polynucleotide can be optionally subjected to any combination of additional treatments, including digestion with restriction endonucleases, size separation, for example by electrophoresis in agarose or polyacrylamide, and affixation to a reaction matrix, such as a blotting material.

Hybridization is allowed to occur by mixing the reagent polynucleotide with a sample suspected of containing a target polynucleotide under appropriate reaction conditions. This may be followed by washing or separation to remove unreacted reagent. Generally, both the target polynucleotide and the reagent must be at least partly equilibrated into the single-stranded form in order for complementary sequences to hybridize efficiently. Thus, it may be useful (particularly in tests for DNA) to prepare the sample by standard denaturation techniques known in the art.

The level of stringency chosen for the hybridization conditions depends on the objective of the test. If it is desired that the test be specific for RFHV or KSHV, then a probe comprising a segment of the respective Glycoprotein B is used, and the reaction is conducted under conditions of high stringency. For example, a preferred set of conditions for use with a preferred probe of 50 nucleotides or more is 6×SSC at 37° C. in 50% formamide, followed by a wash at low ionic strength. This will generally require the target to be at least about 90% identical with the polynucleotide probe for a stable duplex to form. The specificity of the reaction for the particular virus in question can also be increased by increasing the length of the probe used. Thus, longer probes are particularly preferred for this application of the invention. Alternatively, if it is desired that the test also be able to detect other herpes viruses related to KSHV, then a lower stringency is used. Suitable probes include fragments from the KSHV Glycoprotein B polynucleotide, a mixture thereof, or oligonucleotides such as those listed in Table 7.

Appropriate hybridization conditions are determined to permit hybridization of the probe only to Glycoprotein B sequences that have the desired degree of identity with the probe. The stringency required depends on the length of the polynucleotide probe, and the degree of identity between the probe and the desired target sequence. Consider, for example, a probe consisting of the KSHV polynucleotide fragment between the hybridization sites of NIVPA and TVNCB. Conditions requiring a minimum identity of 60% would result in a stable duplex formed with a corresponding polynucleotide of KSHV and other gamma herpes viruses such as sHV1; conditions requiring a minimum identity of 90% would result in a stable duplex forming only with a polynucleotide from KSHV and closely related variants. Conditions of intermediate stringency requiring a minimum identity of 65–70% would permit duplexes to form with a Glycoprotein B polynucleotide of KSHV, and some other members of the RFHV/KSHV subfamily, but not with corresponding polynucleotides of other known herpes viruses, including gamma herpes viruses eHV2, sHV1, mHV68, bHV4, EBV, and other human pathogens such as hCMV, hHV6, hVZV, and HSV1.

Conditions can be estimated beforehand using the formula given earlier. Preferably, the exact conditions are confirmed by testing the probe with separate samples known to contain polynucleotides, both those desired to be detected and those desired to go undetected in the assay. Such samples may be provided either by synthesizing the polynucleotides from published sequences, or by extracting and amplifying DNA from tissues believed to be infected with the respective herpes virus. Determining hybridization conditions is a matter of routine adjustment for a practitioner of ordinary skill, and does not require undue experimentation. Since eHV2, sHV1, mHV68, bHV4 and EBV are more closely identical to the RFHV/KSHV subfamily than alpha and beta herpes viruses, conditions that exclude gamma herpes viruses outside the RFHV/KSHV subfamily will generally also exclude the other herpes viruses listed in Table 1. In addition, if it is believed that certain viruses will not be present in the sample to be tested in the ultimate determination (such as eHV2, mHV68 or bHV4 in a human tissue sample), then the corresponding target sequences may optionally be omitted when working out the conditions of the assay. Thus, conditions can be determined that would permit Type 2 oligonucleotide probes such as those listed in Table 6 to form a stable duplex both with polypeptides comprising SEQ. ID NO: 1 or SEQ. ID NO:3, but not a sequence selected from the group consisting of SEQ. ID NO:5–13. Conditions can also be determined that would permit a suitable fragment comprising at least 21 or more consecutive bases of SEQ. ID NO: 1 or SEQ. ID NO:3 to form a stable duplex both with a polynucleotide comprising SEQ. ID NO:1 and SEQ. ID NO:3, but not a polynucleotide comprising any one of SEQ. ID NO:5–13.

Alternatively, to conduct an assay that is specific due to amplification with a specific primer: DNA or RNA is prepared from the biological sample as before. Optionally, the target polynucleotide is pre-amplified in a PCR using primers which are not species specific, such as those listed in Table 4 or 6. The target is then amplified using specific primers, such as those listed in Table 7, or a combination of primers from Table 4, 6, and 7. In a preferred embodiment, two rounds of amplification are performed, using oligonucleotide primers in a nested fashion: virus-specific or non-specific in the first round; virus-specific in the second round. This provides an assay which is both sensitive and specific.

Use of a specific Type 3 primer during amplification is sufficient to provide the required specificity. A positive test may be indicated by the presence of sufficient reaction product at the end of the amplification series. Amplified polynucleotide can be detected, for example, by blotting the reaction mixture onto a medium such as nitrocellulose and staining with ethidium bromide. Alternatively, a radiolabeled substrate may be added to the mixture during a final amplification cycle; the incorporated label may be separated from unincorporated label (e.g., by blotting or by size separation), and the label may be detected (e.g. by counting or by autoradiography). If run on a gel of agarose or polyacrylamide, the size of the product may help confirm the identity of the amplified fragment. Specific amplification can also be followed by specific hybridization, by using the amplification mixture obtained from the foregoing procedure as a target source for the hybridization reaction outlined earlier.

Use of polynucleotides for gene therapy

Embodied in this invention are pharmaceuticals comprising virus-specific polynucleotides, polypeptides, or antibodies as an active ingredient. Such compositions may decrease the pathology of the virus or infected cells on their own, or render the virus or infected cells more susceptible to treatment by non-specific pharmaceutical compounds.

Polynucleotides of this invention encoding part of a herpes virus Glycoprotein B may be used, for example, for administration to an infected individual for purposes of gene therapy (see generally U.S. Pat. No. 5,399,346: Anderson et al.). The general principle is to administer the polynucleotide in such a way that it ether promotes or attenuates the expression of the polypeptide encoded therein.

A preferred mode of gene therapy is to provide the polynucleotide in such a way that it will be replicated inside the cell, enhancing and prolonging the effect. Thus, the polynucleotide is operatively linked to a suitable promoter, such as the natural promoter of the corresponding gene, a heterologous promoter that is intrinsically active in cells of the target tissue type, or a heterologous promoter that can be induced by a suitable agent. Entry of the polynucleotide into the cell is facilitated by suitable techniques known in the art, such as providing the polynucleotide in the form of a suitable vector, such as a viral expression vector, or encapsulation of the polynucleotide in a liposome. The polynucleotide may be injected systemically, or provided to the site of infection by an antigen-specific homing mechanism, or by direct injection.

In one variation, the polynucleotide comprises a promoter linked to the polynucleotide strand with the same orientation as the strand that is transcribed during the course of a herpes virus infection. Preferably, the Glycoprotein B that is encoded includes an external component, a transmembrane component, and signal sequences for transport to the surface. Virally infected cells transfected with polynucleotides of this kind are expected to express an enhanced level of Glycoprotein B at the surface. Enhancing Glycoprotein B expression in this fashion may enhance recognition of these cells by elements of the immune system, including antibody (and antibody-dependent effectors such as ADCC), and virus-specific cytotoxic T cells.

In another variation, the polynucleotide comprises a promoter linked to the polynucleotide strand with the opposite orientation as the strand that is transcribed during the course of a herpes virus infection. Virally infected cells transfected with polynucleotides of this kind are expected to express a decreased level of Glycoprotein B. The transcript is expected to hybridize with the complementary strand transcribed by the viral gene, and prevent it from being translated. This approach is known as anti-sense therapy.

RFHV/KSHV subfamily polypeptides with Glycoprotein B activity and fragments thereof The RFHV and KSHV polynucleotide sequences shown in FIG. 1 have open reading frames. The polypeptide encoded thereby are shown in SEQ. ID NO:2 and SEQ. ID NO:4, respectively. Encoded between the hybridizing regions of the primers NIVPA and TVNCB used to obtain the polynucleotide sequence is a 106 amino acid fragment of the Glycoprotein B molecule which is 91% identical between RFHV and KSHV. The full protein sequence of KSHV Glycoprotein B is shown in SEQ. ID NO:94. A Glycoprotein B fragment of a third member of the RFHV/KSHV subfamily, RFHV2, is shown in SEQ. ID NO:97.

There are a number of homologous residues to Glycoprotein B molecules of other sequenced herpes viruses. The longest sequence contained in SEQ. ID NO:2 or SEQ. ID NO:4 but not in the known sequences of other herpes viruses is 9 amino acids in length, with two exceptions (SEQ. ID NOS:64 and 65). Longer matching portions are found elsewhere in the Glycoprotein B amino acid sequence. The longest is the 21 amino acid sequence from bHV4 shown in SEQ. ID NO:99; the rest are all 16 amino acids long or less. Other than SEQ. ID NO:99 exception, any fragment of the RFHV and KSHV Glycoprotein B protein sequence that is 17 amino acids or longer is believed to be specific for RFHV or KSHV, respectively, or to closely related strains. Since bHV4 and the other viruses with matching segments are not believed to be capable of infecting primates, any fragment of about 10 amino acids or more found in a primate that was contained in SEQ. ID NO:4 would indicate the presence of an infectious agent closely related to KSHV.

This invention embodies both intact Glycoprotein B from herpes viruses of the RFHV/KSHV subfamily, and any fragment thereof that is specific for the subfamily. Preferred Glycoprotein B fragments of this invention are at least 10 amino acids in length; more preferably they are at least 13 amino acids in length; more preferably they are at least 17 amino acids in length; more preferably they are at least about 20 amino acids in length; even more preferably they are at least about 25 amino acids in length, still more preferably they are at least about 30 amino acids in length.

The amino acid sequence of the RFHV and KSHV Glycoprotein B fragment shown in SEQ. ID NOS:2, 4, 94 and 96 can be used to identify virus-specific and cross-reactive antigenic regions.

In principle, a specific antibody could recognize any amino acid difference between sequences that is not also shared by the species from which the antibody is derived. Antibody binding sites are generally big enough to encompass 5–9 amino acid residues of an antigen, and are quite capable of recognizing a single amino acid difference. Specific antibodies may be part of a polyclonal response arising spontaneously in animals infected with a virus expressing the Glycoprotein B. Specific antibodies may also be induced by injecting an experimental animal with either the intact Glycoprotein B or a Glycoprotein B fragment.

Thus, any peptide of 5 amino acids or more that is unique to KSHV is a potential virus-specific antigen, and could be recognized by a KSHV-specific antibody. Similarly, any peptide of sufficient length shared within the RFHV/KSHV subfamily but not with other herpes viruses is a potential subfamily-specific antigen.

Some examples of preferred peptides are shown in Table 8. Practitioners in the art will immediately recognize that other peptides with similar specificities may be designed by minor alterations to the length of the peptides listed and/or moving the frame of the peptide a few residues in either direction.

The Class I peptides shown in Table 8 are conserved between Glycoprotein B of KSHV and that of certain other members of the gamma herpes virus subfamily. An antibody directed against one such Glycoprotein B in this region may therefore cross-react with some of the others. Class II peptides are conserved between Glycoprotein B of RFHV and KSHV, but not with other gamma herpes viruses. An antibody directed against this region is expected to cross-react between RFHV, KSHV, and other viruses of the RFHV/KSHV subfamily; but not with herpes viruses outside the subfamily. Class III peptides are different between Glycoprotein B of RFHV, KSHV, and other known gamma herpes viruses. An antibody binding to this region, particularly to non-identical residues contained therein, is expected to distinguish RFHV and KSHV Glycoprotein B from each other, and from Glycoprotein B of more distantly related herpes viruses.

TABLE 8

Antigen Peptides

| Specificity | | Sequence | Length | SEQ. ID NO: |
|---|---|---|---|---|
| Class I: | Shared with bHV4 | YRKATSVTVYRG | 13 | 64 |
| | bHV4, mHV68 | RYFSQP | 6 | 66 |
| Shared amongst RFHV/KSHV subfamily and some other gamma herpes viruses | bHV4 | IYAEPGWFPGIYRVR | 15 | 65 |
| | | IYAEPGWFPGIYRVRTTVNCE | 21 | 99 |
| | mHV68 | VLEELSRAWCREQVRD | 16 | 100 |
| Class II: | | VTVYRG | 6 | 67 |
| | | AITNKYE | 7 | 68 |
| Shared amongst RFHV/KSHV subfamily | | SHMDSTY | 7 | 69 |
| | | VENTFTD | 7 | 70 |
| | | TVFLQPV | 7 | 71 |
| | | TDNIQRY | 7 | 72 |
| Class III: | Specific for | | | |
| | RFHV | RGMTEAA | 7 | 73 |
| Virus specific[1] | KSHV | RGLTESA | 7 | 75 |
| | RFHV | PVLYSEP | 7 | 74 |
| | KSHV | PVIYAEP | 7 | 76 |

[1]- Not shared with any other sequenced herpes virus; may be present in some unsequenced RFHV/KSHV subfamily viruses Particularly preferred peptides from Class III are those encompassing regions of Glycoprotein B with the polarity characteristics appropriate for an antigen epitope, as described in the Example section. Given the complete sequence of a Glycoprotein B from KSHV and other members of the RFHV/KSHV subfamily, virus- or subfamily-specific peptides can be predicted for other regions of the molecule by a similar analysis.

Preparation of polypeptides

Polypeptides of this invention may be prepared by several different methods, all of which will be known to a practitioner of ordinary skill.

For example, short polypeptides of about 5–50 amino acids in length are conveniently prepared from sequence data by chemical synthesis. A preferred method is the solid-phase Merrifield technique. Alternatively, a messenger RNA encoding the desired polypeptide may be isolated or synthesized according to one of the methods described earlier, and translated using an in vitro translation system, such as the rabbit reticulocyte system. See, e.g., Dorsky et al.

Longer polypeptides, up to and including the entire Glycoprotein B, are conveniently prepared using a suitable expression system. For example, the encoding strand of a full-length cDNA can be operatively linked to a suitable promoter, inserted into an expression vector, and transfected into a suitable host cell. The host cell is then cultured under conditions that allow transcription and translation to occur, and the polypeptide is subsequently recovered. For examples of the expression and recovery of Glycoprotein B from other species of herpes virus, see, for example, U.S. Pat. No. 4,642,333 (Person); U.S. Pat. No. 5,244,792 (Burke et al.); Manservigi et al.

For many purposes, it is particularly convenient to use a recombinant Glycoprotein B polynucleotide that includes the regions encoding signals for transport to the cell surface, but lacks the region encoding the transmembrane domain of the protein. The polynucleotide may be truncated 5' to the transmembrane encoding region, or it may comprise both extracellular and cytoplasmic encoding region but lack the transmembrane region. Constructs of this nature are expected to be secreted from the cell in a soluble form. Where it is desirable to have a Glycoprotein B fragment that is a monomer, the recombinant may be designed to limit translation to about the first 475 amino acids of the protein.

For example, to express any of these forms of Glycoprotein B in yeast, a cassette may be prepared using the glyceraldehyde-3-phosphate-dehydrogenase (GAPDH) promoter region and terminator region. GAPDH gene fragments are identified in a yeast library, isolated and ligated in the appropriate configuration. The cassette is cloned into pBR322, isolated and confirmed by DNA sequencing. A pCl/l plasmid is constructed containing a Glycoprotein B insert and GAPDH promoter and terminator regions. The plasmid is used to transform yeast strain *S. cerevisiae.* After culture, the yeast cells are pelleted by centrifugation, resuspended in a buffer containing protease inhibitors such as 1 mM phenylmethylsulfonyl fluoride and 0.1 μg/ml pepstatin. The washed cells are disrupted by vortexing with glass beads and recentrifuged. The presence in the supernatant of a Glycoprotein B of the correct size may be confirmed, for example, by Western blot using an antibody against Glycoprotein B, prepared as described in a following section. Glycoprotein B may be purified from the supernatant by a combination of standard protein chemistry techniques, including ion exchange chromatography, affinity chromatography using antibody or substrate, and high-pressure liquid chromatography.

To express Glycoprotein B in mammalian cells, for example, a mammalian expression vector such as pSV1/dhfr may be used. This has an ampicillin-resistance beta-lactamase gene, and a selectable mammalian cell marker, dihydrofolate reductase linked to the SV40 early promoter. Glycoprotein B polynucleotide blunt-end fragments are ligated into the pSV1/dhfr vector and digested with endonucleases to provide a cassette including the SV40 promoter, the Glycoprotein encoding region, and the SV40 splice and polyadenylation sites. The plasmids are used, for example, to transform CHO cells deficient in dhfr, and transfectants are selected. Cells expressing Glycoprotein B may be identified, for example, by immunofluorescence using anti-Glycoprotein B as the primary antibody.

In another example, recombinant plasmids for expressing Glycoprotein B are cloned under control of the Rous sarcoma virus long terminal repeat in the episomal replicating vector pRP-RSV. This plasmid contains the origin of replication and early region of the human papovavirus BK, as well as the dhfr resistance marker. The vector is can then be used, for example, to transform human 293 cells. By using a Glycoprotein B encoding region devoid of the transmembrane spanning domain, the Glycoprotein B polypeptide is constitutively secreted into the culture medium at 0.15–0.25 pg/cell/day. In the presence of 0.6–6 $\mu$M methotrexate, production may be increased 10- to 100-fold, because of an amplification of the episomal recombinant. Glycoprotein B prepared in this way are appropriate, inter alia, for use in diagnosis, and to prepare vaccines protective against new and recurrent herpes virus infections (Manservigi et al).

Use of polypeptides to assess herpes virus infection

The polypeptides embodied in this invention may be used to detect or assess the status of a herpes virus infection in an individual in several different applications.

In one application, a polypeptide encoding a portion of a herpes virus Glycoprotein B is supplied as a reagent for an assay to detect the presence of antibodies that can specifically recognize it. Such antibodies may be present, for example, in the circulation of an individual with current or past herpes virus exposure.

The presence of antibodies to Glycoprotein B in the circulation may provide a sensitive and early indication of viral infection. Since Glycoprotein B is a functional component of the viral envelope, it is produced in greater quantity than other transcripts sequestered within the viral particle. Its distribution is wider than transcripts that appear only transiently in the life cycle of the virus. Furthermore, it may be expressed not only by intact virus, but also by non-infective products of virally infective cells, such as L-particles. Glycoprotein B from various species of herpes virus are known to be strongly immunogenic. Thus, detection of antibody to Glycoprotein B in an individual may be an indication of ongoing active herpes virus infection, latent infection, previous exposure, or treatment with a Glycoprotein B vaccine.

Suitable clinical samples in which to measure antibody levels include serum or plasma from an individual suspected of having a gamma herpes virus infection. The presence of the antibody is determined, for example, by an immunoassay.

A number of immunoassay methods are established in the art for performing the quantitation of antibody using viral peptides (see, e.g., U.S. Pat. No. 5,350,671: Houghton et al.). For example, the test sample potentially containing the specific antibody may be mixed with a pre-determined non-limiting amount of the reagent polypeptide. The reagent may contain a directly attached label, such as an enzyme or a radioisotope. For a liquid-phase assay, unreacted reagents are removed by a separation technique, such as filtration or chromatography. Alternatively, the antibody in the sample may be first captured by a reagent on a solid phase. This may be, for example, the specific polypeptide, an anti-immunoglobulin, or Protein A. The captured antibody is then detected with a second reagent, such as the specific polypeptide, anti-immunoglobulin, or protein A with an attached label. At least one of the capture reagent or the detecting reagent must be the specific polypeptide. In a third variation, cells or tissue sections containing the polypeptide may be overlaid first with the test sample containing the antibody, and then with a detecting reagent such as labeled anti-immunoglobulin. In all these examples, the amount of label captured in the complex is positively related to the amount of specific antibody present in the test sample. Similar assays can be designed in which antibody in the test sample competes with labeled antibody for binding to a limiting amount of the specific peptide. The amount of label in the complex is then negatively correlated with the amount of specific antibody in the test sample. Results obtained using any of these assays are compared between test samples, and control samples from an uninfected source.

By selecting the reagent polypeptide appropriately, antibodies of a desired specificity may be detected. For example, if the intact Glycoprotein B is used, or a fragment comprising regions that are conserved between herpes virus, then antibodies detected in the test samples may be virus specific, cross-reactive, or both. A multi-epitope reagent is preferred for a general screening assay for antibodies related to herpes virus infection. To render the assay specific for antibodies directed either against RFHV or against KSHV, antigen peptides comprising non-conserved regions of the appropriate Glycoprotein B molecule are selected, such as those listed in Class III of Table 8. Preferably, a mixture of such peptides is used. To simultaneously detect antibodies against RFHV, KSHV, and closely related viruses of the gamma herpes family, but not sHV1 and EBV, antigen peptides are selected with the properties of those listed in Class II of Table 8. Preferably, a mixture of such peptides is used.

Antibodies stimulated during a herpes virus infection may subside once the infection resolves, or they may persist as part of the immunological memory of the host. In the latter instance, antibodies due to current infection may be distinguished from antibodies due to immunological memory by determining the class of the antibody. For example, an assay may be conducted in which antibody in the test sample is captured with the specific polypeptide, and then developed with labeled anti-IgM or anti-IgG. The presence of specific antibody in the test sample of the IgM class indicates ongoing infection, while the presence of IgG antibodies alone indicates that the activity is due to immunological memory of a previous infection or vaccination.

Use of polypeptides to design or screen anti-viral drugs

Interfering with the Glycoprotein B gene or gene product would modify the infection process, or the progress of this disease. It is an objective of this invention to provide a method by which useful pharmaceutical compositions and methods of employing such compounds in the treatment of gamma herpes virus infection can be developed and tested. Particularly preferred are pharmaceutical compounds useful in treating infections by RFHV, KSHV and other members of the RFHV/KSHV subfamily. Suitable drugs are those that interfere with transcription or translation of the Glycoprotein B gene, and those that interfere with the biological function of the polypeptide encoded by the gene. It is not necessary that the mechanism of interference be known; only that the interference be preferential for reactions associated with the infectious process.

Preferred drugs include those that competitively interfere with the binding of the Glycoprotein B to its substrate on target cells, such as heparan sulfate and its analogs. Also preferred are drugs that competitively interfere with any interaction of Glycoprotein B to other viral envelope components that may be necessary for the virus to exert one of its biologic functions, such as penetration of target cells. Also preferred are molecules capable of cross-linking or otherwise immobilizing the Glycoprotein B, thereby preventing it from binding its substrate or performing any biological function that plays a role in viral infectivity.

This invention provides methods for screening pharmaceutical candidates to determine which are suitable for clinical use. The methods may be brought to bear on antiviral compounds that are currently known, and those which may be designed in the future.

The method involves combining an active Glycoprotein B with the pharmaceutical candidate, and determining whether the biochemical function is altered by the pharmaceutical candidate. The Glycoprotein B may be any fragment encoded by the Glycoprotein B gene of the RFHV/KSHV subfamily that has Glycoprotein B activity. Suitable fragments may be obtained by expressing a genetically engineered polypeptide encoding an active site of the molecule, or by cleaving the Glycoprotein B with proteases and purifying the active fragments. In a preferred embodiment, the entire Glycoprotein B is provided. The reaction mixture will also comprise other components necessary to measure the biological activity of the protein. For example, in an assay to measure substrate binding, heparan sulfate or an analog thereof may be provided, perhaps linked to a solid support to facilitate measurement of the binding reaction.

One embodiment of the screening method is to measure binding of the pharmaceutical candidate directly to the isolated Glycoprotein B, or a fragment thereof. Compounds that bind to an active site of the molecule are expected to interfere with Glycoprotein B activity. Thus, the entire Glycoprotein B, or a fragment comprising the active site, is mixed with the pharmaceutical candidate. Binding of the candidate can be measured directly, for example, by providing the candidate in a radiolabeled or stable-isotope labeled form. The presence of label bound to the Glycoprotein B can be determined, for example, by precipitating the Glycoprotein B with a suitable antibody, or by providing the molecule attached to a solid phase, and washing the solid phase after the reaction. Binding of the candidate to the Glycoprotein B may also be observed as a conformational change, detected for example by difference spectroscopy, nuclear magnetic resonance, or circular dichroism. Alternatively, binding may be determined in a competitive assay: for example, Glycoprotein B is mixed with the candidate, and then labeled nucleotide or a fragment of a regulatory subunit is added later. Binding of the candidate to the biochemically relevant site should inhibit subsequent binding of the labeled compound.

A second embodiment of the screening method is to measure the ability of the pharmaceutical candidate to inhibit the binding of Glycoprotein B to a substrate or substrate analog. A preferred analog is heparin, coupled a solid support such as Sepharose™ beads. inhibition may be measured, for example, by providing a radiolabel to the Glycoprotein B, incubating it with the pharmaceutical candidate, adding the affinity resin, then washing and counting the resin to determine if the candidate has decreased the amount of radioactivity bound. Pharmaceutical candidates may also be tested for their ability to competitively interfere with interactions between Glycoprotein B and other herpes virus proteins.

A third embodiment of the screening method is to measure the ability of the pharmaceutical candidate to inhibit an activity of an active particle, such as a viral particle, mediated by Glycoprotein B. A particle is engineered to express Glycoprotein B, but not other components that are capable of mediating the same function. The ability of the particle to exhibit a biological function, such as substrate binding or membrane fusion, is then measured in the presence and absence of the pharmaceutical candidate by providing an appropriate target.

This invention also provides for the development of pharmaceuticals for the treatment of herpes infection by rational drug design. See, generally, Hodgson, and Erickson et al. In this embodiment, the three-dimensional structure of the Glycoprotein B is determined, either by predictive modeling based on the amino acid sequence, or preferably, by experimental determination. Experimental methods include antibody mapping, mutational analysis, and the formation of anti-idiotypes. Especially preferred is X-ray crystallography. Knowing the three-dimensional structure of the glycoprotein, especially the orientation of important amino acid groups near the substrate binding site, a compound is designed de novo, or an existing compound is suitably modified. The designed compound will have an appropriate charge balance, hydrophobicity, and/or shape to permit it to attach near an active site of the Glycoprotein B, and sterically interfere with the normal biochemical function of that site. Preferably, compounds designed by this method are subsequently tested in a drug screening assay, such as those outlined above.

Antibodies against Glycoprotein B and their preparation

The amino acid sequence of the Glycoprotein B molecules embodied herein are foreign to the hosts they infect. Glycoprotein B from other species of herpes virus are known to be strongly immunogenic in mammals. Anti-Glycoprotein B is formed in humans, for example, as a usual consequence of infection with hCMV. By analogy, it is expected that Glycoprotein B of RFHV, KSHV, and other members of the RFHV/KSHV subfamily will be immunogenic in mammals, including humans. These expectations are supported by the observations described in the Example section below.

Antibodies against a polypeptide are generally prepared by any method known in the art. To stimulate antibody production in an animal experimentally, it is often preferable to enhance the immunogenicity of a polypeptide by such techniques as polymerization with glutaraldehyde, or combining with an adjuvant, such as Freund's adjuvant. The immunogen is injected into a suitable experimental animal: preferably a rodent for the preparation of monoclonal antibodies; preferably a larger animal such as a rabbit or sheep for preparation of polyclonal antibodies. It is preferable to provide a second or booster injection after about 4 weeks, and begin harvesting the antibody source no less than about 1 week later.

Sera harvested from the immunized animals provide a source of polyclonal antibodies. Detailed procedures for purifying specific antibody activity from a source material are known within the art. If desired, the specific antibody activity can be further purified by such techniques as protein A chromatography, ammonium sulfate precipitation, ion exchange chromatography, high-performance liquid chromatography and immunoaffinity chromatography on a column of the immunizing polypeptide coupled to a solid support.

Polyclonal antibodies raised by immunizing with an intact Glycoprotein B or a fragment comprising conserved sequences may be cross-reactive between herpes viruses. Antibodies that are virus or subfamily specific may be raised by immunizing with a suitably specific antigen, such as those listed above in Table 8. Alternatively, polyclonal antibodies raised against a larger fragment may be rendered specific by removing unwanted activity against other virus Glycoprotein B's, for example, by passing the antibodies over an adsorbent made from Glycoprotein B and collecting the unbound fraction.

Alternatively, immune cells such as splenocytes can be recovered from the immunized animals and used to prepare a monoclonal antibody-producing cell line. See, for example, Harrow & Lane (1988), U.S. Pat. No. 4,472,500 (Milstein et al.), and U.S. Pat. No. 4,444,887 (Hoffman et al.).

Briefly, an antibody-producing line can be produced inter alia by cell fusion, or by transforming antibody-producing cells with Epstein Barr Virus, or transforming with oncogenic DNA. The treated cells are cloned and cultured, and clones are selected that produce antibody of the desired specificity. Specificity testing can be performed on culture supernatants by a number of techniques, such as using the immunizing polypeptide as the detecting reagent in a standard immunoassay, or using cells expressing the polypeptide in immunohistochemistry. A supply of monoclonal antibody from the selected clones can be purified from a large volume of tissue culture supernatant, or from the ascites fluid of suitably prepared host animals injected with the clone.

Effective variations of this method include those in which the immunization with the polypeptide is performed on isolated cells. Antibody fragments and other derivatives can be prepared by methods of standard protein chemistry, such as subjecting the antibody to cleavage with a proteolytic enzyme. Genetically engineered variants of the antibody can be produced by obtaining a polynucleotide encoding the antibody, and applying the general methods of molecular biology to introduce mutations and translate the variant.

Monoclonal antibodies raised by injecting an intact Glycoprotein B or a fragment comprising conserved sequences may be cross-reactive between herpes viruses. Antibodies that are virus or subfamily specific may be raised by immunizing with a suitably specific antigen, as may be selected from Table 8. Alternatively, virus-specific clones may be selected from the cloned hybridomas by using a suitable antigen, such as one selected from Class III of Table 8, in the screening process.

Specific antibodies against herpes virus Glycoprotein B have a number of uses in developmental, diagnostic and therapeutic work. For example, antibodies can be used in drug screening (see U.S. Pat. No. 5,120,639). They may also be used as a component of a passive vaccine, or for detecting herpes virus in a biological sample and for drug targeting, as described in the following sections.

Anti-idiotypes relating to Glycoprotein B may also be prepared. This is accomplished by first preparing a Glycoprotein B antibody, usually a monoclonal antibody, according to the aforementioned methodology. The antibody is then used as an immunogen in a volunteer or experimental animal to raise an anti-idiotype. The anti-idiotype may be either monoclonal or polyclonal, and its development is generally according to the methodology used for the first antibody. Selection of the anti-idiotype or hybridoma clones expressing anti-idiotype is done using the immunogen antibody as a positive selector, and using antibodies of unrelated specificity as negative selectors. Usually, the negative selector antibodies will be a polyclonal immunoglobulin preparation or a pool comprising monoclonal immunoglobulins of the same immunoglobulin class and subclass, and the same species as the immunogen antibody. An anti-idiotype may be used as an alternative component of an active vaccine against Glycoprotein B.

Use of antibodies for detecting Glycoprotein B in biological samples

Antibodies specific for Glycoprotein B can be used to detect Glycoprotein B polypeptides and fragments of viral origin that may be present, for example, in solid tissue samples and cultured cells. Immunohistological techniques to carry out such determinations will be obvious to a practitioner of ordinary skill. Generally, the tissue is preserved by a combination of techniques which may include freezing, exchanging into different solvents, fixing with agents such as paraformaldehyde, drying with agents such as alcohol, or embedding in a commercially available medium such as paraffin or OCT. A section of the sample is suitably prepared and overlaid with a primary antibody specific for the protein.

The primary antibody may be provided directly with a suitable label. More frequently, the primary antibody is detected using one of a number of developing reagents which are easily produced or available commercially. Typically, these developing reagents are anti-immunoglobulin or protein A, and they typically bear labels which include, but are not limited to: fluorescent markers such as fluorescein, enzymes such as peroxidase that are capable of precipitating a suitable chemical compound, electron dense markers such as colloidal gold, or radioisotopes such as $^{125}$I. The section is then visualized using an appropriate microscopic technique, and the level of labeling is compared between the suspected virally infected and a control cell, such as cells surrounding the area of infection or taken from a remote site.

Proteins encoded by a Glycoprotein B gene can also be detected in a standard quantitative immunoassay. If the protein is secreted or shed from infected cell in any appreciable amount, it may be detectable in plasma or serum samples. Alternatively, the target protein may be solubilized or extracted from a solid tissue sample. Before quantitating, the protein may optionally be affixed to a solid phase, such as by a blot technique or using a capture antibody.

A number of immunoassay methods are established in the art for performing the quantitation. For example, the protein may be mixed with a pre-determined non-limiting amount of the reagent antibody specific for the protein. The reagent antibody may contain a directly attached label, such as an enzyme or a radioisotope, or a second labeled reagent may be added, such as anti-immunoglobulin or protein A. For a solid-phase assay, unreacted reagents are removed by washing. For a liquid-phase assay, unreacted reagents are removed by some other separation technique, such as filtration or chromatography. The amount of label captured in the complex is positively related to the amount of target protein present in the test sample. A variation of this technique is a competitive assay, in which the target protein competes with a labeled analog for binding sites on the specific antibody. In this case, the amount of label captured is negatively related to the amount of target protein present in a test sample. Results obtained using any such assay are compared between test samples, and control samples from an uninfected source.

Use of antibodies for drug targeting

An example of how antibodies can be used in therapy of herpes virus infection is in the specific targeting of effector components. Virally infected cells generally display peptides of the virus, especially proteins expressed on the outside of the viral envelope. The peptide therefore provides a marker for infected cells that a specific antibody can bind to. An effector component attached to the antibody therefore becomes concentrated near the infected cells, improving the effect on those cells and decreasing the effect on uninfected cells. Furthermore, if the antibody is able to induce endocytosis, this will enhance entry of the effector into the cell interior.

For the purpose of targeting, an antibody specific for the viral polypeptide (in this case, a region of a Glycoprotein B) is conjugated with a suitable effector component, preferably by a covalent or high-affinity bond. Suitable effector components in such compositions include radionuclides such as $^{131}$I, toxic chemicals, and toxic peptides such as diphtheria toxin. Another suitable effector component is an antisense polynucleotide, optionally encapsulated in a liposome.

Diagnostic kits

Diagnostic procedures using the polynucleotides, oligonucleotides, peptides, or antibodies of this invention may be performed by diagnostic laboratories, experimental laboratories, practitioners, or private individuals. This invention provides diagnostic kits which can be used in these settings. The presence of a herpes virus in the individual may be manifest in a clinical sample obtained from that individual as an alteration in the DNA, RNA, protein, or antibodies contained in the sample. An alteration in one of these components resulting from the presence of a herpes virus may take the form of an increase or decrease of the level of the component, or an alteration in the form of the component, compared with that in a sample from a healthy individual. The clinical sample is optionally pre-treated for enrichment of the target being tested for. The user then applies a reagent contained in the kit in order to detect the changed level or alteration in the diagnostic component.

Each kit necessarily comprises the reagent which renders the procedure specific: a reagent polynucleotide, used for detecting target DNA or RNA; a reagent antibody, used for detecting target protein; or a reagent polypeptide, used for detecting target antibody that may be present in a sample to be analyzed. The reagent is supplied in a solid form or liquid buffer that is suitable for inventory storage, and later for exchange or addition into the reaction medium when the test is performed. Suitable packaging is provided. The kit may optionally provide additional components that are useful in the procedure. These optional components include buffers, capture reagents, developing reagents, labels, reacting surfaces, means for detection, control samples, instructions, and interpretive information.

Other members of the RFHV/KSHV subfamily

RFHV and KSHV are exemplary members of the RFHV/KSHV subfamily. This invention embodies polynucleotide sequences encoding Glycoprotein B of other members of the subfamily, as defined herein. The consensus-degenerate gamma herpes virus oligonucleotide Type 1 and 2 primers, and the methods described herein are designed to be suitable for characterization of the corresponding polynucleotide fragment of other members of the RFHV/KSHV subfamily. One such member is another virus infecting monkeys, designated RFHV2. A segment of the Glycoprotein encoding sequence for this virus was cloned from RF tissue obtained from a *Macaca mulatta* monkey, as described in Example 12.

In order to identify and characterize other members of the family, reagents and methods of this invention are applied to DNA extracted from tissue samples suspected of being infected with such a virus.

Suitable sources of DNA for this purpose include biological samples obtained from a wide range of conditions occurring in humans and other vertebrates. Preferred are conditions in which the agent is suspected of being lymphotrophic, similar to other members of the gamma herpes virus subfamily; for example, infectious mononucleosis of non-EBV origin. More preferred are conditions which resemble in at least one of their clinical or histological features the conditions with which RFHV or KSHV are associated. These include: a) conditions in which fibroproliferation is part of the pathology of the disease, especially in association with collagen deposition, and especially where the fibrous tissue is disorganized; b) conditions involving vascular dysplasia; c) conditions involving malignant transformation, especially but not limited to cells of lymphocyte lineage; d) conditions for which an underlying immunodeficiency contributes to the frequency or severity of the disease; e) conditions which arise idiopathically at multiple sites in an organ or in the body as a whole; f) conditions which epidemiological data suggests are associated with an infectious or environmental agent. Conditions which fulfill more than one of these criteria are comparably more preferred. Some examples of especially preferred conditions include retroperitoneal fibrosis, nodular fibromatosis, pseudosarcomatous fibromatosis, fibrosarcomas, sclerosing mesenteritis, acute respiratory disease syndrome, idiopathic pulmonary fibrosis, diffuse proliferative glomerulonephritis of various types, gliomas, glioblastomas, gliosis, and all types of leukemias and lymphomas.

The type of tissue sample used will depend on the clinical manifestations of the condition. Samples more likely to contain a virus associated with the condition may be taken from the site involved in the disease pathology, or to which there is some other evidence of viral tropism. Peripheral blood mononuclear cells of an infected individual may also act as a carrier of an RFHV/KSHV subfamily virus. KSHV has been detected in PBMC of both Kaposi's Sarcoma (Moore et al. 1995b) and Castleman's disease (Dupin et al.). Other suitable sources are cell cultures developed from such sources, and enriched or isolated preparations of virus obtained from such sources. For negative control samples, tissue may be obtained from apparently unaffected sites on the same individuals, or from matched individuals who apparently do not suffer from the condition.

The process of identification of members of the RFHV/KSHV subfamily preferably involves the use of the methods and reagents provided in this invention, either singularly or in combination.

One method involves amplifying a polynucleotide encoding a herpes virus Glycoprotein B from DNA extracted from the sample. This can be performed, for example, by amplifying the polynucleotide in a reaction such as a PCR. In one variation, the amplification reaction is primed using broadly specific consensus-degenerate Type 1 oligonucleotides, such as those shown in Table 4. This will amplify herpes viruses, primarily of the gamma type. Since the RFHV/KSHV subfamily is a subset of gamma herpes viruses, Glycoprotein B sequences detected by this variation need to be characterized further to determine whether they fall into the RFHV/KSHV subfamily. In a second variation, the amplification is primed with RFHV or KSHV specific Type 3 oligonucleotides, such as those listed in Table 7, or other Glycoprotein B polynucleotide segments taken from these viruses. The amplification is conducted under conditions of medium to low stringency, so that the oligonucleotides will cross-hybridize with related species of viruses. In a more preferred variation, the amplification reaction is primed using RFHV/KSHV subfamily specific Type 2 oligonucleotides, such as those listed in Table 6. Under appropriate hybridization conditions, these primers will preferentially amplify Glycoprotein B from herpes viruses in the subfamily.

Preferred members of the subfamily detected using a Glycoprotein B polynucleotide probe are those that are at least 65% identical with the RFHV or KSHV Glycoprotein B nucleotide sequence between residues 36 and 354 of SEQ. ID NO:1 or SEQ. ID NO:3. More preferred are those that are at least about 67% identical; more preferred are those at least about 70% identical; more preferred are those that are at least about 80% identical; even more preferred are those about 90% identical or more.

Members of the subfamily can also be identified by performing a hybridization assay on the polynucleotide of the sample, using a suitable probe. The polynucleotide to be tested may optionally be amplified before conducting the hybridization assay, such as by using Type 1 or Type 2 oligonucleotides as primers. The target is then tested in a hybridization reaction with a suitable labeled probe. The probe preferably comprises at least 21 nucleotides, preferably at least about 25 nucleotides, more preferably at least about 50 nucleotides contained the RFHV or KSHV Glycoprotein B sequence in SEQ. ID NOS:1 and 3. Even more preferably, the probe comprises nucleotides 36–354 of SEQ. ID NOS: 1 or 3. Other preferred probes include Type 2 oligonucleotides, such as those shown in Table 6. Hybridization conditions are selected to permit the probe to hybridize with Glycoprotein B polynucleotide sequences from the RFHV/KSHV subfamily, but not previously sequenced herpes viruses; particularly sHV1, bHV4, eHV2, mHV68, hEBV, hCMV, hHV6, hVZV, and HSV1. Formation of a stable duplex with the test polynucleotide under these conditions suggests the presence of a polynucleotide in the sample derived from a member of the RFHV/KSHV subfamily.

Members of the subfamily can also be identified by using a Class II antibody, the preparation of which was outlined earlier. A Class II antibody cross-reacts between antigens produced by members of the RFHV/KSHV subfamily, but not with other antigens, including those produced by herpes viruses not members of the subfamily. The test for new subfamily memers is performed, for example, by using the antibodies in an immunohistochemistry study of tissue sections prepared from individuals with the conditions listed above. Positive staining of a tissue section with the antibody suggests the presence of Glycoprotein B in the sample from a member of the RFHV/KSHV subfamily, probably because the tissue is infected with the virus. If, in addition, the tissue section is non-reactive with RFHV and KSHV specific Class III antibodies, the Glycoprotein B in the tissue may be derived from another member of the subfamily. Similarly, if Class II antibodies are found in the circulation of an individual, the individual may have been subject to a present or past infection with a member of the RFHV/KSHV subfamily.

Once a putative new virus is identified by any of the aforementioned methods, its membership in the RFHV/KSHV subfamily may be confirmed by obtaining and sequencing a region of the Glycoprotein B gene of the virus, and comparing it with that of RFHV or KSHV according to the subfamily definition. For new members of the RFHV/KSHV subfamily, other embodiments of this invention may be brought into play for purposes of detection, diagnosis, and pharmaceutical development. Adaptation of the embodiments of the invention for a new subfamily member, if required, is expected to be minor in nature, and will be obvious based on the new sequence data, or a matter of routine adjustment.

Altered forms of Glycoprotein B from the RFHV/KSHV subfamily

This invention also embodies altered forms of Glycoprotein B of the RFHV/KSHV subfamily.

A number of studies on both naturally occurring and induced mutations of the Glycoprotein B of HSV1 and hCMV point to a role of certain regions of the molecule for its the various biochemical functions. See, for example, Reschke et al. and Baghian et al. for a role of carboxyterminal amino acids in fusion; Shiu et al. and Pellett et al. for epitopes for neutralizing antibodies; Gage et al. for regions of the molecule involved in syncytium formation; Navarro et al. (1992) for regions involved in virus penetration and cell-to-cell spread; Quadri et al. and Novarro et al. (1991) for regions involved in intracellular transport of Glycoprotein B during biosynthesis.

Some of the residues described may be conserved between the Glycoprotein B molecules of the viruses investigated previously, and the Glycoprotein B molecules described herein. By analogy, mutation of the same residue in the Glycoprotein B of the RFHV/KSHV subfamily is expected to have a similar effect as described for other viruses. Alternatively, functional regions of different Glycoprotein B molecules may be combined to produce Glycoprotein B recombinants with altered function. For example, replacing the Glycoprotein B gene in a pathogenic virus with that of a non-pathogenic virus may reduce the pathogenicity of the recombinant (Kostal et al.). Either mutation and recombination of Glycoprotein B of the RFHV/KSHV herpes virus subfamily may lead to attenuated strains, in which either the infectivity, replication activity, or pathogenicity is reduced. Alterations in the Glycoprotein B sequence which have these effects are contemplated in this invention.

Attenuated strains of herpes viruses are useful, for example, in developing polyvalent vaccines. It is desirable, especially in developing countries, to provide prophylactic vaccines capable of stimulating the immune system against several potential pathogens simultaneously. Viruses that are engineered to express immunogenic peptides of several different pathogens may accomplish this purpose. Herpes viruses may be especially suitable vectors, because the large genome may easily accommodate several kilobases of extra DNA encoding the peptides. Ideally, the viral vector is sufficiently intact to exhibit some biological activity and attract the attention of the host's immune system, while at the same time being sufficiently attenuated not to cause significant pathology. Thus, an attenuated virus of the RFHV/KSHV subfamily may be useful as a vaccine against like virulent forms, and may be modified to express additional peptides and extend the range of immune protection.

Another use for attenuated forms of herpes viruses is as delivery vehicles for gene therapy (Latchman et al., Glorioso et al.). In order to be effective, polynucleotides in gene therapy must be delivered to the target tissue site. In the treatment of fibrotic diseases, malignancies and related conditions, attenuated viral vectors of the RFHV/KSHV subfamily may be preferable over other targeting mechanisms, including other herpes viruses, since they have the means by which to target towards the affected tissues. In this embodiment, the virus is first attenuated, and then modified to contain the polynucleotide that is desired for gene therapy, such as those that are outlined in a previous section.

Glycoprotein B in RFHV/KSHV subfamily vaccines

Because of its prominence on the envelope of the infectious virus and infected cells, glycoprotein B is predicted to be a useful target for immune effectors. Herpes virus Glycoprotein B is generally immunogenic, giving rise to antibodies capable of neutralizing the virus and preventing it from entering a replicative phase. In addition, Glycoprotein B is capable of eliciting a T-cell response, which may help eradicate an ongoing viral infection by attacking sites of viral replication in host cells.

This invention embodies vaccine compositions and methods for using them in the prevention and management of infection by viruses from the RFHV/KSHV subfamily.

One series of embodiments relate to active vaccines. These compositions are designed to stimulate an immune response in the individual being treated against Glycoprotein B. They generally comprise either the Glycoprotein B molecule, an immunogenic fragment or variant thereof, or a cell or particle capable of expressing the Glycoprotein B molecule. Alternatively, they may comprise a polynucleotide encoding an immunogenic Glycoprotein B fragment (Horn et al.), preferably in the form of an expression vector. Polynucleotide vaccines may optionally comprise a delivery vehicle like a liposome or viral vector particle, or may be administered as naked DNA.

Vaccine compositions of this invention are designed in such a way that the immunogenic fragment is presented to stimulate the proliferation and/or biological function of the appropriate immune cell type. Compositions directed at eliciting an antibody response comprise or encode B cell epitopes, and may also comprise or encode other elements that enhance uptake and display by antigen-presentation cells, or that recruit T cell help. Compositions directed at eliciting helper T cells, especially $CD4^+$ cells, generally comprise T cell epitopes that can be presented in the context of class II histocompatibility molecules. Compositions directed at stimulating cytotoxic T cells and their precursors, especially $CD8^+$ cells, generally comprise T cell epitopes that can be presented in the context of class I histocompatibility molecules.

In the protection of an individual against a future exposure with herpes virus, an antibody response may be sufficient. Prophylactic compositions preferably comprise components that elicit a B cell response. Successful eradication of an ongoing herpes virus infection may involve the participation of cytotoxic T cells, T helper-inducer cells, or both. Infections for treating ongoing infection preferably comprise components capable of eliciting both T helper cells and cytotoxic T cells. Compositions that preferentially stimulate Type 1 helper ($T_{H1}$) cells over Type 2 helper ($T_{H2}$) cells are even more preferred. The preparation and testing of suitable compositions for active vaccines is outlined in the sections that follow.

Another series of embodiments relates to passive vaccines and other materials for adoptive transfer. These compositions generally comprise specific immune components against Glycoprotein B that are immediately ready to participate in viral neutralization or eradication. Therapeutic methods using these compositions are preferred to prevent pathologic consequences of a recent viral exposure. They are also preferred in immunocompromized individuals incapable of mounting a sufficient immune response to an active vaccine. Such individuals include those with congenital immunodeficiencies, acquired immunodeficiencies (such as those infected with HIV or on kidney dialysis), and those on immunosuppressive therapies, for example, with corticosteroids.

Suitable materials for adoptive transfer include specific antibody against Glycoprotein B, as described below. Also included are the adoptive transfer of immune cells. For example, T cells reactive against Glycoprotein B may be taken from a donor individual, optionally cloned or cultured in vitro, and then transferred to a histocompatible recipient. More preferably, the transferred cells are autologous to the recipient, and stimulated in vitro. Thus, T cells are purified from the individual to be treated, cultured in the presence of immunogenic components of Glycoprotein B and suitable stimulatory factors to elicit virus-specific cells, and then readministered.

Certain compositions embodied herein may have properties of both active and passive vaccines. For example, Glycoprotein B antibody given by adoptive transfer may confer immediate protection against herpes virus, and may also stimulate an ongoing response, through an anti-idiotype network, or by enhancing the immune presentation of viral antigen.

Vaccines comprising Glycoprotein B polypeptides

Specific components of vaccines to stimulate an immune response against Glycoprotein B include the intact Glycoprotein B molecule, and fragments of Glycoprotein B that are immunogenic in the host.

Intact Glycoprotein B and longer fragments thereof may be prepared by any of the methods described earlier, especially purification from a suitable expression vector comprising a Glycoprotein B encoding polynucleotide. Isolated Glycoprotein B from other viral strains stimulate a protective immune response (See U.S. Pat. No. 5,171,568: Burke et al.). Preferred fragments comprise regions of the molecule exposed on the outside of the intact viral envelope; located within about 650 amino acids of the N-terminal of the mature protein.

Glycosylation of Glycoprotein B is not required for imnmunogenicity (O'Donnell et al.). Hence, glycosylated and unglycosylated forms of the molecule are equally preferred. Glycosylation may be determined by standard techniques; for example, comparing the mobility of the protein in SDS polyacrylamide gel electrophoresis before and after treating with commercially available endoglycosidase type F or H.

Smaller fragments of 5–50 amino acids comprising particular epitopes of Glycoprotein B are also suitable vaccine components. These may be prepared by any of the methods described earlier; most conveniently, by chemical synthesis. Preferred fragments are those which are immunogenic and expressed on the outside of the viral envelope. Even more preferred are fragments implicated in a biological function of Glycoprotein B, such as binding to cell surface receptors or penetration of the virus into a target cell.

Immunogenicity of various epitopes may be predicted by algorithms known in the art. Antigenic regions for B cell receptors may be determined, for example, by identifying regions of variable polarity (Hopp et al., see Example 9). Antigenic regions for T cell receptors may be determined, for example, by identifying regions capable of forming an amphipathic helix in the presentation groove of a histocompatibility molecule. Antigenic regions may also be identified by analogy with Glycoprotein B molecules of other viral species. See, e.g., Sanchez-Pescador et al. and Mester et al., for B cell epitopes of HSV1; Liu et al. for HLA-restricted helper T cell epitopes of hCMV; and Hanke et al. for cytotoxic T lymphocyte epitopes of HSV1.

Immunogenicity of various epitopes may be measured experimentally by a number of different techniques. Generally, these involve preparing protein fragments of 5–20 amino acids in length comprising potential antigenic regions, and testing them in a specific bioassay. Fragments may be prepared by CNBr and/or proteolytic degradation of a larger segment of Glycoprotein B, and purified, for example, by gel electrophoresis and blotting onto nitrocellulose (Demotz et al.). Fragments may also be prepared by standard peptide synthesis (Schumacher et al., Liu et al.). In a preferred method, consecutive peptides of 12 amino acids overlapping by 8 residues are synthesized according to the entire extracellular domain of the mature Glycoprotein B molecule, using F-Moc chemistry on a nylon membrane support (see Example 11).

Reactivity against the prepared fragment can then be determined in samples from individuals exposed to the intact virus or a Glycoprotein B component. The individual may have been experimentally exposed to the Glycoprotein B component by deliberate administration. Alternatively, the individual may have a naturally occurring viral infection, preferably confirmed by a positive amplification reaction using a virus-specific oligonucleotide probe to Glycoprotein B or DNA Polymerase. Blood samples are obtained from the individual, and used to prepare serum, T cells, and peripheral blood mononuclear cells (PBMC) by standard techniques.

Serum may be tested for the presence of Glycoprotein B specific antibody in an enzyme-linked immunosorbant assay. For example, peptides attached to a solid support such as a nylon membrane are incubated with the serum, washed, incubated with an enzyme-linked anti-immunoglobulin, and developed using an enzyme substrate. The presence of antibody against a particular Glycoprotein B peptide is indicated by a higher level of reaction product in the test well than in a well containing an unrelated peptide (Example 11).

Lymphocyte preparations may be tested for the presence of Glycoprotein B specific helper T cells in a proliferation assay. Approximately $2 \times 10^4$ helper T cells are incubated with the peptide at $10^{-4}$–$10^{-6}$ M in the presence of irradiated autologous or irradiated $10^5$ PBMC as antigen presenting cells for about 3 days. [$^3$H]Thymidine is added for about the last 16 h of culture. The cells are then harvested and washed. Radioactivity in the washed cells at a level of about 10 fold over those cultured in the absence of peptide reflects proliferation of T cells specific for the peptide (Liu et al.). If desired, cells with a $CD3^+4^+8^-$ phenotype may be cloned for further characterization of the helper T cell response.

Lymphocyte preparations may be tested for the presence of Glycoprotein B specific cytotoxic T cells in a $^{51}$Cr release assay. Targets are prepared by infecting allogeneic cells with a herpes virus comprising an expressible Glycoprotein B gene. Alternatively, allogeneic cells transfected with a Glycoprotein B expression vector may be used. The targets are incubated with $^{51}$Cr for about 90 min at 37° C. and then washed. About $5 \times 10^4$ target cells are incubated with $10^{-4}$–$10^{-5}$ M of the peptide and $0.1$–$2 \times 10^4$ test T cells for about 30 min at 37° C. Radioactivity released into the supernatant at a level substantially above that due to spontaneous lysis reflects CTL activity. If desired, cells with a $CD3^+4^-8^+$ phenotype may be cloned for further characterization of the CTL response.

Glycoprotein B peptides may optionally be combined in a vaccine with other peptides of the same virus. Suitable peptides include peptides of any of the other components of the herpes virus, such as Glycoproteins C, D, H, E, I, J, and G. Glycoprotein B peptides may also optionally be combined with immunogenic peptides from different viruses to provide a multivalent vaccine against more than one pathogenic organism. Peptides may be combined by preparing a mixture of the peptides in solution, or by synthesizing a fusion protein in which the various peptide components are linked.

Forms of Glycoprotein B comprising suitable epitopes may optionally be treated chemically to enhance their immunogenicity, especially if they comprise 100 amino acids or less. Such treatment may include cross-linking, for example, with glutaraldehyde; linking to a protein carrier, such as keyhole limpet hemocyanin (KLH) or tetanus toxoid.

The peptide or peptide mixture may be used neat, but normally will be combined with a physiologically and pharmacologically acceptable excipient, such as water, saline, physiologically buffered saline, or sugar solution.

In a preferred embodiment, an active vaccine also comprises an adjuvant which enhances presentation of the immunogen or otherwise accentuates the immune response against the immunogen. Suitable adjuvants include alum, aluminum hydroxide, beta-2 microglobulin (WO 91/16924: Rock et al.), muramyl dipeptides, muramyl tripeptides (U.S. Pat. No. 5,171,568: Burke et al.), and monophosphoryl lipid A (U.S. Pat. No. 4,436,728: Ribi et al.; and WO 92/16231: Francotte et al.). Immunomodulators such as Interleukin 2 may also be present. The peptide and other components (if present) are optionally encapsulated in a liposome or microsphere. For an outline of the experimental testing of various adjuvants, see U.S. Pat. No. 5,171,568 (Burke et al.). A variety of adjuvants may be efficacious. The choice of an adjuvant will depend at least in part on the stability of the vaccine in the presence of the adjuvant, the route of administration, and the regulatory acceptability of the adjuvant, particularly when intended for human use.

Polypeptide vaccines generally have a broad range of effective latitude. The usual route of administration is intramuscular, but preparations may also be developed which are effective given by other routes, including intravenous, intraperitoneal, oral, intranasal, and by inhalation. The total amount of Glycoprotein B polypeptide per dose of vaccine when given intramuscularly will generally be about 10 µg to 5 mg; usually about 50 µg to 2 mg; and more usually about 100 to 500 µg. The vaccine is preferably administered first as a priming dose, and then again as a boosting dose, usually at least four weeks later. Further boosting doses may be given to enhance or rejuvenate the response on a periodic basis.

Vaccines comprising viral particles expressing Glycoprotein B

Active vaccines may also be prepared as particles that express an immunogenic epitope of Glycoprotein B.

One such vaccine comprises the L-particle of a recombinant herpes virus (see U.S. Pat. No. 5,284,122: Cunningham et al.). The genome of the recombinant virus is defective in a capsid component, or otherwise prevented from forming intact virus; however, it retains the ability to make L-particles. The genome is engineered to include a Glycoprotein B encoding polynucleotide of the present invention operatively linked to the controlling elements of the recombinant virus. The virus is then grown, for example, in cultured cells, and the particles are purified by centrifugation on a suitable gradient, such as FICOLL™. Such preparations are free of infective virus, and capable of expressing peptide components of a number of different desirable epitopes.

Another such vaccine comprises a live virus that expresses Glycoprotein B of the present invention as a heterologous antigen. Such viruses include HIV, SIV, FIV, equine infectious anemia, visna virus, and herpes viruses of other species. The virus should be naturally non-pathogenic in the species to be treated; or alternatively, it should be attenuated by genetic modification, for example, to reduce replication or virulence. Herpes virus may be attenuated by mutation of a gene involved in replication, such as the DNA Polymerase gene. Herpes virus may also be attenuated by deletion of an essential late-stage component, such as Glycoprotein H (WO 92/05263: Inglis et al.). A live vaccine may be capable of a low level of replication in the host, particularly if this enhances protein expression, but not to the extent that it causes any pathological manifestation in the subject being treated.

A preferred viral species for preparing a live vaccine is adenovirus. For human therapy, human adenovirus types 4 and 7 have been shown to have no adverse affects, and are suitable for use as vectors. Accordingly, a Glycoprotein B polynucleotide of the present invention may be engineered, for example, into the E1 or E3 region of the viral genome. It is known that adenovirus vectors expressing Glycoprotein B from HSV1 or HSV2 stimulate the production of high titer virus-neutralizing antibody (McDermott et al.). The response protects experimental animals against a lethal challenge with the respective live virus.

Also preferred as a virus for a live recombinant vaccine is a recombinant pox virus, especially vaccinia. Even more preferred are strains of vaccinia virus which have been modified to inactivate a non-essential virulence factor, for example, by deletion or insertion of an open reading frame relating to the factor (U.S. Pat. No. 5,364,773: Paoletti et al.). To prepare the vaccine, a Glycoprotein B encoding polynucleotide of the present invention is genetically engineered into the viral genome and expressed under control of a vaccinia virus promoter. Recombinants of this type may be used directly for vaccination at about $10^7$–$10^8$ plaque-forming units per dose. Single doses may be sufficient to stimulate an antibody response. Vaccinia virus recombinants comprising Glycoprotein B of HSV1 are effective in protecting mice against lethal HSV1 infection (Cantin et al.).

Another vaccine in this category is a self-assembling replication-defective hybrid virus. See, for example, WO 92/05263 (Inglis et al.). The particle may contain, for example, capsid and envelope glycoproteins, but not an intact viral genome. As embodied in this invention, one of the glycoproteins in the viral envelope is Glycoprotein B.

In a preferred embodiment, the particle is produced by a viral vector of a first species, having a sufficient segment of the genome of that species to replicate, along with encoding regions for a capsid and an envelope from a heterologous species (see U.S. Pat. No. 5,420,026: Payne). Genetic elements of the first species are selected such that infection of eukaryotic cells with the vector produces capsid and envelope glycoproteins that self-assemble into replication-defective particles. In a variant of this embodiment, polynucleotides encoding the capsid and envelope glycoproteins are provided in two separate vectors derived from the first viral species. The capsid encoding regions may be derived from a lentivirus, such as HIV, SIV, FIV, equine infectious anemia virus, or visna virus. The envelope encoding regions comprise a Glycoprotein B encoding polynucleotide of the present invention. Preferably, all envelope components are encoded by a herpes virus, particularly of the RFHV/KSHV subfamily. The defective viral particles are obtained by infecting a susceptible eukaryotic cell line such as BSC-40 with the vector(s) and harvesting the supernatant after about 18 hours. Viral particles may be further purified, if desired, by centrifugation through a sucrose cushion. Particles may also be treated with 0.8% formalin at 40° C. for 24 hours prior to administration as a vaccine.

Vaccines comprising a live attenuated virus or virus analog may be lyophilized for refrigeration. Diluents may optionally include tissue culture medium, sorbitol, gelatin, sodium bicarbonate, albumin, gelatin, saline solution, phosphate buffer, and sterile water. Other active components may optionally be added, such as attenuated strains of measles, mumps, and rubella, to produce a polyvalent vaccine. The suspension may be lyophilized, for example, by the gas injection technique. This is performed by placing vials of vaccine in a lyophilizing chamber precooled to about −45° C. with 10–18 Pa of dry sterile argon, raising the temperature about 5–25° C. per h to +30° C., conducting a second lyophilizing cycle with fall vacuum, and then sealing the vials under argon in the usual fashion (see EP 0290197B1: Mcaleer et al.). For vaccines comprising live herpes virus, the final lyophilized preparation will preferably contain 2–8% moisture.

It is recognized that a number of alternative compositions for active vaccines, not limited to those described here in detail, may be efficacious in eliciting specific B- and T-cell immunity. All such compositions are embodied in the spirit of the present invention, providing they include a RFHV/KSHV subfamily Glycoprotein B polynucleotide or polypeptide as an active ingredient.

Vaccines comprising Glycoprotein B antibodies

Antibody against Glycoprotein B of the RFHV/KSHV subfamily may be administered by adoptive transfer to immediately confer a level of humoral immunity in the treated subject. Passively administered anti-glycoprotein B experimentally protects against a lethal challenge with other herpes viruses, even in subjects with compromised T-cell immunity (Eis-Hubinger et al.).

The antibody molecule used should be specific for Glycoprotein B against which protection is desired. It should not cross-reactive with other antigens, particularly endogenous antigens of the subject to be treated. The antibody may be specific for the entire RFHV/KSHV subfamily (Class II antibodies), or for a particular virus species (Class III antibodies), depending on the objective of the treatment. Preferably, the antibody will have an overall affinity for a polyvalent antigen of at least about $10^8$ $M^{-1}$; more preferably it will be at least about $10^{10}$ $M^{-1}$; more preferably it will be at least about $10^{12}$ $M^{-1}$; even more preferably, it will be $10^{13}$ $M^{-1}$ or more. Intact antibody molecules, recombinants, fusion proteins, or antibody fragments may be used; however, intact antibody molecules or recombinants able to express natural antibody effector functions are preferred. Relevant effector functions include but are not limited to virus aggregation; antibody-dependent cellular cytotoxicity; complement activation; and opsonization.

Antibody may be prepared according to the description provided in an earlier section. For systemic protection, the antibody is preferably monomeric, and preferably of the IgG class. For mucosal protection, the antibody may be polymeric, preferably of the IgA class. The antibody may be either monoclonal or polyclonal; typically, a cocktail of monoclonal antibodies is preferred. It is also preferred that the preparation be substantially pure of other biological components from the original antibody source. Other antibody molecules of desired reactivity, and carriers or stabilizers may be added after purification.

In some instances, it is desirable that the antibody resemble as closely as possible an antibody of the species which is to be treated. This is to prevent the administered antibody from becoming itself a target of the recipient's immune response. Antibodies of this type are especially desirable when the subject has an active immune system, or when the antibodies are to be administered in repeat doses.

Accordingly, this invention embodies anti-Glycoprotein B antibody which is human, or which has been humanized. Polyclonal human antibody may be purified from the sera of human individuals previously infected with the respective RFHV/KSHV subfamily herpes virus, or from volunteers administered with an active vaccine. Monoclonal human antibody may be produced from the lymphocytes of such individuals, obtained, for example, from peripheral blood. In general, human hybridomas may be generated according to the methods outlined earlier. Usually, the production of stable human hybridomas will require a combination of manipulative techniques, such as both fusion with a human myeloma cell line and transformation, for example, with EBV.

In a preferred method, human antibody is produced from a chimeric non-primate animal with functional human immunoglobulin loci (WO 91/10741: Jakobovits et al.). The non-primate animal strain (typically a mouse) is incapable of expressing endogenous immunoglobulin heavy chain, and optimally at least one endogenous immunoglobulin light chain. The animals are genetically engineered to express human heavy chain, and optimally also a human light chain. These animals are immunized with a Glycoprotein B of the RFHV/KSHV subfamily of herpes viruses. Their sera can then be used to prepare polyclonal antibody, and their lymphocytes can be used to prepare hybridomas in the usual fashion. After appropriate selection and purification, the resultant antibody is a human antibody with the desired specificity.

In another preferred method, a monoclonal antibody with the desired specificity for Glycoprotein B is first developed in another species, such as a mouse, and then humanized. To humanize the antibody, the polynucleotide encoding the specific antibody is isolated, antigen binding regions are obtained, and then recombined with polynucleotides encoding elements of a human immunoglobulin of unrelated specificity. Alternatively, the nucleotide sequence of the specific antibody is obtained and used to design a related sequence with human characteristics, which can be prepared, for example, by chemical synthesis. The heavy chain constant region or the light chain constant region of the specific antibody, preferably both, are substituted with the constant regions of a human immunoglobulin of the desired class. Preferably, segments of the variable region of both chains outside the complementarity determining regions (CDR) are also substituted with their human equivalents (EP 0329400: Winter).

Even more preferably, segments of the variable region are substituted with their human equivalents, providing they are not involved either in antigen binding or maintaining the structure of the binding site. Important amino acids may be identified, for example, as described by Padlan. In one particular technique (WO 94/11509: Couto et al.), a positional consensus sequence is developed using sequence and crystallography data of known immunoglobulins. The amino acid sequence of the Glycoprotein B specific antibody is compared with the model sequence, and amino acids involved in antigen binding, contact with CDR's, or contact with opposing chains are identified. The other amino acids are altered, where necessary, to make them conform to a consensus of human immunoglobulin sequences. A polynucleotide encoding the humanized sequence is then prepared, transfected into a host cell, and used to produce humanized antibody with the same Glycoprotein B specificity as the originally obtained antibody clone.

Specific antibody obtained using any of these methods is generally sterilized, mixed with a pharmaceutically compatible excipient. Stabilizers such as 0.3 molar glycine, and preservatives such as 1:10,000 thimerosal, may also be present. The suspension may be buffered to neutral pH (~7.0), for example, by sodium carbonate. The potency may optionally be adjusted by the addition of normal human IgG, obtained from large pools of normal plasma, for example, by the Cohn cold ethanol fractionation procedure. Other diluents, such as albumin solution, may be used as an alternative. The concentration is adjusted so that a single dose administration constitutes 0.005–0.2 mg/kg, preferably about 0.06 mg/kg. A single dose preferably results in a circulating level of anti-Glycoprotein B, as detected by ELISA or other suitable technique, which are comparable to those observed in individuals who have received an active Glycoprotein B vaccine or have recovered from an acute infection with the corresponding virus, or which are known from experimental work to be protective against challenges with a pathologic dose of virus.

Administration should generally be performed by intramuscular injection, not intravenously, and care should be taken to assure that the needle is not in a blood vessel. Special care should be taken with individuals who have a history of systemic allergic reactions following administration of human globulin. For prophylactic applications, the antibody preparation may optionally be administered in combination with an active vaccine for Glycoprotein B, as described in the preceding sections. For post-exposure applications, the antibody preparation is preferably administered within one week of the exposure, more preferably within 24 hours, or as soon as possible after the exposure. Subsequent doses may optionally be given at approximately 3 month intervals.

As for all therapeutic instruments described herein, the amount of composition to be used, and the appropriate route and schedule of administration, will depend on the clinical status and requirements of the particular individual being treated. The choice of a particular regimen is ultimately the responsibility of the prescribing physician or veterinarian.

The foregoing description provides, inter alia, a detailed explanation of how Glycoprotein B encoding regions of herpes viruses, particularly those of the RFHV/KSHV subfamily, can be identified and their sequences obtained. Polynucleotide sequences for encoding regions of Glycoprotein B of both RFHV and KSHV are provided.

The polynucleotide sequences listed herein for RFHV and KSHV are believed to be an accurate rendition of the sequences contained in the polynucleotides from the herpes viruses in the tissue samples used for this study. They represent a consensus of sequence data obtained from multiple clones. However, it is recognized that sequences obtained by amplification methods such as PCR may comprise occasional errors in the sequence as a result of amplification. The error rate is estimated to be between about 0.44% and 0.75% for single determinations; about the same rate divided by $\sqrt{(n-1)}$ for the consensus of n different determinations. Nevertheless, the error rate may be as high as 1% or more. Sequences free of amplification errors can be obtained by creating a library of herpes virus polynucleotide sequences, using oligonucleotides such as those provided in Table 7 to select relevant clones, and sequencing the DNA in the selected clones. The relevant methodology is well known to a practitioner of ordinary skill in the art, who may also wish to refer to the description given in the Example section that follows.

It is recognized that allelic variants and escape mutants of herpes viruses occur. Polynucleotides and polypeptides may be isolated or derived that incorporate mutations, either naturally occurring, or accidentally or deliberately induced, without departing from the spirit of this invention.

The examples presented below are provided as a further guide to a practitioner of ordinary skill in the art, and are not meant to be limiting in any way.

EXAMPLES

Example 1

Oligonucleotide Primers for Herpes Virus Glycoprotein B

Amino acid sequences of known herpes virus Glycoprotein B molecules were obtained from the PIR protein database, or derived from DNA sequences obtained from the GenBank database. The sequences were aligned by computer-aided alignment programs and by hand.

Results are shown in FIG. 3. sHV1, bHV4, mHV68, EBV and hHV6 sequences were used to identify regions that were relatively well conserved, particularly amongst the gamma herpes viruses. Nine regions were chosen for design of amplification primers. The DNA sequences for these regions were then used to design the oligonucleotide primers. The primers were designed to have a degenerate segment of 8–14 base pairs at the 3' end, and a consensus segment of 18–30 bases at the 5' end. This provides primers with optimal sensitivity and specificity.

The degenerate segment extended across highly conserved regions of herpes virus Glycoprotein B sequences, encompassing the least number of alternative codons. The primers could therefore be synthesized with alternative nucleotide residues at the degenerate positions and yield a minimum number of combinations. There were no more than 256 alternative forms for each of the primers derived.

The consensus segment was derived from the corresponding flanking region of the Glycoprotein B sequences. Generally, the consensus segment was derived by choosing the most frequently occurring nucleotide at each position of all the Glycoprotein B sequences analyzed. However, selection was biased in favor of C or G nucleotides, to maximize the ability of the primers to form stable duplexes.

Results are shown in FIGS. 4–12, and are summarized in Table 4. In a PCR, oligonucleotides listed in Table 4 as having a "sense" orientation would act as primers by hybridizing with the strand antisense to the coding strand, and initiating polymerization in the same direction as the Glycoprotein B encoding sequence. Oligonucleotides listed in Table 4 as having an "antisense" orientation would hybridize with the coding strand and initiate polymerization in the direction opposite to that of the Glycoprotein B encoding sequence.

Synthetic oligonucleotides according to the designed sequences were ordered and obtained from Oligos Etc, Inc.

Example 2

DNA Extraction

Biopsy specimens were obtained from Kaposi's sarcoma lesions from human subjects diagnosed with AIDS. The specimens were fixed in paraformaldehyde and embedded in paraffin, which were processed for normal histological examination.

Fragments of the paraffin samples were extracted with 500 µL of xylene in a 1.5 mL EPPENDORF™ conical centrifuge tube. The samples were rocked gently for 5 min at room temperature, and the tubes were centrifuged in an EPPENDORF™ bench-top centrifuge at 14,000 rpm for 5 min. After removing the xylene with a Pasteur pipette, 500 µL of 95% ethanol was added, the sample was resuspended, and then re-centrifuged. The ethanol was removed, and the wash step was repeated. Samples were then air-dried for about 1 hour. 500 µL of proteinase-K buffer (0.5% TWEEN™ 20, a detergent; 50 mM Tris buffer pH 7.5, 50 mM NaCl) and 5 µL of proteinase K (20 mg/mL) were added, and the sample was incubated for 3 h at 55° C. The proteinase K was inactivated by incubating at 95° C. for 10 min.

Samples of DNA from KS tissue were pooled to provide a consistent source of polynucleotide for the amplification reactions. This pool was known to contain DNA from KSHV, as detected by amplification of KSHV DNA polymerase sequences, as described in commonly owned U.S. patent application Ser. No. 60/001,148.

Example 3

Obtaining Amplified Segments of KSHV Glycoprotein B

The oligonucleotides obtained in Example 1 were used to amplify segments of the DNA extracted from KSHV tissue in Example 2, according to the following protocol.

A first PCR reaction was conducted using 2 µL of pooled DNA template, 1 µL of oligonucleotide FRFDA (50 pmol/µL), 1 µL of oligonucleotide TVNCB (50 pmol/µL), 10 µL of 10× buffer, 1 µL containing 2.5 mM of each of the deoxyribonucleotide triphosphates (dNTPs), 65 µL distilled water, and 65 µL mineral oil. The mixture was heated to 80° C. in a Perkin-Elmer (model 480) PCR machine. 0.5 µL Taq polymerase (BRL, 5 U/µL) and 19.5 µL water was then added. 35 cycles of amplification were conducted in the following sequence: 1 min at 94° C., 1 min at the annealing temperature, and 1 min at 72° C. The annealing temperature was 60° C. in the first cycle, and decreased by 2° C. each cycle until 50° C. was reached. The remaining cycles were performed using 50° C. as the annealing temperature.

A second PCR reaction was conducted as follows: to 1 µL of the reaction mixture from the previous step was added 1 µL oligonucleotide NIVPA (50 pmol/µL), 1 µL oligonucleotide TVNCB (50 pmol/µL), 10 µL of 10× buffer, 1 µL dNTPs, 66 µL water, and 65 µL mineral oil. The mixture was heated to 80° C., and 0.5 µL Taq polymerase in 19.5 µL water was added. 35 cycles of amplification were conducted using the same temperature step-down procedure as before. The PCR product was analyzed by electrophoresing on a 2% agarose gel and staining with ethidium bromide.

The two-round amplification procedure was performed using fourteen test buffers. Five buffers yielded PCR product of about the size predicted by analogy with other herpes sequences. These included WB4 buffer (10× WB4 buffer is 0.67 M Tris buffer pH 8.8, 40 mM $MgCl_2$, 0.16 M $(NH_4)_2SO_4$, 0.1 M β-mercaptoethanol, 1 mg/mL bovine serum albumin, which is diluted 1 to 10 in the reaction). Also tested was WB2 buffer (the same as WB4 buffer, except with 20 mM $MgCl_2$ in the 10× concentrate). Also tested were buffers that contained 10 mM Tris pH 8.3, 3.5 mM $MgCl_2$ and 25 mM KCl; or 10 mM Tris pH 8.3, 3.5 mM $MbCl_2$ and 75 mM KCl; or 10 mM Tris pH 8.8, 3.5 mM $MgCl_2$ and 75 mM KCl; when diluted to final reaction volume. The WB4 buffer showed the strongest band, and some additional fainter bands. This may have been due to a greater overall amount of labeled amplified polynucleotide in the WB4 sample.

The product from amplification with WB2 buffer was selected for further investigation. A third round of amplification was performed to introduce a radiolabel. The last-used oligonucleotide (TVNCB) is end-labeled with gamma $^{32}$P-ATP, and 1 µL was added to 20 µL of the reaction mixture from the previous amplification step, along with 1 µL 2.5 mM dNTP. The mixture was heated to 80° C., and 0.5 µL Taq polymerase was added. Amplification was conducted through five cycles of 94° C., 60° C. and 72° C. The reaction was stopped using 8.8 µL of loading buffer from a Circumvent sequencing gel kit.

A ~4 µL aliquot of the radiolabeled reaction product was electrophoresed on a 6% polyacrylamide sequencing gel for 1.5 h at 51° C. The gel was dried for 1.5 h, and an autoradiograph was generated by exposure for 12 h. Two bands were identified. The larger band had the size expected for the fragment from analogy with other gamma herpes virus sequences.

The larger band was marked and cut out, and DNA was eluted by incubation in 40 µL TE buffer (10 mM Tris and 1 mM EDTA, pH. 8.0). A further amplification reaction was performed on the extracted DNA, using 1 µL of the eluate, 10 µL 10× WB2 butter, 1 µL 2.5 mM dNTP, 1 µL of each of the second set of oligonucleotide primers (NIVPA and TVNCB), and 65 µL water. The mixture was heated to 80° C., and 0.5 µL Taq polymerase in 19.5 µL water was added.

Amplification was conducted through 35 cycles, using the temperature step-down procedure described earlier.

Example 4

Sequence of the 386 Base Fragment of KSHV Glycoprotein B

The amplified polynucleotide fragment from the Glycoprotein B gene of KSHV was purified and cloned according to the following procedure.

40 μL of amplification product was run on a 2% agarose gel, and stained using 0.125 μg/mL ethydium bromide. The single band at about 400 base pairs was cut out, and purified using a QIAGEN™ II gel extraction kit, according to manufacturer's instructions.

The purified PCR product was ligated into the pGEM™-t cloning vector. The vector was used to transform competent bacteria (E. coli JM-109). Bacterial clones containing the amplified DNA were picked and cultured. The bacteria were lysed and the DNA was extracted using phenol-chloroform followed by precipitation with ethanol. Colonies containing inserts of the correct size were used to obtain DNA for sequencing. The clone inserts were sequenced from both ends using vector-specific oligonucleotides (forward and reverse primers) with a SEQUENASE™ 7-deaza dGTP kit, according to manufacturer's directions. A consensus sequence for the new fragment was obtained by combining sequence data obtained from 5 clones of one KSHV Glycoprotein B amplification product.

The length of the fragment in between the primer hybridizing regions was 319 base pairs. The nucleotide sequence is listed as SEQ. ID NO:3 and shown in FIG. 1. The encoded polypeptide sequence is listed as SEQ. ID NO:4.

FIG. 13 compares the sequence of this Glycoprotein B gene fragment with the corresponding sequence of other gamma herpes viruses. Single dots (.) indicate residues in other gamma herpes viruses that are identical to those of the KSHV sequence. Dashes (-) indicate positions where gaps have been added to provide optimal alignment of the encoded protein. The longest stretch of consecutive nucleotides that is identical between the KSHV sequence and any of the other listed sequences is 14. Short conserved sequences are scattered throughout the fragment. Overall, the polynucleotide fragment is 63% identical between KSHV and the two closest herpes virus sequences, sHV1 and bHV4.

The sequence data was used to design Type 3 oligonucleotide primers of 2040 base pairs in length. The primers were designed to hybridize preferentially with the KSHV Glycoprotein B polynucleotide, but not with other sequenced polynucleotides encoding Glycoprotein B. Example primers of this type were listed earlier in Table 7.

FIG. 14 compares the predicted amino acid sequence encoded by the same Glycoprotein B gene fragment. At the amino acid level, two short segments are shared between KSHV and a previously known gamma herpes virus, bHV4. The first (SEQ. ID NO:64) is 13 amino acids in length and located near the N-terminal end of the fragment. The second (SEQ. ID NO:65) is 15 amino acids in length and located near the C-terminal end of the fragment. All other segments shared between KSHV and other gamma herpes viruses are 9 amino acids or shorter.

Example 5

Sequence of the 386 Base Fragment of RFHV Glycoprotein B

Tissue specimens were obtained from the tumor of a *Macaque nemestrina* monkey at the University of Washington Regional Primate Research Center. The specimens were fixed in paraformaldehyde and embedded in paraffin. DNA was extracted from the specimens according to the procedure of Example 2.

The presence of RFHV polynucleotide in DNA preparations was determined by conducting PCR amplification reactions using oligonucleotide primers hybridizing to the DNA polymerase gene. Details of this procedure are provided in commonly owned U.S. patent application Ser. No. 60/001,148. DNA extracts containing RFHV polynucleotide determined in this fashion were pooled for use in the present study.

DNA preparations containing RFHV polynucleotide served as the template in PCR amplification reactions using Glycoprotein B consensus-degenerate oligonucleotides FRFDA and TVNCB, followed by a second round of amplification using oligonucleotides NIVPA and TVNCB. Conditions were essentially the same as in Example 3, except that only WB4 buffer produced bands of substantial intensity, with the amount of DNA in the initial source and the conditions used. Labeling of the amplified DNA was performed with $^{32}$P end-labeled NIVPA, as before; the product was electrophoresed on a 6% polyacrylamide gel, and an autoradiogram was obtained. A ladder of bands corresponding to about 386 base pairs and about 10 higher mol wt concatemers was observed. The 386 base pair band (with the same mobility as a simultaneously run KSHV fragment) was cut out of the gel and extracted.

To determine whether the DNA in this extract was obtained from a specific amplification reaction, PCR's were set up using NIVPASQ alone, TVNCBSQ alone, or the two primers together. Buffer conditions were the same as for the initial amplification reactions. The mixture was heated to 80° C., Taq polymerase was added, and the amplification was carried through 35 cycles using the temperature step-down procedure. Theoretically, specific amplification reactions accumulate product linearly when one primer is used, and exponentially when using two primers with opposite orientation. Thus, specificity is indicated by more product in the reaction using both primers, whereas equal product in all three mixtures suggests non-specific amplification. Amplification products from these test reactions were analyzed on an agarose gel stained with ethidium bromide. The RF extract showed no product for the NIVPASQ reaction, a moderate staining band for the TVNCBSQ reaction at the appropriate mobility, and an intensely staining band for both primers together. For a KSHV fragment assayed in parallel, there was a faint band for the NIVPASQ reaction, no band for the TVNCBSQ reaction, and an intensely staining band for both primers together. We concluded that the 386 base pair band in the RF extract represented specific amplification product.

Accordingly, 40 μL of the RF extract that had been amplified with both primers was run preparatively on a 2% agarose gel, and the ~386 base pair band was cut out. Agarose was removed using a QIAGEN™ kit, and the product was cloned in *E. coli* and sequenced as in Example 4. A consensus sequence was determined for 3 different clones obtained from the same amplified RFHV product.

The polynucleotide sequence of RFHV Glycoprotein B fragment (SEQ. ID NO:1) is aligned in FIG. 1 with the corresponding sequence from KSHV. Also shown is the encoded RFHV amino acid sequence (SEQ. ID NO:2). Between the primer hybridization regions (nucleotides 36–354), the polynucleotide sequences are 76% identical; and the amino acid sequences are 91% identical. The internal cysteine residue and the potential N-linked glycosylation site are both conserved between the two viruses.

The sequence data was used to design Type 3 oligonucleotide primers of 20–40 base pairs in length. The primers were designed to hybridize preferentially with the RFHV Glycoprotein B polynucleotide, but not with other sequenced polynucleotides encoding Glycoprotein B. Example primers of this type were listed earlier in Table 7.

FIG. 15 compares the predicted amino acid sequence encoded by nucleotides 36–354 of the Glycoprotein B gene fragment. As for the KSHV sequence, two short segments are shared between RFHV and a previously known gamma herpes virus, bHV4. All other segments shared between RFHV and other gamma herpes viruses are shorter than 9 amino acids in length.

FIG. 16 is an alignment of sequence data for the same Glycoprotein B fragment in the spectrum of herpes viruses for which data is available. FIG. 17 shows the phylogenetic relationship between herpes viruses, based on the degree of identity across the partial Glycoprotein B amino acid sequences shown in FIG. 16. By amino acid homology, amongst the viruses shown, RFHV and KSHV are most closely related to bHV4, eHV2, and sHV1.

Example 6

Oligonucleotide Primers and Probes for the RFHV/KSHV Subfamily

Based on the polynucleotide fragment obtained for RFHV and KSHV, seven Type 2 oligonucleotides were designed that could be used either as PCR primers or as hybridization probes with members of the RFHV/KSHV subfamily.

Four consensus-degenerate Type 2 oligonucleotides, SHMDA, CFSSB, ENTFA, and DNIQB are shown in FIG. 17, alongside the sequences they were derived from. Like the oligonucleotides of Example 1, they have a consensus segment towards the 5' end, and a degenerate segment towards the 3' end. However, these oligonucleotides are based only on the RFHV and KSHV sequences, and will therefore preferentially form stable duplexes with Glycoprotein B of the RFHV/KSHV subfamily. A list of exemplary Type 2 oligonucleotides was provided earlier in Table 6.

Different Type 2 oligonucleotides have sense or antisense orientations. Primers with opposing orientations may be used together in PCR amplifications. Alternatively, any Type 2 oligonucleotide may be used in combination with a Type 1 oligonucleotide with an opposite orientation.

Example 7

Upstream and Downstream Glycoprotein B Sequence

Further amplification reactions are conducted to obtain additional sequence data. The source for KSHV DNA is Kaposi's Sarcoma tissue, either frozen tissue blocks or paraffin-embedded tissue, prepared according to Example 2, or cell lines developed from a cancer with a KSHV etiology, such as body cavity lymphoma. Also suitable is KSHV that is propagated in culture (Weiss et al.)

The general strategy to obtain further sequence data in the 5' direction of the coding strand is to conduct amplification reactions using the consensus-degenerate (Type 1) oligonucleotide hybridizing upstream from the fragment as the 5' primer, in combination with the closest virus-specific (Type 3) oligonucleotides as the 3' primers. Thus, a first series of amplification cycles are conducted, for example, using FRFDA and TNKYB as the first set of primers. This may optionally be followed by a second series of amplification cycles, conducted, for example, using FRFDA and GLTEB as a second set of primers.

The conditions used are similar to those described in Examples 3 and 4. The reaction is performed in WB4 buffer, using the temperature step-down procedure described in Example 3. After two rounds of amplification, the product is labeled using the last-used virus-specific oligonucleotide (GLTEB, in this case), end-labeled with gamma $^{32}$P-ATP. The labeled product is electrophoresed on 6% polyacrylamide, and a band corresponding to the appropriate size as predicted by analogy with other herpes viruses is excised. After re-amplification, the product is purified, cloned, and sequenced as before. A consensus sequence for the new fragment is obtained by combining results of about three determinations.

In order to obtain further sequence data in the 3' direction of the coding strand, amplifications are conducted using consensus-degenerate (Type 1) oligonucleotides hybridizing downstream from the fragment as the 3' primer, in combination with the closest virus-specific (Type 3) oligonucleotides as the 5' primers. In one example, a first series of amplification cycles are conducted using NVFDB and TVFLA, optionally followed by a second series conducted using NVFDB and SQPVA. Amplification and sequencing is performed as before. The new sequence is used to design further Type 3 oligonucleotides with a sense orientation, which are used with other downstream-hybridizing Type 1 oligonucleotides (such as FREYB and NVFDB) to obtain further sequence data. Alternatively, further sequence data in the 3' direction is obtained using Type 1 oligonucleotides with opposite orientation: for example, two primers are selected from the group of FRFDA, NIVPA, TVNCA, NIDFB, NVFDB, and FREYB; additional primers may be selected for nested amplification.

To obtain sequence data 3' from the most downstream oligonucleotide primer, Type 1 primers such as CYSRA, or Type 3 primers such as TVFLA, may be used in combination with primers hybridizing towards the 5' end of the DNA polymerase gene. Oligonucleotide primers hybridizing to the DNA polymerase gene of herpes viruses related to RFHV and KSHV are described in commonly owned U.S. patent application Ser. No. 60/001,148. The DNA polymerase encoding region is located 3' to the Glycoprotein B encoding region. PCRs conducted using this primer combination are expected to amplify polynucleotides comprising the 3' end of the Glycoprotein B encoding region, any intervening sequence if present, and the 5' end of the DNA Polymerase encoding region.

This strategy was implemented as follows:

DNA containing KSHV encoding sequences for Glycoprotein B was prepared from a frozen Kaposi's sarcoma sample, designated RiGr, and a cell line derived from a body cavity lymphoma, designated BC-1.

In order to obtain the full 5' sequence, a Type 1 oligonucleotide probe was designed for the encoding sequence suspected of being upstream of Glycoprotein B: namely, the capsid maturation gene (CAPMAT). Known sequences of CAPMAT from other viruses were used to identify a relatively conserved region, and design a consensus-degenerate primer designated FENSA to hybridize with CAPMAT in the sense orientation of Glycoprotein B. A Type 1 oligonucleotide probe was designed for the encoding sequence suspected of being downstream of Glycoprotein B: namely, the DNA polymerase. These oligonucleotides are listed in Table 9:

TABLE 9

Additional Type 1 Oligonucleotides used for Detecting, Amplifying, or Characterizing Herpes Virus Polynucleotides

| Desig-nation | Sequence (5' to 3') | Length | No. of forms | Orien-tation | SEQ ID: |
|---|---|---|---|---|---|
| Target: Capsid/Maturation gene from Herpes Viruses, especially from gamma Herpes Viruses | | | | | |
| FENSAC | GCCTTTGAGAATTCYAARTAYATHAAR | 27 | 48 | sense | 77 |
| FENSAG | GGGUTGAGAAUCYAARTAYATHAAR | 27 | 48 | sense | 78 |
| Target: DNA polymerase gene from Herpes Viruses, especially from gamma Herpes Viruses | | | | | |
| CVNVB | TAAAAGTACAGCTCCTGCCCGAANACRTTNAC RCA | 35 | 64 | antisense | 79 |

Amplification was carried out using pairs of sense and antisense primers that covered the entire Glycoprotein B encoding region. Fragments obtained include those listed in Table 10.

TABLE 10

KSHV Glycoprotein B fragments obtained

| | Fragment | Length | Position |
|---|---|---|---|
| 1 | NIVPA → TVNCB | 0.39 kb | original fragment |
| 2 | FENSA → VNVNB | 0.9 kb | 5' of fragment 1 across to CAPMAT |
| 3 | TVNCA → FREYB | 2.3 kb | 3' of fragment 1' |
| 4 | FAYDA → FREYB | 0.65 kb | 3' of fragment 1 |
| 5 | SQPVA → HVLQB | 2.5 kb | 3' of fragment 1 across to DNA polymerase |
| 6 | FREYA → SCGFB | 1.1 kb | 3' of fragment 2 across to DNA polymerase |

The protocol used for amplifying and sequencing was as follows: PCR amplification was carried out using the DNA template with the primer pair (e.g., FREYA and SCGFB). 35 cycles were conducted of 94° C. for 45 sec. 60° C. for 45 sec. and 72° C. for 45 sec; and then followed by a final extension step at 72° C. for 10 min. PCR products of the predicted length were purified on agarose gels using the QIAQUICK™ PCR purification kit from Quiagen. Purified PCR products were reamplified in a second round of amplification. The second round was conducted alternatively in a nested or non-nested fashion. In the example given, second-round amplification was conducted using FREYA and SCGFB, or with FREYA and HVLQB. Amplification for 35 cycles was conducted at 94° C. for 45 sec, 65° C. for 45 sec, and 72° C. for 45 sec; and then followed by a final extension step at 72° C. for 60 min.

The PCR products were ligated into the Novagen PT7 BLUE™ vector, and transformed into Novablue competent *E. coli.* Ligations and transformations were performed using Novagen protocols. Colonies were screened by PCR using M13 forward and reverse oligonucleotides. Using the Quiaquick plasmid isolation kit, plasmids were isolated from PCR positive colonies that had been grown up overnight in 5 mL LB broth at 37° C. Manual sequencing of the plasmids using M13 forward and reverse sequencing primers was performed following the USB Sequenase Kit protocol (USB). Automated sequencing was performed by ABI methods.

Additional KSHV-specific Type 3 oligonucleotides were designed as the KSHV sequence emerged. Type 3 oligonucleotides were used in various pair combinations or with Type 1 oligonucleotides to PCR amplify, clone, and sequence sections of the KSHV DNA. The Type 3 oligonucleotides used are listed in Table 11:

TABLE 11

Additional Type 3 Oligonucleotides used for Detecting, Amplifying, or Characterizing Herpes Virus Polynucleotides encoding Glycoprotein B

| Desig-nation | Sequence (5' to 3') | Length | No. of forms | Orientation | SEQ ID: |
|---|---|---|---|---|---|
| Target: Glycoprotein B from KSHV | | | | | |
| GAYTA | TGTGGAAACGGGAGCGTACAC | 21 | 1 | sense | 80 |
| DTYSB | TCAGACAAGAGTACGTGTCGG | 21 | 1 | anti-sense | 81 |
| AIYGB | TACAGGTCGACCGTAGATGGC | 21 | 1 | ariti-sense | 82 |
| VTECA | CGCCATTTCCGTGACCGAGTG | 21 | 1 | sense | 83 |
| CEHYB | TGATGAAGTAGTGTTCGCAGG | 21 | 1 | anti-sense | 84 |
| DLGGB | GATGCCACCCAGGTCCGCCAC | 21 | 1 | anti-sense | 85 |
| DLGGA | GTGGCGGACCTGGGTGGCATC | 21 | 1 | sense | 86 |
| RAPPA | CGTAGATCGCAGGGCACCTCC | 21 | 1 | sense | 87 |
| Target: DNA Polymerase from KSHV | | | | | |
| GEVFB | GTCTCTCCCGCGAATACTTCT | 21 | 1 | antisense | 88 |
| HVLQB | GAGGGCCTGCTGGAGGACGTG | 21 | 1 | antisense | 89 |
| SCGFB | CGGTGGAGAAGCCGCAGGATG | 21 | 1 | antisense | 90 |

Figure 18:
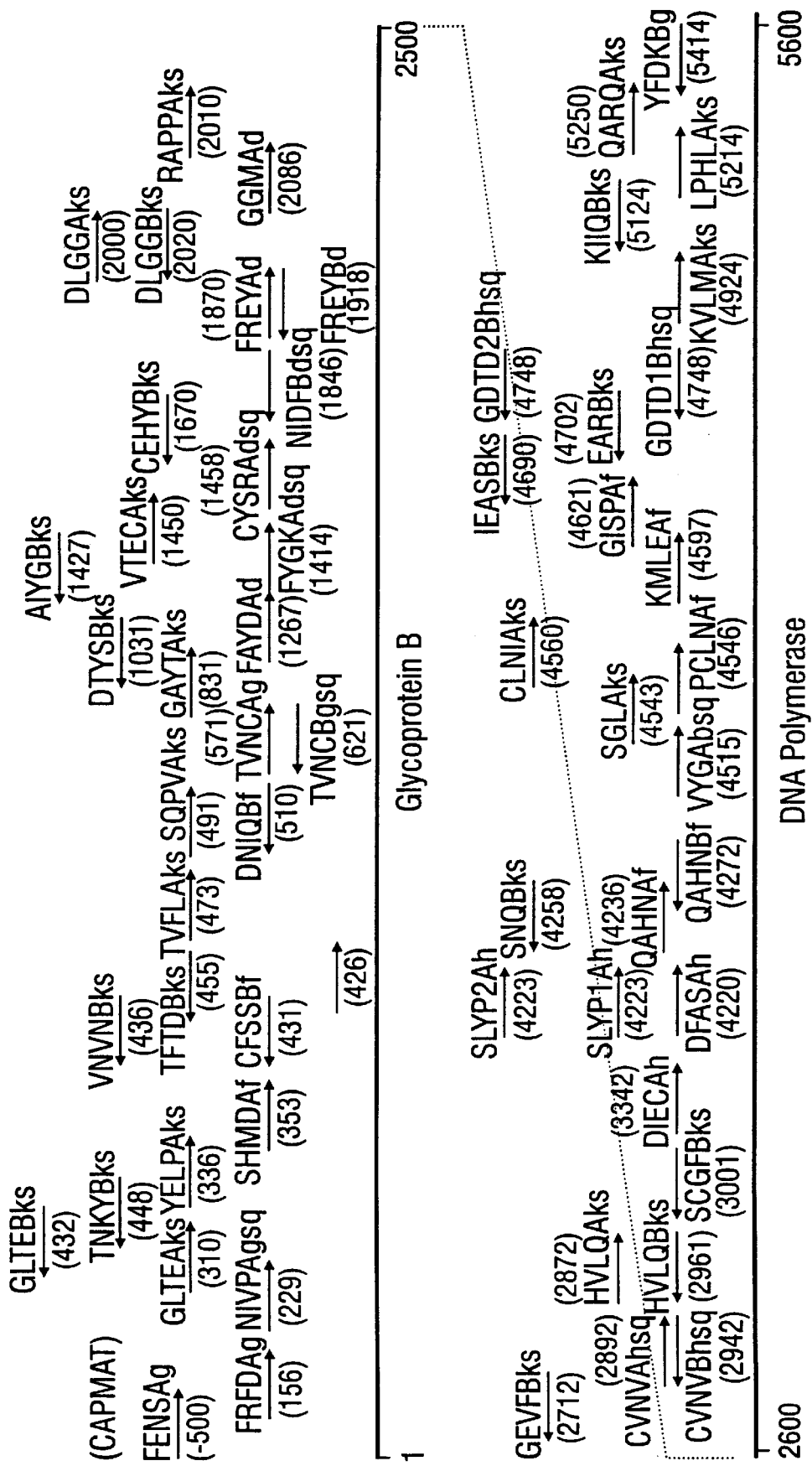
FIG. 18 is an approximate map of Glycoprotein B and DNA polymerase encoding regions as they appear in the KSHV genome, showing the hybridization position of oligonucleotide primers.

FIG. 18 is a map showing the location where oligonucleotides hybridize with the KSHV DNA. Abbreviations used are as follows: d or h=consensus-degenerate probes that hybridize with herpesvirus sequences (Type 1), sq=additional sequencing tail available, g=probes that hybridize with gamma herpesviruses (Type 1), f=probes that hybridize with KSHV/RFHV family of herpesviruses (Type 2), ks=probes specific for KSHV (Type 3).

FIG. 19 lists a consensus sequence obtained by compiling sequence data from each of the characterized fragments. The polynucleotide sequence (SEQ. ID NO:91) is shown. Nucleotides 1–3056 (SEQ. ID NO:92) incorporating the region before the DNA polymerase encoding sequence is an embodiment of this invention. This consensus sequence represents the consensus of data obtained from both the Kaposi's5 sarcoma sample RiGr, and the lymphoma cell line BC-1, with a plurality of clones being sequenced for each sample and each gene segment. Between about 3–9 determinations have been performed at each location.

Also shown in FIG. 19 is the amino acid translation of the three open reading frames (SEQ. ID NOS:93–95). The encoded CAPMAT protein fragment (SEQ. ID NO:93) overlaps the 5' end of the Glycoprotein B encoding sequence (SEQ. ID NO:94) in a different phase. Further upstream, the CAPMAT encoding sequence is also suspected of comprising control elements for Glycoprotein B transcription, due to homology with the binding site for RNA polymerase 2 of Epstein Barr Virus. This putative promoter region is underlined in the Figure. At the 3' end of the Glycoprotein B encoding sequence, there is an untranslated sequence including a polyadenlyation signal. Further downstream is the encoding sequence for a DNA Polymerase fragment (SEQ. ID NO:95).

When the Glycoprotein B encoding sequence was compared with other sequences on GenBank, homology was found only with Glycoprotein B sequences from other herpes viruses. Occasional sequences of 20 nucleotides or less are shared with several herpes viruses. The sequence ATGTTCAGGGAGTACAACTACTACAC (SEQ. ID NO:98) is shared with eHV2. Other than this sequence, segments of the KSHV encoding region 21 nucleotides or longer are apparently unique, compared with other previously known sequences.

Within the Glycoprotein B encoding sequence, four allelic variants were noted at the polynucleotide level between sequence data obtained using the Kaposi's sarcoma sample and that obtained using the body cavity lymphoma cell line. These are indicated in the Figure by arrows. All but one of the variants was silent. The fourth variant causes a difference of Proline to Leucine in the gene product.

The protein product encoded by the KSHV Glycoprotein B gene has the following features: There is a domain at the N-terminus that corresponds to the signal-peptide domain (the "leader") of Glycoprotein B other herpes viruses. The complete KSHV Glycoprotein B amino acid sequence with that known for other herpes viruses is provided in FIG. 3, and reveals areas of homology. Residues highly conserved amongst herpes virus Glycoprotein B sequences are marked with an asterisk (*). The cysteine residues conserved amongst other herpes virus Glycoprotein B sequences are also present in that of KSHV. In addition, there are two additional cysteines which could form an additional internal disulfide and stabilize the three-dimensional structure (marked by "●"). The KSHV Glycoprotein B sequence also has a predicted membrane-spanning domain that corresponds to that on Glycoprotein B of other herpes viruses.

Another feature of the KSHV Glycoprotein B is the presence of an RGD triplet near the N-terminal of the mature protein. The same triplet is present in proteins such as fibrinogen, fibronectin, vitronectin, thrombospondin, osteopontin, and laminin, and has been shown to direct binding of these proteins to cell surfaces via integrin receptors. The RGD domain of lamanin has been shown to bind to endothelial cells and binding of laminin mediates differentiation and the production of capillary-like structures in vitro (Grant et al.). RGD domains are part of the cell adhesion sites of fibronectin and vitronectin (Ruoslahti et al., Humphries et al.).

The upper panel of FIG. 24 provides a comparison of the RGD domain in the KSHV Glycoprotein B protein sequence with other known RGD sequences. The residues flanking the RGD triplet show some similarity between the proteins. In particular, a number of the sequences have serine (S) and threonine (T) residues immediately flanking the RGD triplet, other T, S, F, and P residues to the C-terminal side, and a C residue in the N-terminal direction.

The lower panel of FIG. 24 shows an alignment of the KSHV Glycoprotein B protein sequence with the Glycoprotein B sequence of other gamma herpes viruses. Potential peptidase cleavage sites for the KSHV protein are indicated, based on the possession of cleavage sites in the other sequences. The RGD triplet is located about 3–9 residues from the expected N-terminus of the mature protein. There is no RGD sequence present in the Glycoprotein B of gamma herpes viruses outside the RFHV/KSHV subfamily. If the triplet mediates the infectivity or pathology of the KSHV virus, this property may be unique in comparison to viruses outside the subfamily.

The presence of an RGD domain at the N-terminus of the KSHV glycoprotein B suggests that the domain mediates attachment of KSHV to cells containing an appropriate integrin receptor, such as B-lymphocytes and endothelial cells, leading to infection of these cells. It is also possible that the domain mediates the differentiation of infected endothelial cells into capiflary-like structures that are characteristic of Kaposi's sarcoma lesions. Blocking the attachment of KSHV to cells through the Glycoprotein B RGD domain may inhibit infection, tumor formation, or angiogenesis.

The RGD triplet in Glycoprotein B is potentially important in therapeutic approaches to KSIV infection in several respects. In one example, it may be of benefit to develop vaccines that are based on or enriched for Glycoprotein B peptides that incorporate the RGD sequence. Using a KSHV peptide of 7–20 amino acids encompassing this region, enough immunogenicity may be present to elicit antibodies for which the RGD would be part of the triplet. Circulating antibodies with this specificity may rapidly sequester the RGD site, and decrease any ability of this region to participate in viral infectivity or pathology.

In another example, peptides based on the KSHV Glycoprotein B sequence and including the RGD triplet may also inhibit viral infectivity or pathology, and could be administered immediately to counter an acute exposure. To the extent that binding to the RGD receptor also depends on residues in the ligand that neighbor the RGD triplet, the inhibition may be somewhat selective for KSHV virus in comparison with other RGD-bearing substances.

The full glycoprotein B sequence of RFHV is obtained by a similar strategy to that used for obtaining the KSHV sequence. The source for RFHV DNA is similarly prepared tissue from infected monkeys at the University of Washington Regional Primate Research Center. DNA is extracted as described in Example 5.

In order to obtain further sequence data in the 5' direction of the coding strand, amplifications are conducted using the consensus-degenerate (Type 1) oligonucleotide hybridizing upstream from the fragment as the 5' primer, in combination with the closest virus-specific (Type 3) oligonucleotides as the 3' primers. Thus, a first series of amplification cycles are conducted, for example, using FRFDA and AAITB as the first set of primers. This is followed by a second series of amplification cycles, conducted the same primers, or using the nested set FRFDA and GMTEB. Amplification conditions are similar to those described for KSHV.

In order to obtain further sequence data in the 3' direction of the coding strand, amplifications are conducted using consensus-degenerate (Type 1) oligonucleotides hybridizing downstream from the fragment as the 3' primer, in combination with the closest virus-specific (Type 3) oligonucleotides as the 5' primers. Thus, a first series of amplification cycles are conducted using NVFDB and VEGLA, followed by a second series conducted using NVFDB and PVLYA. Amplification and sequencing is performed as before. The new sequence is used to design further Type 3 oligonucleotides with a sense orientation, which are used with other downstream-hybridizing Type 1 oligonucleotides (namely FREYB and NVFDB) to obtain further sequence data.

Polynucleotide and amino acid sequence data is used to compare the Glycoprotein B of RFHV and KSHV with each other, and with that of other herpes viruses. The RFHV and KSHV sequences may be used to design further subfamily-specific Type 2 oligonucleotides, as in Example 6.

Example 8: Glycoprotein B sequences from DNA libraries

Complete Glycoprotein B sequences can be obtained or confirmed by generating DNA libraries from affected tissue. Sources of DNA for this study are the same as for Example 7.

The DNA lysate is digested with proteinase K, and DNA is extracted using phenol-chloroform. After extensive dialysis, the preparation is partially digested with the Sau3A I restriction endonuclease. The digest is centrifuged on a sucrose gradient, and fragments of about 10–23 kilobases are recovered. The lambda DASH-2™ vector phage (Stratagene) is prepared by cutting with BamHI. The size-selected fragments are then mixed with the vector and ligated using DNA ligase.

The ligated vector is prepared with the packaging extract from Stratagene according to manufacturer's directions. It is used to infect XL1-BLUE™ MRA bacteria. About 200,000 of the phage-infected bacteria are plated onto agar at a density of about 20,000 per plate. After culturing, the plates are overlaid with nitrocellulose, and the nitrocellulose is cut into fragments. Phage are eluted from the fragments and their DNA are subjected to an amplification reaction using appropriate virus-specific primers. The reaction products are run on an agarose gel, and stained with ethidium bromide. Phage are recovered from regions of the plate giving amplified DNA of the expected size. The recovered phage are used to infect new XL1 bacteria and re-plated in fresh cultures. The process is repeated until single clones are obtained at limiting dilution.

Each clone selected by this procedure is then mapped using restriction nucleases to ascertain the size of the fragment incorporated. Inserts sufficiently large to incorporate the entire Glycoprotein B sequence are sequenced at both ends using vector-specific primers. Sequences are compared with the known polynucleotide sequence of the entire EBV genome to determine whether the fragment spans the intact Glycoprotein B sequence. DNA is obtained from suitable clones, sheared, and sequenced by shot-gun cloning according to standard techniques.

Example 9: Antigenic regions of Glycoprotein B

The polynucleotide fragments between the hybridization sites for NIVPA and TVNCB in the Glycoprotein B gene have the predicted amino acid sequences shown in FIG. 14. Based on these sequences, peptides that are unique for RFHV or KSHV, or that are shared between species can be identified.

FIG. 14 shows example peptides of 6 or 7 amino acids in length. Some of the peptides comprise one or more residues that are distinct either for RFHV or KSHV (Class III), or for the RFHV/KSHV subfamily (Class II) compared with the corresponding gamma herpes virus peptides.

To confirm that regions contained within this 106-amino acid region of Glycoprotein B may be recognized by antibody, computer analysis was performed to generate Hopp and Woods antigenicity plots. The Hopp and Woods determination is based in part on the relative hydrophilicity and hydrophobicity of consecutive amino acid residues (Hopp et al).

Figure 20:
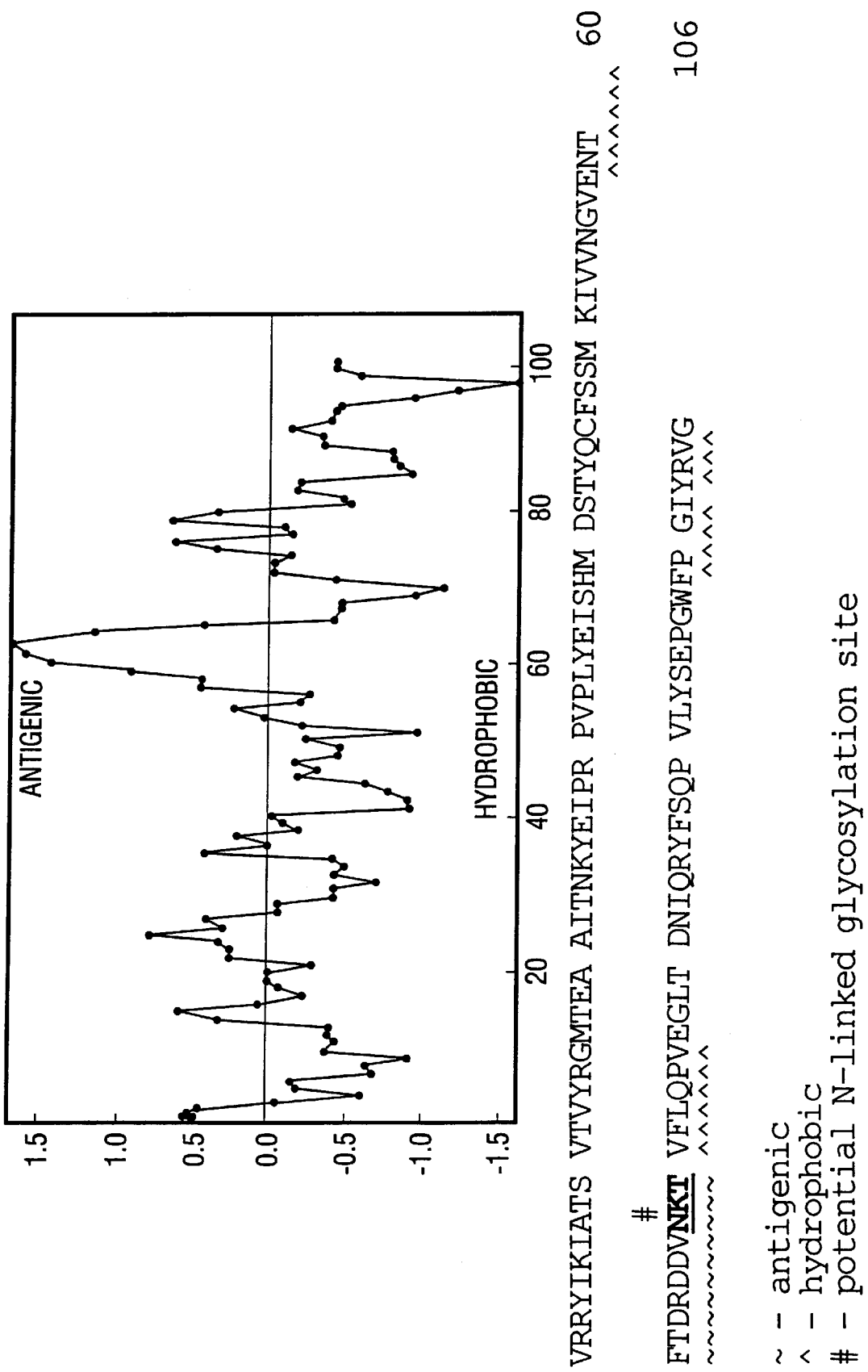
FIG. 20 is a Hopp-Woods antigenicity plot for the 106 nucleotide Glycoprotein B polypeptide fragment of RFHV encoded between NIVPA and TVNCB. Indicated below are spans of hydrophobic and antigenic residues in the sequence.
Figure 21:
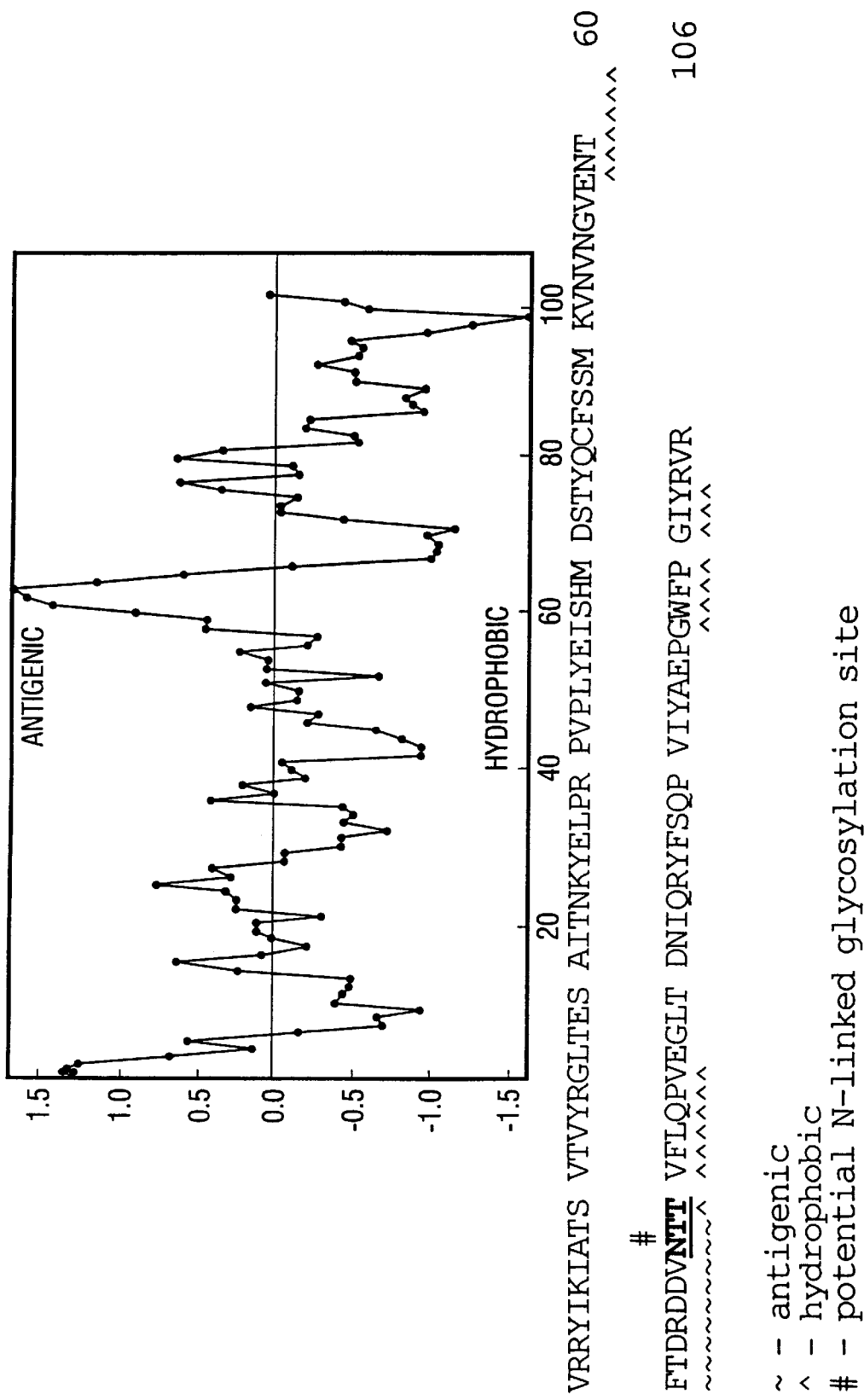
FIG. 21 is a Hopp-Woods antigenicity plot for the 106 nucleotide Glycoprotein B polypeptide fragment of KSHV encoded between NIVPA and TVNCB.
Figure 22:
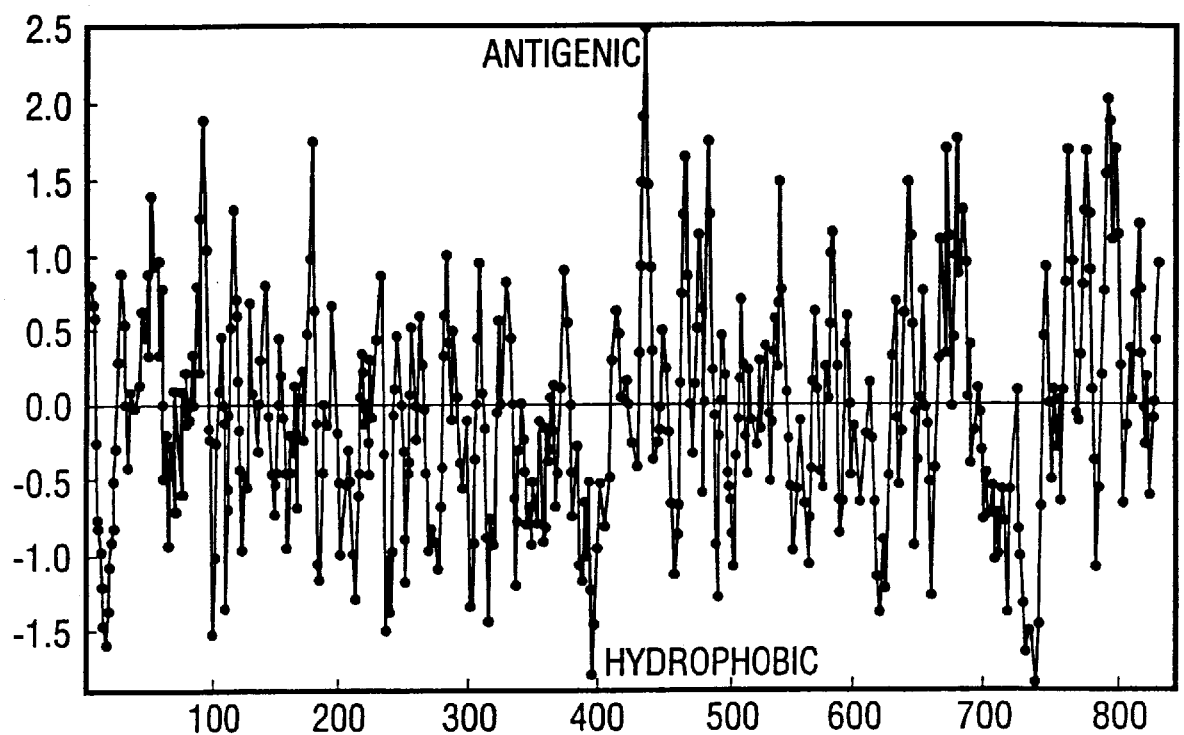
FIG. 22 is a Hopp-Woods antigenicity plot for the complete Glycoprotein B from KSHV.

Results are shown in FIGS. 20, 21 and 22. Key: ~=antigenic; ^=hydrophobic; #=potential N-linked glycosylation site. FIG. 20 shows the analysis of the 106 amino acid Glycoprotein B fragment from RFHV; FIG. 21 shows the analysis of the KSHV fragment, and FIG. 22 shows the analysis of the full KSHV sequence.

Both RFHV and KSHV contain several regions predicted to be likely antibody target sites. In particular, the KSHV sequence shows an antigenic region near the N-terminal end of this fragment, and near the potential N-linked glycosylation site. The full-length KSHV sequence shows hydrophobic minima corresponding both to the signal peptide (residue ~25) and the transmembrane domain (residue ~750). A number of putative antigenic regions with scores >1.0 or >1.5 are observed. Particularly notable is a region scoring up to ~2.5 that appears at about residues 440–460.

Example 10: Virus specific Glycoprotein B amplification assays

Type 3 oligonucleotides are used in nested virus-specific amplification reactions to detect the presence of RFHV or KSHV in a panel of tissue samples from potentially affected subjects.

For KSHV, DNA is extracted from tissue suspected of harboring the virus; particularly biopsy samples from human subjects with Kaposi's Sarcoma lesions and body cavity B-cell lymphoma. A number of different tissue samples are used, including some from KS lesions, some from apparently unaffected tissue in the same individuals, some from HIV positive individuals with no apparent KS lesions, and some from HIV negative individuals. Five samples are obtained in each category. DNA is prepared as described in Example 2.

The oligonucleotide primers GLTEA, YELPA, VNVNB, and ENTFB are ordered from Oligos Etc., Inc. The DNA is amplified in two stages, using primers GLTEA and ENTFB in the first stage, and YELPA and VNVNB in the second stage. The conditions of the amplification are similar to those of Example 3. The reaction product is electrophoresed on a 2% agarose gel, stained with ethidium bromide, and examined under U.V. light. A positive result is indicated by the presence of abundant polynucleotide in the reaction product, as detected by ethidium bromide staining. This reflects the presence of KSHV derived DNA in the sample; specifically, the Glycoprotein B encoding fragment from YELPA to VNVNB. Results are matched with patient history and sample histopathology to determine whether positive assay results correlate with susceptibility to KS.

For RFHV, DNA is extracted from frozen tissue samples taken from Macaca nemestrina and Macaca fascicularis monkeys living in the primate colony at the Washington Regional Primate Research Center. Ten samples are taken each from tissue sites showing overt symptoms of fibromatosis, apparently unaffected sites in the same monkeys, and corresponding sites in monkeys showing no symptomatology. Nested PCR amplification is conducted first using GMTEA and VEGLB, then using KYEIA and TDRDB. Amplification product is electrophoresed and stained as before, to determine whether RFHV polynucleotide is present in the samples.

Example 11: Immunogenic regions of Glycoprotein B

To identify what antibodies may be generated during the natural course of infection with KSHV, serum samples are obtained from 10–20 AIDS subjects with Kaposi's Sarcoma lesions, from 10–20 HIV-positive symptom-negative subjects, and 10–20 HIV-negative controls. In initial studies, sera in each population are pooled for antibody analysis.

Peptides 12 residues long are synthesized according to the entire predicted extracellular domain of the mature KSHV Glycoprotein B molecule. Sequential peptides are prepared covering the entire sequence, and overlapping by 8 residues. The peptides are prepared on a nylon membrane support by standard F-Moc chemistry, using a SPOTS™ kit from Genosys according to manufacturer's directions. Prepared membranes are overlaid with the serum, washed, and overlaid with beta-galactose conjugated anti-human IgG. The test is developed by adding the substrate X-gal. Positive staining indicates IgG antibody reactivity in the serum against the corresponding peptide.

Similarly, to identify antibodies formed in the natural course of RFHV infection, blood samples are collected from 10 Macaca nemestrina and 10 Macaca fascicularis monkeys, a proportion of which display overt symptoms of fibromatosis. The presence or absence of an ongoing RFHV infection is confirmed by conducting PCR amplification assays using RFHV-specific oligonucleotides as in Example 10. Plasma and blood cells are separated by centrifugation. These sera are used to test for antibodies in a method similar to that for KSHV, except that 12-mers are synthesized based on the RFHV Glycoprotein B sequence.

Select RFHV and KSHV peptides are also tested in animal models to determine immunogenicity when administered in combination with desirable adjuvants such as alum and DETOX™. Suitable peptides include those identified in the aforementioned experiment as eliciting antibody during the natural course of viral infection. Other candidates include those believed to participate in a biological function of Glycoprotein B, and those corresponding to peptides of other herpes viruses known to elicit viral neutralizing antibodies. The peptides are coupled onto keyhole limpet hemocyanin (KLH) as a carrier, combined with adjuvant according to standard protocols, and 100 μg peptide equivalent in 1–2 mL inoculum is injected intramuscularly into rabbits. The animals are boosted with a second dose 4 weeks later, and test-bled after a further 2 weeks.

Microtiter plate wells are prepared for ELISA by coating with the immunogen or unrelated peptide-KLH control. The wells are overlaid with serial dilutions of the plasma from the test bleeds, washed, and developed using beta-galactose anti-human IgG and X-gal. Positive staining in the test wells but not the control wells indicates that the peptide is immunogenic under the conditions used.

Example 12: Identification and characterization of Glycoprotein B from other members of the RFHV/KSHV subfamily Tissue samples suspected of containing a previously undescribed gamma herpes virus, particularly fibroproliferative conditions, lymphocyte malignancies, and conditions associated with immunodeficiency and immunosuppression, such as acute respiratory disease syndrome (ARDS), are preserved by freezing, and the DNA is extracted as in Example 2. Two rounds of PCR amplification are conducted using Type 1 oligonucleotides FRFDA and TVNCB in the first round, then using nested Type 1 or Type 2 oligonucleotides in the second round.

Optionally, the presence of an RFHV/KSHV family Glycoprotein B polynucleotide is confirmed by probing the amplification product with a suitable probe. The amplified polynucleotide is electrophoresed in agarose and blotted onto a nylon membrane. The blot is hybridized with a probe comprising the polynucleotide fragment obtained from the KSHV polynucleotide encoding Glycoprotein B (residues 36–354 of SEQ. ID NO:3), labeled with $^{32}P$. The hybridization reaction is done under conditions that will permit a stable complex forming between the probe and Glycoprotein B from a herpes virus, but not between the probe and Glycoprotein B encoding polynucleotides from sources outside the RFHV/KSHV subfamily. Hybridization conditions will require approximately 70% identity between hybridizing segments of the probe and the target for a stable complex to form. These conditions are calculated using the formula given earlier, depending on the length and sequence of the probe and the corresponding sequence of the target. The conditions are estimated to be: a) allowing the probe to hybridize with the target in 6×SSC (0.15M NaCl, 15 mM sodium citrate buffer) at room temperature in the absence of formamide; and b) washing newly formed duplexes for a brief period (5–10 min) in 2×SSC at room temperature.

Amplified polynucleotides that hybridize to the labeled probe under these conditions are selected for further characterization. Alternatively, PCR amplification products having about the same size as that predicted from the KSHV are suspected of having a related sequence. Samples may also be suspected of having a related sequence if they have been used to obtain polynucleotides encompassing other regions of a herpes virus genome, such as DNA polymerase. Samples containing fragments potentially different from RFHV or KSHV, either due to a size difference or different origin, are sequenced across the fragment as in Example 4. Those with novel sequences are used to determine the entire Glycoprotein B gene sequence by a method similar to that in Example 7 or 8.

A Glycoprotein B encoding sequence from a third member of the RFHV/KSHV herpes virus subfamily was obtained as follows.

DNA was extracted from two frozen tissue samples from a *Macaca mulatta* monkey with retroperitoneal fibromatosis. Extraction was conducted according to Example 1. The extracted DNA was precipitated with ethanol in the presence of 40 μg glycogen as carrier, washed in 70% ethanol, and resuspended in 10 mM Tris buffer, pH 8.0. The extracted DNA was used to obtain a 151 base pair fragment of a herpes virus DNA polymerase gene, which was non-identical to that of KSHV, RFHV, or any other previously characterized DNA polymerase. This lead to the suspicion that the sample contained genomic DNA from a different herpes virus, that could be used to identify and characterize a new Glycoprotein B gene.

A 386 base pair fragment of a Glycoprotein B encoding sequence was amplified from the sample using a heminested PCR. The procedure was similar to that used in Examples 4 and 5, with a first round of amplification using FRFDA and TVNCB, followed by a second round of amplification using NIVPA and TVNCB. The final PCR product was sequenced as before.

FIG. 23 lists the polynucleotide sequence (SEQ. ID NO:96) along with the corresponding amino acid translation (SEQ. ID NO:97). Underlined is the 319 base pair sequence in between the two primer hybridization sites. The sequences are different from those of KSHV and RFHV. The Glycoprotein B is from a new member of the RFHV/KSHV subfamily of herpes viruses, designated RFHV2.

REFERENCES:

Altschul et al. (1986). *Bull. Math. Bio.* 48:603–616.
Ambroziuk et al. (1995). *Science* 268:582–583.
A. M. Eis-Hubinger et al. (1993). *J. Gen. Virol.* 74:379–385.
Baghian A. et al. (1993). *J. Virol.* 67:2396–2401.
Basco et al. (1992). *J. Biol. Chem.* 267:19427–19434.
Basco et al. (1993). *Chromosoma* 102:32–38.
Beaucage et al. (1981). *Tetra. Lett.* 22:1859–1862.
Berel V. et al. (1990). *Lancet* 335:123–128.
Bernard et al. (1989). *Cell* 59:219–228.
Bernard et al. (1990). *Proc. Natl. Acad. Sci. USA* 87:4610–4614.
Boshoff et al. (1995). *Nature Medicine* 1:1274–1278.
Byrne K. M. et al. (1995). *Virology* 290:230–235.
Cantin E. M. et al. (1987). *Proc. Natl. Acad. Sci. USA* 84:5908–5912.
Cesarman E. et al. (1995). *New Engl. J. Med.* 332:1186–1191.
Chang Y. et al. (1994). *Science* 266:1865–1869.
Demotz S. et al. (1989). *J. Immunol. Methods* 122:67–72.
Derbyshire et al. (1991). *EMBO J.,* 10:17–24.
Digard P. et al. (1995). *Proc. Natl. Acad. Sci. USA* 92:1456–1460.
Dorsky D. I. et al. (1988). *J. Virol.* 62:3224–3232.
Dorsky D. I. et al. (1990). *J. Virol.* 64:1394–1397.
Dupin N. et al. (1995). *New Engl. J. Med.* 333:798.
Emery V. C. et al. (1992). pp. 257–277 in *Molecular and Cell Biology of Opportunistic Infections in AIDS;* S. Myint & A. Cann, eds, Chapman & Hall.
Erickson et al. (1990). *Science* 249:527–533.
Fields B. N. & Knipe D. M., eds. (1991). *Fundamental Virology,* 2nd Edition, Raven Press.
Finesmith T. H. et al. (1994). *Int. J. Dermatol.* 33:755–762.
Gage P. J. et al. (1993). *J. Virol.* 67:2191–2201.
Gao S. J. et al. (1996). *New Engl. J. Med.* 335:233–241.
Gibbs J. S. et al. (1988a). *Proc. Natl. Acad. Sci. USA* 85:6672–6676.
Gibbs J. S. et al. (1988b). *Proc. Natl. Acad. Sci. USA* 85:7969–7973.
Giddens W. E. Jr. et al. (1983). pp. 249–253 in *Viral and Immnunological Diseases in Nonhuman Primates;* Alan R. Liss Inc.
Glorioso J. C. et al. (1994). *Dev. Biol. Stand* 82:79–87.
Haanes E. J. et al. (1994). *J. Virol.* 68:5825–5834.
Haffey M. L. et al. (1988). *J. Virol.* 62:4493–4498.
Hall J. D. et al. (1989). *Nucl. Acids Res.* 17:9231–9244.
Hanke T. et al. (1991). *J. Virol.* 65:1177–1186.
Henikoff et al. (1992) *Proc. Natl. Acad. Sci. USA* 89:10915–10919.
Herold B. C. et al. (1994). *J. Gen. Virol.* 75:1211–1222.
Hirose et al. (1978). *Tetra. Lett* (1978) 19:2449–2452.
Hodgson (1991). *Bio/Technology* 9:19–21.
Horn et al. (1995). *Human Gene Therapy* 6:565–573.
Hopp T. P. et al. (1981). *Proc. Natl. Acad. Sci. USA* 78:3824–3828.
Johnson P. A. et al. (1994). *Methods Cell Biol.* 43A: 191–210.
Karlin S. et al. (1994). *J. Virol.* 68:1886–1902.
Kedes D. H. et al. (1996). *Nature Medicine* 2:918–924.
Knopf C. W. et al. (1988). *Biochim. Biophys. Acta* 951:298–314.
Kostal M. et al. (1994). *Acta Virologica* 38:77–88.
Kumar et al. (1984). *J. Org. Chem.* 49:4905–4912.
Larder B. A. et al. (1987). *EMBO J.* 6:169–175.
Latchman D. S. et al. (1994). *Molec. Biotechnol.* 2:179–195.
Lin L. S. et al. (1995). *J. Med. Virol.* 45:99–105.
Lisitsyn N. et al. (1993). *Science* 259:946.
Liu M. Y. et al. (1989). *J. Med Virol.* 28:101–105.
Liu Y. N. C. et al. (1993). *J. Gen. Virol.* 74:2207–2214.
Manservigi R. et al. (1990). *J. Virol.* 64:431–436.
Marcy A. I. et al. (1990). *J. Virol.* 64:5883–5890.
Martin R. W. et al. (1993). *Medicine* 72:245–26.
McDermott M. R. et al. (1989). *Virology* 169:244–247.
Meier J. L. et al. (1993). *J. Virol.* 67:7573–7581.
Meinkoth J. et al. (1984). *Anal. Biochem.* 138:267.
Mester J. C. et al. (1990). *J. Virol.* 64:5277–5283.
Miles S. A. (1994). *Curr. Opin. Oncol.* 6:497–502.
Miller G. (1996). *New Engl. J. Med.* 334:1292–1297.
Mitsuyasu R. T. (1993). *Curr. Opin. Oncol.* 5:835–844.
Moore P. S. et al. (1995a). *New Engl. J. Med.* 332:1181–1185.
Moore P. S. et al. (1995b). *New Engl. J. Med.* 333:798–799.
Moore P. S. et al. (1996). *J. Virol.* 70:549–558.
Navarro D. et al. (1991). *Virology* 184:253–264.
Navarro D. et al. (1992). *Virology* 186:99–112.
Northfelt. D. W. (1994). *Drugs* (New Zealand) 48:569–582.
Nugent C. T. et al. (1994). *J. Virol.* 68:7644–7648.
O'Donnell C. A. et al. (1991). *Clin. exp. Immunol.* 86:30–36.
O'Donnell M. E. et al. (1987). *J. Biol. Chem.* 262:4252–4259.
O'Leary J. J. (1996). *Nature Medicine* 2:862–863.
Padlan E. A. (1991). *Molec. Immunol.* 28:489–494.
Pellett P. E. et al. (1985). *J. Virol.* 53:243–253.
Pereira L. (1994). *Infect. Agents Dis.* 3:9–28.
Qadri I. et al. (1991). *Virology* 180:135–152.
Reardon J. E. et al. (1989). *J. Biol. Chem.* 264:7405–7411.
Reschke M. et al. (1995). *J. Gen. Virol.* 76:113–122.
Sanchez-Pescador L. et al. (1992). *J. Infec. Dis.* 166:623–627.
Schumacher T. N. et al. (1992). *Eur. J. Immunol.* 22:1405–1412.
Shiu S. Y. W. et al. (1994). *Arch. Virol.* 137:133–138.
Simon et al. (1991). *EMBO J.* 10:2165–2171.
Soengas et al. (1992). *EMBO J.* 11:4227–4237.
Stow N. D. (1993). *Nucl. Acids Res.* 21:87–92.
Tsai C. C. et al. (1986). *Lab. Animal Sci.* 36:119–124.
VanDevanter et al. (1996). *J. Clin. Microbiol.* 34:1666–1671.
Wang T. S. F. et al. (1989). *FASEB J.* 3:14–21.

Ward P. L. et al. (1994). *Trends Genet.* 10:267–274.
Weiss R. A. et al. (1996). *Nature Medicine* 2:277–278.
Yeung K. C. et al. (1991). *Curr. Eye Res.* 10 (Suppl.) 31–37.
Zhong W. et al. (1996). *Proc. Natl. Acad. Sci. USA* 93:6641–6646.
Grant D. S. et al. (1989). *Cell* 58:933–943.
Huang T. F. et al. (1989). *Biochemistry* 28:661–666.
Humphries M. et al. (1986). *J. Cell Biol.* 103:2637–2647.
Ingber D. E. et al. (1989). *Cell* 58:803–805.
Koller et al. (1989). *EMBO J.* 8:1073–1077.
Maeda T. (1989). *J. Biol. Chem.* 264:15165–15166.
Pytela R. (1988). *EMBO J.* 7:1371–1378.
Ruoslahti E. et al. (1987). *Science* 238:491–497.

| US 4762708 | Cohen et al. | (Gd vaccine) |
|---|---|---|
| US 4415732 | Caruthers M. H. et al. | (polynucleotide synthesis) |
| US 4444887 | Hoffman M. K. | (mAb method) |
| US 4472500 | Milstein C. et al. | (mAb cell) |
| US 4642333 | Person S. | (HSV Gb expression) |
| US 4683195 | Mullis K. B. | (PCR) |
| US 4683202 | Mullis K. B. et al. | (PCR) |
| US 5124246 | Urdea M. S. et al. | (branched DNA) |

-continued

| US 5171568 | Burke R. L. et al. | (HSV Gb/Gd vaccine) |
|---|---|---|
| US 5176995 | Sninsky J. J. et al. | (PCR method for viruses) |
| US 5244792 | Burke R. L. et al. | (HSV Gb expression) |
| US 5350671 | Houghton M. et al | (HCV diagnostics) |
| US 5354653 | Matsumoto T. et al. | (HSV strain probe assay) |
| US 5364773 | Paoletti et al. | (Vaccinia vaccine) |
| US 5384122 | Cunningham et al. | (Herpes L-particle vaccine) |
| US 5399346 | Anderson W. F. et al. | (Assembling defective particles) |
| WO 91/16420 | Blum et al. | (Polymerase mutations) |
| WO 92/05263 | Inglis et al. | (Attentuated herpes) |
| WO 92/16231 | Francotte et al. | (Gd/MPL-A vaccine) |
| WO 94/11509 | Couto et al. | (Humanizing ab) |
| EP 0239400 | Winter | (Humanizing ab) |
| EP 0290197 | Mcaleer et al. | (Live herpes vaccine) |
| JP 5309000 | Iatron Lab Inc. | (PCR assay for EBV POL) |

U.S. provisional Patent Application 60/001,148; and continuation-in-part application filed on Jul. 11, 1996 [Serial No. Pending; Attorney Docket 29938-20001.00]: T. M. Rose, M. Bosch, K. Strand & G. Todaro. "DNA Polymerase of gamma herpes viruses associated with Kaposi's Sarcoma and Retroperitoneal Fibromatosis"

SEQUENCES

| SEQ. ID | Designation | Description | Type | Source |
|---|---|---|---|---|
| 1 | RFHV | Glycoprotein B PCR segment | dsDNA | FIG. 1 |
| 2 | RFHV | Glycoprotein B PCR segment | Protein | FIG. 1 |
| 3 | KSHV | Glycoprotein B PCR segment | dsDNA | FIG. 1 |
| 4 | KSHV | Glycoprotein B PCR segment | Protein | FIG. 1 |
| 5 | sHV1 | Glycoprotein B sequence | dSDNA | GenBank HSVSPOLGBP |
| 6 | bHV4 | Glycoprotein B sequence | dsDNA | GenBank BHT4GLYB |
| 7 | eHV2 | Glycoprotein B sequence | dsDNA | GenBank EHVU20824 |
| 8 | mHV68 | Glycoprotein B sequence | dsDNA | GenBank MVU08990 |
| 9 | hEBV | Glycoprotein B sequence | dsDNA | GenBank EBV |
| 10 | hCMV | Glycoprotein B sequence | dsDNA | GenBank HEHCMVGB |
| 11 | hHV6 | Glycoprotein B sequence | dsDNA | GenBank HH6GBXA |
| 12 | hVZV | Glycoprotein B sequence | dsDNA | GenBank HEVZVXX |
| 13 | HSV1 | Glycoprotein B sequence | dsDNA | GenBank HS1GLYB |
| 14 | sHV1 | Glycoprotein B sequence | Protein | Translation |
| 15 | bHV4 | Glycoprotein B sequence | Protein | Translation |
| 16 | eHV2 | Glycoprotein B sequence | Protein | Translation |
| 17 | mHV68 | Glycoprotein B sequence | Protein | Translation |
| 18 | hEBV | Glycoprotein B sequence | Protein | Translation |
| 19 | hCMV | Glycoprotein B sequence | Protein | Translation |
| 20 | hHV6 | Glycoprotein B sequence | Protein | Translation |
| 21 | hVZV | Glycoprotein B sequence | Protein | Translation |
| 22 | HSV1 | Glycoprotein B sequence | Protein | Translation |
| 23 | sHVSA8 | Glycoprotein B sequence | Protein | Translation |
| 24–40 | | TYPE 1 oligonucleotides (Gamma herpes Glycoprotein B) | ssDNA (IUPAC) | Table 4 |
| 41–47 | | TYPE 2 oligonucleotide (RFHV/KSHV subfamily Glycoprotein B) | ssDNA (IUPAC) | Table 6 |
| 48–55 | | TYPE 3 oligonucleotides - RFHV specific Glycoprotein B | ssDNA | Table 7 |
| 56–63 | | TYPE 3 oligonucleotides - KSHV specific Glycoprotein B | ssDNA | Table 7 |
| 64–66 | | CLASS I antigen peptides (Gamma herpes Glycoprotein B) | Protein | Table 8 |
| 67–72 | | CLASS II antigen peptides (RFHVIKSHV subfamily Glycoprotein B) | Protein | Table 8 |
| 73–74 | | CLASS III antigen peptides- RFHV specific Glycoprotein B | Protein | Table 8 |

SEQUENCES

| SEQ. ID | Designation | Description | Type | Source |
|---|---|---|---|---|
| 75–76 | | CLASS III antigen peptide s-KSHV specific Glycoprotein B | Protein | Table 8 |
| 77–78 | | TYPE 1 oligonucleotide (Gamma herpes Capsid maturation) | ssDNA (IUPAC) | Table 9 |
| 79 | | TYPE 1 oligonucleotide (Gamma herpes DNA

```
Ile Lys Ile Ala Thr Ser Val Thr Val Tyr Arg Gly Met Thr Glu Ala
            20                  25                  30

Ala Ile Thr Asn Lys Tyr Glu Ile Pro Arg Pro Val Pro Leu Tyr Glu
            35                  40                  45

Ile Ser His Met Asp Ser Thr Tyr Gln Cys Phe Ser Ser Met Lys Ile
            50                  55                  60

Val Val Asn Gly Val Glu Asn Thr Phe Thr Asp Arg Asp Asp Val Asn
 65              70                  75                  80

Lys Thr Val Phe Leu Gln Pro Val Glu Gly Leu Thr Asp Asn Ile Gln
                85                  90                  95

Arg Tyr Phe Ser Gln Pro Val Leu Tyr Ser Glu Pro Gly Trp Phe Pro
               100                 105                 110

Gly Ile Tyr Arg Val Gly Thr Thr Val Asn Cys Glu Ile Val Asp Met
               115                 120                 125
```

(2) INFORMATION FOR SEQ ID NO:3:

(i) SEQUENCE CHARACTERISTICS:
        (A) LENGTH: 386 base pairs
        (B) TYPE: nucleic acid
        (C) STRANDEDNESS: double
        (D) TOPOLOGY: linear (xi) SEQUENCE DESCRIPTION: SEQ ID NO:3:

```
GTGTACAAGA AGAACATCGT GCCGTATATT TTTAAGGTGC GGCGCTATAG GAAAATTGCC    60

ACCTCTGTCA CGGTCTACAG GGGCTTGACA GAGTCCGCCA TCACCAACAA GTATGAACTC   120

CCGAGACCCG TGCCACTCTA TGAGATAAGC CACATGGACA GCACCTATCA GTGCTTTAGT   180

TCCATGAAGG TAAATGTCAA CGGGGTAGAA AACACATTTA CTGACAGAGA CGATGTTAAC   240

ACCACAGTAT TCCTCCAACC AGTAGAGGGG CTTACGGATA ACATTCAAAG GTACTTTAGC   300

CAGCCGGTCA TCTACGCGGA ACCCGGCTGG TTTCCCGGCA TATACAGAGT TAGGACAACA   360

GTCAACTGTG AGATTGTAGA CATGTT                                        386
```

(2) INFORMATION FOR SEQ ID NO:4:

(i) SEQUENCE CHARACTERISTICS:
        (A) LENGTH: 128 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

```
Val Tyr Lys Lys Asn Ile Val Pro Tyr Ile Phe Lys Val Arg Arg Tyr
 1               5                  10                  15

Arg Lys Ile Ala Thr Ser Val Thr Val Tyr Arg Gly Leu Thr Glu Ser
            20                  25                  30

Ala Ile Thr Asn Lys Tyr Glu Leu Pro Arg Pro Val Pro Leu Tyr Glu
            35                  40                  45

Ile Ser His Met Asp Ser Thr Tyr Gln Cys Phe Ser Ser Met Lys Val
            50                  55                  60

Asn Val Asn Gly Val Glu Asn Thr Phe Thr Asp Arg Asp Asp Val Asn
 65              70                  75                  80

Thr Thr Val Phe Leu Gln Pro Val Glu Gly Leu Thr Asp Asn Ile Gln
                85                  90                  95

Arg Tyr Phe Ser Gln Pro Val Ile Tyr Ala Glu Pro Gly Trp Phe Pro
               100                 105                 110
```

```
        Gly Ile Tyr Arg Val Arg Thr Thr Val Asn Cys Glu Ile Val Asp Met
            115                 120                 125

(2) INFORMATION FOR SEQ ID NO:5:

(i) SEQUENCE CHARACTERISTICS:
        (A) LENGTH: 2425 base pairs
        (B) TYPE: nucleic acid
        (C) STRANDEDNESS: double
        (D) TOPOLOGY: linear (xi) SEQUENCE DESCRIPTION: SEQ ID NO:5:

ATGGTACCTA ATAAACACTT ACTGCTTATA ATTTTGTCGT TTTCTACTGC ATGTGGACAA      60

ACGACACCTA CTACAGCTGT TGAAAAAAAT AAAACTCAAG CTATATACCA AGAGTATTTC     120

AAATATCGTG TATGTAGTGC ATCAACTACT GGAGAATTGT TTAGATTTGA TTTAGACAGA     180

ACTTGTCCAA GTACTGAAGA CAAAGTTCAT AAGGAAGGCA TTCTTTTAGT GTACAAAAAA     240

AATATAGTTC CATATATCTT TAAAGTCAGA AGATACAAAA AAATCACAAC ATCAGTCCGT     300

ATTTTTAATG GCTGGACTAG AGAAGGTGTT GCTATTACAA ACAAATGGGA ACTTTCTAGA     360

GCTGTTCCAA AATATGAGAT AGATATTATG GATAAGACTT ACCAATGTCA TAATTGCATG     420

CAGATAGAAG TAAACGGAAT GTTAAATTCT TACTATGACA GAGATGGAAA TAACAAAACT     480

GTAGACTTAA AGCCTGTAGA TGGTCTAACG GGTGCAATTA CAAGATACAT TAGCCAACCT     540

AAAGTTTTTG CTGATCCTGG CTGGCTATGG GGAACTTACA GGACTCGAAC TACCGTTAAC     600

TGTGAAATTG TAGACATGTT TGCTAGGTCT GCTGACCCTT ACACATACTT TGTGACTGCG     660

CTTGGCGACA CAGTAGAAGT GTCTCCTTTC TGTGATGTAG ATAATTCATG CCCAAATGCA     720

ACTGACGTGT TGTCAGTACA AATAGACTTA AATCACACTG TTGTTGACTA TGGAAATAGA     780

GCTACATCAC AGCAGCATAA AAAAGAATA TTTGCTCATA CTTTAGATTA TTCTGTTTCT     840

TGGGAAGCTG TAAACAAATC CGCGTCAGTA TGCTCAATGG TTTTTTGGAA GAGTTTTCAA     900

CGAGCTATCC AAACTGAACA TGACTTAACT TATCATTTCA TTGCTAATGA ATAACAGCA     960

GGATTCTCTA CAGTGAAAGA ACCCTTAGCA AATTTTACAA GTGATTACAA TTGTCTTATG    1020

ACTCATATCA ACACTACTTT AGAGGATAAG ATAGCAAGAG TCAACAATAC TCACACTCCA    1080

AATGGTACAG CAGAATATTA TCAAACAGAA GGTGGAATGA TTTTAGTGTG GCAGCCATTA    1140

ATAGCAATAG AATTAGAAGA AGCAATGTTG GAAGCAACTA CATCTCCAGT AACTCCTAGT    1200

GCACCAACTA GCTCATCTAG AAGTAAGCGA GCAATAAGAA GCATAAGAGA TGTGAGTGCA    1260

GGTTCAGAAA ATAATGTGTT TCTATCACAA ATACAATATG CATATGATAA GCTACGTCAA    1320

AGTATCAACA ACGTGCTAGA AGAGTTAGCT ATAACATGGT GTAGAACA AGTGAGACAA      1380

ACAATGGTGT GGTATGAGAT AGCAAAAATT AATCCAACAA GTGTTATGAC AGCAATATAT    1440

GGAAAACCTG TCTCTCGTAA AGCTTTAGGA GATGTAATCT CTGTTACAGA ATGTATAAAT    1500

GTTGACCAAT CTAGTGTGAG CATACACAAG AGTCTTAAAA CAGAAAATAA TGACATATGC    1560

TATTCACGGC CTCCAGTTAC ATTTAAATTT GTTAACAGTA GTCAGCTGTT TAAAGGACAG    1620

TTAGGGCTA GAAATGAAAT TCTTCTGTCA GAAAGTCTTG TAGAAAATTG CCACCAAAAT    1680

GCAGAGACTT TTTTTACAGC TAAAAATGAA ACTTACCACT TTAAAAATTA TGTGCATGTA    1740

GAAACTTTGC CAGTGAATAA CATTTCAACT TTAGACACTT TTTTAGCTCT TAACCTAACT    1800

TTCATAGAAA ATATTGACTT TAAAGCTGTT GAATTGTATT CAAGTGGAGA GAGAAAGTTA    1860

GCAAACGTGT TTGATTTAGA GACTATGTTT AGAGAATATA ACTATTACGC TCAGAGTATA    1920

TCTGGCTTAA GAAAAGATTT TGATAACTCT CAAAGAAACA ACAGAGACAG AATCATTCAA    1980
```

```
GATTTTTCAG AAATTCTAGC AGACTTAGGC TCTATCGGCA AAGTTATTGT TAATGTGGCA    2040

AGCGGCGCAT TTTCTCTTTT TGGAGGTATT GTAACAGGCA TATTAAATTT TATTAAAAAT    2100

CCTTTAGGTG GCATGTTCAC ATTTCTATTA ATAGGAGCAG TTATAATCTT AGTAATTCTA    2160

CTAGTACGGC GCACAAATAA TATGTCTCAA GCTCCAATTA GAATGATTTA CCCAGATGTT    2220

GAGAAATCTA AATCTACTGT GACGCCTATG GAGCCTGAAA CAATTAAACA AATTTTGCTT    2280

GGAATGCATA ACATGCAGCA AGAAGCATAT AAGAAAAAAG AAGAACAAAG AGCTGCTAGA    2340

CCGTCTATTT TTAGACAAGC TGCTGAGACA TTTTTGCGTA AGCGATCTGG TTACAAACAG    2400

ATTTCAACCG AAGACAAAAT AGTAT                                         2425
```

(2) INFORMATION FOR SEQ ID NO:6:

(i) SEQUENCE CHARACTERISTICS:
        (A) LENGTH: 2623 base pairs
        (B) TYPE: nucleic acid
        (C) STRANDEDNESS: double
        (D) TOPOLOGY: linear (xi) SEQUENCE DESCRIPTION: SEQ ID NO:6:

```
ATGTATTATA AGACTATCTT ATTCTTCGCT CTAATTAAGG TATGCAGTTT CAACCAGACC      60

ACTACACACT CAACCACAAC CTCACCAAGT ATTTCATCAA CCACCTCTTC CACAACAACA     120

TCAACAAGCA AGCCATCAAA CACAACCTCA ACAAATAGTT CATTAGCTGC CTCTCCCCAG     180

AACACGTCAA CAAGCAAGCC ATCCACTGAT AATCAGGGTA CCAGTACCCC CACTATTCCA     240

ACTGTTACTG ATGACACAGC CAGTAAAAAT TTTTATAAAT ACAGAGTATG CAGTGCATCA     300

TCTTCCTCTG GAGAACTATT CAGATTTGAC CTTGATCAGA CATGTCCAGA TACAAAAGAT     360

AAAAAACATG TGGAAGGCAT CCTGCTGGTA CTAAAAAAGA ATATTGTCCC ATACATCTTC     420

AAAGTGAGGA AATATAGAAA AATTGCCACC TCAGTGACAG TTTACAGAGG GTGGTCCCAG     480

GCAGCTGTTA CCAATAGGGA TGATATCAGC AGAGCCATAC CCTATAATGA AATTTCAATG     540

ATAGATAGGA CCTATCATTG TTTCTCTGCT ATGGCAACAG TCATTAATGG GATTCTGAAC     600

ACCTATATAG ACAGGGATTC TGAAAATAAG TCTGTTCCCC TCCAGCCAGT GGCCGGACTG     660

ACTGAGAACA TAAACAGATA CTTTAGTCAA CCTCTCATAT ATGCAGAACC TGGCTGGTTT     720

CCAGGGATTT ATAGAGTGAG AACAACTGTT AATTGTGAGG TTGTTGACAT GTATGCCCGC     780

TCTGTGGAAC CATATACTCA CTTTATTACA GCTCTGGGGG ACACTATTGA AATCTCCCCA     840

TTCTGTCACA ACAATTCTCA ATGCACCACT GGTAATTCCA CCTCAAGGGA TGCCACAAAG     900

GTATGGATAG AAGAAAATCA CCAAACTGTT GACTATGAAA GACGGGGGCA TCCCACTAAA     960

GATAAAGAA TCTTTCTAAA AGATGAGGAA TATACCATCT CCTGGAAAGC AGAAGATAGA    1020

GAGAGAGCTA TTTGTGATTT TGTGATATGG AAAACCTTTC CCAGGGCCAT ACAAACAATC    1080

CATAATGAGA GCTTTCACTT TGTGGCAAAT GAAGTCACAG CCAGCTTTTT AACATCCAAC    1140

CAAGAAGAAA CGGAGCTACG TGGAAATACC GAGATATTGA ATTGCATGAA TAGTACCATA    1200

AATGAAACTC TAGAAGAGAC AGTCAAAAAA TTTAACAAAT CCCATATCAG AGATGGGGAG    1260

GTAAAGTACT ATAAAACAAA TGGGGGACTA TTCCTTATCT GGCAGGCAAT GAAACCCCTT    1320

AATCTGTCAG AACACACAAA CTACACTATT GAAAGGAATA ACAAGACTGG AAATAAATCA    1380

AGACAAAAAA GGTCTGTAGA TACAAAGACC TTCCAAGGCG CCAAGGGCCT GTCCACTGCC    1440

CAGGTTCAAT ATGCCTATGA CCATTTAAGA ACAAGCATGA ATCACATCCT AGAGGAATTA    1500

ACCAAAACAT GGTGCCGGGA ACAAAAAAAG GACAATCTAA TGTGGTATGA GCTGAGTAAA    1560
```

```
ATTAACCCAG TGAGTGTCAT GGCAGCCATT TATGGGAAAC CTGTGGCAGT GAAAGCCATG   1620

GGAGATGCAT TCATGGTTTC TGAGTGCATC AATGTTGACC AGGCAAGTGT CAATATCCAT   1680

AAAAGTATGA GAACGGATGA TCCCAAGGTA TGTTACTCCA GACCCCTGGT CACATTTAAA   1740

TTTGTGAATA GTACTGCCAC CTTCAGGGGT CAGCTTGGAA CAAGGAATGA AATCTTGCTC   1800

ACAAACACAC ACGTGGAAAC TTGTAGACCA ACAGCAGATC ATTATTTTTT TGTAAAGAAC   1860

ATGACACACT ATTTTAAGGA CTATAAATTT GTGAAGACAA TGGATACCAA TAACATATCC   1920

ACCCTGGATA CATTTTTAAC TCTCAATTTA ACTTTTATAG ACAATATAGA TTTCAAGACA   1980

GTGGAACTTT ACAGTGAGAC TGAAAGAAAG ATGGCCAGTG CCCTCGACCT GGAGACGATG   2040

TTTAGAGAGT ATAATTACTA CACACAGAAG CTTGCAAGTC TGAGAGAAGA TCTAGACAAC   2100

ACCATTGACC TGAACAGGGA CAGACTAGTT AAAGATCTCT CTGAAATGAT GGCAGACCTT   2160

GGAGACATTG GAAAAGTGGT GGTCAACACA TTCAGTGGCA TTGTCACTGT TTTTGGGTCT   2220

ATAGTTGGTG GATTTGTCAG TTTTTTCACA AACCCCATTG GGGGCGTGAC GATCATCCTC   2280

CTTCTCATAG TTGTGGTTTT TGTTGTTTTT ATAGTCTCCA GGAGAACCAA TAACATGAAC   2340

GAGGCCCCCA TAAAAATGAT CTATCCAAAC ATTGACAAAG CCTCTGAGCA GGAGAACATT   2400

CAGCCCCTAC CCGGAGAGGA GATTAAGCGC ATCCTCCTTG GAATGCACCA GCTCCAGCAA   2460

AGTGAGCACG GCAAATCTGA GGAAGAGGCT AGCCATAAAC CAGGGTTGTT CCAACTATTG   2520

GGGGATGGCC TACAATTGCT GCGCAGGCGC GGGTATACTA GGTTACCAAC TTTTGACCCC   2580

AGTCCAGGCA ATGACACATC TGAGACACAC CAAAAATATG TTT                    2623
```

(2) INFORMATION FOR SEQ ID NO:7:

(i) SEQUENCE CHARACTERISTICS:
        (A) LENGTH: 2625 base pairs
        (B) TYPE: nucleic acid
        (C) STRANDEDNESS: double
        (D) TOPOLOGY: linear (xi) SEQUENCE DESCRIPTION: SEQ ID NO:7:

```
ATGGGGGTCG GGGGCGGGCC TCGCGTCGTC CTCTGTCTAT GGTGCGTCGC TGCGCTTCTC     60

TGCCAGGGGG TGGCGCAAGA AGTTGTGGCT GAAACGACCA CCCCGTTCGC AACCCACAGA    120

CCAGAAGTGG TGGCCGAGGA GAACCCGGCC AACCCCTTTC TGCCGTTCAG GGTATGCGGG    180

GCCTCGCCTA CGGGCGGAGA GATATTCAGG TTCCCCCTGG AGGAGAGCTG CCCCAACACG    240

GAAGACAAGG ACCACATAGA GGGCATAGCT CTCATCTACA AGACCAACAT AGTGCCTTAT    300

GTTTTTAATG TCAGAAAGTA TAGGAAGATC ATGACCTCGA CCACCATCTA CAAGGGTTGG    360

AGCGAGGATG CCATAACAAA CCAGCACACG AGGAGCTACG CCGTCCCCCT GTACGAGGTC    420

CAGATGATGG ACCACTATTA TCAGTGCTTT AGCGCCGTAC AGGTCAACGA GGGGGGGCAC    480

GTCAACACCT ACTATGACAG GGACGGGTGG AACGAGACCC CCTTCCTCAA ACCGGCCGAT    540

GGTCTCACCT CTAGCATAAC GCGCTATCAG AGTCAACCAG AGGTGTACGC CACCCCCAGA    600

AACCTGTTGT GGTCTTACAC AACAAGAACC ACAGTCAACT GCGAGGTGAC AGAGATGTCT    660

GCGAGATCCA TGAAACCATT TGAGTTCTTT GTGACGTCTG TTGGTGACAC TATAGAGATG    720

TCGCCCTTTT TAAAAGAAAA TGGCACAGAG CCAGAGAAAA TCTTGAAAAG ACCACACTCT    780

ATTCAACTGC TGAAAAACTA TGCTGTCACA AAGTACGGTG TGGGGTTGGG GCAGGCTGAT    840

AACGCTACCA GATTCTTTGC AATATTTGGG GACTATTCCC TGTCTTGGAA AGCCACCACT    900

GAAAACAGCT CCTACTGTGA TTTAATTTTA TGGAAGGGGT TTTCCAATGC CATTCAAACT    960

CAACACAATA GCAGTCTCCA TTTTATTGCC AATGATATAA CAGCCTCCTT CTCTACTCCT   1020
```

```
TTAGAAGAAG AGGCTAATTT TAACGAGACA TTTAAGTGTA TATGGAACAA CACCCAAGAA    1080

GAAATTCAAA AAAAGTTAAA AGAGGTTGAA AAAACTCACA GACCTAACGG TACTGCGAAG    1140

GTCTATAAAA CAACAGGCAA TCTGTACATT GTTTGGCAAC CGCTTATACA GATAGACCTG    1200

CTAGATACTC ATGCCAAGCT GTACAATCTC ACAAACGCTA CAGCTTCACC TACATCAACA    1260

CCCACAACAT CTCCCAGGAG AAGACGCAGG GATACTTCAA GTGTTAGTGG CGGTGGAAAT    1320

AATGGAGACA ACTCAACTAA GGAAGAGAGT GTGGCGGCCT CCCAGGTTCA GTTTGCCTAT    1380

GACAATCTCA GAAAGAGCAT CAACAGGGTG TTGGGAGAGC TGTCCAGGGC ATGGTGCAGG    1440

GAACAGTACA GGGCCTCGCT CATGTGGTAC GAGCTGAGCA AGATCAACCC CACCAGCGTC    1500

ATGAGCGCCA TCTATGGCAG GCCAGTGTCT GCCAAGTTGA TAGGGACGT GGTGTCAGTG     1560

TCAGATTGTA TCAGTGTTGA CCAAAAGAGC GTGTTTGTGC ACAAAAATAT GAAGGTGCCT    1620

GGCAAAGAAG ACCTGTGTTA CACCAGGCCT GTGGTGGGCT TCAAGTTTAT CAATGGGAGC    1680

GAACTGTTTG CTGGCCAGCT GGGTCCCAGG AACGAGATTG TGCTGTCCAC CTCTCAGGTG    1740

GAGGTCTGCC AGCACAGCTG CGAGCACTAC TTCCAGGCCG GAACCAGAT GTACAAGTAC     1800

AAGGACTACT ACTATGTCAG TACCCTCAAC CTGACTGACA TACCCACCCT ACACACCATG    1860

ATTACCCTGA ACCTGTCTCT GGTAGAGAAT ATAGATTTTA AGGTGATTGA GCTCTATTCT    1920

AAAACAGAGA AAGGCTGTC CAACGTGTTT GACATCGAGA CCATGTTCAG GGAGTACAAC     1980

TACTACACTC AGAACCTCAA CGGGCTGAGG AAGGACCTGG ATGACAGCAT AGATCATGGC    2040

AGGGACAGCT TCATCCAGAC CCTGGGTGAC ATCATGCAGG ACCTGGGCAC CATAGGCAAG    2100

GTGGTGGTCA ATGTGGCCAG CGGAGTGTTC TCCCTCTTTG GGAGCATAGT CTCGGGGGTG    2160

ATAAGCTTTT TCAAAAATCC CTTTGGGGGC ATGCTGCTCA TAGTCCTCAT CATAGCCGGG    2220

GTAGTGGTGG TGTACCTGTT TATGACCAGG TCCAGGAGCA TATACTCTGC CCCCATTAGA    2280

ATGCTCTACC CCGGGGTGGA GAGGCGGCC CAGGAGCCGG GCGCGCACCC GGTGTCAGAA     2340

GACCAAATCA GGAACATCCT GATGGGAATG CACCAATTTC AGCAGCGGCA GCGGGCGGAA    2400

GAGGAGGCCC GACGAGAGGA AGAAGTAAAA GGAAAAAGAA CTCTCTTTGA AGTGATAAGA    2460

GACTCTGCGA CCAGCGTTCT GAGGAGGAGA AGAGGGGGTG GTGGGTACCA GCGCCTACAG    2520

CGAGACGGGA GCGACGATGA GGGGGATTAT GAGCCATTGA GGCGACAAGA TGGAGGCTAC    2580

GACGACGTGG ACGTGGAGGC AGGCACGGCG GATACCGGTG TGTAA                   2625

(2) INFORMATION FOR SEQ ID NO:8:

(i) SEQUENCE CHARACTERISTICS:
        (A) LENGTH: 2548 base pairs
        (B) TYPE: nucleic acid
        (C) STRANDEDNESS: double
        (D) TOPOLOGY: linear (xi) SEQUENCE DESCRIPTION: SEQ ID NO:8:

ATGTACCCTA CAGTGAAAAG TATGAGAGTC GCCCACCTAA CCAATCTCCT AACCCTTCTG      60

TGTCTGCTGT GCCACACGCA TCTCTACGTA TGTCAGCCAA CCACTCTGAG GCAGCCATCA    120

GACATGACCC CAGCCCAGGA CGCTCCAACA GAGACTCCCC CACCCCTCTC AACTAACACT    180

AACAGAGGAT TTGAGTACTT TCGCGTGTGT GGGGTGGCTG CCACGGGGGA GACCTTCAGG    240

TTTGATTTAG ACAAAACATG CCCCAGTACA CAAGATAAGA AGCATGTGGA GGGCATCTTG    300

CTCGTGTATA AGATCAACAT CGTGCCCTAC ATCTTCAAAA TCAGGAGATA TAGAAAAATA    360

ATTACTCAAC TGACCATCTG GCGAGGCCTA ACCACTAGTT CAGTCACTGG TAAATTTGAA    420
```

```
ATGGCCACTC AGGCCCACGA GTGGGAAGTG GGCGACTTTG ACAGCATCTA TCAGTGCTAC        480

AATAGCGCCA CCATGGTGGT AAACAACGTC AGACAGGTGT ATGTGGACAG AGATGGGTC         540

AATAAAACTG TGAACATACG CCCTGTTGAT GGTCTAACAG GAATATCCA AAGATACTTT         600

AGTCAGCCCA CCCTTTATTC AGAACCTGGT TGGATGCCTG GCTTTTATCG TGTTCGAACC        660

ACCGTTAACT GTGAAATTGT AGACATGGTG GCACGCTCCA TGGATCCCTA TAACTACATC        720

GCTACCGCCC TGGGAGACAG CCTGGAGCTC TCCCCGTTTC AAACCTTTGA CAACACCAGC        780

CAGTGTACTG CGCCTAAGAG AGCTGATATG AGGGTCAGGG AGGTCAAGAA TTACAAGTTT       840

GTAGATTATA ATAACAGGGG AACTGCCCCC GCTGGACAAA GCAGGACCTT TCTAGAGACT       900

CCCTCTGCCA CTTACTCCTG GAAAACAGCC ACCAGACAAA CTGCCACGTG CGACCTGGTG       960

CACTGGAAAA CATTCCCTCG CGCCATCCAA ACTGCTCATG AACATAGCTA CCATTTTGTG      1020

GCCAATGAAG TCACCGCCAC CTTCAATACA CCCCTGACTG AGGTAGAAAA TTTCACCAGC      1080

ACGTATAGCT GCGTCAGTGA CCAGATCAAT AAGACCATCT CTGAATATAT CCAAAAGTTG      1140

AACAACTCCT ACGTGGCCAG TGGGAAAACA CAGTATTTCA AGACTGATGG TAACCTGTAC      1200

CTCATCTGGC AACCACTCGA ACATCCAGAG ATTGAAGACA TAGACGAGGA CAGCGACCCA      1260

GAACCAACCC CCGCCCCACC AAAGTCCACA AGGAGAAAAA GAGAGGCAGC TGACAATGGA      1320

AACTCAACAT CTGAGGTCTC AAAGGGCTCA GAAAATCCGC TCATTACGGC CCAAATTCAA      1380

TTTGCCTATG ACAAGCTGAC CACCAGCGTC AACAACGTGC TTGAGGAGTT GTCCAGGGCG      1440

TGGTGTAGAG AACAGGTCAG AGACACCCTC ATGTGGTATG AGCTTAGCAA GGTCAACCCT      1500

ACGAGTGTGA TGTCTGCCAT TTATGAAAG CCTGTCGCTG CCAGGTACGT GGGCGACGCC        1560

ATATCTGTGA CAGACTGTAT CTATGTGGAC CAAAGTTCAG TCAACATCCA CCAGAGCTTG      1620

CGGCTGCAGC ATGATAAAAC CACCTGCTAC TCGAGACCTA GAGTCACCTT CAAATTTATA      1680

AACAGTACAG ACCCGCTAAC TGGCCAGTTG GGTCCTAGAA AAGAAATTAT CCTCTCCAAC      1740

ACAAACATAG AAACATGCAA GGATGAGAGT GAACACTACT TCATTGTGGG GGAATACATT      1800

TACTATTATA AAAATTACAT TTTTGAAGAA AAGCTAAACC TCTCAAGCAT CGCTACCCTA      1860

GACACATTTA TAGCCCTCAA TATCTCATTT ATTGAAAATA TCGACTTCAA AACAGTAGAA      1920

CTGTACTCCT CTACTGAAAG GAAACTCGCA TCGAGCGTCT TTGATATAGA ATCCATGTTT      1980

AGGGAATATA ACTATTACAC CTACAGCCTC GCGGGCATTA AGAAGGACCT AGACAACACC      2040

ATCGACTACA ATAGAGACAG ACTGGTTCAG GACCTGTCAG ACATGATGGC TGATCTGGGA      2100

GACATTGGAA GATCTGTGGT GAATGTGGTC AGCTCGGTAG TCACATTTTT CAGTAGTATT      2160

GTGACAGGGT TCATTAAATT CTTTACCAAC CCTCTAGGGG AATATTCAT TCTCCTAATT       2220

ATTGGTGGAA TAATCTTCTT GGTGGTAGTC CTAAATAGAA GAAACTCACA GTTTCACGAT      2280

GCACCCATCA AAATGCTGTA CCCTTCTGTT GAAAACTACG CTGCCAGACA GGCGCCACCT      2340

CCCTATAGCG CATCACCTCC AGCTATAGAC AAAGAGGAAA TTAAGCGCAT ACTTTTGGGC      2400

ATGCATCAGG TACACCAGGA AGAAAAGGAA GCACAGAAAC AACTAACCAA CTCTGGCCCT      2460

ACTTTGTGGC AGAAAGCCAC AGGATTCCTT AGAAATCGCC GGAAGGGATA CAGCCAACTT     2520

CCTCTGGAAG ATGAATCAAC TTCCCTCT                                        2548
```

(2) INFORMATION FOR SEQ ID NO:9:

(i) SEQUENCE CHARACTERISTICS:
        (A) LENGTH: 2572 base pairs
        (B) TYPE: nucleic acid
        (C) STRANDEDNESS: double
        (D) TOPOLOGY: linear -continued (xi) SEQUENCE DESCRIPTION: SEQ ID NO:9:

| | | | | |
|---|---|---|---|---|
| ATGACTCGGC | GTAGGGTGCT | AAGCGTGGTC | GTGCTGCTAG | CCGCCCTGGC GTGCCGTCTC 60 |
| GGTGCGCAGA | CCCCAGAGCA | GCCCGCACCC | CCCGCCACCA | CGGTGCAGCC TACCGCCACG 120 |
| CGTCAGCAAA | CCAGCTTTCC | TTTCCGAGTC | TGCGAGCTCT | CCAGCCACGG CGACCTGTTC 180 |
| CGCTTCTCCT | CGGACATCCA | GTGTCCCTCG | TTTGGCACGC | GGGAGAATCA CACGGAGGGC 240 |
| CTGTTGATGG | TGTTTAAAGA | CAACATTATT | CCCTACTCGT | TTAAGGTCCG CTCCTACACC 300 |
| AAGATAGTGA | CCAACATTCT | CATCTACAAT | GGCTGGTACG | CGGACTCCGT GACCAACCGG 360 |
| CACGAGGAGA | AGTTCTCCGT | TGACAGCTAC | GAAACTGACC | AGATGGATAC CATCTACCAG 420 |
| TGCTACAACG | CGGTCAAGAT | GACAAAAGAT | GGGCTGACGC | GCGTGTATGT AGACCGCGAC 480 |
| GGAGTTAACA | TCACCGTCAA | CCTAAAGCCC | ACCGGGGGCC | TGGCCAACGG GGTGCGCCGC 540 |
| TACGCCAGCC | AGACGGAGCT | CTATGACGCC | CCCGGGTGGT | TGATATGGAC TTACAGAACA 600 |
| AGAACTACCG | TCAACTGCCT | GATAACTGAC | ATGATGGCCA | AGTCCAACAG CCCCTTCGAC 660 |
| TTCTTTGTGA | CCACCACCGG | GCAGACTGTG | GAAATGTCCC | CTTTCTATGA CGGGAAAAAT 720 |
| AAGGAAACCT | TCCATGAGCG | GGCAGACTCC | TTCCACGTGA | GAACTAACTA CAAGATAGTG 780 |
| GACTACGACA | ACCGAGGGAC | GAACCCGCAA | GGCGAACGCC | GAGCCTTCCT GGACAAGGGC 840 |
| ACTTACACGC | TATCTTGGAA | GCTCGAGAAC | AGGACAGCCT | ACTGCCCGCT TCAACACTGG 900 |
| CAAACCTTTG | ACTCGACCAT | CGCCACGAAA | ACAGGGAAGT | CAATACATTT TGTGACTGAC 960 |
| GAGGGCACCT | CTAGCTTCGT | GACCAACACA | ACCGTGGGCA | TAGAGCTCCC GGACGCCTTC 1020 |
| AAGTGCATCG | AAGAGCAGGT | GAACAAGACC | ATGCATGAGA | AGTACGAGGC CGTCCAGGAT 1080 |
| CGTTACACGA | AGGGCCAGGA | AGCCATTACA | TATTTTATAA | CGAGCGGAGG ATTGTTATTA 1140 |
| GCTTGGCTAC | CTCTGACCCC | GCGCTCGTTG | GCCACCGTCA | AGAACCTGAC GGAGCTTACC 1200 |
| ACTCCGACTT | CCTCACCCCC | CAGCAGTCCA | TCGCCCCCAG | CCCCATCCGC GGCCCGCGGG 1260 |
| AGCACCCCCG | CCGCCGTTCT | GAGGCGTCGG | AGGCGGGATG | CGGGGAACGC CACCACACCG 1320 |
| GTGCCCCCCA | CGGCCCCCGG | GAAGTCCCTG | GGCACCCTCA | ACAATCCCGC CACCGTCCAG 1380 |
| ATCCAATTTG | CCTACGACTC | CCTGCGCCGC | CAGATCAACC | GCATGCTGGG AGACCTTGCG 1440 |
| CGGGCCTGGT | GCCTGGAGCA | GAAGAGGCAG | AACATGGTGC | TGAGAGAACT AACCAAGATT 1500 |
| AATCCAACCA | CCGTCATGTC | CAGCATCTAC | GGTAAGGCGG | TGGCGGCCAA GCGCCTGGGG 1560 |
| GATGTCATCT | CAGTCTCCCA | GTGCGTGCCC | GTTAACCAGG | CCACCGTCAC CCTGCGCAAG 1620 |
| AGCATGAGGG | TCCCTGGCTC | CGAGACCATG | TGCTACTCGC | GCCCCCTGGT GTCCTTCAGC 1680 |
| TTTATCAACG | ACACCAAGAC | CTACGAGGGA | CAGCTGGGCA | CCGACAACGA GATCTTCCTC 1740 |
| ACAAAAAAGA | TGACGGAGGT | GTGCCAGGCG | ACCAGCCAGT | ACTACTTCCA GTCCGGCAAC 1800 |
| GAGATCCACG | TCTACAACGA | CTACCACCAC | TTTAAAACCA | TCGAGCTGGA CGGCATTGCC 1860 |
| ACCCTGCAGA | CCTTCATCTC | ACTAAACACC | TCCCTCATCG | AGAACATTGA CTTTGCCTCC 1920 |
| CTGGAGCTGT | ACTCACGGGA | CGAACAGCGT | GCCTCCAACG | TCTTTGACCT GGAGGGCATC 1980 |
| TTCCGGGAGT | ACAACTTCCA | GGCGCAAAAC | ATCGCCGGCC | TGCGGAAGGA TTTGGACAAT 2040 |
| GCAGTGTCAA | ACGGAAGAAA | TCAATTCGTG | GACGGCCTGG | GGAACTTAT GGACAGTCTG 2100 |
| GGTAGCGTGG | GTCAGTCCAT | CACCAACCTA | GTCAGCACGG | TGGGGGGTTT GTTTAGCAGC 2160 |
| CTGGTCTCTG | GTTTCATCTC | CTTCTTCAAA | AACCCCTTCG | GCGGCATGCT CATTCTGGTC 2220 |
| CTGGTGGCGG | GGGTGGTGAT | CCTGGTTATT | CCCTCACGA | GGCGCACGCG CCAGATGTCG 2280 |
| CAGCAGCCGG | TGCAGATGCT | CTACCCCGGG | ATCGACGAGC | TCGCTCAGCA ACATGCCTCT 2340 |

```
GGTGAGGGTC CAGGCATTAA TCCCATTAGT AAGACAGAAT TACAAGCCAT CATGTTAGCG    2400

CTGCATGAGC AAAACCAGGA GCAAAAGAGA GCAGCTCAGA GGGCGGCCGG ACCCTCAGTG    2460

GCCAGCAGAG CATTGCAGGC AGCCAGGGAC CGTTTTCCAG GCCTACGCAG AAGACGCTAT    2520

CACGATCCAG AGACCGCCGC CGCACTGCTT GGGGAGGCAG AGACTGAGTT TT           2572

(2) INFORMATION FOR SEQ ID NO:10:

(i) SEQUENCE CHARACTERISTICS:
        (A) LENGTH: 2722 base pairs
        (B) TYPE: nucleic acid
        (C) STRANDEDNESS: double
        (D) TOPOLOGY: linear (xi) SEQUENCE DESCRIPTION: SEQ ID NO:10:

ATGGAATCCA GGATCTGGTG CCTGGTAGTC TGCGTTAACC TGTGTATCGT CTGTCTGGGT      60

GCTGCGGTTT CCTCTTCTAG TACTTCCCAT GCAACTTCTT CTACTCACAA TGGAAGCCAT     120

ACTTCTCGTA CGACGTCTGC TCAAACCCGG TCAGTCTATT CTCAACACGT AACGTCTTCT     180

GAAGCCGTCA GTCATAGAGC CAACGAGACT ATCTACAACA CTACCCTCAA GTACGGAGAT     240

GTGGTGGGAG TCAACACTAC CAAGTACCCC TATCGCGTGT GTTCTATGGC CCAGGGTACG     300

GATCTTATTC GCTTTGAACG TAATATCATC TGCACCTCGA TGAAGCCTAT CAATGAAGAC     360

TTGGATGAGG GCATCATGGT GGTCTACAAG CGCAACATCG TGGCGCACAC CTTTAAGGTA     420

CGGGTCTACC AAAAGGTTTT GACGTTTCGT CGTAGCTACG CTTACATCTA CACCACTTAT     480

CTGCTGGGCA GCAATACGGA ATACGTGGCG CCTCCTATGT GGGAGATTCA TCACATCAAC     540

AAGTTTGCTC AATGCTACAG TTCCTACAGC CGCGTTATAG GAGGCACGGT TTTCGTGGCA     600

TATCATAGGG ACAGTTATGA AAACAAAACC ATGCAATTAA TTCCCGACGA TTATTCCAAC     660

ACCCACAGTA CCCGTTACGT GACGGTCAAG GATCAGTGGC ACAGCCGCGG CAGCACCTGG     720

CTCTATCGTG AGACCTGTAA TCTGAACTGT ATGCTGACCA TCACTACTGC GCGCTCCAAG     780

TATCCTTATC ATTTTTTTGC AACTTCCACG GGTGATGTGG TTTACATTTC TCCTTTCTAC     840

AACGGAACCA ATCGCAATGC CAGCTACTTT GGAGAAAACG CCGACAAGTT TTTCATTTTC     900

CCGAACTACA CCATCGTTTC CGACTTTGGA AGACCCAACG CTGCGCCAGA AACCCATAGG     960

TTGGTGGCTT TTCTCGAACG TGCCGACTCG GTGATCTCTT GGGATATACA GGACGAGAAG    1020

AATGTCACCT GCCAGCTCAC CTTCTGGGAA GCCTCGGAAC GTACTATCCG TTCCGAAGCC    1080

GAAGACTCGT ACCACTTTTC TTCTGCCAAA ATGACTGCAA CTTTTCTGTC TAAGAAACAA    1140

GAAGTGAACA TGTCCGACTC CGCGCTGGAC TGCGTACGTG ATGAGGCTAT AAATAAGTTA    1200

CAGCAGATTT TCAATACTTC ATACAATCAA ACATATGAAA AATACGGAAA CGTGTCCGTC    1260

TTCGAAACCA GCGGCGGTCT GGTGGTGTTC TGGCAAGGCA TCAAGCAAAA ATCTTTGGTG    1320

GAATTGGAAC GTTTGGCCAA TCGATCCAGT CTGAATATCA CTCATAGGAC CAGAAGAAGT    1380

ACGAGTGACA ATAATACAAC TCATTTGTCC AGCATGGAAT CGGTGCACAA TCTGGTCTAC    1440

GCCCAGCTGC AGTTCACCTA TGACACGTTG CGCGGTTACA TCAACCGGGC GCTGGCGCAA    1500

ATCGCAGAAG CCTGGTGTGT GGATCAACGG CGCACCCTAG AGGTCTTCAA GGAACTCAGC    1560

AAGATCAACC CGTCAGCCAT TCTCTCGGCC ATTTACAACA AACCGATTGC CGCGCGTTTC    1620

ATGGGTGATG TCTTGGGCCT GGCCAGCTGC GTGACCATCA ACCAAACCAG CGTCAAGGTG    1680

CTGCGTGATA TGAACGTGAA GGAATCGCCA GGACGCTGCT ACTCACGACC CGTGGTCATC    1740

TTTAATTTCG CCAACAGCTC GTACGTGCAG TACGGTCAAC TGGGCGAGGA CAACGAAATC    1800
```

-continued

```
CTGTTGGGCA ACCACCGCAC TGAGGAATGT CAGCTTCCCA GCCTCAAGAT CTTCATCGCC      1860

GGGAACTCGG CCTACGAGTA CGTGGACTAC CTCTTCAAAC GCATGATTGA CCTCAGCAGT      1920

ATCTCCACCG TCGACAGCAT GATCGCCCTG GATATCGACC CGCTGGAAAA TACCGACTTC      1980

AGGGTACTGG AACTTTACTC GCAGAAAGAG CTGCGTTCCA GCAACGTTTT TGACCTCGAA      2040

GAGATCATGC GCGAATTCAA CTCGTACAAG CAGCGGGTAA AGTACGTGGA GGACAAGGTA      2100

GTCGACCCGC TACCGCCCTA CCTCAAGGGT CTGGACGACC TCATGAGCGG CCTGGGCGCC      2160

GCGGGAAAGG CCGTTGGCGT AGCCATTGGG GCCGTGGGTG GCGCGGTGGC CTCCGTGGTC      2220

GAAGGCGTTG CCACCTTCCT CAAAAACCCC TTCGGAGCCT TCACCATCAT CCTCGTGGCC      2280

ATAGCCGTAG TCATTATCAC TTATTTGATC TATACTCGAC AGCGGCGTCT GTGCACGCAG      2340

CCGCTGCAGA ACCTCTTTCC CTATCTGGTG TCCGCCGACG GGACCACCGT GACGTCGGGC      2400

AGCACCAAAG ACACGTCGTT ACAGGCTCCG CCTTCCTACG AGGAAAGTGT TTATAATTCT      2460

GGTCGCAAAG GACCGGGACC ACCGTCGTCT GATGCATCCA CGGCGGCTCC GCCTTACACC      2520

AACGAGCAGG CTTACCAGAT GCTTCTGGCC CTGGCCCGTC TGGACGCAGA GCAGCGAGCG      2580

CAGCAGAACG GTACAGATTC TTTGGACGGA CAGACTGGCA CGCAGGACAA GGGACAGAAG      2640

CCTAACCTGC TAGACCGGCT GCGACATCGC AAAAACGGCT ACAGACACTT GAAAGACTCC      2700

GACGAAGAAG AGAACGTCTG AA                                              2722
```

(2) INFORMATION FOR SEQ ID NO:11:

(i) SEQUENCE CHARACTERISTICS:
        (A) LENGTH: 2493 base pairs
        (B) TYPE: nucleic acid
        (C) STRANDEDNESS: double
        (D) TOPOLOGY: linear (xi) SEQUENCE DESCRIPTION: SEQ ID NO:11:

```
ATGAGCAAGA TGAGAGTATT ATTCCTGGCT GTCTTTTTGA TGAATAGTGT TTTAATGATA        60

TATTGCGATT CGGATGATTA TATCAGAGCG GGCTATAATC ACAAATATCC TTTTCGGATT       120

TGTTCGATTG CCAAAGGCAC TGATTTGATG CGGTTCGACA GAGATATTTC GTGTTCGCCA       180

TATAAGTCTA ATGCAAAGAT GTCGGAGGGT TTTTTCATCA TTTACAAAAC AAATATCGAG       240

ACCTACACTT TTCCAGTGAG AACATATAAA AACGAGCTGA CGTTCCAAAC CAGTTACCGT       300

GATGTGGGTG TGGTTTATTT TCTGGATCGG ACGGTGATGG GTTTGGCCAT GCCGGTGTAC       360

GAAGCAAATT TAGTTAATTC TCGTGCGCAG TGTTATTCAG CCGTAGCGAT AAAACGACCC       420

GATGGTACGG TGTTTAGTGC CTATCATGAG GATAATAATA AAAACGAAAC TCTAGAATTA       480

TTTCCTCTGA ATTTCAAGTC TGTTACTAAT AAAAGATTTA TCACTACGAA AGAACCCTAC       540

TTTGCAAGGG GTCCTTTGTG GCTCTATTCT ACATCGACGT CTCTCAATTG TATTGTGACG       600

GAGGCTACGG CTAAGGCGAA ATATCCGTTT AGTTACTTTG CTTTGACGAC TGGTGAAATC       660

GTGGAAGGGT CTCCGTTCTT CGACGGTTCA AACGGTAAAC ATTTTGCAGA GCCGTTAGAA       720

AAATTGACAA TCTTGGAAAA CTATACTATG ATAGAAGATC TAATGAATGG TATGAATGGG       780

GCTACTACGT TAGTAAGGAA GATCGCTTTT CTGGAGAAAG GGGATACTTT GTTTTCTTGG       840

GAAATCAAGG AAGAGAATGA ATCGGTGTGT ATGCTAAAGC ACTGGACTAC GGTGACTCAC       900

GGGCTTCGAG CGGAGACGGA TGAGACTTAT CACTTTATTT CTAAGGAGTT GACAGCCGCT       960

TTCGTCGCCT CCAAGGAGTC TTTAAATCTT ACCGATCCCA AACAAACGTG TATTAAGAAT      1020

GAATTTGAGA AGATAATTAC AGATGTCTAT ATGTCAGATT ATAATGATGA CTACAGCATG      1080

AACGGTAGTT ATCAAATTTT TAAGACTACG GGAGATCTGA TTTTGATTTG GCAGCCTCTT      1140
```

```
GTGCAAAAAT CTCTTATGGT TCTTGAGCAG GGTTCAGTAA ACTTACGTAG GAGGCGAGAT      1200

TTGGTGGATG TCAAGTCTAG ACATGATATT CTTTATGTGC AATTACAGTA CCTCTATGAT      1260

ACTTTGAAAG ATTATATCAA CGATGCCTTG GGGAATTTGG CAGAATCTTG GTGCCTCGAT      1320

CAAAAACGAA CGATAACGAT GTTGCACGAA CTTAGTAAGA TCAGTCCATC GAGTATCGTG      1380

TCTGAGGTTT ACGGTCGTCC GATATCTGCA CAGTTGCATG GTGATGTGTT AGCTATCTCG      1440

AAATGCATAG AAGTTAATCA ATCATCCGTT CAGCTTTATA AGAGTATGCG GGTCGTCGAT      1500

GCGAAGGGAG TAAGGAGTGA AACGATGTGT TATAATCGGC CCTTGGTGAC GTTTAGCTTT      1560

GTGAACTCCA CGCCTGAGGT TGTCCTTGGT CAGCTAGGGT TAGATAATGA GATTCTGTTG      1620

GGTGATCATA GGACAGAGGA ATGTGAGATA CCTAGTACAA AGATATTTCT ATCTGGAAAT      1680

CATGCACACG TGTATACCGA TTATACGCAT ACGAATTCGA CGCCCATAGA AGACATTGAG      1740

GTATTGGATG CTTTTATTAG ACTAAAGATC GACCCTCTCG AAAATGCTGA TTTTAAACTA      1800

CTTGATTTAT ATTCGCCGGA CGAATTGAGT AGAGCAAACG TTTTCGATTT AGAGAATATT      1860

CTTCGTGAAT ATAACTCATA TAAGAGCGCA CTATATACTA TAGAAGCTAA AATTGCTACT      1920

AATACGCCGT CGTATGTCAA TGGGATTAAT TCTTTTTTAC AAGGGCTTGG GGCTATAGGC      1980

ACTGGATTGG GCTCGGTTAT AAGTGTTACG GCAGGAGCAC TTGGGGATAT TGTGGGTGGA      2040

GTGGTGTCTT TTTTAAAAAA TCCATTCGGG GGTGGTCTCA TGTTGATTTT AGCGATAGTA      2100

GTTGTCGTTA TAATAATTGT GGTTTTCGTT AGACAAAAAC ATGTGCTTAG TAAGCCTATT      2160

GACATGATGT TTCCTTATGC CACCAATCCG GTGACTACTG TGTCCAGTGT TACGGGGACC      2220

ACTGTCGTCA AGACGCCTAG TGTTAAAGAT GCTGACGGGG GCACATCTGT TGCGGTTTCG      2280

GAAAAGAGG AGGGTATGGC TGACGTCAGT GGACAAATAA GTGGTGATGA ATATTCACAA      2340

GAAGATGCTT TAAAAATGCT CAAGGCCATA AAGTCTTTAG ACGAGTCCTA CAGAAGAAAA      2400

CCTTCGTCTT CTGAGTCTCA TGCCTCAAAA CCTAGTTTGA TAGACAGGAT CAGGTATAGA      2460

GGTTATAAGA GTGTAAATGT AGAAGAAGCG TGA                                  2493

(2) INFORMATION FOR SEQ ID NO:12:

(i) SEQUENCE CHARACTERISTICS:
        (A) LENGTH: 2608 base pairs
        (B) TYPE: nucleic acid
        (C) STRANDEDNESS: double
        (D) TOPOLOGY: linear (xi) SEQUENCE DESCRIPTION: SEQ ID NO:12:

ATGTTTGTTA CGGCGGTTGT GTCGGTCTCT CCAAGCTCGT TTTATGAGAG TTTACAAGTA       60

GAGCCCACAC AATCAGAAGA TATAACCCGG TCTGCTCATC TGGGCGATGG TGATGAAATC      120

AGAGAAGCTA TACACAAGTC CCAGGACGCC GAAACAAAAC CCACGTTTTA CGTCTGCCCA      180

CCGCCAACAG GCTCCACAAT CGTACGATTA GAACCAACTC GGACATGTCC GGATTATCAC      240

CTTGGTAAAA ACTTTACAGA GGGTATTGCT GTTGTTTATA AGAAAAACAT TGCAGCGTAC      300

AAGTTTAAGG CGACGGTATA TTACAAAGAT GTTATCGTTA GCACGGCGTG GGCCGGAAGT      360

TCTTATACGC AAATTACTAA TAGATATGCG GATAGGGTAC CAATTCCCGT TTCAGAGATC      420

ACGGACACCA TTGATAAGTT TGGCAAGTGT TCTTCTAAAG CAACGTACGT ACGAAATAAC      480

CACAAAGTTG AAGCCTTTAA TGAGGATAAA AATCCACAGG ATATGCCTCT AATCGCATCA      540

AAATATAATT CTGTGGGATC CAAAGCATGG CATACTACCA ATGACACGTA CATGGTTGCC      600

GGAACCCCCG GAACATATAG GACGGGCACG TCGGTGAATT GCATCATTGA GGAAGTTGAA      660
```

```
GCCAGATCAA TATTCCCTTA TGATAGTTTT GGACTTTCCA CGGGAGATAT AATATACATG      720

TCCCCGTTTT TTGGCCTACG GGATGGTGCA TACAGAGAAC ATTCCAATTA TGCAATGGAT      780

CGTTTTCACC AGTTTGAGGG TTATAGACAA AGGGATCTTG ACACTAGAGC ATTACTGGAA      840

CCTGCAGCGC GGAACTTTTT AGTCACGCCT CATTTAACGG TTGGTTGGAA CTGGAAGCCA      900

AAACGAACGG AAGTTTGTTC GCTTGTCAAG TGGCGTGAGG TTGAAGACGT AGTTCGCGAT      960

GAGTATGCAC ACAATTTTCG CTTTACAATG AAAACACTTT CTACCACGTT TATAAGTGAA     1020

ACAAACGAGT TTAATCTTAA CCAAATCCAT CTCAGTCAAT GTGTAAAGGA GGAAGCCCGG     1080

GCTATTATTA ACCGGATCTA TACAACCAGA TACAACTCAT CTCATGTTAG AACCGGGGAT     1140

ATCCAGACCT ACCTTGCCAG AGGGGGGTTT GTTGTGGTGT TTCAACCCCT GCTGAGCAAT     1200

TCCCTCGCCC GTCTCTATCT CCAAGAATTG GTCCGTGAAA ACACTAATCA TTCACCACAA     1260

AAACACCCGA CTCGAAATAC CAGATCCCGA CGAAGCGTGC CAGTTGAGTT GCGTGCCAAT     1320

AGAACAATAA CAACCACCTC ATCGGTGGAA TTTGCTATGC TCCAGTTTAC ATATGACCAC     1380

ATTCAAGAGC ATGTTAATGA AATGTTGGCA CGTATCTCCT CGTCGTGGTG CCAGCTACAA     1440

AATCGCGAAC GCGCCCTTTG GAGCGGACTA TTTCCAATTA ACCCAAGTGC TTTAGCGAGC     1500

ACCATTTTGG ATCAACGTGT TAAAGCTCGT ATTCTCGGCG ACGTTATCTC CGTTTCTAAT     1560

TGTCCAGAAC TGGGATCAGA TACACGCATT ATACTTCAAA ACTCTATGAG GGTATCTGGT     1620

AGTACTACGC GTTGTTATAG CCGTCCTTTA ATTTCAATAG TTAGTTTAAA TGGGTCCGGG     1680

ACGGTGGAGG GCCAGCTTGG AACAGATAAC GAGTTAATTA TGTCCAGAGA TCTGTTAGAA     1740

CCATGCGTGG CTAATCACAA GCGATATTTT CTATTTGGGC ATCACTACGT ATATTATGAG     1800

GATTATCGTT ACGTCCGTGA AATCGCAGTC CATGATGTGG GAATGATTAG CACTTACGTA     1860

GATTTAAACT TAACACTTCT TAAAGATAGA GAGTTTATGC CGCTGCAAGT ATATACAAGA     1920

GACGAGCTGC GGGATACAGG ATTACTAGAC TACAGTGAAA TTCAACGCCG AAATCAAATG     1980

CATTCGCTGC GTTTTTATGA CATAGACAAG GTTGTGCAAT ATGATAGCGG AACGGCCATT     2040

ATGCAGGGCA TGGCTCAGTT TTTCCAGGGA CTTGGGACCG CGGGCCAGGC CGTTGGACAT     2100

GTGGTTCTTG GGGCCACGGG AGCGCTGCTT TCCACCGTAC ACGGATTTAC CACGTTTTTA     2160

TCTAACCCAT TTGGGGCATT GGCCGTGGGA TTATTGGTTT TGGCGGGACT GGTAGCGGCC     2220

TTTTTTGCGT ACCGGTACGT GCTTAAACTT AAAACAAGCC CGATGAAGGC ATTATATCCA     2280

CTCACAACCA AGGGGTTAAA ACAGTTACCG GAAGGAATGG ATCCCTTTGC CGAGAAACCC     2340

AACGCTACTG ATACCCCAAT AGAAGAAATT GGCGACTCAC AAAACACTGA ACCGTCGGTA     2400

AATAGCGGGT TTGATCCCGA TAAATTTCGA GAAGCCCAGG AAATGATTAA ATATATGACG     2460

TTAGTATCTG CGGCTGAGCG CCAAGAATCT AAAGCCCGCA AAAAAAATAA GACTAGCGCC     2520

CTTTTAACTT CACGTCTTAC CGGCCTTGCT TTACGAAATC GCCGAGGATA CTCCCGTGTT     2580

CGCACCGAGA ATGTAACGGG GGTGTAAA                                       2608

(2) INFORMATION FOR SEQ ID NO:13:

(i) SEQUENCE CHARACTERISTICS:
        (A) LENGTH: 2713 base pairs
        (B) TYPE: nucleic acid
        (C) STRANDEDNESS: double
        (D) TOPOLOGY: linear (xi) SEQUENCE DESCRIPTION: SEQ ID NO:13:

ATGCGCCAGG GCGCCGCGCG GGGGTGCCGG TGGTTCGTCG TATGGGCGCT CTTGGGGTTG       60

ACGCTGGGGG TCCTGGTGGC GTCGGCGGCT CCGAGTTCCC CCGGCACGCC TGGGGTCGCG      120
```

```
GCCGCGACCC AGGCGGCGAA CGGGGGACCT GCCACTCCGG CGCCGCCCGC CCCTGGCCCC    180

GCCCCAACGG GGGACACGAA ACCGAAGAAG AACAAAAAAC CGAAAAACCC ACCGCCGCCG    240

CGCCCCGCCG GCGACAACGC GACCGTCGCC GCGGGCCACG CCACCCTGCG CGAGCACCTG    300

CGGGACATCA AGGCGGAGAA CACCGATGCA AACTTTTACG TGTGCCCACC CCCCACGGGC    360

GCCACGGTGG TGCAGTTCGA GCAGCCGCGC CGCTGCCCGA CCCGGCCCGA GGGTCAGAAC    420

TACACGGAGG GCATCGCGGT GGTCTTCAAG GAGAACATCG CCCCGTACAA GTTCAAGGCC    480

ACCATGTACT ACAAAGACGT CACCGTTTCG CAGGTGTGGT TCGGCCACCG CTACTCCCAG    540

TTTATGGGGA TCTTTGAGGA CCGCGCCCCC GTCCCCTTCG AGGAGGTGAT CGACAAGATC    600

AACGCCAAGG GGTCTGTCG GTCCACGGCC AAGTACGTGC GCAACAACCT GGAGACCACC     660

GCGTTTCACC GGGACGACCA CGAGACCGAC ATGGAGCTGA AACCGGCCAA CGCCGCGACC    720

CGCACGAGCC GGGGCTGGCA CACCACCGAC CTCAAGTACA ACCCCTCGCG GGTGGAGGCG    780

TTCCACCGGT ACGGGACGAC GGTAAACTGC ATCGTCGAGG AGGTGGACGC GCGCTCGGTG    840

TACCCGTACG ACGAGTTTGT GCTGGCGACT GGCGACTTTG TGTACATGTC CCCGTTTTAC    900

GGCTACCGGG AGGGGTCGCA CACCGAACAC ACCAGCTACG CCGCCGACCG CTTCAAGCAG    960

GTTGACGGCT TCTACGCGCG CGACCTCACC ACCAAGGCCC GGGCCACGGC GCCGACCACC   1020

CGGAACCTGC TCACGACCCC CAAGTTCACC GTGGCCTGGG ACTGGGTGCC AAAGCGCCCG   1080

TCGGTCTGCA CCATGACCAA GTGGCAGGAG GTGGACGAGA TGCTGCGCTC CGAGTACGGC   1140

GGCTCCTTCC GATTCTCCTC CGACGCCATA TCCACCACCT TCACCACCAA CCTGACCGAG   1200

TACCCGCTCT CGCGCGTGGA CCTGGGGGAC TGCATCGGCA AGGACGCCCG CGACGCCATG   1260

GACCGCATCT TCGCCCGCAG GTACAACGCG ACGCACATCA AGGTGGGCCA GCCGCAGTAC   1320

TACCTGGCCA ATGGGGGCTT TCTGATCGCG TACCAGCCCC TTCTCAGCAA CACGCTCGCG   1380

GAGCTGTACG TGCGGGAACA CCTCCGAGAG CAGAGCCGCA AGCCCCCAAA CCCCACGCCC   1440

CCGCCGCCCG GGCCAGCGC CAACGCGTCC GTGGAGCGCA TCAAGACCAC CTCCTCCATC    1500

GAGTTCGCCC GGCTGCAGTT TACGTACAAC CACATACAGC GCCATGTCAA CGATATGTTG   1560

GGCCGCGTTG CCATCGCGTG GTGCGAGCTG CAGAATCACG AGCTGACCCT GTGGAACGAG   1620

GCCCGCAAGC TGAACCCCAA CGCCATCGCC TCGGCCACCG TGGGCCGGCG GGTGAGCGCG   1680

CGGATGCTCG GCGACGTGAT GGCCGTCTCC ACGTGCGTGC CGGTCGCCGC GGACAACGTG   1740

ATCGTCCAAA ACTCGATGCG CATCAGCTCG CGGCCCGGGG CCTGCTACAG CCGCCCCCTG   1800

GTCAGCTTTC GGTACGAAGA CCAGGGCCCG TTGGTCGAGG GGCAGGTGGG GGAGAACAAC   1860

GAGCTGCGGC TGACGCGCGA TGCGATCGAG CCGTGCACCG TGGGACACCG GCGCTACTTC   1920

ACCTTCGGTG GGGGCTACGT GTACTTCGAG GAGTACGCGT ACTCCCACCA GCTGAGCCGC   1980

GCCGACATCA CCACCGTCAG CACCTTCATC GACCTCAACA TCACCATGCT GGAGGATCAC   2040

GAGTTTGTCC CCCTGGAGGT GTACACCCGC CACGAGATCA AGGACAGCGG CCTGCTGGAC   2100

TACACGGAGG TCCAGCGCCG CAACCAGCTG CACGACCTGC GCTTCGCCGA CATCGACACG   2160

GTCATCCACG CCGACGCCAA CGCCGCCATG TTCGCGGGCC TGGGCGCGTT CTTCGAGGGG   2220

ATGGGCGACC TGGGGCGCGC GGTCGGCAAG GTGGTGATGG GCATCGTGGG CGGCGTGGTA   2280

TCGGCCGTGT CGGGCGTGTC CTCCTTCATG TCCAACCCCT TTGGGGCGCT GGCCGTGGGT   2340

CTGTTGGTCC TGGCCGGCCT GGCGGCGGCT TTCTTCGCCT TTCGCTACGT CATGCGGCTG   2400

CAGAGCAACC CCATGAAGGC CCTGTACCCG CTAACCACCA AGGAGCTCAA GAACCCCACC   2460

AACCCGGACG CGTCCGGGGA GGGCGAGGAG GGCGGCGACT TTGACGAGGC CAAGCTAGCC   2520
```

```
GAGGCCCGGG AGATGATACG GTACATGGCC CTGGTGTCTG CCATGGAGCG CACGGAACAC      2580

AAGGCCAAGA AGAAGGGCAC GAGCGCGCTG CTCAGCGCCA AGGTCACCGA CATGGTCATG      2640

CGCAAGCGCC GCAACACCAA CTACACCCAA GTTCCCAACA AGACGGTGA CGCCGACGAG      2700

GACGACCTGT GAC                                                         2713
```

(2) INFORMATION FOR SEQ ID NO:14:

(i) SEQUENCE CHARACTERISTICS:
        (A) LENGTH: 808 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:14:

```
Met Val Pro Asn Lys His Leu Leu Ile Ile Leu Ser Phe Ser Thr
1               5                   10                  15

Ala Cys Gly Gln Thr Thr Pro Thr Thr Ala Val Glu Lys Asn Lys Thr
            20                  25                  30

Gln Ala Ile Tyr Gln Glu Tyr Phe Lys Tyr Arg Val Cys Ser Ala Ser
            35                  40                  45

Thr Thr Gly Glu Leu Phe Arg Phe Asp Leu Asp Arg Thr Cys Pro Ser
50                  55                  60

Thr Glu Asp Lys Val His Lys Glu Gly Ile Leu Leu Val Tyr Lys Lys
65                  70                  75                  80

Asn Ile Val Pro Tyr Ile Phe Lys Val Arg Arg Tyr Lys Lys Ile Thr
                85                  90                  95

Thr Ser Val Arg Ile Phe Asn Gly Trp Thr Arg Glu Gly Val Ala Ile
            100                 105                 110

Thr Asn Lys Trp Glu Leu Ser Arg Ala Val Pro Lys Tyr Glu Ile Asp
            115                 120                 125

Ile Met Asp Lys Thr Tyr Gln Cys His Asn Cys Met Gln Ile Glu Val
130                 135                 140

Asn Gly Met Leu Asn Ser Tyr Tyr Asp Arg Asp Gly Asn Asn Lys Thr
145                 150                 155                 160

Val Asp Leu Lys Pro Val Asp Gly Leu Thr Gly Ala Ile Thr Arg Tyr
                165                 170                 175

Ile Ser Gln Pro Lys Val Phe Ala Asp Pro Gly Trp Leu Trp Gly Thr
            180                 185                 190

Tyr Arg Thr Arg Thr Thr Val Asn Cys Glu Ile Val Asp Met Phe Ala
            195                 200                 205

Arg Ser Ala Asp Pro Tyr Thr Tyr Phe Val Thr Ala Leu Gly Asp Thr
210                 215                 220

Val Glu Val Ser Pro Phe Cys Asp Val Asp Asn Ser Cys Pro Asn Ala
225                 230                 235                 240

Thr Asp Val Leu Ser Val Gln Ile Asp Leu Asn His Thr Val Val Asp
                245                 250                 255

Tyr Gly Asn Arg Ala Thr Ser Gln Gln His Lys Lys Arg Ile Phe Ala
            260                 265                 270

His Thr Leu Asp Tyr Ser Val Ser Trp Glu Ala Val Asn Lys Ser Ala
            275                 280                 285

Ser Val Cys Ser Met Val Phe Trp Lys Ser Phe Gln Arg Ala Ile Gln
290                 295                 300

Thr Glu His Asp Leu Thr Tyr His Phe Ile Ala Asn Glu Ile Thr Ala
```

-continued

```
305                 310                 315                 320
Gly Phe Ser Thr Val Lys Glu Pro Leu Ala Asn Phe Thr Ser Asp Tyr
                325                 330                 335

Asn Cys Leu Met Thr His Ile Asn Thr Thr Leu Glu Asp Lys Ile Ala
                340                 345                 350

Arg Val Asn Asn Thr His Thr Pro Asn Gly Thr Ala Glu Tyr Tyr Gln
                355                 360                 365

Thr Glu Gly Gly Met Ile Leu Val Trp Gln Pro Leu Ile Ala Ile Glu
370                 375                 380

Leu Glu Glu Ala Met Leu Glu Ala Thr Thr Ser Pro Val Thr Pro Ser
385                 390                 395                 400

Ala Pro Thr Ser Ser Arg Ser Lys Arg Ala Ile Arg Ser Ile Arg
                405                 410                 415

Asp Val Ser Ala Gly Ser Glu Asn Asn Val Phe Leu Ser Gln Ile Gln
                420                 425                 430

Tyr Ala Tyr Asp Lys Leu Arg Gln Ser Ile Asn Asn Val Leu Glu Glu
                435                 440                 445

Leu Ala Ile Thr Trp Cys Arg Glu Gln Val Arg Gln Thr Met Val Trp
                450                 455                 460

Tyr Glu Ile Ala Lys Ile Asn Pro Thr Ser Val Met Thr Ala Ile Tyr
465                 470                 475                 480

Gly Lys Pro Val Ser Arg Lys Ala Leu Gly Asp Val Ile Ser Val Thr
                485                 490                 495

Glu Cys Ile Asn Val Asp Gln Ser Ser Val Ser Ile His Lys Ser Leu
                500                 505                 510

Lys Thr Glu Asn Asn Asp Ile Cys Tyr Ser Arg Pro Pro Val Thr Phe
                515                 520                 525

Lys Phe Val Asn Ser Ser Gln Leu Phe Lys Gly Gln Leu Gly Ala Arg
                530                 535                 540

Asn Glu Ile Leu Leu Ser Glu Ser Leu Val Glu Asn Cys His Gln Asn
545                 550                 555                 560

Ala Glu Thr Phe Phe Thr Ala Lys Asn Glu Thr Tyr His Phe Lys Asn
                565                 570                 575

Tyr Val His Val Glu Thr Leu Pro Val Asn Asn Ile Ser Thr Leu Asp
                580                 585                 590

Thr Phe Leu Ala Leu Asn Leu Thr Phe Ile Glu Asn Ile Asp Phe Lys
                595                 600                 605

Ala Val Glu Leu Tyr Ser Ser Gly Glu Arg Lys Leu Ala Asn Val Phe
                610                 615                 620

Asp Leu Glu Thr Met Phe Arg Glu Tyr Asn Tyr Tyr Ala Gln Ser Ile
625                 630                 635                 640

Ser Gly Leu Arg Lys Asp Phe Asp Asn Ser Gln Arg Asn Asn Arg Asp
                645                 650                 655

Arg Ile Ile Gln Asp Phe Ser Glu Ile Leu Ala Asp Leu Gly Ser Ile
                660                 665                 670

Gly Lys Val Ile Val Asn Val Ala Ser Gly Ala Phe Ser Leu Phe Gly
                675                 680                 685

Gly Ile Val Thr Gly Ile Leu Asn Phe Ile Lys Asn Pro Leu Gly Gly
                690                 695                 700

Met Phe Thr Phe Leu Leu Ile Gly Ala Val Ile Ile Leu Val Ile Leu
705                 710                 715                 720

Leu Val Arg Arg Thr Asn Asn Met Ser Gln Ala Pro Ile Arg Met Ile
                725                 730                 735
```

```
Tyr Pro Asp Val Glu Lys Ser Lys Ser Thr Val Thr Pro Met Glu Pro
            740                 745                 750

Glu Thr Ile Lys Gln Ile Leu Leu Gly Met His Asn Met Gln Gln Glu
            755                 760                 765

Ala Tyr Lys Lys Lys Glu Glu Gln Arg Ala Ala Arg Pro Ser Ile Phe
770                 775                 780

Arg Gln Ala Ala Glu Thr Phe Leu Arg Lys Arg Ser Gly Tyr Lys Gln
785                 790                 795                 800

Ile Ser Thr Glu Asp Lys Ile Val
                805
```

(2) INFORMATION FOR SEQ ID NO:15:

(i) SEQUENCE CHARACTERISTICS:
        (A) LENGTH: 874 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:15:

```
Met Tyr Tyr Lys Thr Ile Leu Phe Phe Ala Leu Ile Lys Val Cys Ser
1                   5                   10                  15

Phe Asn Gln Thr Thr Thr His Ser Thr Thr Ser Pro Ser Ile Ser
            20                  25                  30

Ser Thr Thr Ser Ser Thr Thr Ser Thr Ser Lys Pro Ser Asn Thr
            35                  40                  45

Thr Ser Thr Asn Ser Ser Leu Ala Ala Ser Pro Gln Asn Thr Ser Thr
50                  55                  60

Ser Lys Pro Ser Thr Asp Asn Gln Gly Thr Ser Thr Pro Thr Ile Pro
65                  70                  75                  80

Thr Val Thr Asp Asp Thr Ala Ser Lys Asn Phe Tyr Lys Tyr Arg Val
                85                  90                  95

Cys Ser Ala Ser Ser Ser Gly Glu Leu Phe Arg Phe Asp Leu Asp
                100                 105                 110

Gln Thr Cys Pro Asp Thr Lys Asp Lys Lys His Val Glu Gly Ile Leu
            115                 120                 125

Leu Val Leu Lys Lys Asn Ile Val Pro Tyr Ile Phe Lys Val Arg Lys
130                 135                 140

Tyr Arg Lys Ile Ala Thr Ser Val Thr Val Tyr Arg Gly Trp Ser Gln
145                 150                 155                 160

Ala Ala Val Thr Asn Arg Asp Asp Ile Ser Arg Ala Ile Pro Tyr Asn
                165                 170                 175

Glu Ile Ser Met Ile Asp Arg Thr Tyr His Cys Phe Ser Ala Met Ala
            180                 185                 190

Thr Val Ile Asn Gly Ile Leu Asn Thr Tyr Ile Asp Arg Asp Ser Glu
            195                 200                 205

Asn Lys Ser Val Pro Leu Gln Pro Val Ala Gly Leu Thr Glu Asn Ile
            210                 215                 220

Asn Arg Tyr Phe Ser Gln Pro Leu Ile Tyr Ala Glu Pro Gly Trp Phe
225                 230                 235                 240

Pro Gly Ile Tyr Arg Val Arg Thr Val Asn Cys Glu Val Val Asp
                245                 250                 255

Met Tyr Ala Arg Ser Val Glu Pro Tyr Thr His Phe Ile Thr Ala Leu
            260                 265                 270

Gly Asp Thr Ile Glu Ile Ser Pro Phe Cys His Asn Asn Ser Gln Cys
```

-continued

```
                275                     280                     285
Thr Thr Gly Asn Ser Thr Ser Arg Asp Ala Thr Lys Val Trp Ile Glu
    290                     295                     300
Glu Asn His Gln Thr Val Asp Tyr Glu Arg Arg Gly His Pro Thr Lys
305                     310                     315                 320
Asp Lys Arg Ile Phe Leu Lys Asp Glu Tyr Thr Ile Ser Trp Lys
                325                     330                     335
Ala Glu Asp Arg Glu Arg Ala Ile Cys Asp Phe Val Ile Trp Lys Thr
                340                     345                     350
Phe Pro Arg Ala Ile Gln Thr Ile His Asn Gly Ser Phe His Phe Val
                355                     360                     365
Ala Asn Glu Val Thr Ala Ser Phe Leu Thr Ser Asn Gln Glu Glu Thr
    370                     375                     380
Glu Leu Arg Gly Asn Thr Glu Ile Leu Asn Cys Met Asn Ser Thr Ile
385                     390                     395                 400
Asn Glu Thr Leu Glu Glu Thr Val Lys Lys Phe Asn Lys Ser His Ile
                    405                     410                     415
Arg Asp Gly Glu Val Lys Tyr Tyr Lys Thr Asn Gly Gly Leu Phe Leu
                420                     425                     430
Ile Trp Gln Ala Met Lys Pro Leu Asn Leu Ser Glu His Thr Asn Tyr
                435                     440                     445
Thr Ile Glu Arg Asn Asn Lys Thr Gly Asn Lys Ser Arg Gln Lys Arg
    450                     455                     460
Ser Val Asp Thr Lys Thr Phe Gln Gly Ala Lys Gly Leu Ser Thr Ala
465                     470                     475                 480
Gln Val Gln Tyr Ala Tyr Asp His Leu Arg Thr Ser Met Asn His Ile
                    485                     490                     495
Leu Glu Glu Leu Thr Lys Thr Trp Cys Arg Glu Gln Lys Lys Asp Asn
                500                     505                     510
Leu Met Trp Tyr Glu Leu Ser Lys Ile Asn Pro Val Ser Val Met Ala
                515                     520                     525
Ala Ile Tyr Gly Lys Pro Val Ala Val Lys Ala Met Gly Asp Ala Phe
                530                     535                     540
Met Val Ser Glu Cys Ile Asn Val Asp Gln Ala Ser Val Asn Ile His
545                     550                     555                 560
Lys Ser Met Arg Thr Asp Pro Lys Val Cys Tyr Ser Arg Pro Leu
                    565                     570                     575
Val Thr Phe Lys Phe Val Asn Ser Thr Ala Thr Phe Arg Gly Gln Leu
                580                     585                     590
Gly Thr Arg Asn Glu Ile Leu Leu Thr Asn Thr His Val Glu Thr Cys
                595                     600                     605
Arg Pro Thr Ala Asp His Tyr Phe Val Lys Asn Met Thr His Tyr
    610                     615                     620
Phe Lys Asp Tyr Lys Phe Val Lys Thr Met Asp Thr Asn Asn Ile Ser
625                     630                     635                 640
Thr Leu Asp Thr Phe Leu Thr Leu Asn Leu Thr Phe Ile Asp Asn Ile
                    645                     650                     655
Asp Phe Lys Thr Val Glu Leu Tyr Ser Glu Thr Glu Arg Lys Met Ala
                660                     665                     670
Ser Ala Leu Asp Leu Glu Thr Met Phe Arg Glu Tyr Asn Tyr Tyr Thr
                675                     680                     685
Gln Lys Leu Ala Ser Leu Arg Glu Asp Leu Asp Asn Thr Ile Asp Leu
                690                     695                     700
```

-continued

```
Asn Arg Asp Arg Leu Val Lys Asp Leu Ser Glu Met Met Ala Asp Leu
705                 710                 715                 720

Gly Asp Ile Gly Lys Val Val Asn Thr Phe Ser Gly Ile Val Thr
            725                 730                 735

Val Phe Gly Ser Ile Val Gly Gly Phe Val Ser Phe Phe Thr Asn Pro
            740                 745                 750

Ile Gly Gly Val Thr Ile Ile Leu Leu Leu Ile Val Val Val Phe Val
            755                 760                 765

Val Phe Ile Val Ser Arg Arg Thr Asn Asn Met Asn Glu Ala Pro Ile
        770                 775                 780

Lys Met Ile Tyr Pro Asn Ile Asp Lys Ala Ser Glu Gln Glu Asn Ile
785                 790                 795                 800

Gln Pro Leu Pro Gly Glu Glu Ile Lys Arg Ile Leu Leu Gly Met His
                805                 810                 815

Gln Leu Gln Gln Ser Glu His Gly Lys Ser Glu Glu Ala Ser His
            820                 825                 830

Lys Pro Gly Leu Phe Gln Leu Leu Gly Asp Gly Leu Gln Leu Leu Arg
            835                 840                 845

Arg Arg Gly Tyr Thr Arg Leu Pro Thr Phe Asp Pro Ser Pro Gly Asn
850                 855                 860

Asp Thr Ser Glu Thr His Gln Lys Tyr Val
865                 870
```

(2) INFORMATION FOR SEQ ID NO:16:

(i) SEQUENCE CHARACTERISTICS:
        (A) LENGTH: 874 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:16:

```
Met Gly Val Gly Gly Gly Pro Arg Val Val Leu Cys Leu Trp Cys Val
1               5                   10                  15

Ala Ala Leu Leu Cys Gln Gly Val Ala Gln Glu Val Val Ala Glu Thr
            20                  25                  30

Thr Thr Pro Phe Ala Thr His Arg Pro Glu Val Val Ala Glu Glu Asn
            35                  40                  45

Pro Ala Asn Pro Phe Leu Pro Arg Val Cys Gly Ala Ser Pro Thr
50                  55                  60

Gly Gly Glu Ile Phe Arg Phe Pro Leu Glu Glu Ser Cys Pro Asn Thr
65                  70                  75                  80

Glu Asp Lys Asp His Ile Glu Gly Ile Ala Leu Ile Tyr Lys Thr Asn
                85                  90                  95

Ile Val Pro Tyr Val Phe Asn Val Arg Lys Tyr Arg Lys Ile Met Thr
            100                 105                 110

Ser Thr Thr Ile Tyr Lys Gly Trp Ser Glu Asp Ala Ile Thr Asn Gln
            115                 120                 125

His Thr Arg Ser Tyr Ala Val Pro Leu Tyr Glu Val Gln Met Met Asp
        130                 135                 140

His Tyr Tyr Gln Cys Phe Ser Ala Val Gln Val Asn Glu Gly Gly His
145                 150                 155                 160

Val Asn Thr Tyr Tyr Asp Arg Asp Gly Trp Asn Glu Thr Ala Phe Leu
                165                 170                 175

Lys Pro Ala Asp Gly Leu Thr Ser Ser Ile Thr Arg Tyr Gln Ser Gln
```

-continued

```
            180                 185                 190
Pro Glu Val Tyr Ala Thr Pro Arg Asn Leu Leu Trp Ser Tyr Thr Thr
            195                 200                 205
Arg Thr Thr Val Asn Cys Glu Val Thr Glu Met Ser Ala Arg Ser Met
210                 215                 220
Lys Pro Phe Glu Phe Phe Val Thr Ser Val Gly Asp Thr Ile Glu Met
225                 230                 235                 240
Ser Pro Phe Leu Lys Glu Asn Gly Thr Glu Pro Lys Ile Leu Lys
                245                 250                 255
Arg Pro His Ser Ile Gln Leu Leu Lys Asn Tyr Ala Val Thr Lys Tyr
                260                 265                 270
Gly Val Gly Leu Gly Gln Ala Asp Asn Ala Thr Arg Phe Phe Ala Ile
            275                 280                 285
Phe Gly Asp Tyr Ser Leu Ser Trp Lys Ala Thr Thr Glu Asn Ser Ser
290                 295                 300
Tyr Cys Asp Leu Ile Leu Trp Lys Gly Phe Ser Asn Ala Ile Gln Thr
305                 310                 315                 320
Gln His Asn Ser Ser Leu His Phe Ile Ala Asn Asp Ile Thr Ala Ser
                325                 330                 335
Phe Ser Thr Pro Leu Glu Glu Ala Asn Phe Asn Glu Thr Phe Lys
                340                 345                 350
Cys Ile Trp Asn Asn Thr Gln Glu Glu Ile Gln Lys Lys Leu Lys Glu
            355                 360                 365
Val Glu Lys Thr His Arg Pro Asn Gly Thr Ala Lys Val Tyr Lys Thr
            370                 375                 380
Thr Gly Asn Leu Tyr Ile Val Trp Gln Pro Leu Ile Gln Ile Asp Leu
385                 390                 395                 400
Leu Asp Thr His Ala Lys Leu Tyr Asn Leu Thr Asn Ala Thr Ala Ser
                405                 410                 415
Pro Thr Ser Thr Pro Thr Thr Ser Pro Arg Arg Arg Arg Asp Thr
                420                 425                 430
Ser Ser Val Ser Gly Gly Asn Asn Gly Asp Asn Ser Thr Lys Glu
            435                 440                 445
Glu Ser Val Ala Ala Ser Gln Val Gln Phe Ala Tyr Asp Asn Leu Arg
450                 455                 460
Lys Ser Ile Asn Arg Val Leu Gly Glu Leu Ser Arg Ala Trp Cys Arg
465                 470                 475                 480
Glu Gln Tyr Arg Ala Ser Leu Met Trp Tyr Glu Leu Ser Lys Ile Asn
                485                 490                 495
Pro Thr Ser Val Met Ser Ala Ile Tyr Gly Arg Pro Val Ser Ala Lys
                500                 505                 510
Leu Ile Gly Asp Val Val Ser Val Ser Asp Cys Ile Ser Val Asp Gln
            515                 520                 525
Lys Ser Val Phe Val His Lys Asn Met Lys Val Pro Gly Lys Glu Asp
530                 535                 540
Leu Cys Tyr Thr Arg Pro Val Gly Phe Lys Phe Ile Asn Gly Ser
545                 550                 555                 560
Glu Leu Phe Ala Gly Gln Leu Gly Pro Arg Asn Glu Ile Val Leu Ser
                565                 570                 575
Thr Ser Gln Val Glu Val Cys Gln His Ser Cys Glu His Tyr Phe Gln
                580                 585                 590
Ala Gly Asn Gln Met Tyr Lys Tyr Lys Asp Tyr Tyr Val Ser Thr
            595                 600                 605
```

-continued

```
Leu Asn Leu Thr Asp Ile Pro Thr Leu His Thr Met Ile Thr Leu Asn
    610                 615                 620

Leu Ser Leu Val Glu Asn Ile Asp Phe Lys Val Ile Glu Leu Tyr Ser
625                 630                 635                 640

Lys Thr Glu Lys Arg Leu Ser Asn Val Phe Asp Ile Glu Thr Met Phe
                645                 650                 655

Arg Glu Tyr Asn Tyr Tyr Thr Gln Asn Leu Asn Gly Leu Arg Lys Asp
                660                 665                 670

Leu Asp Asp Ser Ile Asp His Gly Arg Asp Ser Phe Ile Gln Thr Leu
            675                 680                 685

Gly Asp Ile Met Gln Asp Leu Gly Thr Ile Gly Lys Val Val Val Asn
690                 695                 700

Val Ala Ser Gly Val Phe Ser Leu Phe Gly Ser Ile Val Ser Gly Val
705                 710                 715                 720

Ile Ser Phe Phe Lys Asn Pro Phe Gly Gly Met Leu Leu Ile Val Leu
                725                 730                 735

Ile Ile Ala Gly Val Val Val Tyr Leu Phe Met Thr Arg Ser Arg
                740                 745                 750

Ser Ile Tyr Ser Ala Pro Ile Arg Met Leu Tyr Pro Gly Val Glu Arg
        755                 760                 765

Ala Ala Gln Glu Pro Gly Ala His Pro Val Ser Glu Asp Gln Ile Arg
770                 775                 780

Asn Ile Leu Met Gly Met His Gln Phe Gln Gln Arg Gln Arg Ala Glu
785                 790                 795                 800

Glu Glu Ala Arg Arg Glu Glu Val Lys Gly Lys Arg Thr Leu Phe
                805                 810                 815

Glu Val Ile Arg Asp Ser Ala Thr Ser Val Leu Arg Arg Arg Gly
            820                 825                 830

Gly Gly Gly Tyr Gln Arg Leu Gln Arg Asp Gly Ser Asp Asp Glu Gly
            835                 840                 845

Asp Tyr Glu Pro Leu Arg Arg Gln Asp Gly Gly Tyr Asp Asp Val Asp
850                 855                 860

Val Glu Ala Gly Thr Ala Asp Thr Gly Val
865                 870
```

(2) INFORMATION FOR SEQ ID NO:17:

(i) SEQUENCE CHARACTERISTICS:
        (A) LENGTH: 849 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:17:

```
Met Tyr Pro Thr Val Lys Ser Met Arg Val Ala His Leu Thr Asn Leu
1               5                   10                  15

Leu Thr Leu Leu Cys Leu Leu Cys His Thr His Leu Tyr Val Cys Gln
                20                  25                  30

Pro Thr Thr Leu Arg Gln Pro Ser Asp Met Thr Pro Ala Gln Asp Ala
            35                  40                  45

Pro Thr Glu Thr Pro Pro Leu Ser Thr Asn Thr Asn Arg Gly Phe
    50                  55                  60

Glu Tyr Phe Arg Val Cys Gly Val Ala Ala Thr Gly Glu Thr Phe Arg
65                  70                  75                  80

Phe Asp Leu Asp Lys Thr Cys Pro Ser Thr Gln Asp Lys Lys His Val
```

-continued

```
                85                   90                   95
Glu Gly Ile Leu Leu Val Tyr Lys Ile Asn Ile Val Pro Tyr Ile Phe
            100                 105                 110
Lys Ile Arg Arg Tyr Arg Lys Ile Ile Thr Gln Leu Thr Ile Trp Arg
        115                 120                 125
Gly Leu Thr Thr Ser Ser Val Thr Gly Lys Phe Glu Met Ala Thr Gln
    130                 135                 140
Ala His Glu Trp Glu Val Gly Asp Phe Asp Ser Ile Tyr Gln Cys Tyr
145                 150                 155                 160
Asn Ser Ala Thr Met Val Val Asn Val Arg Gln Val Tyr Val Asp
                165                 170                 175
Arg Asp Gly Val Asn Lys Thr Val Asn Ile Arg Pro Val Asp Gly Leu
            180                 185                 190
Thr Gly Asn Ile Gln Arg Tyr Phe Ser Gln Pro Thr Leu Tyr Ser Glu
        195                 200                 205
Pro Gly Trp Met Pro Gly Phe Tyr Arg Val Arg Thr Thr Val Asn Cys
    210                 215                 220
Glu Ile Val Asp Met Val Ala Arg Ser Met Asp Pro Tyr Asn Tyr Ile
225                 230                 235                 240
Ala Thr Ala Leu Gly Asp Ser Leu Glu Leu Ser Pro Phe Gln Thr Phe
                245                 250                 255
Asp Asn Thr Ser Gln Cys Thr Ala Pro Lys Arg Ala Asp Met Arg Val
            260                 265                 270
Arg Glu Val Lys Asn Tyr Lys Phe Val Asp Tyr Asn Asn Arg Gly Thr
        275                 280                 285
Ala Pro Ala Gly Gln Ser Arg Thr Phe Leu Glu Thr Pro Ser Ala Thr
    290                 295                 300
Tyr Ser Trp Lys Thr Ala Thr Arg Gln Thr Ala Thr Cys Asp Leu Val
305                 310                 315                 320
His Trp Lys Thr Phe Pro Arg Ala Ile Gln Thr Ala His Glu His Ser
                325                 330                 335
Tyr His Phe Val Ala Asn Glu Val Thr Ala Thr Phe Asn Thr Pro Leu
            340                 345                 350
Thr Glu Val Glu Asn Phe Thr Ser Thr Tyr Ser Cys Val Ser Asp Gln
        355                 360                 365
Ile Asn Lys Thr Ile Ser Glu Tyr Ile Gln Lys Leu Asn Asn Ser Tyr
    370                 375                 380
Val Ala Ser Gly Lys Thr Gln Tyr Phe Lys Thr Asp Gly Asn Leu Tyr
385                 390                 395                 400
Leu Ile Trp Gln Pro Leu Glu His Pro Glu Ile Glu Asp Ile Asp Glu
                405                 410                 415
Asp Ser Asp Pro Glu Pro Thr Pro Ala Pro Pro Lys Ser Thr Arg Arg
            420                 425                 430
Lys Arg Glu Ala Ala Asp Asn Gly Asn Ser Thr Ser Glu Val Ser Lys
        435                 440                 445
Gly Ser Glu Asn Pro Leu Ile Thr Ala Gln Ile Gln Phe Ala Tyr Asp
    450                 455                 460
Lys Leu Thr Thr Ser Val Asn Asn Val Leu Glu Glu Leu Ser Arg Ala
465                 470                 475                 480
Trp Cys Arg Glu Gln Val Arg Asp Thr Leu Met Trp Tyr Glu Leu Ser
                485                 490                 495
Lys Val Asn Pro Thr Ser Val Met Ser Ala Ile Tyr Gly Lys Pro Val
            500                 505                 510
```

-continued

```
Ala Ala Arg Tyr Val Gly Asp Ala Ile Ser Val Thr Asp Cys Ile Tyr
        515                 520                 525

Val Asp Gln Ser Ser Val Asn Ile His Gln Ser Leu Arg Leu Gln His
530                 535                 540

Asp Lys Thr Thr Cys Tyr Ser Arg Pro Arg Val Thr Phe Lys Phe Ile
545                 550                 555                 560

Asn Ser Thr Asp Pro Leu Thr Gly Gln Leu Gly Pro Arg Lys Glu Ile
                565                 570                 575

Ile Leu Ser Asn Thr Asn Ile Glu Thr Cys Lys Asp Glu Ser Glu His
                580                 585                 590

Tyr Phe Ile Val Gly Glu Tyr Ile Tyr Tyr Lys Asn Tyr Ile Phe
        595                 600                 605

Glu Glu Lys Leu Asn Leu Ser Ser Ile Ala Thr Leu Asp Thr Phe Ile
        610                 615                 620

Ala Leu Asn Ile Ser Phe Ile Glu Asn Ile Asp Phe Lys Thr Val Glu
625                 630                 635                 640

Leu Tyr Ser Ser Thr Glu Arg Lys Leu Ala Ser Ser Val Phe Asp Ile
                645                 650                 655

Glu Ser Met Phe Arg Glu Tyr Asn Tyr Thr Tyr Ser Leu Ala Gly
                660                 665                 670

Ile Lys Lys Asp Leu Asp Asn Thr Ile Asp Tyr Asn Arg Asp Arg Leu
        675                 680                 685

Val Gln Asp Leu Ser Asp Met Met Ala Asp Leu Gly Asp Ile Gly Arg
690                 695                 700

Ser Val Val Asn Val Val Ser Ser Val Val Thr Phe Phe Ser Ser Ile
705                 710                 715                 720

Val Thr Gly Phe Ile Lys Phe Phe Thr Asn Pro Leu Gly Gly Ile Phe
                725                 730                 735

Ile Leu Leu Ile Ile Gly Gly Ile Ile Phe Leu Val Val Val Leu Asn
                740                 745                 750

Arg Arg Asn Ser Gln Phe His Asp Ala Pro Ile Lys Met Leu Tyr Pro
                755                 760                 765

Ser Val Glu Asn Tyr Ala Ala Arg Gln Ala Pro Pro Tyr Ser Ala
        770                 775                 780

Ser Pro Pro Ala Ile Asp Lys Glu Glu Ile Lys Arg Ile Leu Leu Gly
785                 790                 795                 800

Met His Gln Val His Gln Glu Glu Lys Glu Ala Gln Lys Gln Leu Thr
                805                 810                 815

Asn Ser Gly Pro Thr Leu Trp Gln Lys Ala Thr Gly Phe Leu Arg Asn
                820                 825                 830

Arg Arg Lys Gly Tyr Ser Gln Leu Pro Leu Glu Asp Glu Ser Thr Ser
        835                 840                 845

Leu
```

(2) INFORMATION FOR SEQ ID NO:18:

(i) SEQUENCE CHARACTERISTICS:
        (A) LENGTH: 857 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:18:

```
Met Thr Arg Arg Arg Val Leu Ser Val Val Leu Leu Ala Ala Leu
1               5                   10                  15
```

```
Ala Cys Arg Leu Gly Ala Gln Thr Pro Glu Gln Pro Ala Pro Pro Ala
            20                  25                  30
Thr Thr Val Gln Pro Thr Ala Thr Arg Gln Gln Thr Ser Phe Pro Phe
        35                  40                  45
Arg Val Cys Glu Leu Ser Ser His Gly Asp Leu Phe Arg Phe Ser Ser
 50                  55                  60
Asp Ile Gln Cys Pro Ser Phe Gly Thr Arg Glu Asn His Thr Glu Gly
 65                  70                  75                  80
Leu Leu Met Val Phe Lys Asp Asn Ile Ile Pro Tyr Ser Phe Lys Val
            85                  90                  95
Arg Ser Tyr Thr Lys Ile Val Thr Asn Ile Leu Ile Tyr Asn Gly Trp
            100                 105                 110
Tyr Ala Asp Ser Val Thr Asn Arg His Glu Glu Lys Phe Ser Val Asp
            115                 120                 125
Ser Tyr Glu Thr Asp Gln Met Asp Thr Ile Tyr Gln Cys Tyr Asn Ala
    130                 135                 140
Val Lys Met Thr Lys Asp Gly Leu Thr Arg Val Tyr Val Asp Arg Asp
145                 150                 155                 160
Gly Val Asn Ile Thr Val Asn Leu Lys Pro Thr Gly Gly Leu Ala Asn
                165                 170                 175
Gly Val Arg Arg Tyr Ala Ser Gln Thr Glu Leu Tyr Asp Ala Pro Gly
            180                 185                 190
Trp Leu Ile Trp Thr Tyr Arg Thr Arg Thr Thr Val Asn Cys Leu Ile
            195                 200                 205
Thr Asp Met Met Ala Lys Ser Asn Ser Pro Phe Asp Phe Val Thr
    210                 215                 220
Thr Thr Gly Gln Thr Val Glu Met Ser Pro Phe Tyr Asp Gly Lys Asn
225                 230                 235                 240
Lys Glu Thr Phe His Glu Arg Ala Asp Ser Phe His Val Arg Thr Asn
                245                 250                 255
Tyr Lys Ile Val Asp Tyr Asp Asn Arg Gly Thr Asn Pro Gln Gly Glu
            260                 265                 270
Arg Arg Ala Phe Leu Asp Lys Gly Thr Tyr Thr Leu Ser Trp Lys Leu
        275                 280                 285
Glu Asn Arg Thr Ala Tyr Cys Pro Leu Gln His Trp Gln Thr Phe Asp
    290                 295                 300
Ser Thr Ile Ala Thr Glu Thr Gly Lys Ser Ile His Phe Val Thr Asp
305                 310                 315                 320
Glu Gly Thr Ser Ser Phe Val Thr Asn Thr Val Gly Ile Glu Leu
                325                 330                 335
Pro Asp Ala Phe Lys Cys Ile Glu Glu Gln Val Asn Lys Thr Met His
            340                 345                 350
Glu Lys Tyr Glu Ala Val Gln Asp Arg Tyr Thr Lys Gly Gln Glu Ala
        355                 360                 365
Ile Thr Tyr Phe Ile Thr Ser Gly Gly Leu Leu Leu Ala Trp Leu Pro
 370                 375                 380
Leu Thr Pro Arg Ser Leu Ala Thr Val Lys Asn Leu Thr Glu Leu Thr
385                 390                 395                 400
Thr Pro Thr Ser Ser Pro Ser Ser Ser Pro Ala Pro Ser
                405                 410                 415
Ala Ala Arg Gly Ser Thr Pro Ala Ala Val Leu Arg Arg Arg Arg
            420                 425                 430
Asp Ala Gly Asn Ala Thr Thr Pro Val Pro Pro Thr Ala Pro Gly Lys
```

```
                435                 440                 445
Ser Leu Gly Thr Leu Asn Asn Pro Ala Thr Val Gln Ile Gln Phe Ala
    450                 455                 460

Tyr Asp Ser Leu Arg Arg Gln Ile Asn Arg Met Leu Gly Asp Leu Ala
465                 470                 475                 480

Arg Ala Trp Cys Leu Glu Gln Lys Arg Gln Asn Met Val Leu Arg Glu
                485                 490                 495

Leu Thr Lys Ile Asn Pro Thr Thr Val Met Ser Ser Ile Tyr Gly Lys
                500                 505                 510

Ala Val Ala Ala Lys Arg Leu Gly Asp Val Ile Ser Val Ser Gln Cys
            515                 520                 525

Val Pro Val Asn Gln Ala Thr Val Thr Leu Arg Lys Ser Met Arg Val
530                 535                 540

Pro Gly Ser Glu Thr Met Cys Tyr Ser Arg Pro Leu Val Ser Phe Ser
545                 550                 555                 560

Phe Ile Asn Asp Thr Lys Thr Tyr Glu Gly Gln Leu Gly Thr Asp Asn
                565                 570                 575

Glu Ile Phe Leu Thr Lys Lys Met Thr Glu Val Cys Gln Ala Thr Ser
                580                 585                 590

Gln Tyr Tyr Phe Gln Ser Gly Asn Glu Ile His Val Tyr Asn Asp Tyr
            595                 600                 605

His His Phe Lys Thr Ile Glu Leu Asp Gly Ile Ala Thr Leu Gln Thr
        610                 615                 620

Phe Ile Ser Leu Asn Thr Ser Leu Ile Glu Asn Ile Asp Phe Ala Ser
625                 630                 635                 640

Leu Glu Leu Tyr Ser Arg Asp Glu Gln Arg Ala Ser Asn Val Phe Asp
                645                 650                 655

Leu Glu Gly Ile Phe Arg Glu Tyr Asn Phe Gln Ala Gln Asn Ile Ala
                660                 665                 670

Gly Leu Arg Lys Asp Leu Asp Asn Ala Val Ser Asn Gly Arg Asn Gln
            675                 680                 685

Phe Val Asp Gly Leu Gly Glu Leu Met Asp Ser Leu Gly Ser Val Gly
        690                 695                 700

Gln Ser Ile Thr Asn Leu Val Ser Thr Val Gly Gly Leu Phe Ser Ser
705                 710                 715                 720

Leu Val Ser Gly Phe Ile Ser Phe Phe Lys Asn Pro Phe Gly Gly Met
                725                 730                 735

Leu Ile Leu Val Leu Val Ala Gly Val Val Ile Leu Val Ile Ser Leu
                740                 745                 750

Thr Arg Arg Thr Arg Gln Met Ser Gln Gln Pro Val Gln Met Leu Tyr
            755                 760                 765

Pro Gly Ile Asp Glu Leu Ala Gln Gln His Ala Ser Gly Glu Gly Pro
        770                 775                 780

Gly Ile Asn Pro Ile Ser Lys Thr Glu Leu Gln Ala Ile Met Leu Ala
785                 790                 795                 800

Leu His Glu Gln Asn Gln Glu Gln Lys Arg Ala Ala Gln Arg Ala Ala
                805                 810                 815

Gly Pro Ser Val Ala Ser Arg Ala Leu Gln Ala Ala Arg Asp Arg Phe
                820                 825                 830

Pro Gly Leu Arg Arg Arg Arg Tyr His Asp Pro Glu Thr Ala Ala Ala
            835                 840                 845

Leu Leu Gly Glu Ala Glu Thr Glu Phe
        850                 855
```

(2) INFORMATION FOR SEQ ID NO:19:

(i) SEQUENCE CHARACTERISTICS:
        (A) LENGTH: 907 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:19:

```
Met Glu Ser Arg Ile Trp Cys Leu Val Val Cys Val Asn Leu Cys Ile
1               5                   10                  15

Val Cys Leu Gly Ala Ala Val Ser Ser Ser Thr Arg Gly Thr Ser
            20                  25                  30

Ala Thr His Ser His His Ser Ser His Thr Thr Ser Ala Ala His Ser
            35                  40                  45

Arg Ser Gly Ser Val Ser Gln Arg Val Thr Ser Ser Gln Thr Val Ser
        50                  55                  60

His Gly Val Asn Glu Thr Ile Tyr Asn Thr Thr Leu Lys Tyr Gly Asp
65                  70                  75                  80

Val Val Gly Val Asn Thr Thr Lys Tyr Pro Tyr Arg Val Cys Ser Met
                85                  90                  95

Ala Gln Gly Thr Asp Leu Ile Arg Phe Glu Arg Asn Ile Val Cys Thr
            100                 105                 110

Ser Met Lys Pro Ile Asn Glu Asp Leu Asp Glu Gly Ile Met Val Val
        115                 120                 125

Tyr Lys Arg Asn Ile Val Ala His Thr Phe Lys Val Arg Val Tyr Gln
130                 135                 140

Lys Val Leu Thr Phe Arg Arg Ser Tyr Ala Tyr Ile His Thr Thr Tyr
145                 150                 155                 160

Leu Leu Gly Ser Asn Thr Glu Tyr Val Ala Pro Pro Met Trp Glu Ile
                165                 170                 175

His His Ile Asn Ser His Ser Gln Cys Tyr Ser Ser Tyr Ser Arg Val
            180                 185                 190

Ile Ala Gly Thr Val Phe Val Ala Tyr His Arg Asp Ser Tyr Glu Asn
        195                 200                 205

Lys Thr Met Gln Leu Met Pro Asp Asp Tyr Ser Asn Thr His Ser Thr
210                 215                 220

Arg Tyr Val Thr Val Lys Asp Gln Trp His Ser Arg Gly Ser Thr Trp
225                 230                 235                 240

Leu Tyr Arg Glu Thr Cys Asn Leu Asn Cys Met Val Thr Ile Thr Thr
                245                 250                 255

Ala Arg Ser Lys Tyr Pro Tyr His Phe Phe Ala Thr Ser Thr Gly Asp
            260                 265                 270

Val Val Asp Ile Ser Pro Phe Tyr Asn Gly Thr Asn Arg Asn Ala Ser
        275                 280                 285

Tyr Phe Gly Glu Asn Ala Asp Lys Phe Ile Phe Pro Asn Tyr Thr
290                 295                 300

Ile Val Ser Asp Phe Gly Arg Pro Asn Ser Ala Leu Glu Thr His Arg
305                 310                 315                 320

Leu Val Ala Phe Leu Glu Arg Ala Asp Ser Val Ile Ser Trp Asp Ile
                325                 330                 335

Gln Asp Glu Lys Asn Val Thr Cys Gln Leu Thr Phe Trp Glu Ala Ser
            340                 345                 350

Glu Arg Thr Ile Arg Ser Glu Ala Glu Asp Ser Tyr His Phe Ser Ser
```

-continued

```
            355                 360                 365
Ala Lys Met Thr Ala Thr Phe Leu Ser Lys Lys Gln Glu Val Asn Met
    370                 375                 380
Ser Asp Ser Ala Leu Asp Cys Val Arg Asp Glu Ala Ile Asn Lys Leu
385                 390                 395                 400
Gln Gln Ile Phe Asn Thr Ser Tyr Asn Gln Thr Tyr Glu Lys Tyr Gly
                405                 410                 415
Asn Val Ser Val Phe Glu Thr Thr Gly Gly Leu Val Val Phe Trp Gln
                420                 425                 430
Gly Ile Lys Gln Lys Ser Leu Val Glu Leu Glu Arg Leu Ala Asn Arg
            435                 440                 445
Ser Ser Leu Asn Leu Thr His Asn Arg Thr Lys Arg Ser Thr Asp Gly
450                 455                 460
Asn Asn Ala Thr His Leu Ser Asn Met Glu Ser Val His Asn Leu Val
465                 470                 475                 480
Tyr Ala Gln Leu Gln Phe Thr Tyr Asp Thr Leu Arg Gly Tyr Ile Asn
                485                 490                 495
Arg Ala Leu Ala Gln Ile Ala Glu Ala Trp Cys Val Asp Gln Arg Arg
            500                 505                 510
Thr Leu Glu Val Phe Lys Glu Leu Ser Lys Ile Asn Pro Ser Ala Ile
            515                 520                 525
Leu Ser Ala Ile Tyr Asn Lys Pro Ile Ala Arg Phe Met Gly Asp
530                 535                 540
Val Leu Gly Leu Ala Ser Cys Val Thr Ile Asn Gln Thr Ser Val Lys
545                 550                 555                 560
Val Leu Arg Asp Met Asn Val Lys Glu Ser Pro Gly Arg Cys Tyr Ser
                565                 570                 575
Arg Pro Val Val Ile Phe Asn Phe Ala Asn Ser Ser Tyr Val Gln Tyr
                580                 585                 590
Gly Gln Leu Gly Glu Asp Asn Glu Ile Leu Leu Gly Asn His Arg Thr
            595                 600                 605
Glu Glu Cys Gln Leu Pro Ser Leu Lys Ile Phe Ile Ala Gly Asn Ser
            610                 615                 620
Ala Tyr Glu Tyr Val Asp Tyr Leu Phe Lys Arg Met Ile Asp Leu Ser
625                 630                 635                 640
Ser Ile Ser Thr Val Asp Ser Met Ile Ala Leu Asp Ile Asp Pro Leu
                645                 650                 655
Glu Asn Thr Asp Phe Arg Val Leu Glu Leu Tyr Ser Gln Lys Glu Leu
                660                 665                 670
Arg Ser Ser Asn Val Phe Asp Leu Glu Glu Ile Met Arg Glu Phe Asn
            675                 680                 685
Ser Tyr Lys Gln Arg Val Lys Tyr Val Glu Asp Lys Val Val Asp Pro
            690                 695                 700
Leu Pro Pro Tyr Leu Lys Gly Leu Asp Asp Leu Met Ser Gly Leu Gly
705                 710                 715                 720
Ala Ala Gly Lys Ala Val Gly Val Ala Ile Gly Ala Val Gly Gly Ala
                725                 730                 735
Val Ala Ser Val Val Glu Gly Val Ala Thr Phe Leu Lys Asn Pro Phe
            740                 745                 750
Gly Ala Phe Thr Ile Ile Leu Val Ala Ile Ala Val Val Ile Ile Ile
            755                 760                 765
Tyr Leu Ile Tyr Thr Arg Gln Arg Arg Leu Cys Met Gln Pro Leu Gln
770                 775                 780
```

-continued

```
Asn Leu Phe Pro Tyr Leu Val Ser Ala Asp Gly Thr Val Thr Ser
785                 790                 795                 800

Gly Asn Thr Lys Asp Thr Ser Leu Gln Ala Pro Ser Tyr Glu Glu
                805                 810                 815

Ser Val Tyr Asn Ser Gly Arg Lys Gly Pro Gly Pro Ser Ser Asp
            820                 825                 830

Ala Ser Thr Ala Ala Pro Pro Tyr Thr Asn Glu Gln Ala Tyr Gln Met
        835                 840                 845

Leu Leu Ala Leu Val Arg Leu Asp Ala Glu Gln Arg Ala Gln Gln Asn
850                 855                 860

Gly Thr Asp Ser Leu Asp Gly Gln Thr Gly Thr Gln Asp Lys Gly Gln
865                 870                 875                 880

Lys Pro Asn Leu Leu Asp Arg Leu Arg His Arg Lys Asn Gly Tyr Arg
                885                 890                 895

His Leu Lys Asp Ser Asp Glu Glu Asn Val
                900                 905
```

(2) INFORMATION FOR SEQ ID NO:20:

(i) SEQUENCE CHARACTERISTICS:
        (A) LENGTH: 830 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:20:

```
Met Ser Lys Met Val Val Leu Phe Leu Ala Val Phe Leu Met Asn Ser
1               5                   10                  15

Val Leu Met Ile Tyr Cys Asp Pro Asp His Tyr Ile Arg Ala Gly Tyr
            20                  25                  30

Asn His Lys Tyr Pro Phe Arg Ile Cys Ser Ile Ala Lys Gly Thr Asp
        35                  40                  45

Leu Met Arg Phe Asp Arg Asp Ile Ser Cys Ser Pro Tyr Lys Ser Asn
50                  55                  60

Ala Lys Met Ser Glu Gly Phe Phe Ile Ile Tyr Lys Thr Asn Ile Glu
65                  70                  75                  80

Thr Tyr Thr Phe Pro Val Arg Thr Tyr Lys Glu Leu Thr Phe Gln
                85                  90                  95

Ser Ser Tyr Arg Asp Val Gly Val Val Tyr Phe Leu Asp Arg Thr Val
            100                 105                 110

Met Gly Leu Ala Met Pro Val Tyr Glu Ala Asn Leu Val Asn Ser His
        115                 120                 125

Ala Gln Cys Tyr Ser Ala Val Ala Met Lys Arg Pro Asp Gly Thr Val
    130                 135                 140

Phe Ser Ala Phe His Glu Asp Asn Asn Lys Asn Asn Thr Leu Asn Leu
145                 150                 155                 160

Phe Pro Leu Asn Phe Lys Ser Ile Thr Asn Lys Arg Phe Ile Thr Thr
                165                 170                 175

Lys Glu Pro Tyr Phe Ala Arg Gly Pro Leu Trp Leu Tyr Ser Thr Ser
            180                 185                 190

Thr Ser Leu Asn Cys Ile Val Thr Glu Ala Thr Ala Lys Ala Lys Tyr
        195                 200                 205

Pro Phe Ser Tyr Phe Ala Leu Thr Thr Gly Glu Ile Val Glu Gly Ser
    210                 215                 220

Pro Phe Phe Asn Gly Ser Asn Gly Lys His Phe Ala Glu Pro Leu Glu
```

-continued

```
            225                 230                 235                 240
Lys Leu Thr Ile Leu Glu Asn Tyr Thr Met Ile Glu Asp Leu Met Asn
                    245                 250                 255
Gly Met Asn Gly Ala Thr Thr Leu Val Arg Lys Ile Ala Phe Leu Glu
                260                 265                 270
Lys Ala Asp Thr Leu Phe Ser Trp Glu Ile Lys Glu Glu Asn Glu Ser
            275                 280                 285
Val Cys Met Leu Lys His Trp Thr Val Thr His Gly Leu Arg Ala
        290                 295                 300
Glu Thr Asp Glu Tyr His Phe Ile Ser Lys Glu Leu Thr Ala Ala
305                 310                 315                 320
Phe Val Ala Pro Lys Glu Ser Leu Asn Leu Thr Asp Pro Lys Gln Thr
                    325                 330                 335
Cys Ile Lys Asp Glu Phe Glu Lys Ile Ile Asn Glu Val Tyr Met Ser
                340                 345                 350
Asp Tyr Asn Asp Thr Tyr Ser Met Asn Gly Ser Tyr Gln Ile Phe Lys
                355                 360                 365
Thr Thr Gly Asp Leu Ile Leu Ile Trp Gln Pro Leu Val Gln Lys Ser
        370                 375                 380
Leu Met Phe Leu Glu Gln Gly Ser Glu Lys Ile Arg Arg Arg Arg Asp
385                 390                 395                 400
Val Val Asp Val Lys Ser Arg His Asp Ile Leu Tyr Val Gln Leu Gln
                    405                 410                 415
Tyr Leu Tyr Asp Thr Leu Lys Asp Tyr Ile Asn Asp Ala Leu Gly Asn
                420                 425                 430
Leu Ala Glu Ser Trp Cys Leu Asp Gln Lys Arg Thr Ile Thr Met Leu
            435                 440                 445
His Glu Leu Ser Lys Ile Ser Pro Ser Ser Ile Val Ser Glu Val Tyr
        450                 455                 460
Gly Arg Pro Ile Ser Ala Gln Leu His Gly Asp Val Leu Ala Ile Ser
465                 470                 475                 480
Lys Cys Ile Glu Val Asn Gln Ser Ser Val Gln Leu His Lys Ser Met
                    485                 490                 495
Arg Val Val Asp Ala Lys Gly Val Arg Ser Glu Thr Met Cys Tyr Asn
                500                 505                 510
Arg Pro Leu Val Thr Phe Ser Phe Val Asn Ser Thr Pro Glu Val Val
            515                 520                 525
Pro Gly Gln Leu Gly Leu Asp Asn Glu Ile Leu Leu Gly Asp His Arg
        530                 535                 540
Thr Glu Glu Cys Glu Ile Pro Ser Thr Lys Ile Phe Leu Ser Gly Asn
545                 550                 555                 560
His Ala His Val Tyr Thr Asp Tyr Thr His Thr Asn Ser Thr Pro Ile
                    565                 570                 575
Glu Asp Ile Glu Val Leu Asp Ala Phe Ile Arg Leu Lys Ile Asp Pro
                580                 585                 590
Leu Glu Asn Ala Asp Phe Lys Val Leu Asp Leu Tyr Ser Pro Asp Glu
            595                 600                 605
Leu Ser Arg Ala Asn Val Phe Asp Leu Glu Asn Ile Leu Arg Glu Tyr
        610                 615                 620
Asn Ser Tyr Lys Ser Ala Leu Tyr Thr Ile Glu Ala Lys Ile Ala Thr
625                 630                 635                 640
Asn Thr Pro Ser Tyr Val Asn Gly Ile Asn Ser Phe Leu Gln Gly Leu
                    645                 650                 655
```

-continued

```
Gly Ala Ile Gly Thr Gly Leu Gly Ser Val Ile Ser Val Thr Ala Gly
            660                 665                 670

Ala Leu Gly Asp Ile Val Gly Val Val Ser Phe Leu Lys Asn Pro
        675                 680                 685

Phe Gly Gly Leu Met Leu Ile Leu Ala Ile Val Val Val Ile
690                 695                 700

Ile Ile Val Val Phe Val Arg Gln Arg His Val Leu Ser Lys Pro Ile
705                 710                 715                 720

Asp Met Met Phe Pro Tyr Ala Thr Asn Pro Val Thr Val Ser Ser
                725                 730                 735

Val Thr Gly Thr Thr Val Val Lys Thr Pro Ser Val Lys Asp Val Asp
            740                 745                 750

Gly Gly Thr Ser Val Ala Val Ser Glu Lys Glu Glu Gly Met Ala Asp
            755                 760                 765

Val Ser Gly Gln Val Ser Asp Asp Glu Tyr Ser Gln Glu Ala Ala Leu
770                 775                 780

Lys Met Leu Lys Ala Ile Lys Ser Leu Asp Glu Ser Tyr Arg Arg Lys
785                 790                 795                 800

Pro Ser Ser Ser Glu Ser His Ala Ser Lys Pro Ser Leu Ile Asp Arg
                805                 810                 815

Ile Arg Tyr Arg Gly Tyr Lys Ser Val Asn Val Glu Glu Ala
                820                 825                 830

(2) INFORMATION FOR SEQ ID NO:21:

(i) SEQUENCE CHARACTERISTICS:
        (A) LENGTH: 868 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:21:

Met Phe Val Thr Ala Val Val Ser Val Ser Pro Ser Ser Phe Tyr Glu
1               5                   10                  15

Ser Leu Gln Val Glu Pro Thr Gln Ser Glu Asp Ile Thr Arg Ser Ala
                20                  25                  30

His Leu Gly Asp Gly Asp Glu Ile Arg Glu Ala Ile His Lys Ser Gln
            35                  40                  45

Asp Ala Glu Thr Lys Pro Thr Phe Tyr Val Cys Pro Pro Thr Gly
50                  55                  60

Ser Thr Ile Val Arg Leu Glu Pro Thr Arg Thr Cys Pro Asp Tyr His
65                  70                  75                  80

Leu Gly Lys Asn Phe Thr Glu Gly Ile Ala Val Val Tyr Lys Glu Asn
                85                  90                  95

Ile Ala Ala Tyr Lys Phe Lys Ala Thr Val Tyr Tyr Lys Asp Val Ile
            100                 105                 110

Val Ser Thr Ala Trp Ala Gly Ser Ser Tyr Thr Gln Ile Thr Asn Arg
            115                 120                 125

Tyr Ala Asp Arg Val Pro Ile Pro Val Ser Glu Ile Thr Asp Thr Ile
130                 135                 140

Asp Lys Phe Gly Lys Cys Ser Ser Lys Ala Thr Tyr Val Arg Asn Asn
145                 150                 155                 160

His Lys Val Glu Ala Phe Asn Glu Asp Lys Asn Pro Gln Asp Met Pro
                165                 170                 175

Leu Ile Ala Ser Lys Tyr Asn Ser Val Gly Ser Lys Ala Trp His Thr
```

```
                    180                 185                 190
Thr Asn Asp Thr Tyr Met Val Ala Gly Thr Pro Gly Thr Tyr Arg Thr
                195                 200                 205
Gly Thr Ser Val Asn Cys Ile Ile Glu Glu Val Glu Ala Arg Ser Ile
            210                 215                 220
Phe Pro Tyr Asp Ser Phe Gly Leu Ser Thr Gly Asp Ile Ile Tyr Met
225                 230                 235                 240
Ser Pro Phe Phe Gly Leu Arg Asp Gly Ala Tyr Arg Glu His Ser Asn
                245                 250                 255
Tyr Ala Met Asp Arg Phe His Gln Phe Glu Gly Tyr Arg Gln Arg Asp
            260                 265                 270
Leu Asp Thr Arg Ala Leu Leu Glu Pro Ala Ala Arg Asn Phe Leu Val
        275                 280                 285
Thr Pro His Leu Thr Val Gly Trp Asn Trp Lys Pro Lys Arg Thr Glu
    290                 295                 300
Val Cys Ser Leu Val Lys Trp Arg Glu Val Glu Asp Val Val Arg Asp
305                 310                 315                 320
Glu Tyr Ala His Asn Phe Arg Phe Thr Met Lys Thr Leu Ser Thr Thr
                325                 330                 335
Phe Ile Ser Glu Thr Asn Glu Phe Asn Leu Asn Gln Ile His Leu Ser
            340                 345                 350
Gln Cys Val Lys Glu Glu Ala Arg Ala Ile Ile Asn Arg Ile Tyr Thr
        355                 360                 365
Thr Arg Tyr Asn Ser Ser His Val Arg Thr Gly Asp Ile Gln Thr Tyr
    370                 375                 380
Leu Ala Arg Gly Gly Phe Val Val Phe Gln Pro Leu Leu Ser Asn
385                 390                 395                 400
Ser Leu Ala Arg Leu Tyr Leu Gln Glu Leu Val Arg Glu Asn Thr Asn
                405                 410                 415
His Ser Pro Gln Lys His Pro Thr Arg Asn Thr Arg Ser Arg Arg Ser
            420                 425                 430
Val Pro Val Glu Leu Arg Ala Asn Arg Thr Ile Thr Thr Thr Ser Ser
        435                 440                 445
Val Glu Phe Ala Met Leu Gln Phe Thr Tyr Asp His Ile Gln Glu His
    450                 455                 460
Val Asn Glu Met Leu Ala Arg Ile Ser Ser Ser Trp Cys Gln Leu Gln
465                 470                 475                 480
Asn Arg Glu Arg Ala Leu Trp Ser Gly Leu Phe Pro Ile Asn Pro Ser
                485                 490                 495
Ala Leu Ala Ser Thr Ile Leu Asp Gln Arg Val Lys Ala Arg Ile Leu
            500                 505                 510
Gly Asp Val Ile Ser Val Ser Asn Cys Pro Glu Leu Gly Ser Asp Thr
        515                 520                 525
Arg Ile Ile Leu Gln Asn Ser Met Arg Val Ser Gly Ser Thr Thr Arg
    530                 535                 540
Cys Tyr Ser Arg Pro Leu Ile Ser Ile Val Ser Leu Asn Gly Ser Gly
545                 550                 555                 560
Thr Val Glu Gly Gln Leu Gly Thr Asp Asn Glu Leu Ile Met Ser Arg
                565                 570                 575
Asp Leu Leu Glu Pro Cys Val Ala Asn His Lys Arg Tyr Phe Leu Phe
            580                 585                 590
Gly His His Tyr Val Tyr Tyr Glu Asp Tyr Arg Tyr Val Arg Glu Ile
        595                 600                 605
```

```
Ala Val His Asp Val Gly Met Ile Ser Thr Tyr Val Asp Leu Asn Leu
    610                 615                 620

Thr Leu Leu Lys Asp Arg Glu Phe Met Pro Leu Gln Val Tyr Thr Arg
625                 630                 635                 640

Asp Glu Leu Arg Asp Thr Gly Leu Leu Asp Tyr Ser Glu Ile Gln Arg
                645                 650                 655

Arg Asn Gln Met His Ser Leu Arg Phe Tyr Asp Ile Asp Lys Val Val
            660                 665                 670

Gln Tyr Asp Ser Gly Thr Ala Ile Met Gln Gly Met Ala Gln Phe Phe
        675                 680                 685

Gln Gly Leu Gly Thr Ala Gly Gln Ala Val Gly His Val Val Leu Gly
690                 695                 700

Ala Thr Gly Ala Leu Leu Ser Thr Val His Gly Phe Thr Thr Phe Leu
705                 710                 715                 720

Ser Asn Pro Phe Gly Ala Leu Ala Val Gly Leu Leu Val Leu Ala Gly
                725                 730                 735

Leu Val Ala Ala Phe Phe Ala Tyr Arg Tyr Val Leu Lys Leu Lys Thr
            740                 745                 750

Ser Pro Met Lys Ala Leu Tyr Pro Leu Thr Thr Lys Gly Leu Lys Gln
        755                 760                 765

Leu Pro Glu Gly Met Asp Pro Phe Ala Glu Lys Pro Asn Ala Thr Asp
770                 775                 780

Thr Pro Ile Glu Glu Ile Gly Asp Ser Gln Asn Thr Glu Pro Ser Val
785                 790                 795                 800

Asn Ser Gly Phe Asp Pro Asp Lys Phe Arg Glu Ala Gln Glu Met Ile
                805                 810                 815

Lys Tyr Met Thr Leu Val Ser Ala Glu Arg Gln Glu Ser Lys Ala
            820                 825                 830

Arg Lys Lys Asn Lys Thr Ser Ala Leu Leu Thr Ser Arg Leu Thr Gly
        835                 840                 845

Leu Ala Leu Arg Asn Arg Arg Gly Tyr Ser Arg Val Arg Thr Glu Asn
850                 855                 860

Val Thr Gly Val
865

(2) INFORMATION FOR SEQ ID NO:22:

(i) SEQUENCE CHARACTERISTICS:
        (A) LENGTH: 903 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:22:

Met Arg Gln Gly Ala Ala Arg Gly Cys Arg Trp Phe Val Val Trp Ala
1               5                   10                  15

Leu Leu Gly Leu Thr Leu Gly Val Leu Val Ala Ser Ala Ala Pro Ser
            20                  25                  30

Ser Pro Gly Thr Pro Gly Val Ala Ala Thr Gln Ala Ala Asn Gly
        35                  40                  45

Gly Pro Ala Thr Pro Ala Pro Ala Pro Gly Pro Ala Pro Thr Gly
50                  55                  60

Asp Thr Lys Pro Lys Lys Asn Lys Pro Lys Asn Pro Pro Pro
65                  70                  75                  80

Arg Pro Ala Gly Asp Asn Ala Thr Val Ala Ala Gly His Ala Thr Leu
```

-continued

```
                85                  90                  95
Arg Glu His Leu Arg Asp Ile Lys Ala Glu Asn Thr Asp Ala Asn Phe
                    100                 105                 110

Tyr Val Cys Pro Pro Thr Gly Ala Thr Val Gln Phe Glu Gln
        115                 120                 125

Pro Arg Arg Cys Pro Thr Arg Pro Glu Gly Gln Asn Tyr Thr Glu Gly
        130                 135                 140

Ile Ala Val Val Phe Lys Glu Asn Ile Ala Pro Tyr Lys Phe Lys Ala
145                 150                 155                 160

Thr Met Tyr Tyr Lys Asp Val Thr Val Ser Gln Val Trp Phe Gly His
                    165                 170                 175

Arg Tyr Ser Gln Phe Met Gly Ile Phe Glu Asp Arg Ala Pro Val Pro
                180                 185                 190

Phe Glu Glu Val Ile Asp Lys Ile Asn Ala Lys Gly Val Cys Arg Ser
                    195                 200                 205

Thr Ala Lys Tyr Val Arg Asn Asn Leu Glu Thr Thr Ala Phe His Arg
210                 215                 220

Asp Asp His Glu Thr Asp Met Glu Leu Lys Pro Ala Asn Ala Ala Thr
225                 230                 235                 240

Arg Thr Ser Arg Gly Trp His Thr Thr Asp Leu Lys Tyr Asn Pro Ser
                    245                 250                 255

Arg Val Glu Ala Phe His Arg Tyr Gly Thr Thr Val Asn Cys Ile Val
                    260                 265                 270

Glu Glu Val Asp Ala Arg Ser Val Tyr Pro Tyr Asp Glu Phe Val Leu
                275                 280                 285

Ala Thr Gly Asp Phe Val Tyr Met Ser Pro Phe Tyr Gly Tyr Arg Glu
                290                 295                 300

Gly Ser His Thr Glu His Thr Ser Tyr Ala Ala Asp Arg Phe Lys Gln
305                 310                 315                 320

Val Asp Gly Phe Tyr Ala Arg Asp Leu Thr Thr Lys Ala Arg Ala Thr
                    325                 330                 335

Ala Pro Thr Thr Arg Asn Leu Leu Thr Thr Pro Lys Phe Thr Val Ala
                340                 345                 350

Trp Asp Trp Val Pro Lys Arg Pro Ser Val Cys Thr Met Thr Lys Trp
                355                 360                 365

Gln Glu Val Asp Glu Met Leu Arg Ser Glu Tyr Gly Gly Ser Phe Arg
                370                 375                 380

Phe Ser Ser Asp Ala Ile Ser Thr Thr Phe Thr Thr Asn Leu Thr Glu
385                 390                 395                 400

Tyr Pro Leu Ser Arg Val Asp Leu Gly Asp Cys Ile Gly Lys Asp Ala
                    405                 410                 415

Arg Asp Ala Met Asp Arg Ile Phe Ala Arg Arg Tyr Asn Ala Thr His
                420                 425                 430

Ile Lys Val Gly Gln Pro Gln Tyr Tyr Leu Ala Asn Gly Gly Phe Leu
                435                 440                 445

Ile Ala Tyr Gln Pro Leu Leu Ser Asn Thr Leu Ala Glu Leu Tyr Val
                450                 455                 460

Arg Glu His Leu Arg Glu Gln Ser Arg Lys Pro Pro Asn Pro Thr Pro
465                 470                 475                 480

Pro Pro Pro Gly Ala Ser Ala Asn Ala Ser Val Glu Arg Ile Lys Thr
                    485                 490                 495

Thr Ser Ser Ile Glu Phe Ala Arg Leu Gln Phe Thr Tyr Asn His Ile
                500                 505                 510
```

```
Gln Arg His Val Asn Asp Met Leu Gly Arg Val Ala Ile Ala Trp Cys
        515                 520                 525
Glu Leu Gln Asn His Glu Leu Thr Leu Trp Asn Glu Ala Arg Lys Leu
        530                 535                 540
Asn Pro Asn Ala Ile Ala Ser Ala Thr Val Gly Arg Arg Val Ser Ala
545                 550                 555                 560
Arg Met Leu Gly Asp Val Met Ala Val Ser Thr Cys Val Pro Val Ala
                565                 570                 575
Ala Asp Asn Val Ile Val Gln Asn Ser Met Arg Ile Ser Ser Arg Pro
            580                 585                 590
Gly Ala Cys Tyr Ser Arg Pro Leu Val Ser Phe Arg Tyr Glu Asp Gln
        595                 600                 605
Gly Pro Leu Val Glu Gly Gln Val Gly Glu Asn Asn Glu Leu Arg Leu
610                 615                 620
Thr Arg Asp Ala Ile Glu Pro Cys Thr Val Gly His Arg Arg Tyr Phe
625                 630                 635                 640
Thr Phe Gly Gly Gly Tyr Val Tyr Phe Glu Glu Tyr Ala Tyr Ser His
                645                 650                 655
Gln Leu Ser Arg Ala Asp Ile Thr Thr Val Ser Thr Phe Ile Asp Leu
            660                 665                 670
Asn Ile Thr Met Leu Glu Asp His Glu Phe Val Pro Leu Glu Val Tyr
        675                 680                 685
Thr Arg His Glu Ile Lys Asp Ser Gly Leu Leu Asp Tyr Thr Glu Val
690                 695                 700
Gln Arg Arg Asn Gln Leu His Asp Leu Arg Phe Ala Asp Ile Asp Thr
705                 710                 715                 720
Val Ile His Ala Asp Ala Asn Ala Met Phe Ala Gly Leu Gly Ala
                725                 730                 735
Phe Phe Glu Gly Met Gly Asp Leu Gly Arg Ala Val Gly Lys Val Val
            740                 745                 750
Met Gly Ile Val Gly Gly Val Val Ser Ala Val Ser Gly Val Ser Ser
        755                 760                 765
Phe Met Ser Asn Pro Phe Gly Ala Leu Ala Val Gly Leu Leu Val Leu
770                 775                 780
Ala Gly Leu Ala Ala Ala Phe Phe Ala Phe Arg Tyr Val Met Arg Leu
785                 790                 795                 800
Gln Ser Asn Pro Met Lys Ala Leu Tyr Pro Leu Thr Thr Lys Glu Leu
                805                 810                 815
Lys Asn Pro Thr Asn Pro Asp Ala Ser Gly Glu Gly Glu Glu Gly Gly
            820                 825                 830
Asp Phe Asp Glu Ala Lys Leu Ala Glu Ala Arg Glu Met Ile Arg Tyr
        835                 840                 845
Met Ala Leu Val Ser Ala Met Glu Arg Thr Glu His Lys Ala Lys Lys
850                 855                 860
Lys Gly Thr Ser Ala Leu Leu Ser Ala Lys Val Thr Asp Met Val Met
865                 870                 875                 880
Arg Lys Arg Arg Asn Thr Asn Tyr Thr Gln Val Pro Asn Lys Asp Gly
                885                 890                 895
Asp Ala Asp Glu Asp Asp Leu
                900
```

(2) INFORMATION FOR SEQ ID NO:23:

(i) SEQUENCE CHARACTERISTICS:
        (A) LENGTH: 885 amino acids (B) TYPE: amino acid
          (C) STRANDEDNESS: single
          (D) TOPOLOGY: linear (ii) MOLECULE TYPE: protein (xi) SEQUENCE DESCRIPTION: SEQ ID NO:23:

Met Arg Pro Arg Gly Thr Pro Pro Ser Phe Leu Pro Leu Pro Val Leu
 1               5                  10                  15

Leu Ala Leu Ala Val Ile Ala Ala Gly Arg Ala Ala Pro Ala Ala
                20                  25                  30

Ala Ala Ala Pro Thr Ala Asp Pro Ala Ala Thr Pro Ala Leu Pro Glu
        35                  40                  45

Asp Glu Glu Val Pro Asp Glu Asp Gly Glu Gly Val Ala Thr Pro Ala
50                  55                  60

Pro Ala Ala Asn Ala Ser Val Glu Ala Gly Arg Ala Thr Leu Arg Glu
65                  70                  75                  80

Asp Leu Arg Glu Ile Lys Ala Arg Asp Gly Asp Ala Thr Phe Tyr Val
                85                  90                  95

Cys Pro Pro Pro Thr Gly Ala Thr Val Val Gln Phe Glu Gln Pro Arg
                100                 105                 110

Pro Cys Pro Arg Ala Pro Asp Gly Gln Asn Tyr Thr Glu Gly Ile Ala
                115                 120                 125

Val Val Phe Lys Glu Asn Ile Ala Pro Tyr Lys Phe Lys Ala Thr Met
130                 135                 140

Tyr Tyr Lys Asp Val Thr Val Ser Gln Val Trp Phe Gly His Arg Tyr
145                 150                 155                 160

Ser Gln Phe Met Gly Ile Phe Glu Asp Arg Ala Pro Val Pro Phe Glu
                165                 170                 175

Glu Val Met Asp Lys Ile Asn Ala Lys Gly Val Cys Arg Ser Thr Ala
                180                 185                 190

Lys Tyr Val Arg Asn Asn Met Glu Ser Thr Ala Phe His Arg Asp Asp
                195                 200                 205

His Glu Ser Asp Met Ala Leu Lys Pro Ala Lys Ala Ala Thr Arg Thr
210                 215                 220

Ser Arg Gly Trp His Thr Thr Asp Leu Lys Tyr Asn Pro Ala Arg Val
225                 230                 235                 240

Glu Ala Phe His Arg Tyr Gly Thr Thr Val Asn Cys Ile Val Glu Glu
                245                 250                 255

Val Glu Ala Arg Ser Val Tyr Pro Tyr Asp Glu Phe Val Leu Ala Thr
                260                 265                 270

Gly Asp Phe Val Tyr Met Ser Pro Phe Tyr Gly Tyr Arg Asp Gly Ser
                275                 280                 285

His Gly Glu His Thr Ala Tyr Ala Ala Asp Arg Phe Arg Gln Val Asp
                290                 295                 300

Gly Tyr Tyr Glu Arg Asp Leu Ser Thr Gly Arg Arg Ala Ala Ala Pro
305                 310                 315                 320

Val Thr Arg Asn Leu Leu Thr Thr Pro Lys Phe Thr Val Gly Trp Asp
                325                 330                 335

Trp Ala Pro Lys Arg Pro Ser Val Cys Thr Leu Thr Lys Trp Arg Glu
                340                 345                 350

Val Asp Glu Met Leu Arg Ala Glu Tyr Gly Pro Ser Phe Arg Phe Ser
                355                 360                 365

Ser Ala Ala Leu Ser Thr Thr Phe Thr Ala Asn Arg Thr Glu Tyr Ala
                370                 375                 380

-continued

```
Leu Ser Arg Val Asp Leu Ala Asp Cys Val Gly Arg Glu Ala Arg Glu
385                 390                 395                 400

Ala Val Asp Arg Ile Phe Leu Arg Arg Tyr Asn Gly Thr His Val Lys
                405                 410                 415

Val Gly Gln Val Gln Tyr Tyr Leu Ala Thr Gly Gly Phe Leu Ile Ala
            420                 425                 430

Tyr Gln Pro Leu Leu Ser Asn Ala Leu Val Glu Leu Tyr Val Arg Glu
        435                 440                 445

Leu Val Arg Glu Gln Thr Arg Arg Pro Ala Gly Gly Asp Pro Gly Glu
450                 455                 460

Ala Ala Thr Pro Gly Pro Ser Val Asp Pro Ser Val Glu Arg Ile
465                 470                 475                 480

Lys Thr Thr Ser Ser Val Glu Phe Ala Arg Leu Gln Phe Thr Tyr Asp
                485                 490                 495

His Ile Gln Arg His Val Asn Asp Met Leu Gly Arg Ile Ala Thr Ala
            500                 505                 510

Trp Cys Glu Leu Gln Asn Arg Glu Leu Thr Leu Trp Asn Glu Ala Arg
        515                 520                 525

Arg Leu Asn Pro Gly Ala Ile Ala Ser Ala Thr Val Gly Arg Arg Val
530                 535                 540

Ser Ala Arg Met Leu Gly Asp Val Met Ala Val Ser Thr Cys Val Pro
545                 550                 555                 560

Val Ala Pro Asp Asn Val Ile Met Gln Asn Ser Ile Gly Val Ala Ala
                565                 570                 575

Arg Pro Gly Thr Cys Tyr Ser Arg Pro Leu Val Ser Phe Arg Tyr Glu
            580                 585                 590

Ala Asp Gly Pro Leu Val Glu Gly Gln Leu Gly Glu Asp Asn Glu Ile
        595                 600                 605

Arg Leu Glu Arg Asp Ala Leu Glu Pro Cys Thr Val Gly His Arg Arg
610                 615                 620

Tyr Phe Thr Phe Gly Ala Gly Tyr Val Tyr Phe Glu Glu Tyr Ala Tyr
625                 630                 635                 640

Ser His Gln Leu Gly Arg Ala Asp Val Thr Thr Val Ser Thr Phe Ile
                645                 650                 655

Asn Leu Asn Leu Thr Met Leu Glu Asp His Glu Phe Val Pro Leu Glu
            660                 665                 670

Val Tyr Thr Arg Gln Glu Ile Lys Asp Ser Gly Leu Leu Asp Tyr Thr
        675                 680                 685

Glu Val Gln Arg Arg Asn Gln Leu His Ala Leu Arg Phe Ala Asp Ile
690                 695                 700

Asp Thr Val Ile Lys Ala Asp Ala His Ala Ala Leu Phe Ala Gly Leu
705                 710                 715                 720

Tyr Ser Phe Phe Glu Gly Leu Gly Asp Val Gly Arg Ala Val Gly Lys
                725                 730                 735

Val Val Met Gly Ile Val Gly Val Val Ser Ala Val Ser Gly Val
            740                 745                 750

Ser Ser Phe Leu Ser Asn Pro Phe Gly Ala Leu Ala Val Gly Leu Leu
        755                 760                 765

Val Leu Ala Gly Leu Ala Ala Phe Phe Ala Phe Arg Tyr Val Met
770                 775                 780

Arg Leu Gln Arg Asn Pro Met Lys Ala Leu Tyr Pro Leu Thr Thr Lys
785                 790                 795                 800

Glu Leu Lys Ser Asp Gly Ala Pro Leu Ala Gly Gly Glu Asp Gly
                805                 810                 815
```

```
Ala Glu Asp Phe Asp Glu Ala Lys Leu Ala Gln Ala Arg Glu Met Ile
            820                 825                 830

Arg Tyr Met Ala Leu Val Ser Ala Met Glu Arg Thr Glu His Lys Ala
        835                 840                 845

Arg Lys Lys Gly Thr Ser Ala Leu Leu Ser Ala Lys Val Thr Asp Ala
    850                 855                 860

Val Met Arg Lys Arg Ala Arg Pro Arg Tyr Ser Pro Leu Arg Asp Thr
865                 870                 875                 880

Asp Glu Glu Glu Leu
            885
```

(2) INFORMATION FOR SEQ ID NO:24:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:24:

GCTGTTCAGA TTTGACTTAG AYMANMCNTG YCC                                              33

(2) INFORMATION FOR SEQ ID NO:25:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:25:

GTGTACAAGA AGAACATCGT GCCNTAYATN TTYAA                                          35

(2) INFORMATION FOR SEQ ID NO:26:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:26:

GTGTACAAGA AGAACATCGT GCC                                                      23

(2) INFORMATION FOR SEQ ID NO:27:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:27:

AACATGTCTA CAATCTCACA RTTNACNGTN GT                                             32

(2) INFORMATION FOR SEQ ID NO:28:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:28:

AACATGTCTA CAATCTCACA                                                                20

(2) INFORMATION FOR SEQ ID NO:29:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:29:

AATAACCTCT TTACGGCCCA AATTCARTWY GCNTAYGA                              38

(2) INFORMATION FOR SEQ ID NO:30:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:30:

CCAACGAGTG TGATGTCAGC CATTTAYGGN AARCCNGT                              38

(2) INFORMATION FOR SEQ ID NO:31:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:31:

CCAACGAGTG TGATGTCAGC C                                                  21

(2) INFORMATION FOR SEQ ID NO:32:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:32:

TGCTACTCGC GACCTCTAGT CACCTTYAAR TTYRTNAA                              38

(2) INFORMATION FOR SEQ ID NO:33:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:33:

TGCTACTCGC GACCTCTAGT CACC                                        24

(2) INFORMATION FOR SEQ ID NO:34:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:34:

ACCGGAGTAC AGTTCCACTG TYTTRAARTC DATRTT                                36

(2) INFORMATION FOR SEQ ID NO:35:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:35:

TGTCACCTTG ACATGAGGCC A        21

(2) INFORMATION FOR SEQ ID NO:36:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:36:

TTTGACCTGG AGACTATGTT YMGNGARTAY AA        32

(2) INFORMATION FOR SEQ ID NO:37:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:37:

GCTCTGGGTG TAGTAGTTRT AYTCYCTRAA CAT        33

(2) INFORMATION FOR SEQ ID NO:38:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:38:

TCTCGGAACA TGCTCTCCAG RTCRAAMACR TT        32

(2) INFORMATION FOR SEQ ID NO:39:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:39:

ACCTTCATCA AAAATCCCTT NGGNGGNATG YT        32

(2) INFORMATION FOR SEQ ID NO:40:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:40:

TGGACTTACA GGACTCGAAC NACNGTNAAY TG        32

(2) INFORMATION FOR SEQ ID NO:41:

```
    (i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:41:

AGACCCGTGC CACTCTATGA RATHAGYCAY ATGGA                               35

(2) INFORMATION FOR SEQ ID NO:42:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:42:

AGACCCGTGC CACTCTATGA                                                20

(2) INFORMATION FOR SEQ ID NO:43:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:43:

GTTCACAACA ATCTTCATNG ARCTRAARCA                                     30

(2) INFORMATION FOR SEQ ID NO:44:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:44:

GTTCACAACA ATCTTCAT                                                  18

(2) INFORMATION FOR SEQ ID NO:45:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:45:

GTCAACGGAG TAGARAAYAC NTTYACNGA                                      29

(2) INFORMATION FOR SEQ ID NO:46:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:46:

ACTGGCTGGC TAAAGTACCT TTGAATRTTR TCNGT                               35

(2) INFORMATION FOR SEQ ID NO:47:

(i) SEQUENCE CHARACTERISTICS:
        (A) LENGTH: 23 base pairs
```

(B) TYPE: nucleic acid
        (C) STRANDEDNESS: single
        (D) TOPOLOGY: linear (xi) SEQUENCE DESCRIPTION: SEQ ID NO:47:

ACTGGCTGGC TAAAGTACCT TTG                                            23

(2) INFORMATION FOR SEQ ID NO:48:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:48:

TGCTGCTTCT GTCATACCGC G                                              21

(2) INFORMATION FOR SEQ ID NO:49:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:49:

TATTTGTTTG TGATTGCTGC T                                              21

(2) INFORMATION FOR SEQ ID NO:50:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:50:

GCGGTATGAC AGAAGCAGCA A                                              21

(2) INFORMATION FOR SEQ ID NO:51:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:51:

AACAAATATG AGATCCCCAG G                                              21

(2) INFORMATION FOR SEQ ID NO:52:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:52:

TCATCCCGAT CGGTGAACGT A                                              21

(2) INFORMATION FOR SEQ ID NO:53:

(i) SEQUENCE CHARACTERISTICS:
        (A) LENGTH: 21 base pairs
        (B) TYPE: nucleic acid
        (C) STRANDEDNESS: single (D) TOPOLOGY: linear (xi) SEQUENCE DESCRIPTION: SEQ ID NO:53:

TTGTCAGTTA GACCTTCGAC G                                              21

(2) INFORMATION FOR SEQ ID NO:54:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO:54:

CCCGTCGAAG GTCTAACTGA C                                              21

(2) INFORMATION FOR SEQ ID NO:55:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO:55:

AGCCAACCAG TACTGTACTC T                                              21

(2) INFORMATION FOR SEQ ID NO:56:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO:56:

TGATGGCGGA CTCTGTCAAG C                                              21

(2) INFORMATION FOR SEQ ID NO:57:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO:57:

GTTCATACTT GTTGGTGATG G                                              21

(2) INFORMATION FOR SEQ ID NO:58:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO:58:

GGGCTTGACA GAGTCCGCCA T                                              21

(2) INFORMATION FOR SEQ ID NO:59:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO:59:

ACAAGTATGA ACTCCCGAGA C                                      21

(2) INFORMATION FOR SEQ ID NO:60:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:60:

ACCCCGTTGA CATTTACCTT C                                      21

(2) INFORMATION FOR SEQ ID NO:61:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:61:

TCGTCTCTGT CAGTAAATGT G                                      21

(2) INFORMATION FOR SEQ ID NO:62:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:62:

CCACAGTATT CCTCCAACCA G                                      21

(2) INFORMATION FOR SEQ ID NO:63:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:63:

GGTACTTTAG CCAGCCGGTC A                                      21

(2) INFORMATION FOR SEQ ID NO:64:

(i) SEQUENCE CHARACTERISTICS:
        (A) LENGTH: 13 amino acids
        (B) TYPE: amino acid
        (C) STRANDEDNESS: single
        (D) TOPOLOGY: linear (xi) SEQUENCE DESCRIPTION: SEQ ID NO:64:

Tyr Arg Lys Ile Ala Thr Ser Val Thr Val Tyr Arg Gly
1               5                   10

(2) INFORMATION FOR SEQ ID NO:65:

(i) SEQUENCE CHARACTERISTICS:
        (A) LENGTH: 15 amino acids
        (B) TYPE: amino acid
        (C) STRANDEDNESS: single
        (D) TOPOLOGY: linear (xi) SEQUENCE DESCRIPTION: SEQ ID NO:65:

```
Ile Tyr Ala Glu Pro Gly Trp Phe Pro Gly Ile Tyr Arg Val Arg
1               5                   10                  15
```

(2) INFORMATION FOR SEQ ID NO:66:

(i) SEQUENCE CHARACTERISTICS:
        (A) LENGTH: 6 amino acids
        (B) TYPE: amino acid
        (C) STRANDEDNESS: single
        (D) TOPOLOGY: linear (xi) SEQUENCE DESCRIPTION: SEQ ID NO:66:

```
Arg Tyr Phe Ser Gln Pro
1               5
```

(2) INFORMATION FOR SEQ ID NO:67:

(i) SEQUENCE CHARACTERISTICS:
        (A) LENGTH: 6 amino acids
        (B) TYPE: amino acid
        (C) STRANDEDNESS: single
        (D) TOPOLOGY: linear (xi) SEQUENCE DESCRIPTION: SEQ ID NO:67:

```
Val Thr Val Tyr Arg Gly
1               5
```

(2) INFORMATION FOR SEQ ID NO:68:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:68:

```
Ala Ile Thr Asn Lys Tyr Glu
1               5
```

(2) INFORMATION FOR SEQ ID NO:69:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:69:

```
Ser His Met Asp Ser Thr Tyr
1               5
```

(2) INFORMATION FOR SEQ ID NO:70:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:70:

```
Val Glu Asn Thr Phe Thr Asp
1               5
```

(2) INFORMATION FOR SEQ ID NO:71:

(i) SEQUENCE CHARACTERISTICS:
        (A) LENGTH: 7 amino acids
        (B) TYPE: amino acid

```
            (C) STRANDEDNESS: single
            (D) TOPOLOGY: linear (xi) SEQUENCE DESCRIPTION: SEQ ID NO:71:

Thr Val Phe Leu Gln Pro Val
1               5

(2) INFORMATION FOR SEQ ID NO:72:

(i) SEQUENCE CHARACTERISTICS:
            (A) LENGTH: 7 amino acids
            (B) TYPE: amino acid
            (C) STRANDEDNESS: single
            (D) TOPOLOGY: linear (xi) SEQUENCE DESCRIPTION: SEQ ID NO:72:

Thr Asp Asn Ile Gln Arg Tyr
1               5

(2) INFORMATION FOR SEQ ID NO:73:

(i) SEQUENCE CHARACTERISTICS:
            (A) LENGTH: 7 amino acids
            (B) TYPE: amino acid
            (C) STRANDEDNESS: single
            (D) TOPOLOGY: linear (xi) SEQUENCE DESCRIPTION: SEQ ID NO:73:

Arg Gly Met Thr Glu Ala Ala
1               5

(2) INFORMATION FOR SEQ ID NO:74:

(i) SEQUENCE CHARACTERISTICS:
            (A) LENGTH: 7 amino acids
            (B) TYPE: amino acid
            (C) STRANDEDNESS: single
            (D) TOPOLOGY: linear (xi) SEQUENCE DESCRIPTION: SEQ ID NO:74:

Pro Val Leu Tyr Ser Glu Pro
1               5

(2) INFORMATION FOR SEQ ID NO:75:

(i) SEQUENCE CHARACTERISTICS:
            (A) LENGTH: 7 amino acids
            (B) TYPE: amino acid
            (C) STRANDEDNESS: single
            (D) TOPOLOGY: linear (xi) SEQUENCE DESCRIPTION: SEQ ID NO:75:

Arg Gly Leu Thr Glu Ser Ala
1               5

(2) INFORMATION FOR SEQ ID NO:76:

(i) SEQUENCE CHARACTERISTICS:
            (A) LENGTH: 7 amino acids
            (B) TYPE: amino acid
            (C) STRANDEDNESS: single
            (D) TOPOLOGY: linear (xi) SEQUENCE DESCRIPTION: SEQ ID NO:76:

Pro Val Ile Tyr Ala Glu Pro
1               5

(2) INFORMATION FOR SEQ ID NO:77:
```

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:77:

GCCTTTGAGA ATTCYAARTA YATHAAR                                              27

(2) INFORMATION FOR SEQ ID NO:78:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:78:

GGGTTTGAGA ATTCYAARTA YATHAAR                                              27

(2) INFORMATION FOR SEQ ID NO:79:

(i) SEQUENCE CHARACTERISTICS:
        (A) LENGTH: 35 amino acids
        (B) TYPE: amino acid
        (C) STRANDEDNESS: single
        (D) TOPOLOGY: linear (xi) SEQUENCE DESCRIPTION: SEQ ID NO:79:

Thr Ala Ala Ala Ala Gly Thr Ala Cys Ala Gly Cys Thr Cys Thr
1               5                  10                  15

Gly Cys Cys Cys Gly Ala Ala Asn Ala Cys Arg Thr Thr Asn Ala Cys
            20                  25                  30

Arg Cys Ala
        35

(2) INFORMATION FOR SEQ ID NO:80:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:80:

TGTGGAAACG GGAGCGTACA C                                                    21

(2) INFORMATION FOR SEQ ID NO:81:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:81:

TCAGACAAGA GTACGTGTCG G                                                    21

(2) INFORMATION FOR SEQ ID NO:82:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:82:

TACAGGTCGA CCGTAGATGG C                                                    21

(2) INFORMATION FOR SEQ ID NO:83:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:83:

CGCCATTTCC GTGACCGAGT G                                                    21

(2) INFORMATION FOR SEQ ID NO:84:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:84:

TGATGAAGTA GTGTTCGCAG G                                                    21

(2) INFORMATION FOR SEQ ID NO:85:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:85:

GATGCCACCC AGGTCCGCCA C                                                    21

(2) INFORMATION FOR SEQ ID NO:86:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:86:

GTGGCGGACC TGGGTGGCAT C                                                    21

(2) INFORMATION FOR SEQ ID NO:87:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:87:

CGTAGATCGC AGGGCACCTC C                                                    21

(2) INFORMATION FOR SEQ ID NO:88:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:88:

GTCTCTCCCG CGAATACTTC T                                                    21

(2) INFORMATION FOR SEQ ID NO:89:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:89:

```
GAGGGCCTGC TGGAGGACGT G                                       21
```

(2) INFORMATION FOR SEQ ID NO:90:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:90:

```
CGGTGGAGAA GCCGCAGGAT G                                       21
```

(2) INFORMATION FOR SEQ ID NO:91:

(i) SEQUENCE CHARACTERISTICS:
        (A) LENGTH: 3612 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 2..406
        (D) OTHER INFORMATION: /function=
            "Capsid/Maturation/Transport gene"

(ix) FEATURE:
        (A) NAME/KEY: CDS
        (B) LOCATION: 393..2927
        (D) OTHER INFORMATION: /function= "Glycoprotein B gene"

(ix) FEATURE:
        (A) NAME/KEY: CDS
        (B) LOCATION: 3057..3611
        (D) OTHER INFORMATION: /product= "DNA Polymerase"

(xi) SEQUENCE DESCRIPTION: SEQ ID NO:91:

```
TGGGGGCATG TTTCCCATTC AAAAGATGAT GGTATCAGAG ATGATCTGGC CCAGCATAGA     60

GCGGAAGGAC TGGATAGAGC CCAACTTCAA CCAGTTCTAT AGCTTTGAGA ATCAAGACAT    120

AAACCATCTG CAAAAGAGAG CTTGGGAATA TATCAGAGAG CTGGTATTAT CGGTTTCTCT    180

GAACAACAGA ACTTGGGAGA GGGAGCTAAA AATACTTCTC ACGCCTCAGG GCTCACCGGG    240

GTTTGAGGAA CCGAAACCCG CAGGACTCAC AACGGGGCTG TACCTAACAT TTGAGATATC    300

TGCGCCCTTG GTGTTGGTGG ATAAAAAATA TGGCTGGATA TTTAAAGACC TGTACGCCCT    360

TCTGTACCAC CACCTGCAAC TGAGCAACCA CAATGACTCC CAGGTCTAGA TTGGCCACCC    420

TGGGGACTGT CATCCTGTTG GTCTGCTTTT GCGCAGGCGC GGCGCACTCG AGGGGTGACA    480

CCTTTCAGAC GTCCAGTTCC CCCACACCCC CAGGATCTTC CTCTAAGGCC CCCACCAAAC    540

CTGGTGAGGA AGCATCTGGT CCTAAGAGTG TGGACTTTTA CCAGTTCAGA GTGTGTAGTG    600

CATCGATCAC CGGGGAGCTT TTTCGGTTCA ACCTGGAGCA GACGTGCCCA GACACCAAAG    660

ACAAGTACCA CCAAGAAGGA ATTTACTGG TGTACAAAAA AACATAGTG CCTCATATCT    720

TTAAGGTGCG GCGCTATAGG AAAAATTGCCA CCTCTGTCAC GGTCTACAGG GGCTTGACAG    780
```

```
AGTCCGCCAT CACCAACAAG TATGAACTCC CGAGACCCGT GCCACTCTAT GAGATAAGCC       840

ACATGGACAG CACCTATCAG TGCTTTAGTT CCATGAAGGT AAATGTCAAC GGGGTAGAAA       900

ACACATTTAC TGACAGAGAC GATGTTAACA CCACAGTATT CCTCCAACCA GTAGAGGGGC       960

TTACGGATAA CATTCAAAGG TACTTTAGCC AGCCGGTCAT CTACGCGGAA CCCGGCTGGT      1020

TTCCCGGCAT ATACAGAGTT AGGACCACYG TCAATTGCGA GATAGTGGAC ATGATAGCCA      1080

GGTCTGCTGA ACCATACAAT TACTTTGTCA CGTCACTGGG TGACACGGTG GAAGTCTCCC      1140

CTTTTTGCTA TAACGAATCC TCATGCAGCA CAACCCCCAG CAACAAAAAT GGCCTTAGCG      1200

TCCAAGTAGT TCTCAACCAC ACTGTGGTCA CGTACTCTGA CAGAGGAACC AGTCCCACTC      1260

CCCAAAACAG GATCTTTGTG GAAACGGGAG CGTACACGCT TTCGTGGGCC TCCGAGAGCA      1320

AGACCACGGC CGTGTGTCCG CTGGCACTGT GGAAAACCTT CCCGCGCTCC ATCCAGACTA      1380

CCCACGAGGA CAGCTTCCAC TTTGTGGCCA ACGAGATCAC GGCCACCTTC ACGGCTCCTC      1440

TAACGCCAGT GGCCAACTTT ACCGACACGT ACTCTTGTCT GACCTCGGAT ATCAACACCA      1500

CGCTTAACGC CAGCAAGGCC AAACTGGCGA GCACTCACGT CCCTAACGGG ACGGTCCAGT      1560

ACTTCCACAC AACAGGCGGA CTCTATTTGG TCTGGCAGCC CATGTCCGCG ATTAACCTGA      1620

CTCACGCTCA GGGCGACAGC GGGAACCCCA CGTCATCGCC GCCCCCCTCC GCATCCCCCA      1680

TGACCACCTC TGCCAGCCGC AGAAAGAGAC GGTCAGCCAG TACCGCTGCT GCCGGCGGCG      1740

GGGGGTCCAC GGACAACCTG TCTTACACGC AGCTGCAGTT TGCCTACGAC AAACTGCGGG      1800

ATGGCATTAA TCAGGTGTTA GAAGAACTCT CCAGGGCATG GTGTCGCGAG CAGGTCAGGG      1860

ACAACCTAAT GTGGTACGAG CTCAGTAAAA TCAACCCCAC CAGCGTTATG ACAGCCATCT      1920

ACGGTCGACC TGTATCCGCC AAGTTCGTAG GAGACGCCAT TTCCGTGACC GAGTGCATTA      1980

ACGTGGACCA GAGCTCCGTA ACATCCACA AGAGCCTCAG AACCAATAGT AAGGACGTGT      2040

GTTACGCGCG CCCCCTGGTG ACGTTTAAGT TTTTGAACAG TTCCAACCTA TTCACCGGCC      2100

AGCTGGGCGC GCGCAATGAG ATAATACTGA CCAACAACCA GGTGGAAACC TGCAAAGACA      2160

CCTGCGAACA CTACTTCATC ACCCGCAACG AGACTCTGGT GTATAAGGAC TACGCGTACC      2220

TGCGCACTAT AAACACCACT GACATATCCA CCCTGAACAC TTTTATCGCC CTGAATCTAT      2280

CCTTTATTCA AAACATAGAC TTCAAGGCCA TCGAGCTGTA CAGCAGTGCA GAGAAACGAC      2340

TCGCGAGTAG CGTGTTTGAC CTGGAGACGA TGTTCAGGGA GTACAACTAC TACACACATC      2400

GTCTCGCGGG TTTGCGCGAG GATCTGGACA ACACCATAGA TATGAACAAG GAGCGCTTCG      2460

TAAGGGACTT GTCGGAGATA GTGGCGGACC TGGGTGGCAT CGGAAAAACG GTKGTGAACG      2520

TGGCCAGCAG CGTGGTCACT CTATGTGGCT CATTGGTTAC CGGATTCATA AATTTTATTA      2580

AACACCCCCT AGGTGGCATG CTGATGATCA TTATCGTTAT AGCAATCATC CTGATCATTT      2640

TTATGCTCAG TCGCCGCACC AATACCATAG CCCAGGCGCC GGTGAAGATG ATCTACCCCG      2700

ACGTAGATCG CAGGGCACCT CCTAGCGGCG GAGCCCCAAC ACGGGAGGAA ATCAAAAACA      2760

TCCTGCTGGG AATGCACCAG CTACAACAAG AGGAGAGGCA GAAGGCGGAT GATYTGAAAA      2820

AAAGTACACC CTCGGTGTTT CAGCGTACCG CAAACGGCCT TCGTCAGCGT CTGAGAGGAT      2880

ATAAACCTCT GACTCAATCG CTAGACATCA GTCYGGAAAC GGGGGAGTGA CAGTGGATTC      2940

GAGGTTATTG TTTGATGTAA ATTTAGGAAA CACGGCCCGC CTCTGAAGCA CCACATACAG      3000

ACTGCAGTTA TCAACCCTAC TCGTTGCACA CAGACACAAA TTACCGTCCG CAGATCATGG      3060

ATTTTTTCAA TCCATTTATC GACCCAACTC GCGGAGGCCC GAGAAACACT GTGAGGCAAC      3120

CCACGCCGTC ACAGTCGCCA ACTGTCCCCT CGGAGACAAG AGTATGCAGG CTTATACCGG      3180
```

```
CCTGTTTCCA AACCCCGGGG CGACCCGGCG TGGTTGCCGT GGACACCACA TTTCCACCCA        3240

CCTACTTCCA GGGCCCCAAG CGGGGAGAAG TATTCGCGGG AGAGACTGGG TCTATCTGGA        3300

AAACAAGGCG CGGACAGGCA CGCAATGCTC CTATGTCGCA CCTCATATTC CACGTATACG        3360

ACATCGTGGA GACCACCTAC ACGGCCGACC GCTGCGAGGA CGTGCCATTT AGCTTCCAGA        3420

CTGATATCAT TCCCAGCGGC ACCGTCCTCA AGCTGCTCGG CAGAACACTA GATGGCGCCA        3480

GTGTCTGCGT GAACGTTTTC AGGCAGCGCT GCTACTTCTA CACACTAGCA CCCCAGGGGG        3540

TAAACCTGAC CCACGTCCTC CAGCAGGCCC TCCAGGCTGG CTTCGGTCGC GCATCCTGCG        3600

GCTTCTCCAC CG                                                            3612

(2) INFORMATION FOR SEQ ID NO:92:

(i) SEQUENCE CHARACTERISTICS:
        (A) LENGTH: 3056 base pairs
        (B) TYPE: nucleic acid
        (C) STRANDEDNESS: double
        (D) TOPOLOGY: linear (xi) SEQUENCE DESCRIPTION: SEQ ID NO:92:

TGGGGGCATG TTTCCCATTC AAAAGATGAT GGTATCAGAG ATGATCTGGC CCAGCATAGA          60

GCGGAAGGAC TGGATAGAGC CCAACTTCAA CCAGTTCTAT AGCTTTGAGA ATCAAGACAT         120

AAACCATCTG CAAAAGAGAG CTTGGGAATA TATCAGAGAG CTGGTATTAT CGGTTTCTCT         180

GAACAACAGA ACTTGGGAGA GGGAGCTAAA AATACTTCTC ACGCCTCAGG GCTCACCGGG         240

GTTTGAGGAA CCGAAACCCG CAGGACTCAC AACGGGGCTG TACCTAACAT TTGAGATATC         300

TGCGCCCTTG GTGTTGGTGG ATAAAAAATA TGGCTGGATA TTTAAAGACC TGTACGCCCT         360

TCTGTACCAC CACCTGCAAC TGAGCAACCA CAATGACTCC CAGGTCTAGA TTGGCCACCC         420

TGGGGACTGT CATCCTGTTG GTCTGCTTTT GCGCAGGCGC GGCGCACTCG AGGGGTGACA         480

CCTTTCAGAC GTCCAGTTCC CCCACACCCC CAGGATCTTC CTCTAAGGCC CCCACCAAAC         540

CTGGTGAGGA AGCATCTGGT CCTAAGAGTG TGGACTTTTA CCAGTTCAGA GTGTGTAGTG         600

CATCGATCAC CGGGGAGCTT TTTCGGTTCA ACCTGGAGCA GACGTGCCCA GACACCAAAG         660

ACAAGTACCA CCAAGAAGGA ATTTTACTGG TGTACAAAAA AAACATAGTG CCTCATATCT         720

TTAAGGTGCG GCGCTATAGG AAAATTGCCA CCTCTGTCAC GGTCTACAGG GGCTTGACAG         780

AGTCCGCCAT CACCAACAAG TATGAACTCC CGAGACCCGT GCCACTCTAT GAGATAAGCC         840

ACATGGACAG CACCTATCAG TGCTTTAGTT CCATGAAGGT AAATGTCAAC GGGGTAGAAA         900

ACACATTTAC TGACAGAGAC GATGTTAACA CCACAGTATT CCTCCAACCA GTAGAGGGGC         960

TTACGGATAA CATTCAAAGG TACTTTAGCC AGCCGGTCAT CTACGCGGAA CCCGGCTGGT        1020

TTCCCGGCAT ATACAGAGTT AGGACCACYG TCAATTGCGA GATAGTGGAC ATGATAGCCA        1080

GGTCTGCTGA ACCATACAAT TACTTTGTCA CGTCACTGGG TGACACGGTG GAAGTCTCCC        1140

CTTTTTGCTA TAACGAATCC TCATGCAGCA CAACCCCCAG CAACAAAAAT GGCCTTAGCG        1200

TCCAAGTAGT TCTCAACCAC ACTGTGGTCA CGTACTCTGA CAGAGGAACC AGTCCCACTC        1260

CCCAAAACAG GATCTTTGTG GAAACGGGAG CGTACACGCT TTCGTGGGCC TCCGAGAGCA        1320

AGACCACGGC CGTGTGTCCG CTGGCACTGT GGAAAACCTT CCCGCGCTCC ATCCAGACTA        1380

CCCACGAGGA CAGCTTCCAC TTTGTGGCCA ACGAGATCAC GGCCACCTTC ACGGCTCCTC        1440

TAACGCCAGT GGCCAACTTT ACCGACACGT ACTCTTGTCT GACCTCGGAT ATCAACACCA        1500

CGCTTAACGC CAGCAAGGCC AAACTGGCGA GCACTCACGT CCCTAACGGG ACGGTCCAGT        1560

ACTTCCACAC AACAGGCGGA CTCTATTTGG TCTGGCAGCC CATGTCCGCG ATTAACCTGA        1620
```

```
CTCACGCTCA GGGCGACAGC GGGAACCCCA CGTCATCGCC GCCCCCCTCC GCATCCCCCA      1680

TGACCACCTC TGCCAGCCGC AGAAAGAGAC GGTCAGCCAG TACCGCTGCT GCCGGCGGCG      1740

GGGGGTCCAC GGACAACCTG TCTTACACGC AGCTGCAGTT TGCCTACGAC AAACTGCGGG      1800

ATGGCATTAA TCAGGTGTTA GAAGAACTCT CCAGGGCATG GTGTCGCGAG CAGGTCAGGG      1860

ACAACCTAAT GTGGTACGAG CTCAGTAAAA TCAACCCCAC CAGCGTTATG ACAGCCATCT      1920

ACGGTCGACC TGTATCCGCC AAGTTCGTAG GAGACGCCAT TTCCGTGACC GAGTGCATTA      1980

ACGTGGACCA GAGCTCCGTA ACATCCACA AGAGCCTCAG AACCAATAGT AAGGACGTGT       2040

GTTACGCGCG CCCCCTGGTG ACGTTTAAGT TTTTGAACAG TTCCAACCTA TTCACCGGCC      2100

AGCTGGGCGC GCGCAATGAG ATAATACTGA CCAACAACCA GGTGGAAACC TGCAAAGACA      2160

CCTGCGAACA CTACTTCATC ACCCGCAACG AGACTCTGGT GTATAAGGAC TACGCGTACC      2220

TGCGCACTAT AAACACCACT GACATATCCA CCCTGAACAC TTTTATCGCC CTGAATCTAT      2280

CCTTTATTCA AAACATAGAC TTCAAGGCCA TCGAGCTGTA CAGCAGTGCA GAGAAACGAC      2340

TCGCGAGTAG CGTGTTTGAC CTGGAGACGA TGTTCAGGGA GTACAACTAC TACACACATC      2400

GTCTCGCGGG TTTGCGCGAG GATCTGGACA ACACCATAGA TATGAACAAG GAGCGCTTCG      2460

TAAGGGACTT GTCGGAGATA GTGGCGGACC TGGGTGGCAT CGGAAAAACG GTKGTGAACG      2520

TGGCCAGCAG CGTGGTCACT CTATGTGGCT CATTGGTTAC CGGATTCATA AATTTTATTA      2580

AACACCCCCT AGGTGGCATG CTGATGATCA TTATCGTTAT AGCAATCATC CTGATCATTT      2640

TTATGCTCAG TCGCCGCACC AATACCATAG CCCAGGCGCC GGTGAAGATG ATCTACCCCG      2700

ACGTAGATCG CAGGGCACCT CCTAGCGGCG GAGCCCCAAC ACGGGAGGAA ATCAAAAACA      2760

TCCTGCTGGG AATGCACCAG CTACAACAAG AGGAGAGGCA GAAGGCGGAT GATYTGAAAA      2820

AAAGTACACC CTCGGTGTTT CAGCGTACCG CAAACGGCCT TCGTCAGCGT CTGAGAGGAT      2880

ATAAACCTCT GACTCAATCG CTAGACATCA GTCYGGAAAC GGGGGAGTGA CAGTGGATTC      2940

GAGGTTATTG TTTGATGTAA ATTTAGGAAA CACGGCCCGC CTCTGAAGCA CCACATACAG      3000

ACTGCAGTTA TCAACCCTAC TCGTTGCACA CAGACACAAA TTACCGTCCG CAGATC         3056

(2) INFORMATION FOR SEQ ID NO:93:

(i) SEQUENCE CHARACTERISTICS:
        (A) LENGTH: 135 amino acids
        (B) TYPE: amino acid
        (C) STRANDEDNESS: single
        (D) TOPOLOGY: linear (xi) SEQUENCE DESCRIPTION: SEQ ID NO:93:

Gly Gly Met Phe Pro Ile Gln Lys Met Met Val Ser Glu Met Ile Trp
1               5                   10                  15

Pro Ser Ile Glu Arg Lys Asp Trp Ile Glu Pro Asn Phe Asn Gln Phe
            20                  25                  30

Tyr Ser Phe Glu Asn Gln Asp Ile Asn His Leu Gln Lys Arg Ala Trp
        35                  40                  45

Glu Tyr Ile Arg Glu Leu Val Leu Ser Val Ser Leu Asn Asn Arg Thr
    50                  55                  60

Trp Glu Arg Glu Leu Lys Ile Leu Leu Thr Pro Gln Gly Ser Pro Gly
65                  70                  75                  80

Phe Glu Glu Pro Lys Pro Ala Gly Leu Thr Thr Gly Leu Tyr Leu Thr
                85                  90                  95

Phe Glu Ile Ser Ala Pro Leu Val Leu Val Asp Lys Lys Tyr Gly Trp
            100                 105                 110
```

Ile Phe Lys Asp Leu Tyr Ala Leu Leu Tyr His His Leu Gln Leu Ser
            115                 120                 125

Asn His Asn Asp Ser Gln Val
            130                 135

(2) INFORMATION FOR SEQ ID NO:94:

(i) SEQUENCE CHARACTERISTICS:
        (A) LENGTH: 845 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 841
        (D) OTHER INFORMATION: /note= "Proline or Leucine
            depending on codon"

(xi) SEQUENCE DESCRIPTION: SEQ ID NO:94:

Met Thr Pro Arg Ser Arg Leu Ala Thr Leu Gly Thr Val Ile Leu Leu
1               5                   10                  15

Val Cys Phe Cys Ala Gly Ala Ala His Ser Arg Gly Asp Thr Phe Gln
            20                  25                  30

Thr Ser Ser Ser Pro Thr Pro Pro Gly Ser Ser Ser Lys Ala Pro Thr
            35                  40                  45

Lys Pro Gly Glu Glu Ala Ser Gly Pro Lys Ser Val Asp Phe Tyr Gln
50                  55                  60

Phe Arg Val Cys Ser Ala Ser Ile Thr Gly Glu Leu Phe Arg Phe Asn
65                  70                  75                  80

Leu Glu Gln Thr Cys Pro Asp Thr Lys Asp Lys Tyr His Gln Glu Gly
                85                  90                  95

Ile Leu Leu Val Tyr Lys Lys Asn Ile Val Pro His Ile Phe Lys Val
            100                 105                 110

Arg Arg Tyr Arg Lys Ile Ala Thr Ser Val Thr Val Tyr Arg Gly Leu
            115                 120                 125

Thr Glu Ser Ala Ile Thr Asn Lys Tyr Glu Leu Pro Arg Pro Val Pro
            130                 135                 140

Leu Tyr Glu Ile Ser His Met Asp Ser Thr Tyr Gln Cys Phe Ser Ser
145                 150                 155                 160

Met Lys Val Asn Val Asn Gly Val Glu Asn Thr Phe Thr Asp Arg Asp
            165                 170                 175

Asp Val Asn Thr Thr Val Phe Leu Gln Pro Val Glu Gly Leu Thr Asp
            180                 185                 190

Asn Ile Gln Arg Tyr Phe Ser Gln Pro Val Ile Tyr Ala Glu Pro Gly
            195                 200                 205

Trp Phe Pro Gly Ile Tyr Arg Val Arg Thr Thr Val Asn Cys Glu Ile
            210                 215                 220

Val Asp Met Ile Ala Arg Ser Ala Glu Pro Tyr Asn Tyr Phe Val Thr
225                 230                 235                 240

Ser Leu Gly Asp Thr Val Glu Val Ser Pro Phe Cys Tyr Asn Glu Ser
            245                 250                 255

Ser Cys Ser Thr Thr Pro Ser Asn Lys Asn Gly Leu Ser Val Gln Val
            260                 265                 270

Val Leu Asn His Thr Val Val Thr Tyr Ser Asp Arg Gly Thr Ser Pro
            275                 280                 285

Thr Pro Gln Asn Arg Ile Phe Val Glu Thr Gly Ala Tyr Thr Leu Ser
            290                 295                 300

```
Trp Ala Ser Glu Ser Lys Thr Thr Ala Val Cys Pro Leu Ala Leu Trp
305                 310                 315                 320

Lys Thr Phe Pro Arg Ser Ile Gln Thr Thr His Glu Asp Ser Phe His
            325                 330                 335

Phe Val Ala Asn Glu Ile Thr Ala Thr Phe Thr Ala Pro Leu Thr Pro
        340                 345                 350

Val Ala Asn Phe Thr Asp Thr Tyr Ser Cys Leu Thr Ser Asp Ile Asn
        355                 360                 365

Thr Thr Leu Asn Ala Ser Lys Ala Lys Leu Ala Ser Thr His Val Pro
    370                 375                 380

Asn Gly Thr Val Gln Tyr Phe His Thr Gly Gly Leu Tyr Leu Val
385                 390                 395                 400

Trp Gln Pro Met Ser Ala Ile Asn Leu Thr His Ala Gln Gly Asp Ser
                405                 410                 415

Gly Asn Pro Thr Ser Ser Pro Pro Ser Ala Ser Pro Met Thr Thr
            420                 425                 430

Ser Ala Ser Arg Arg Lys Arg Arg Ser Ala Ser Thr Ala Ala Gly
        435                 440                 445

Gly Gly Gly Ser Thr Asp Asn Leu Ser Tyr Thr Gln Leu Gln Phe Ala
450                 455                 460

Tyr Asp Lys Leu Arg Asp Gly Ile Asn Gln Val Leu Glu Glu Leu Ser
465                 470                 475                 480

Arg Ala Trp Cys Arg Glu Gln Val Arg Asp Asn Leu Met Trp Tyr Glu
                485                 490                 495

Leu Ser Lys Ile Asn Pro Thr Ser Val Met Thr Ala Ile Tyr Gly Arg
            500                 505                 510

Pro Val Ser Ala Lys Phe Val Gly Asp Ala Ile Ser Val Thr Glu Cys
        515                 520                 525

Ile Asn Val Asp Gln Ser Ser Val Asn Ile His Lys Ser Leu Arg Thr
        530                 535                 540

Asn Ser Lys Asp Val Cys Tyr Ala Arg Pro Leu Val Thr Phe Lys Phe
545                 550                 555                 560

Leu Asn Ser Ser Asn Leu Phe Thr Gly Gln Leu Gly Ala Arg Asn Glu
                565                 570                 575

Ile Ile Leu Thr Asn Asn Gln Val Glu Thr Cys Lys Asp Thr Cys Glu
            580                 585                 590

His Tyr Phe Ile Thr Arg Asn Glu Thr Leu Val Tyr Lys Asp Tyr Ala
        595                 600                 605

Tyr Leu Arg Thr Ile Asn Thr Thr Asp Ile Ser Thr Leu Asn Thr Phe
        610                 615                 620

Ile Ala Leu Asn Leu Ser Phe Ile Gln Asn Ile Asp Phe Lys Ala Ile
625                 630                 635                 640

Glu Leu Tyr Ser Ser Ala Glu Lys Arg Leu Ala Ser Ser Val Phe Asp
                645                 650                 655

Leu Glu Thr Met Phe Arg Glu Tyr Asn Tyr Tyr Thr His Arg Leu Ala
            660                 665                 670

Gly Leu Arg Glu Asp Leu Asp Asn Thr Ile Asp Met Asn Lys Glu Arg
        675                 680                 685

Phe Val Arg Asp Leu Ser Glu Ile Val Ala Asp Leu Gly Gly Ile Gly
        690                 695                 700

Lys Thr Val Val Asn Val Ala Ser Ser Val Val Thr Leu Cys Gly Ser
705                 710                 715                 720

Leu Val Thr Gly Phe Ile Asn Phe Ile Lys His Pro Leu Gly Gly Met
```

```
                        725                 730                 735
Leu Met Ile Ile Ile Val Ile Ala Ile Ile Leu Ile Ile Phe Met Leu
            740                 745                 750

Ser Arg Arg Thr Asn Thr Ile Ala Gln Ala Pro Val Lys Met Ile Tyr
        755                 760                 765

Pro Asp Val Asp Arg Arg Ala Pro Pro Ser Gly Gly Ala Pro Thr Arg
    770                 775                 780

Glu Glu Ile Lys Asn Ile Leu Leu Gly Met His Gln Leu Gln Gln Glu
785                 790                 795                 800

Glu Arg Gln Lys Ala Asp Asp Leu Lys Lys Ser Thr Pro Ser Val Phe
                805                 810                 815

Gln Arg Thr Ala Asn Gly Leu Arg Gln Arg Leu Arg Gly Tyr Lys Pro
            820                 825                 830

Leu Thr Gln Ser Leu Asp Ile Ser Xaa Glu Thr Gly Glu
        835                 840                 845

(2) INFORMATION FOR SEQ ID NO:95:

(i) SEQUENCE CHARACTERISTICS:
        (A) LENGTH: 185 amino acids
        (B) TYPE: amino acid
        (C) STRANDEDNESS: single
        (D) TOPOLOGY: linear (xi) SEQUENCE DESCRIPTION: SEQ ID NO:95:

Met Asp Phe Phe Asn Pro Phe Ile Asp Pro Thr Arg Gly Gly Pro Arg
1               5                   10                  15

Asn Thr Val Arg Gln Pro Thr Pro Ser Gln Ser Pro Thr Val Pro Ser
            20                  25                  30

Glu Thr Arg Val Cys Arg Leu Ile Pro Ala Cys Phe Gln Thr Pro Gly
        35                  40                  45

Arg Pro Gly Val Val Ala Val Asp Thr Thr Phe Pro Pro Thr Tyr Phe
    50                  55                  60

Gln Gly Pro Lys Arg Gly Glu Val Phe Ala Gly Glu Thr Gly Ser Ile
65                  70                  75                  80

Trp Lys Thr Arg Arg Gly Gln Ala Arg Asn Ala Pro Met Ser His Leu
                85                  90                  95

Ile Phe His Val Tyr Asp Ile Val Glu Thr Thr Tyr Thr Ala Asp Arg
            100                 105                 110

Cys Glu Asp Val Pro Phe Ser Phe Gln Thr Asp Ile Ile Pro Ser Gly
        115                 120                 125

Thr Val Leu Lys Leu Leu Gly Arg Thr Leu Asp Gly Ala Ser Val Cys
    130                 135                 140

Val Asn Val Phe Arg Gln Arg Cys Tyr Phe Tyr Thr Leu Ala Pro Gln
145                 150                 155                 160

Gly Val Asn Leu Thr His Val Leu Gln Gln Ala Leu Gln Ala Gly Phe
                165                 170                 175

Gly Arg Ala Ser Cys Gly Phe Ser Thr
                180                 185

(2) INFORMATION FOR SEQ ID NO:96:

(i) SEQUENCE CHARACTERISTICS:
        (A) LENGTH: 386 base pairs
        (B) TYPE: nucleic acid
        (C) STRANDEDNESS: double
        (D) TOPOLOGY: linear (ix) FEATURE:
```

(A) NAME/KEY: CDS
              (B) LOCATION: 1..384

(xi) SEQUENCE DESCRIPTION: SEQ ID NO:96:

```
GTG TAC AAG AAG AAC ATC GTG CCT AAC ATG TTC AAG GTA CGC AGG TAC          48
Val Tyr Lys Lys Asn Ile Val Pro Asn Met Phe Lys Val Arg Arg Tyr
 1               5                  10                  15

AGA AAA GTA GCA ACG CCT GTC ACA CTC TAC CGC GGT ATG ACA GAC GCA          96
Arg Lys Val Ala Thr Pro Val Thr Leu Tyr Arg Gly Met Thr Asp Ala
                 20                  25                  30

GCA ATA ACT AAC AAA TAT GAA ATT CCC AGA CCC GTA CCA CTA TAC GAG         144
Ala Ile Thr Asn Lys Tyr Glu Ile Pro Arg Pro Val Pro Leu Tyr Glu
             35                  40                  45

ATC AGT CAC ATG GAC AGC ACC TAC CAG TGC TTT AGT TCC ATG AAA ATT         192
Ile Ser His Met Asp Ser Thr Tyr Gln Cys Phe Ser Ser Met Lys Ile
 50                  55                  60

GTA GTG AAC GGA GTC GAA AAC ACG TTC ACC GGT CGG GAT GAC GTA AAC         240
Val Val Asn Gly Val Glu Asn Thr Phe Thr Gly Arg Asp Asp Val Asn
 65                  70                  75                  80

AAA AGC GTA TTT CTC CAG CCA GTC GAA GGT CTA ACT GAC AAC ATA AAG         288
Lys Ser Val Phe Leu Gln Pro Val Glu Gly Leu Thr Asp Asn Ile Lys
                 85                  90                  95

AGA TAC TTT AGC CAG CCA GTG CTA TAT TCT GAA CCC GGA TGG TTT CCA         336
Arg Tyr Phe Ser Gln Pro Val Leu Tyr Ser Glu Pro Gly Trp Phe Pro
             100                 105                 110

GGT ATC TAC AGG GTT AGG ACA ACA GTT AAT TGT GAG ATT GTA GAC ATG         384
Gly Ile Tyr Arg Val Arg Thr Thr Val Asn Cys Glu Ile Val Asp Met
         115                 120                 125

TT                                                                      386
```

(2) INFORMATION FOR SEQ ID NO:97:

(i) SEQUENCE CHARACTERISTICS:
              (A) LENGTH: 128 amino acids
              (B) TYPE: amino acid
              (D) TOPOLOGY: linear (ii) MOLECULE TYPE: protein (xi) SEQUENCE DESCRIPTION: SEQ ID NO:97:

```
Val Tyr Lys Lys Asn Ile Val Pro Asn Met Phe Lys Val Arg Arg Tyr
 1               5                  10                  15

Arg Lys Val Ala Thr Pro Val Thr Leu Tyr Arg Gly Met Thr Asp Ala
                 20                  25                  30

Ala Ile Thr Asn Lys Tyr Glu Ile Pro Arg Pro Val Pro Leu Tyr Glu
             35                  40                  45

Ile Ser His Met Asp Ser Thr Tyr Gln Cys Phe Ser Ser Met Lys Ile
 50                  55                  60

Val Val Asn Gly Val Glu Asn Thr Phe Thr Gly Arg Asp Asp Val Asn
 65                  70                  75                  80

Lys Ser Val Phe Leu Gln Pro Val Glu Gly Leu Thr Asp Asn Ile Lys
                 85                  90                  95

Arg Tyr Phe Ser Gln Pro Val Leu Tyr Ser Glu Pro Gly Trp Phe Pro
             100                 105                 110

Gly Ile Tyr Arg Val Arg Thr Thr Val Asn Cys Glu Ile Val Asp Met
         115                 120                 125
```

(2) INFORMATION FOR SEQ ID NO:98:

(i) SEQUENCE CHARACTERISTICS:
              (A) LENGTH: 26 base pairs (B) TYPE: nucleic acid
            (C) STRANDEDNESS: single
            (D) TOPOLOGY: linear (xi) SEQUENCE DESCRIPTION: SEQ ID NO:98:

ATGTTCAGGG AGTACAACTA CTACAC                                              26

(2) INFORMATION FOR SEQ ID NO:99:

(i) SEQUENCE CHARACTERISTICS:
            (A) LENGTH: 21 amino acids
            (B) TYPE: amino acid
            (C) STRANDEDNESS: single
            (D) TOPOLOGY: linear (xi) SEQUENCE DESCRIPTION: SEQ ID NO:99:

Ile Tyr Ala Glu Pro Gly Trp Phe Pro Gly Ile Tyr Arg Val Arg Thr
1               5                   10                  15

Thr Val Asn Cys Glu
            20

(2) INFORMATION FOR SEQ ID NO:100:

(i) SEQUENCE CHARACTERISTICS:
            (A) LENGTH: 16 amino acids
            (B) TYPE: amino acid
            (C) STRANDEDNESS: single
            (D) TOPOLOGY: linear (xi) SEQUENCE DESCRIPTION: SEQ ID NO:100:

Val Leu Glu Glu Leu Ser Arg Ala Trp Cys Arg Glu Gln Val Arg Asp
1               5                   10                  15

(2) INFORMATION FOR SEQ ID NO:101:

(i) SEQUENCE CHARACTERISTICS:
            (A) LENGTH: 48 amino acids
            (B) TYPE: amino acid
            (C) STRANDEDNESS: single
            (D) TOPOLOGY: linear (xi) SEQUENCE DESCRIPTION: SEQ ID NO:101:

Met Thr Pro Arg Ser Arg Leu Ala Thr Leu Gly Thr Val Ile Leu Leu
1               5                   10                  15

Val Cys Phe Cys Ala Gly Ala Ala His Ser Arg Gly Asp Thr Phe Gln
                20                  25                  30

Thr Ser Ser Ser Pro Thr Pro Pro Gly Ser Ser Ser Lys Ala Pro
            35                  40                  45

(2) INFORMATION FOR SEQ ID NO:102:

(i) SEQUENCE CHARACTERISTICS:
            (A) LENGTH: 42 amino acids
            (B) TYPE: amino acid
            (C) STRANDEDNESS: single
            (D) TOPOLOGY: linear (xi) SEQUENCE DESCRIPTION: SEQ ID NO:102:

Met Val Pro Asn Lys His Leu Leu Ile Leu Ser Phe Ser Thr Ala
1               5                   10                  15

Cys Gly Gln Thr Thr Pro Thr Thr Ala Val Glu Lys Asn Lys Thr Gln
                20                  25                  30

Ala Ile Tyr Gln Glu Tyr Phe Lys Tyr Arg
            35                  40

(2) INFORMATION FOR SEQ ID NO:103:

(i) SEQUENCE CHARACTERISTICS:
        (A) LENGTH: 45 amino acids
        (B) TYPE: amino acid
        (C) STRANDEDNESS: single
        (D) TOPOLOGY: linear (xi) SEQUENCE DESCRIPTION: SEQ ID NO:103:

Met Tyr Tyr Lys Thr Ile Leu Phe Phe Ala Leu Ile Lys Val Cys Ser
1               5                   10                  15

Phe Asn Gln Thr Thr Thr His Ser Thr Thr Thr Ser Pro Ser Ile Ser
            20                  25                  30

Ser Thr Thr Ser Ser Thr Thr Thr Ser Thr Ser Lys Pro
        35                  40                  45

(2) INFORMATION FOR SEQ ID NO:104:

(i) SEQUENCE CHARACTERISTICS:
        (A) LENGTH: 49 amino acids
        (B) TYPE: amino acid
        (C) STRANDEDNESS: single
        (D) TOPOLOGY: linear (xi) SEQUENCE DESCRIPTION: SEQ ID NO:104:

Met Tyr Pro Thr Val Lys Ser Met Arg Val Ala His Leu Thr Asn Leu
1               5                   10                  15

Leu Thr Leu Leu Cys Leu Leu Cys His Thr His Leu Tyr Val Cys Gln
            20                  25                  30

Pro Thr Thr Leu Arg Gln Pro Ser Asp Met Thr Pro Ala Gln Asp Ala
        35                  40                  45

Pro (2) INFORMATION FOR SEQ ID NO:105:

(i) SEQUENCE CHARACTERISTICS:
        (A) LENGTH: 48 amino acids
        (B) TYPE: amino acid
        (C) STRANDEDNESS: single
        (D) TOPOLOGY: linear (xi) SEQUENCE DESCRIPTION: SEQ ID NO:105:

Met Thr Arg Arg Arg Val Leu Ser Val Val Leu Leu Ala Ala Leu
1               5                   10                  15

Ala Cys Arg Leu Gly Ala Gln Thr Pro Glu Gln Pro Ala Pro Pro Ala
            20                  25                  30

Thr Thr Val Gln Pro Thr Ala Thr Arg Gln Gln Leu Ser Val Val Val
        35                  40                  45

(2) INFORMATION FOR SEQ ID NO:106:

(i) SEQUENCE CHARACTERISTICS:
        (A) LENGTH: 19 amino acids
        (B) TYPE: amino acid
        (C) STRANDEDNESS: single
        (D) TOPOLOGY: linear (xi) SEQUENCE DESCRIPTION: SEQ ID NO:106:

Cys Ala Gly Ala Ala His Ser Arg Gly Asp Thr Phe Gln Thr Ser Ser
1               5                   10                  15

Ser Pro Thr (2) INFORMATION FOR SEQ ID NO:107:

(i) SEQUENCE CHARACTERISTICS:
            (A) LENGTH: 18 amino acids
            (B) TYPE: amino acid
            (C) STRANDEDNESS: single
            (D) TOPOLOGY: linear (xi) SEQUENCE DESCRIPTION: SEQ ID NO:107:

Asn Ile Met Glu Ile Leu Arg Gly Asp Phe Ser Ser Ala Asn Asn Arg
1               5                   10                  15

Asp Asn (2) INFORMATION FOR SEQ ID NO:108:

(i) SEQUENCE CHARACTERISTICS:
            (A) LENGTH: 18 amino acids
            (B) TYPE: amino acid
            (C) STRANDEDNESS: single
            (D) TOPOLOGY: linear (xi) SEQUENCE DESCRIPTION: SEQ ID NO:108:

Ser Ser Thr Ser Tyr Asn Arg Gly Asp Ser Thr Phe Glu Ser Lys Ser
1               5                   10                  15

Tyr Lys (2) INFORMATION FOR SEQ ID NO:109:

(i) SEQUENCE CHARACTERISTICS:
            (A) LENGTH: 20 amino acids
            (B) TYPE: amino acid
            (C) STRANDEDNESS: single
            (D) TOPOLOGY: linear (xi) SEQUENCE DESCRIPTION: SEQ ID NO:109:

Ala Leu Gly Gly Asp Val Glu Lys Arg Gly Asp Arg Glu Glu Ala His
1               5                   10                  15

Val Pro Phe Phe
            20

(2) INFORMATION FOR SEQ ID NO:110:

(i) SEQUENCE CHARACTERISTICS:
            (A) LENGTH: 19 amino acids
            (B) TYPE: amino acid
            (C) STRANDEDNESS: single
            (D) TOPOLOGY: linear (xi) SEQUENCE DESCRIPTION: SEQ ID NO:110:

Cys Gln Ala Gly Thr Phe Ala Leu Arg Gly Asp Ser Thr Phe Glu Glu
1               5                   10                  15

Ser Lys Ser (2) INFORMATION FOR SEQ ID NO:111:

(i) SEQUENCE CHARACTERISTICS:
            (A) LENGTH: 20 amino acids
            (B) TYPE: amino acid
            (C) STRANDEDNESS: single
            (D) TOPOLOGY: linear (xi) SEQUENCE DESCRIPTION: SEQ ID NO:111:

Ile Thr Val Tyr Ala Val Thr Gly Arg Gly Asp Ser Pro Ala Ser Ser
1               5                   10                  15

Lys Pro Ile Ser
            20

(2) INFORMATION FOR SEQ ID NO:112:

(i) SEQUENCE CHARACTERISTICS:
        (A) LENGTH: 20 amino acids
        (B) TYPE: amino acid
        (C) STRANDEDNESS: single
        (D) TOPOLOGY: linear (xi) SEQUENCE DESCRIPTION: SEQ ID NO:112:

Cys Glu Val Val Thr Gly Ser Pro Arg Gly Asp Ser Gln Ser Ser Trp
1               5                   10                  15

Lys Ser Val Gly
            20

(2) INFORMATION FOR SEQ ID NO:113:

(i) SEQUENCE CHARACTERISTICS:
        (A) LENGTH: 18 amino acids
        (B) TYPE: amino acid
        (C) STRANDEDNESS: single
        (D) TOPOLOGY: linear (xi) SEQUENCE DESCRIPTION: SEQ ID NO:113:

Cys Lys Pro Gln Val Thr Arg Gly Asp Val Phe Thr Met Pro Glu Asp
1               5                   10                  15

Glu Tyr

What is claimed is:

1. An isolated polynucleotide comprising a sequence as set forth as nucleotides 36 to 354 of SEQ. ID NO:1 or SEQ. ID NO:3.

2. An isolated polynucleotide comprising a sequence selected from the group consisting of: SEQ. ID NO:41, SEQ. ID NO:43, SEQ. ID NO.:45 and SEQ. ID NO:46.

3. An isolated polynucleotide comprising a sequence set forth in a member of the group consisting of nucleotides 36 to 354 inclusive of SEQ. ID NO1, nucleotides 36 to 354 inclusive of SEQ ID NO:3, nucleotides 36 to 354 inclusive of SEQ ID NO:92 and SEQ. ID NO:96.

4. An isolated or non-naturally occurring polynucleotide encoding a polypeptide comprising a sequence as set forth in a member of the group consisting of amino acids 13 to 118 inclusive of SEQ ID NO:2, amino acids 13 to 118 inclusive of SEQ ID NO:4, amino acids 13 to 118 inclusive of SEQ ID NO:97, and SEQ ID NO: 94.

5. A recombinant cloning or expression vector comprising the polynucleotide of claim 4.

6. A host cell transformed by the polynucleotide of claim 4.

7. An oligonucleotide selected from the group consisting of SEQ. ID NOS:24–63, SEQ. ID NOS.77–78, and SEQ. ID NOS:80–90.

8. An isolated polynucleotide, where said polynucleotide is capable of hybridizing under conditions of high stringency with a second polynucleotide comprising a sequence selected from the group consisting of SEQ. ID NOS:1, 3, 92, and 94, and their respective complementary sequences, but is not capable of hybridizing under conditions of high stringency with a polynucleotide having a sequence of any of SEQ. ID NOS:5–13.

9. The isolated polynucleotide of claim 8, the nucleotide sequence of which is contained in the genome of a naturally occurring virus.

10. A monoclonal or isolated polyclonal antibody specific for a Glycoprotein B polypeptide encoded in said encoding region of the polynucleotide of claim 1.

11. A monoclonal or isolated polyclonal antibody specific for the polypeptide encoded by the polynucleotide of claim 4.

12. A diagnostic kit for detecting a herpes virus polynucleotide in a biological sample, comprising a reagent in suitable packaging, wherein the reagent comprises the polynucleotide of claim 3.

13. A diagnostic kit for detecting a herpes virus polypeptide present in a biological sample, comprising a reagent in suitable packaging, wherein the reagent comprises the antibody of claim 11.

14. A method of inhibiting attachment of a herpes virus to a cell, comprising contacting the cell with a polypeptide encoded by the polynucleotide of claim 4, wherein said polypeptide comprises an arginine-glycine-aspartic acid sequence.

15. A method of detecting infection of an individual by a herpes virus, comprising the steps of:
   a) contacting antibody from a sample obtained from the individual with the polypeptide encoded by the polynucleotide of claim 4 under conditions that permit the formation of a stable antigen-antibody complex; and
   b) detecting said stable complexes formed in step a), if any.

16. A method of detecting infection of an individual by a herpes virus, comprising the steps of:
   a) contacting a polypeptide from a sample obtained from the individual with the antibody of claim 11 under conditions that permit the formation of a stable antigen-antibody complex; and
   b) detecting said stable complexes formed in step a), if any.

17. A method of producing a Glycoprotein B polypeptide, comprising expressing the polynucleotide of claim 4 in a eukaryotic cell.

* * * * *